(12) United States Patent
Ross, Jr. et al.

(10) Patent No.: US 6,313,339 B1
(45) Date of Patent: Nov. 6, 2001

(54) ARYL AND HETEROARYLCYLOPROPYL OXIME ETHERS AND THEIR USE AS FUNGICIDES AND INSECTICIDES

(76) Inventors: Ronald Ross, Jr., 2198 Jericho Dr., Jamison, PA (US) 18929; Duyan Vuong Nguyen, 7600 Stenton Ave. Apt. 7D, Philadelphia, PA (US) 19118; Steve Howard Shaber, 44 Ash Stoker La., Horsham, PA (US) 19044

( * ) Notice: Subject to any disclaimer, the term of this patent is extended or adjusted under 35 U.S.C. 154(b) by 0 days.

(21) Appl. No.: 09/506,094

(22) Filed: Feb. 17, 2000

(51) Int. Cl.$^7$ .................. C07C 229/08; A01N 37/44
(52) U.S. Cl. ................. 560/35; 514/256; 514/357; 514/438; 514/461; 514/521; 514/522; 514/538; 514/624; 544/242; 544/335; 544/336; 546/329; 546/335; 549/76; 549/496; 558/391; 558/414; 558/434; 564/163; 564/164

(58) Field of Search ................ 514/256, 357, 514/438, 461, 521, 522, 538, 624; 544/242, 335, 336; 546/329, 335; 549/76, 496; 558/391, 434, 414; 560/35; 564/163, 164

(56) References Cited

U.S. PATENT DOCUMENTS

| 5,756,426 | 5/1998 | Ziegler et al. ............ 504/312 |
| 5,874,467 | 2/1999 | Bayer et al. ............. 514/538 |
| 5,889,059 | 3/1999 | Bayer et al. ............. 514/619 |

*Primary Examiner*—Shailendra Kumar

(57) ABSTRACT

Certain cyclopropyl oxime ethers substituted by aryl and heterocyclic moieties possess broad spectrum fungicidal and insecticidal properties. These compounds are disclosed along with compositions containing these compounds and methods for controlling fungi and insects by the use of a fungitoxic or insecticidal amount of these compounds.

10 Claims, No Drawings

ARYL AND HETEROARYLCYLOPROPYL OXIME ETHERS AND THEIR USE AS FUNGICIDES AND INSECTICIDES

The present invention relates to certain aryl cyclopropyl oxime ether structures, compositions containing these compounds and methods for controlling fungi and insects by the use of a fungitoxic or insecticidal amount of these compounds.

Compounds having certain bis oxime ether structures have been disclosed in U.S. Pat. No. 5,756,426. We have discovered certain new bis oxime ethers which possess a cyclopropane substituted by aryl and heterocyclic moieties. These novel derivatives possess broad spectrum fungicidal and insecticidal properties.

The novel cyclopropyloxime ethers of the present invention have the Formula I:

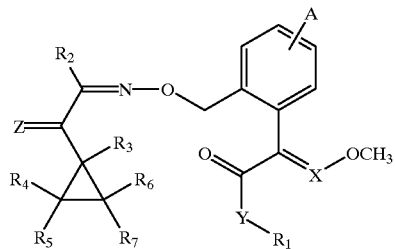

(I)

wherein

X is N or CH; Y is O, S or $NR_8$;

A is selected from the group consisting of hydrogen, halo, cyano, $(C_1-C_{12})$alkyl, and $(C_1-C_{12})$alkoxy;

Z is O, N—$OR_9$ or N—$R_{10}$;

$R_1$ and $R_8$ are independently selected from the group consisting of hydrogen and $(C_1-C_4)$alkyl;

$R_2$ is selected from the group consisting of hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, cyano, $(C_1-C_4)$alkoxycarbonyl, aryl, aralkyl, heterocyclic, and heterocyclic$(C_1-C_4)$alkyl;

$R_3$ and $R_7$ are each independently selected from the group consisting of hydrogen, $(C_1-C_{12})$alkyl, halo$(C_1-C_{12})$alkyl, $(C_2-C_8)$alkenyl, halo$(C_2-C_8)$alkenyl, $(C_2-C_8)$alkynyl, halo$(C_2-C_8)$alkynyl, aryl, aralkyl, heterocyclic and heterocyclic$(C_1-C_4)$alkyl, provided that at least one of $R_3$ and $R_7$ is aryl, aralkyl, heterocyclic, or heterocyclic $(C_1-C_4)$alkyl;

$R_4$, $R_5$, and $R_6$ are each independently selected from the group consisting of hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, halo, cyano, $(C_1-C_4)$alkoxycarbonyl, aryl, aralkyl, heterocyclic and heterocyclic$(C_1-C_4)$alkyl;

$R_9$ is selected from the group consisting of hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, $(C_1-C_4)$alkylcarbonyl, arylcarbonyl, aralkylcarbonyl, heterocyclic carbonyl, $(C_1-C_4)$alkoxycarbonyl, aryl, aralkyl, heterocyclic and heterocyclic$(C_1-C_4)$alkyl;

$R_{10}$ is selected from the group consisting of hydrogen, $(C_1-C_{12})$alkyl, halo$(C_1-C_{12})$alkyl, $(C_2-C_8)$alkenyl, halo$(C_2-C_8)$alkenyl, $(C_2-C_8)$alkynyl, halo$(C_2-C_8)$alkynyl, aryl, aralkyl, heterocyclic or heterocyclic $(C_1-C_4)$alkyl, $(C_1-C_4)$alkylcarbonyl, and $(C_1-C_4)$alkoxycarbonyl, arylcarbonyl, aralkylcarbonyl, heterocyclic carbonyl, $(C_1-C_4)$alkylaminocarbonyl, arylaminocarbonyl, N—$R_8R_9$, N=$CR_1R_{12}$, $(C_1-C_4)$alkylsulfonyl, N=cyclopropyl, N=cyclobutyl, N=cyclopentyl, N=cyclohexyl, and arylsulfonyl;

$R_{11}$ and $R_{12}$ are each independently selected from the group consisting of hydrogen, $(C_1-C_{12})$alkyl, halo$(C_1-C_{12})$alkyl, $(C_1-C_{12})$alkoxy, halo$(C_1-C_{12})$alkoxy, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, cyano, $(C_1-C_4)$alkoxycarbonyl, $(C_1-C_4)$alkylamino, aryl, aralkyl, heterocyclic, and heterocyclic$(C_1-C_4)$alkyl.

The aforementioned $(C_1-C_{12})$alkyl, $(C_2-C_8)$alkenyl, $(C_2-C_8)$alkynyl and $(C_3-C_7)$cycloalkyl groups may be optionally substituted with up to three substituents selected from the group consisting of nitro, halomethyl, $(C_1-C_4)$alkoxycarbonyl, and cyano.

Unless otherwise limited, the following terms, as used herein, have the following meanings.

The term "alkyl" means both branched and straight chain alkyl groups from 1 to 12 carbon atoms. Typical alkyl groups are methyl, ethyl, n-propyl, iso-propyl, n-butyl, sec-butyl, isobutyl, t-butyl, n-pentyl, isopentyl, n-hexyl, n-heptyl, isooctyl, nonyl, decyl, undecyl, dodecyl and the like. The term haloalkyl refers to an alkyl group substituted with 1 to 3 halogens.

The term "alkenyl" means an ethylenically unsaturated hydrocarbon group, straight or branched, having a chain length of 2 to 8 carbon atoms and 1 or 2 ethylenic bonds. The term "haloalkenyl" means an alkenyl group substituted with 1 to 3 halogen atoms. The term "alkynyl" means an unsaturated hydrocarbon group, straight or branched, having a chain length of 2 to 12 carbon atoms and 1 or 2 acetylenic bonds.

The term "aryl" means phenyl or naphthyl, which maybe substituted with up to three substituents independently selected from the group consisting of halogen, cyano, trihalomethyl, phenyl, phenoxy, $(C_1-C_4)$alkyl, $(C_1-C_4)$alkoxy, $(C_1-C_4)$alkylthio, $(C_1-C_4)$alkylsulfoxide, halo $(C_1-C_4)$alkyl and halo$(C_1-C_4)$alkoxy.

Typical aryl substituents include but are not limited to 2-chlorophenyl, 3-chlorophenyl, 4-chlorophenyl, 2-fluorophenyl, 3-fluorophenyl, 4-fluorophenyl, 4-bromophenyl, 2-methylphenyl, 3-methyphenyl, 4-methylphenyl, 2,4-dibromophenyl, 3,5-difluorophenyl, 2,4,6-trichlorophenyl, 2-chloronapthyl, 3-(trifluoromethyl) phenyl, 4-(trifluoromethyl)phenyl and 2-iodo-4-methylphenyl.

The term "heterocyclic" means a substituted or unsubstituted 6 membered unsaturated ring containing one, two or three heteroatoms independently selected from oxygen, nitrogen and sulfur or to a bicyclic unsaturated ring system containing up to 10 atoms including one heteroatom selected from oxygen, nitrogen and sulfur. The term "heterocyclic" also refers to a 5-membered unsaturated ring containing one, two, or three heteroatoms independently selected from oxygen, nitrogen, and sulfur, preferably one or two heteroatoms. Examples of heterocycles include but are not limited to 2-, 3- or 4-pyridinyl, pyrazinyl, 2-, 4-, or 5-pyrimidinyl, pyridazinyl, pyrazole, triazolyl, imidazolyl, 2 or 3-thienyl, 2 or 3-furyl, pyrrolyl, oxazolyl, isoxazolyl, thiazolyl, isothiazolyl, oxadiazolyl, thiadiazolyl, quinolyl and isoquinolyl. If the heterocyclic ring is substituted there may be up to two substituents independently selected from $(C_1-C_4)$ alkyl, halogen, cyano, nitro, and trihalomethyl.

The term "aralkyl" means a group having an alkyl chain and an aryl portion wherein the alkyl chain is from 1 to 10 carbon atoms and can be branched or straight chain, preferably a straight chain, with the aryl portion, as defined above, forming a terminal portion of the aralkyl moiety. Typical aralkyl moieties are optionally substituted benzyl, phenethyl, phenpropyl and phenbutyl moieties. Typical benzyl moieties are 2-chlorobenzyl, 3-chlorobenzyl, 4-chlorobenzyl, 2-fluorobenzyl, 3-fluorobenzyl, 4-fluorobenzyl, 4-trifluoromethylbenzyl, 2,4-dichlorobenzyl, 2,4-dibromobenzyl, 2-methylbenzyl, 3-methylbenzyl, and 4-methylbenzyl. Typical phenethyl moieties are 2-(2-chlorophenyl)ethyl, 2-(3-chlorophenyl) ethyl, 2-(4-chlorophenyl)ethyl, 2-(2-fluorophenyl)ethyl, 2-(3-fluorophenyl)ethyl, 2-(4-fluorophenyl)ethyl, 2-(2-methylphenyl)ethyl, 2-(3-methyl-phenyl)ethyl, 2-(4-methylphenyl)ethyl, 2-(4-trifluoromethylphenyl)ethyl, 2-(2,4-dichlorophenyl)-ethyl, 2-(3,5-dimethoxyphenyl)ethyl. Typical phenpropyl moieties are 3-phenylpropyl, 3-(2-chlorophenyl)propyl, 3-(3-chlorophenyl)propyl, 3-(4-chlorophenyl)propyl, 3-(2,4-dichloro-phenyl)propyl, 3-(2-fluorophenyl)propyl, 3-(3-fluorophenyl)propyl, 3-(4-fluorophenyl)propyl, 3-(2-methylphenyl)propyl, 3-(3-methylphenyl)propyl, 3-(4-methylphenyl)ethyl, 3-(4-trifluoromethylphenyl)propyl, 3-(2,4-dichlorophenyl)propyl and 3-(3,5-dimethylphenyl)propyl. Typical phenbutyl moieties include are 4-phenylbutyl, 4-(2-chlorophenyl)butyl, 4-(3-chlorophenyl)butyl, 4-(4-chlorophenyl)butyl, 4-(2-fluorophenyl)butyl, 4-(3-fluorophenyl)butyl, 4-(4-fluorophenyl)butyl, 4-(2-methylphenyl)butyl, 4-(3-methylphenyl)butyl, 4-(4-methylphenyl)butyl and 4-(2,4-dichlorophenyl)butyl.

Halogen or halo is meant to include iodo, fluoro, bromo and chloro moieties.

Because of the C=C or C=N double bonds, the novel compounds of the general Formula I may be obtained in preparation as E/Z isomeric mixtures. These isomers can be separated into individual components by conventional means. The cyclopropanes of Formula I may be obtained in preparation as cis and trans isomeric mixtures which can be separated into individual components by conventional means. Both the individual isomeric compounds and mixtures thereof form subjects of the invention and can be used as fungicides and insecticides.

The present invention also includes the enantiomorphs, salts and complexes of Formula I.

A preferred embodiment of this invention are the compounds, enantiomorphs, salts and complexes of Formula II where A is hydrogen, $R_1$ and $R_2$ are hydrogen or $(C_1-C_4)$ alkyl, $R_3$, $R_4$, $R_5$ and $R_6$ are hydrogen, $R_7$ is aryl, aralkyl, or heterocyclic, Z is N—$OR_9$ where $R_9$ is $(C_1-C_4)$alkyl, and X and Y are as defined above.

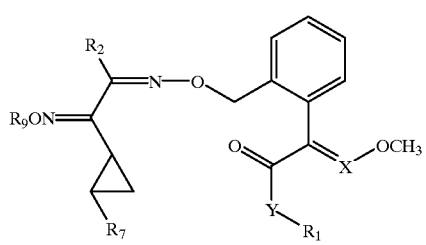

Formula II

A more preferred embodiment of this invention are the compounds, enantiomorphs, salts and complexes of Formula III where (in Formula II) X is N, Y is NH, $R_1$, $R_2$ and $R_9$ are methyl, A is hydrogen, and $R_7$ is aryl.

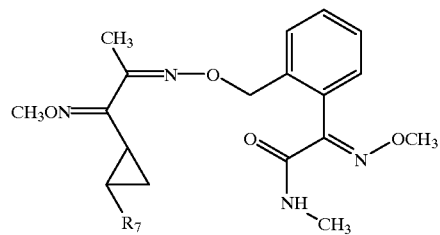

Formula III

Typical compounds encompassed by the present invention of Formula I include those compounds of Formula IV, which is Formula I with A=$R_4$=$R_5$=$R_6$=H, $R_1$=$CH_3$, X=CH, Y=Z=O, and where $R_2$, $R_3$, and $R_7$ are defined in Table 1.

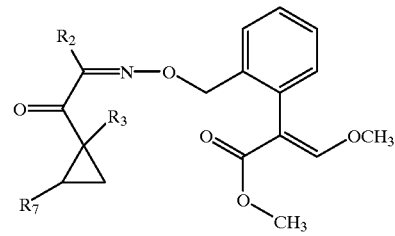

Formula IV

TABLE 1

| Compd. | $R_2$ | $R_3$ | $R_7$ |
|---|---|---|---|
| 1.1 | H | H | Ph |
| 1.2 | H | H | 4-Cl(Ph) |
| 1.3 | H | H | 4-Br(Ph) |
| 1.4 | H | H | 4-F(Ph) |
| 1.5 | H | H | 4-OCH$_3$(Ph) |
| 1.6 | H | H | 4-CF$_3$(Ph) |
| 1.7 | H | H | 4-NO$_2$(Ph) |
| 1.8 | H | H | 2,4-Cl(Ph) |
| 1.9 | H | H | 2,4-F(Ph) |
| 1.10 | H | H | 3,4-F(Ph) |
| 1.11 | CH$_3$ | H | Ph |
| 1.12 | CH$_3$ | H | 2-Cl(Ph) |
| 1.13 | CH$_3$ | H | 3-Cl(Ph) |
| 1.14 | CH$_3$ | H | 4-Cl(Ph) |
| 1.15 | CH$_3$ | H | 2-Br(Ph) |
| 1.16 | CH$_3$ | H | 3-Br(Ph) |
| 1.17 | CH$_3$ | H | 4-Br(Ph) |
| 1.18 | CH$_3$ | H | 2-F(Ph) |
| 1.19 | CH$_3$ | H | 3-F(Ph) |
| 1.20 | CH$_3$ | H | 4-F(Ph) |
| 1.21 | CH$_3$ | H | 2-OCH$_3$(Ph) |
| 1.22 | CH$_3$ | H | 3-OCH$_3$(Ph) |
| 1.23 | CH$_3$ | H | 4-OCH$_3$(Ph) |
| 1.24 | CH$_3$ | H | 2-CH$_3$(Ph) |
| 1.25 | CH$_3$ | H | 3-CH$_3$(Ph) |
| 1.26 | CH$_3$ | H | 4-CH$_3$(Ph) |
| 1.27 | CH$_3$ | H | 2-CF$_3$(Ph) |
| 1.28 | CH$_3$ | H | 3-CF$_3$(Ph) |
| 1.29 | CH$_3$ | H | 4-CF$_3$(Ph) |
| 1.30 | CH$_3$ | H | 2-NO$_2$(Ph) |
| 1.31 | CH$_3$ | H | 3-NO$_2$(Ph) |
| 1.32 | CH$_3$ | H | 4-NO$_2$(Ph) |
| 1.33 | CH$_3$ | H | 2,3-Cl(Ph) |
| 1.34 | CH$_3$ | H | 2,4-Cl(Ph) |
| 1.35 | CH$_3$ | H | 2,5-Cl(Ph) |
| 1.36 | CH$_3$ | H | 2,6-Cl(Ph) |

TABLE 1-continued

| Compd. | $R_2$ | $R_3$ | $R_7$ |
|---|---|---|---|
| 1.37 | $CH_3$ | H | 3,4-Cl(Ph) |
| 1.38 | $CH_3$ | H | 3,5-Cl(Ph) |
| 1.39 | $CH_3$ | H | 2,3-F(Ph) |
| 1.40 | $CH_3$ | H | 2,4-F(Ph) |
| 1.41 | $CH_3$ | H | 2,5-F(Ph) |
| 1.42 | $CH_3$ | H | 2,6-F(Ph) |
| 1.43 | $CH_3$ | H | 3,4-F(Ph) |
| 1.44 | $CH_3$ | H | 3,5-F(Ph) |
| 1.45 | $C_2H_5$ | H | Ph |
| 1.46 | $C_2H_5$ | H | 2-Cl(Ph) |
| 1.47 | $C_2H_5$ | H | 3-Cl(Ph) |
| 1.48 | $C_2H_5$ | H | 4-Cl(Ph) |
| 1.49 | $C_2H_5$ | H | 4-Br(Ph) |
| 1.50 | $C_2H_5$ | H | 4-F(Ph) |
| 1.51 | $C_2H_5$ | H | 4-$OCH_3$(Ph) |
| 1.52 | $C_2H_5$ | H | 4-$CH_3$(Ph) |
| 1.53 | $C_2H_5$ | H | 4-$NO_2$(Ph) |
| 1.54 | $C_2H_5$ | H | 2,4-Cl(Ph) |
| 1.55 | $C_2H_5$ | H | 2,4-F(Ph) |
| 1.56 | n-$C_3H_7$ | H | Ph |
| 1.57 | n-$C_3H_7$ | H | 2-Cl(Ph) |
| 1.58 | n-$C_3H_7$ | H | 3-Cl(Ph) |
| 1.59 | n-$C_3H_7$ | H | 4-Cl(Ph) |
| 1.60 | n-$C_3H_7$ | H | 4-F(Ph) |
| 1.61 | n-$C_3H_7$ | H | 3-$OCH_3$(Ph) |
| 1.62 | n-$C_3H_7$ | H | 4-$OCH_3$(Ph) |
| 1.63 | n-$C_3H_7$ | H | 4-$CH_3$(Ph) |
| 1.64 | n-$C_3H_7$ | H | 4-$NO_2$(Ph) |
| 1.65 | n-$C_3H_7$ | H | 2,4-Cl(Ph) |
| 1.66 | n-$C_3H_7$ | H | 2,4-F(Ph) |
| 1.67 | iso-$C_3H_7$ | H | Ph |
| 1.68 | iso-$C_3H_7$ | H | 2-Cl(Ph) |
| 1.69 | iso-$C_3H_7$ | H | 3-Cl(Ph) |
| 1.70 | iso-$C_3H_7$ | H | 4-Cl(Ph) |
| 1.71 | iso-$C_3H_7$ | H | 4-Br(Ph) |
| 1.72 | iso-$C_3H_7$ | H | 4-F(Ph) |
| 1.73 | iso-$C_3H_7$ | H | 4-$OCH_3$(Ph) |
| 1.74 | iso-$C_3H_7$ | H | 4-$CH_3$(Ph) |
| 1.75 | iso-$C_3H_7$ | H | 4-$NO_2$(Ph) |
| 1.76 | iso-$C_3H_7$ | H | 2,4-Cl(Ph) |
| 1.77 | iso-$C_3H_7$ | H | 2,4-F(Ph) |
| 1.78 | n-$C_4H_9$ | H | Ph |
| 1.79 | n-$C_4H_9$ | H | 2-Cl(Ph) |
| 1.80 | n-$C_4H_9$ | H | 3-Cl(Ph) |
| 1.81 | n-$C_4H_9$ | H | 4-Cl(Ph) |
| 1.82 | n-$C_4H_9$ | H | 4-Br(Ph) |
| 1.83 | n-$C_4H_9$ | H | 4-F(Ph) |
| 1.84 | n-$C_4H_9$ | H | 4-$OCH_3$(Ph) |
| 1.85 | n-$C_4H_9$ | H | 4-$CH_3$(Ph) |
| 1.86 | n-$C_4H_9$ | H | 4-$NO_2$(Ph) |
| 1.87 | n-$C_4H_9$ | H | 2,4-Cl(Ph) |
| 1.88 | n-$C_4H_9$ | H | 2,4-F(Ph) |
| 1.89 | iso-$C_4H_9$ | H | Ph |
| 1.90 | iso-$C_4H_9$ | H | 2-Cl(Ph) |
| 1.91 | iso-$C_4H_9$ | H | 3-Cl(Ph) |
| 1.92 | iso-$C_4H_9$ | H | 4-Cl(Ph) |
| 1.93 | iso-$C_4H_9$ | H | 4-F(Ph) |
| 1.94 | iso-$C_4H_9$ | H | 3-$OCH_3$(Ph) |
| 1.95 | iso-$C_4H_9$ | H | 4-$OCH_3$(Ph) |
| 1.96 | iso-$C_4H_9$ | H | 4-$CH_3$(Ph) |
| 1.97 | iso-$C_4H_9$ | H | 4-$NO_2$(Ph) |
| 1.98 | iso-$C_4H_9$ | H | 2,4-Cl(Ph) |
| 1.99 | iso-$C_4H_9$ | H | 2,4-F(Ph) |
| 1.100 | $C(CH_3)_3$ | H | Ph |
| 1.101 | $C(CH_3)_3$ | H | 2-Cl(Ph) |
| 1.102 | $C(CH_3)_3$ | H | 3-Cl(Ph) |
| 1.103 | $C(CH_3)_3$ | H | 4-Cl(Ph) |
| 1.104 | $C(CH_3)_3$ | H | 4-F(Ph) |
| 1.105 | $C(CH_3)_3$ | H | 3-$OCH_3$(Ph) |
| 1.106 | $C(CH_3)_3$ | H | 4-$OCH_3$(Ph) |
| 1.107 | $C(CH_3)_3$ | H | 4-$CH_3$(Ph) |
| 1.108 | $C(CH_3)_3$ | H | 4-$NO_2$(Ph) |
| 1.109 | $C(CH_3)_3$ | H | 2,4-Cl(Ph) |
| 1.110 | $C(CH_3)_3$ | H | 2,4-F(Ph) |
| 1.111 | cyclopropyl | H | Ph |
| 1.112 | cyclopropyl | H | 2-Cl(Ph) |
| 1.113 | cyclopropyl | H | 3-Cl(Ph) |
| 1.114 | cyclopropyl | H | 4-Cl(Ph) |
| 1.115 | cyclopropyl | H | 4-Br(Ph) |
| 1.116 | cyclopropyl | H | 3-$OCH_3$(Ph) |
| 1.117 | cyclopropyl | H | 4-$OCH_3$(Ph) |
| 1.118 | cyclopropyl | H | 4-$CH_{3(Ph)}$ |
| 1.119 | cyclopropyl | H | 4-$NO_2$(Ph) |
| 1.120 | cyclopropyl | H | 2,4-Cl(Ph) |
| 1.121 | cyclopropyl | H | 2,4-F(Ph) |
| 1.122 | 1-$CH_3$-cyclopropyl | H | Ph |
| 1.123 | 1-$CH_3$-cyclopropyl | H | 2-Cl(Ph) |
| 1.124 | 1-$CH_3$-cyclopropyl | H | 3-Cl(Ph) |
| 1.125 | 1-$CH_3$-cyclopropyl | H | 4-Cl(Ph) |
| 1.126 | 1-$CH_3$-cyclopropyl | H | 4-Br(Ph) |
| 1.127 | 1-$CH_3$-cyclopropyl | H | 4-F(Ph) |
| 1.128 | 1-$CH_3$-cyclopropyl | H | 4-$OCH_3$(Ph) |
| 1.129 | 1-$CH_3$-cyclopropyl | H | 4-$CH_3$(Ph) |
| 1.130 | 1-$CH_3$-cyclopropyl | H | 4-$NO_2$(Ph) |
| 1.131 | 1-$CH_3$-cyclopropyl | H | 2,4-Cl(Ph) |
| 1.132 | 1-$CH_3$-cyclopropyl | H | 2,4-F(Ph) |
| 1.133 | $CH_3$ | $CH_3$ | Ph |
| 1.134 | $CH_3$ | $CH_3$ | 2-Cl(Ph) |
| 1.135 | $CH_3$ | $CH_3$ | 3-Cl(Ph) |
| 1.136 | $CH_3$ | $CH_3$ | 4-Cl(Ph) |
| 1.137 | $CH_3$ | $CH_3$ | 4-Br(Ph) |
| 1.138 | $CH_3$ | $CH_3$ | 4-F(Ph) |
| 1.139 | $CH_3$ | $CH_3$ | 4-$OCH_3$(Ph) |
| 1.140 | $CH_3$ | $CH_3$ | 4-$CH_3$(Ph) |
| 1.141 | $CH_3$ | $CH_3$ | 4-$NO_2$(Ph) |
| 1.142 | $CH_3$ | $CH_3$ | 2,4-Cl(Ph) |
| 1.143 | $CH_3$ | $CH_3$ | 2,4-F(Ph) |
| 1.144 | $C_2H_5$ | $CH_3$ | Ph |
| 1.145 | $C_2H_5$ | $CH_3$ | 2-Cl(Ph) |
| 1.146 | $C_2H_5$ | $CH_3$ | 3-Cl(Ph) |
| 1.147 | $C_2H_5$ | $CH_3$ | 4-Cl(Ph) |
| 1.148 | $C_2H_5$ | $CH_3$ | 4-Br(Ph) |
| 1.149 | $C_2H_5$ | $CH_3$ | 4-F(Ph) |
| 1.150 | $C_2H_5$ | $CH_3$ | 4-$OCH_3$(Ph) |
| 1.151 | $C_2H_5$ | $CH_3$ | 4-$CH_3$(Ph) |
| 1.152 | $C_2H_5$ | $CH_3$ | 4-$NO_2$(Ph) |
| 1.153 | $C_2H_5$ | $CH_3$ | 2,4-Cl(Ph) |
| 1.154 | $C_2H_5$ | $CH_3$ | 2,4-F(Ph) |
| 1.155 | n-$C_3H_7$ | $CH_3$ | Ph |
| 1.156 | n-$C_3H_7$ | $CH_3$ | 2-Cl(Ph) |
| 1.157 | N-$C_3H_7$ | $CH_3$ | 3-Cl(Ph) |
| 1.158 | n-$C_3H_7$ | $CH_3$ | 4-C#Ph) |
| 1.159 | N-$C_3H_7$ | $CH_3$ | 4-Br(Ph) |
| 1.160 | N-$C_3H_7$ | $CH_3$ | 4-F(Ph) |
| 1.161 | N-$C_3H_7$ | $CH_3$ | 4-$OCH_3$(Ph) |
| 1.162 | N-$C_3H_7$ | $CH_3$ | 4-$CH_3$(Ph) |
| 1.163 | N-$C_3H_7$ | $CH_3$ | 4-$NO_2$(Ph) |
| 1.164 | N-$C_3H_7$ | $CH_3$ | 2,4-Cl(Ph) |
| 1.165 | N-$C_3H_7$ | $CH_3$ | 2,4-F(Ph) |
| 1.166 | iso-$C_3H_7$ | $CH_3$ | Ph |
| 1.167 | iso-$C_3H_7$ | $CH_3$ | 2-Cl(Ph) |
| 1.168 | iso-$C_3H_7$ | $CH_3$ | 3-Cl(Ph) |
| 1.169 | iso-$C_3H_7$ | $CH_3$ | 4-Cl(Ph) |
| 1.170 | iso-$C_3H_7$ | $CH_3$ | 4-Br(Ph) |
| 1.171 | iso-$C_3H_7$ | $CH_3$ | 4-F(Ph) |
| 1.172 | iso-$C_3H_7$ | $CH_3$ | 4-$OCH_3$(Ph) |
| 1.173 | iso-$C_3H_7$ | $CH_3$ | 4-$CH_3$(Ph) |
| 1.174 | iso-$C_3H_7$ | $CH_3$ | 4-$NO_2$(Ph) |
| 1.175 | iso-$C_3H_7$ | $CH_3$ | 2,4-Cl(Ph) |
| 1.176 | iso-$C_3H_7$ | $CH_3$ | 2,4-F(Ph) |
| 1.177 | n-$C_4H_9$ | $CH_3$ | Ph |
| 1.178 | n-$C_4H_9$ | $CH_3$ | 2-Cl(Ph) |
| 1.179 | n-$C_4H_9$ | $CH_3$ | 3-Cl(Ph) |
| 1.180 | n-$C_4H_9$ | $CH_3$ | 4-Cl(Ph) |
| 1.181 | n-$C_4H_9$ | $CH_3$ | 4-Br(Ph) |
| 1.182 | n-$C_4H_9$ | $CH_3$ | 4-F(Ph) |
| 1.183 | n-$C_4H_9$ | $CH_3$ | 4-$OCH_3$(Ph) |
| 1.184 | n-$C_4H_9$ | $CH_3$ | 4-$CH_3$(Ph) |
| 1.185 | n-$C_4H_9$ | $CH_3$ | 4-$NO_2$(Ph) |
| 1.186 | n-$C_4H_9$ | $CH_3$ | 2,4-Cl(Ph) |
| 1.187 | n-$C_4H_9$ | $CH_3$ | 2,4-F(Ph) |
| 1.188 | n-$C_4H_9$ | $CH_3$ | 4-$CF_3$(Ph) |
| 1.189 | Ph | H | Ph |
| 1.190 | Ph | H | 2-Cl(Ph) |

TABLE 1-continued

| Compd. | R$_2$ | R$_3$ | R$_7$ |
|---|---|---|---|
| 1.191 | Ph | H | 3-Cl(Ph) |
| 1.192 | Ph | H | 4-Cl(Ph) |
| 1.193 | Ph | H | 4-Br(Ph) |
| 1.194 | Ph | H | 4-F(Ph) |
| 1.195 | Ph | H | 4-OCH$_3$(Ph) |
| 1.196 | Ph | H | 4-CH$_3$(Ph) |
| 1.197 | Ph | H | 4-NO$_2$(Ph) |
| 1.198 | Ph | H | 2,4-Cl(Ph) |
| 1.199 | Ph | H | 2,4-F(Ph) |
| 1.200 | Ph | CH$_3$ | Ph |
| 1.201 | Ph | CH$_3$ | 2-Cl(Ph) |
| 1.202 | Ph | CH$_3$ | 3-Cl(Ph) |
| 1.203 | Ph | CH$_3$ | 4-Cl(Ph) |
| 1.204 | Ph | CH$_3$ | 4-Br(Ph) |
| 1.205 | Ph | CH$_3$ | 4-F(Ph) |
| 1.206 | Ph | CH$_3$ | 4-OCH$_3$(Ph) |
| 1.207 | Ph | CH$_3$ | 4-CH$_3$(Ph) |
| 1.208 | Ph | CH$_3$ | 4-NO$_2$(Ph) |
| 1.209 | Ph | CH$_3$ | 2,4-Cl(Ph) |
| 1.210 | Ph | CH$_3$ | 2,4-F(Ph) |
| 1.211 | CN | H | Ph |
| 1.212 | CN | H | 2-Cl(Ph) |
| 1.213 | CN | H | 3-Cl(Ph) |
| 1.214 | CN | H | 4-Cl(Ph) |
| 1.215 | CN | H | 4-Br(Ph) |
| 1.216 | CN | H | 4-F(Ph) |
| 1.217 | CN | H | 4-OCH$_3$(Ph) |
| 1.218 | CN | H | 4-CH$_3$(Ph) |
| 1.219 | CN | H | 4-NO$_2$(Ph) |
| 1.220 | CN | H | 2,4-Cl(Ph) |
| 1.221 | CN | H | 2,4-F(Ph) |
| 1.222 | CN | CH$_3$ | Ph |
| 1.223 | CN | CH$_3$ | 2-Cl(Ph) |
| 1.224 | CN | CH$_3$ | 3-Cl(Ph) |
| 1.225 | CN | CH$_3$ | 4-Cl(Ph) |
| 1.226 | CN | CH$_3$ | 4-Br(Ph) |
| 1.227 | CN | CH$_3$ | 4-F(Ph) |
| 1.228 | CN | CH$_3$ | 4-OCH$_3$(Ph) |
| 1.229 | CN | CH$_3$ | 4-CH$_3$(Ph) |
| 1.230 | CN | CH$_3$ | 4-NO$_2$(Ph) |
| 1.231 | CN | CH$_3$ | 2,4-Cl(Ph) |
| 1.232 | CN | CH$_3$ | 2,4-F(Ph) |
| 1.233 | H | H | 1-napthyl |
| 1.234 | CH$_3$ | H | 1-napthyl |
| 1.235 | C$_2$H$_5$ | H | 1-napthyl |
| 1.236 | n-C$_3$H$_7$ | H | 1-napthyl |
| 1.237 | iso-C$_3$H$_7$ | H | 1-napthyl |
| 1.238 | n-C$_4$H$_9$ | H | 1-napthyl |
| 1.239 | iso-C$_4$H$_9$ | H | 1-napthyl |
| 1.240 | cyclopropyl | H | 1-napthyl |
| 1.241 | 1-CH$_3$-cyclopropyl | H | 1-napthyl |
| 1.242 | CN | H | 1-napthyl |
| 1.243 | Ph | CH$_3$ | 1-napthyl |
| 1.244 | H | CH$_3$ | 1-napthyl |
| 1.245 | CH$_3$ | CH$_3$ | 1-napthyl |
| 1.246 | C$_2$H$_5$ | CH$_3$ | 1-napthyl |
| 1.247 | n-C$_3$H$_7$ | CH$_3$ | 1-napthyl |
| 1.248 | iso-C$_3$H$_7$ | CH$_3$ | 1-napthyl |
| 1.249 | n-C$_4$H$_9$ | CH$_3$ | 1-napthyl |
| 1.250 | iso-C$_4$H$_9$ | CH$_3$ | 1-napthyl |
| 1.251 | cyclopropyl | CH$_3$ | 1-napthyl |
| 1.252 | 1-CH$_3$-cyclopropyl | CH$_3$ | 1-napthyl |
| 1.253 | CN | CH$_3$ | 1-napthyl |
| 1.254 | Ph | CH$_3$ | 1-napthyl |
| 1.255 | H | H | 2-napthyl |
| 1.256 | CH$_3$ | H | 2-napthyl |
| 1.257 | C$_2$H$_5$ | H | 2-napthyl |
| 1.258 | n-C$_3$H$_7$ | H | 2-napthyl |
| 1.259 | iso-C$_3$H$_7$ | H | 2-napthyl |
| 1.260 | n-C$_4$H$_9$ | H | 2-napthyl |
| 1.261 | iso-C$_4$H$_9$ | H | 2-napthyl |
| 1.262 | cyclopropyl | H | 2-napthyl |
| 1.263 | 1-CH$_3$-cyclopropyl | H | 2-napthyl |
| 1.264 | CN | H | 2-napthyl |
| 1.265 | Ph | H | 2-napthyl |
| 1.266 | H | CH$_3$ | 2-napthyl |
| 1.267 | CH$_3$ | CH$_3$ | 2-napthyl |
| 1.268 | C$_2$H$_5$ | CH$_3$ | 2-napthyl |
| 1.269 | n-C$_3$H$_7$ | CH$_3$ | 2-napthyl |
| 1.270 | iso-C$_3$H$_7$ | CH$_3$ | 2-napthyl |
| 1.271 | n-C$_4$H$_9$ | CH$_3$ | 2-napthyl |
| 1.272 | iso-C$_4$H$_9$ | CH$_3$ | 2-napthyl |
| 1.273 | cyclopropyl | CH$_3$ | 2-napthyl |
| 1.274 | 1-CH$_3$-cyclopropyl | CH$_3$ | 2-napthyl |
| 1.275 | CN | CH$_3$ | 2-napthyl |
| 1.276 | Ph | CH5 | 2-napthyl |
| 1.277 | 2-Cl(Ph) | CH$_3$ | 2-napthyl |
| 1.278 | 3-Cl(Ph) | CH$_3$ | 2-napthyl |
| 1.279 | 4-Cl(Ph) | CH$_3$ | 2-napthyl |
| 1.280 | 4-Br(Ph) | CH$_3$ | 2-napthyl |
| 1.281 | 4-F(Ph) | CH$_3$ | 2-napthyl |
| 1.282 | 4-OCH$_3$(Ph) | CH$_3$ | 2-napthyl |
| 1.283 | 4-CH$_3$(Ph) | CH$_3$ | 2-napthyl |
| 1.284 | 3-CF$_3$(Ph) | CH$_3$ | 2-napthyl |
| 1.285 | CH$_3$ | C$_2$H$_5$ | Ph |
| 1.286 | CH$_3$ | C$_2$H$_5$ | 2-Cl(Ph) |
| 1.287 | CH$_3$ | C$_2$H$_5$ | 3-Cl(Ph) |
| 1.288 | CH$_3$ | C$_2$H$_5$ | 4-Cl(Ph) |
| 1.289 | CH$_3$ | C$_2$H$_5$ | 4-Br(Ph) |
| 1.290 | CH$_3$ | C$_2$H$_5$ | 4-F(Ph) |
| 1.291 | CH$_3$ | C$_2$H$_5$ | 4-OCH$_3$(Ph) |
| 1.292 | CH$_3$ | C$_2$H$_5$ | 4-CH$_3$(Ph) |
| 1.293 | CH$_3$ | C$_2$H$_5$ | 4-NO$_2$(Ph) |
| 1.294 | CH$_3$ | C$_2$H$_5$ | 2,4-Cl(Ph) |
| 1.295 | CH$_3$ | C$_2$H$_5$ | 2,4-F(Ph) |
| 1.296 | CH$_3$ | n-C$_3$H$_7$ | Ph |
| 1.297 | CH$_3$ | n-C$_3$H$_7$ | 2-Cl(Ph) |
| 1.298 | CH$_3$ | n-C$_3$H$_7$ | 3-Cl(Ph) |
| 1.299 | CH$_3$ | n-C$_3$H$_7$ | 4-Cl(Ph) |
| 1.300 | CH$_3$ | n-C$_3$H$_7$ | 4-Br(Ph) |
| 1.301 | CH$_3$ | n-C$_3$H$_7$ | 4-F(Ph) |
| 1.302 | CH$_3$ | n-C$_3$H$_7$ | 4-OCH$_3$(Ph) |
| 1.303 | CH$_3$ | n-C$_3$H$_7$ | 4-CH$_3$(Ph) |
| 1.304 | CH$_3$ | N-C$_3$H$_7$ | 4-NO$_2$(Ph) |
| 1.305 | CH$_3$ | N-C$_3$H$_7$ | 2,4-Cl(Ph) |
| 1.306 | CH$_3$ | N-C$_3$H$_7$ | 2,4-F(Ph) |
| 1.307 | CH$_3$ | iso-C$_3$H$_7$ | Ph |
| 1.308 | CH$_3$ | iso-C$_3$H$_7$ | 2-Cl(Ph) |
| 1.309 | CH$_3$ | iso-C$_3$H$_7$ | 3-Cl(Ph) |
| 1.310 | CH$_3$ | iso-C$_3$H$_7$ | 4-Cl(Ph) |
| 1.311 | CH$_3$ | iso-C$_3$H$_7$ | 4-Br(Ph) |
| 1.312 | CH$_3$ | iso-C$_3$H$_7$ | 4-F(Ph) |
| 1.313 | CH$_3$ | iso-C$_3$H$_7$ | 4-OCH$_3$(Ph) |
| 1.314 | CH$_3$ | iso-C$_3$H$_7$ | 4-CH$_3$(Ph) |
| 1.315 | CH$_3$ | iso-C$_3$H$_7$ | 4-NO$_2$(Ph) |
| 1.316 | CH$_3$ | iso-C$_3$H$_7$ | 2,4-Cl(Ph) |
| 1.317 | CH$_3$ | iso-C$_3$H$_7$ | 2,4-F(Ph) |
| 1.318 | CH$_3$ | n-C$_4$H$_9$ | Ph |
| 1.319 | CH$_3$ | n-C$_4$H$_9$ | 2-Cl(Ph) |
| 1.320 | CH$_3$ | n-C$_4$H$_9$ | 3-Cl(Ph) |
| 1.321 | CH$_3$ | n-C$_4$H$_9$ | 4-Cl(Ph) |
| 1.322 | CH$_3$ | n-C$_4$H$_9$ | 4-Br(Ph) |
| 1.323 | CH$_3$ | n-C$_4$H$_9$ | 4-F(Ph) |
| 1.324 | CH$_3$ | n-C$_4$H$_9$ | 4-OCH$_3$(Ph) |
| 1.325 | CH$_3$ | n-C$_4$H$_9$ | 4-CH$_3$(Ph) |
| 1.326 | CH$_3$ | n-C$_4$H$_9$ | 4-NO$_2$(Ph) |
| 1.327 | CH$_3$ | n-C$_4$H$_9$ | 2,4-Cl(Ph) |
| 1.328 | CH$_3$ | n-C$_4$H$_9$ | 2,4-F(Ph) |
| 1.329 | CH$_3$ | cyclopropyl | Ph |
| 1.330 | CH$_3$ | cyclopropyl | 2-Cl(Ph) |

Typical compounds encompassed by the present invention of Formula I include those compounds of Formula V, which is Formula I with A=R$_4$=R$_5$=R$_6$=H, R$_1$=CH$_3$, X=N, Y=Z=O, and where R$_2$, R$_3$, and R$_7$ are defined in Table 2.

Formula V

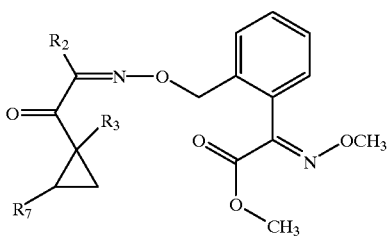

TABLE 2

| Compd. | $R_2$ | $R_3$ | $R_7$ |
|---|---|---|---|
| 2.1 | H | H | Ph |
| 2.2 | H | H | 4-Cl(Ph) |
| 2.3 | H | H | 4-Br(Ph) |
| 2.4 | H | H | 4-F(Ph) |
| 2.5 | H | H | 4-OCH$_3$(Ph) |
| 2.6 | H | H | 4-CF$_3$(Ph) |
| 2.7 | H | H | 4-NO$_2$(Ph) |
| 2.8 | H | H | 2,4-Cl(Ph) |
| 2.9 | H | H | 2,4-F(Ph) |
| 2.10 | H | H | 3,4-F(Ph) |
| 2.11 | CH$_3$ | H | Ph |
| 2.12 | CH$_3$ | H | 2-Cl(Ph) |
| 2.13 | CH$_3$ | H | 3-Cl(Ph) |
| 2.14 | CH$_3$ | H | 4-Cl(Ph) |
| 2.15 | CH$_3$ | H | 2-Br(Ph) |
| 2.16 | CH$_3$ | H | 3-Br(Ph) |
| 2.17 | CH$_3$ | H | 4-Br(Ph) |
| 2.18 | CH$_3$ | H | 2-F(Ph) |
| 2.19 | CH$_3$ | H | 3-F(Ph) |
| 2.20 | CH$_3$ | H | 4-F(Ph) |
| 2.21 | CH$_3$ | H | 2-OCH$_3$(Ph) |
| 2.22 | CH$_3$ | H | 3-OCH$_3$(Ph) |
| 2.23 | CH$_3$ | H | 4-OCH$_3$(Ph) |
| 2.24 | CH$_3$ | H | 2-CH$_3$(Ph) |
| 2.25 | CH$_3$ | H | 3-CH$_3$(Ph) |
| 2.26 | CH$_3$ | H | 4-CH$_3$(Ph) |
| 2.27 | CH$_3$ | H | 2-CF$_3$(Ph) |
| 2.28 | CH$_3$ | H | 3-CF$_3$(Ph) |
| 2.29 | CH$_3$ | H | 4-CF$_3$(Ph) |
| 2.30 | CH$_3$ | H | 2-NO$_2$(Ph) |
| 2.31 | CH$_3$ | H | 3-NO$_2$(Ph) |
| 2.32 | CH$_3$ | H | 4-NO$_2$(Ph) |
| 2.33 | CH$_3$ | H | 2,3-Cl(Ph) |
| 2.34 | CH$_3$ | H | 2,4-Cl(Ph) |
| 2.35 | CH$_3$ | H | 2,5-Cl(Ph) |
| 2.36 | CH$_3$ | H | 2,6-Cl(Ph) |
| 2.37 | CH$_3$ | H | 3,4-Cl(Ph) |
| 2.38 | CH$_3$ | H | 3,5-Cl(Ph) |
| 2.39 | CH$_3$ | H | 2,3-F(Ph) |
| 2.40 | CH$_3$ | H | 2,4-F(Ph) |
| 2.41 | CH$_3$ | H | 2,5-F(Ph) |
| 2.42 | CH$_3$ | H | 2,6-F(Ph) |
| 2.43 | CH$_3$ | H | 3,4-F(Ph) |
| 2.44 | CH$_3$ | H | 3,5-F(Ph) |
| 2.45 | C$_2$H$_5$ | H | Ph |
| 2.46 | C$_2$H$_5$ | H | 2-Cl(Ph) |
| 2.47 | C$_2$H$_5$ | H | 3-Cl(Ph) |
| 2.48 | C$_2$H$_5$ | H | 4-Cl(Ph) |
| 2.49 | C$_2$H$_5$ | H | 4-Br(Ph) |
| 2.50 | C$_2$H$_5$ | H | 4-F(Ph) |
| 2.51 | C$_2$H$_5$ | H | 4-OCH$_3$(Ph) |
| 2.52 | C$_2$H$_5$ | H | 4-CH$_3$(Ph) |
| 2.53 | C$_2$H$_5$ | H | 4-NO$_2$(Ph) |
| 2.54 | C$_2$H$_5$ | H | 2,4-Cl(Ph) |
| 2.55 | C$_2$H$_5$ | H | 2,4-F(Ph) |
| 2.56 | N-C$_3$H$_7$ | H | Ph |
| 2.57 | N-C$_3$H$_7$ | H | 2-Cl(Ph) |
| 2.58 | N-C$_3$H$_7$ | H | 3-Cl(Ph) |
| 2.59 | N-C$_3$H$_7$ | H | 4-Cl(Ph) |
| 2.60 | N-C$_3$H$_7$ | H | 4-F(Ph) |
| 2.61 | N-C$_3$H$_7$ | H | 3-OCH$_3$(Ph) |
| 2.62 | N-C$_3$H$_7$ | H | 4-OCH$_3$(Ph) |
| 2.63 | N-C$_3$H$_7$ | H | 4-CH$_3$(Ph) |
| 2.64 | N-C$_3$H$_7$ | H | 4-NO$_2$(Ph) |
| 2.65 | N-C$_3$H$_7$ | H | 2,4-Cl(Ph) |
| 2.66 | N-C$_3$H$_7$ | H | 2,4-F(Ph) |
| 2.67 | iso-C$_3$H$_7$ | H | Ph |
| 2.68 | iso-C$_3$H$_7$ | H | 2-Cl(Ph) |
| 2.69 | iso-C$_3$H$_7$ | H | 3-Cl(Ph) |
| 2.70 | iso-C$_3$H$_7$ | H | 4-Cl(Ph) |
| 2.71 | iso-C$_3$H$_7$ | H | 4-Br(Ph) |
| 2.72 | iso-C$_3$H$_7$ | H | 4-F(Ph) |
| 2.73 | iso-C$_3$H$_7$ | H | 4-OCH$_3$(Ph) |
| 2.74 | iso-C$_3$H$_7$ | H | 4-CH$_3$(Ph) |
| 2.75 | iso-C$_3$H$_7$ | H | 4-NO$_2$(Ph) |
| 2.76 | iso-C$_3$H$_7$ | H | 2,4-Cl(Ph) |
| 2.77 | iso-C$_3$H$_7$ | H | 2,4-F(Ph) |
| 2.78 | n-C$_4$H$_9$ | H | Ph |
| 2.79 | n-C$_4$H$_9$ | H | 2-Cl(Ph) |
| 2.80 | n-C$_4$H$_9$ | H | 3-Cl(Ph) |
| 2.81 | n-C$_4$H$_9$ | H | 4-Cl(Ph) |
| 2.82 | n-C$_4$H$_9$ | H | 4-Br(Ph) |
| 2.83 | n-C$_4$H$_9$ | H | 4-F(Ph) |
| 2.84 | n-C$_4$H$_9$ | H | 4-OCH$_3$(Ph) |
| 2.85 | n-C$_4$H$_9$ | H | 4-CH$_3$(Ph) |
| 2.86 | n-C$_4$H$_9$ | H | 4-NO$_2$(Ph) |
| 2.87 | n-C$_4$H$_9$ | H | 2,4-Cl(Ph) |
| 2.88 | n-C$_4$H$_9$ | H | 2,4-F(Ph) |
| 2.89 | iso-C$_4$H$_9$ | H | Ph |
| 2.90 | iso-C$_4$H$_9$ | H | 2-Cl(Ph) |
| 2.91 | iso-C$_4$H$_9$ | H | 3-Cl(Ph) |
| 2.92 | iso-C$_4$H$_9$ | H | 4-Cl(Ph) |
| 2.93 | iso-C$_4$H$_9$ | H | 4-F(Ph) |
| 2.94 | iso-C$_4$H$_9$ | H | 3-OCH$_3$(Ph) |
| 2.95 | iso-C$_4$H$_9$ | H | 4-OCH$_3$(Ph) |
| 2.96 | iso-C$_4$H$_9$ | H | 4-CH$_3$(Ph) |
| 2.97 | iso-C$_4$H$_9$ | H | 4-NO$_2$(Ph) |
| 2.98 | iso-C$_4$H$_9$ | H | 2,4-Cl(Ph) |
| 2.99 | iso-C$_4$H$_9$ | H | 2,4-F(Ph) |
| 2.100 | C(CH$_3$)$_3$ | H | Ph |
| 2.101 | C(CH$_3$)$_3$ | H | 2-Cl(Ph) |
| 2.102 | C(CH$_3$)$_3$ | H | 3-Cl(Ph) |
| 2.103 | C(CH$_3$)$_3$ | H | 4-Cl(Ph) |
| 2.104 | C(CH$_3$)$_3$ | H | 4-F(Ph) |
| 2.105 | C(CH$_3$)$_3$ | H | 3-OCH$_3$(Ph) |
| 2.106 | C(CH$_3$)$_3$ | H | 4-OCH$_3$(Ph) |
| 2.107 | C(CH$_3$)$_3$ | H | 4-CH$_3$(Ph) |
| 2.108 | C(CH$_3$)$_3$ | H | 4-NO$_2$(Ph) |
| 2.109 | C(CH$_3$)$_3$ | H | 2,4-Cl(Ph) |
| 2.110 | C(CH$_3$)$_3$ | H | 2,4-F(Ph) |
| 2.111 | cyclopropyl | H | Ph |
| 2.112 | cyclopropyl | H | 2-Cl(Ph) |
| 2.113 | cyclopropyl | H | 3-Cl(Ph) |
| 2.114 | cyclopropyl | H | 4-Cl(Ph) |
| 2.115 | cyclopropyl | H | 4-Br(Ph) |
| 2.116 | cyclopropyl | H | 3-OCH$_3$(Ph) |
| 2.117 | cyclopropyl | H | 4-OCH$_3$(Ph) |
| 2.118 | cyclopropyl | H | 4-CH$_3$(Ph) |
| 2.119 | cyclopropyl | H | 4-NO$_2$(Ph) |
| 2.120 | cyclopropyl | H | 2,4-Cl(Ph) |
| 2.121 | cyclopropyl | H | 2,4-F(Ph) |
| 2.122 | 1-CH$_3$-cyclopropyl | H | Ph |
| 2.123 | 1-CH$_3$-cyclopropyl | H | 2-Cl(Ph) |
| 2.124 | 1-CH$_3$-cyclopropyl | H | 3-Cl(Ph) |
| 2.125 | 1-CH$_3$-cyclopropyl | H | 4-Cl(Ph) |
| 2.126 | 1-CH$_3$-cyclopropyl | H | 4-Br(Ph) |
| 2.127 | 1-CH$_3$-cyclopropyl | H | 4-F(Ph) |
| 2.128 | 1-CH$_3$-cyclopropyl | H | 4-OCH$_3$(Ph) |
| 2.129 | 1-CH$_3$-cyclopropyl | H | 4-CH$_3$(Ph) |
| 2.130 | 1-CH$_3$-cyclopropyl | H | 4-NO$_2$(Ph) |
| 2.131 | 1-CH$_3$-cyclopropyl | H | 2,4-Cl(Ph) |
| 2.132 | 1-CH$_3$-cyclopropyl | H | 2,4-F(Ph) |
| 2.133 | CH$_3$ | CH$_3$ | Ph |
| 2.134 | CH$_3$ | CH$_3$ | 2-Cl(Ph) |
| 2.135 | CH$_3$ | CH$_3$ | 3-Cl(Ph) |
| 2.136 | CH$_3$ | CH$_3$ | 4-Cl(Ph) |
| 2.137 | CH$_3$ | CH$_3$ | 4-Br(Ph) |
| 2.138 | CH$_3$ | CH$_3$ | 4-F(Ph) |

TABLE 2-continued

| Compd. | R₂ | R₃ | R₇ |
|---|---|---|---|
| 2.139 | CH₃ | CH₃ | 4-OCH₃(Ph) |
| 2.140 | CH₃ | CH₃ | 4-CH₃(Ph) |
| 2.141 | CH₃ | CH₃ | 4-NO₂(Ph) |
| 2.142 | CH₃ | CH₃ | 2,4-Cl(Ph) |
| 2.143 | CH₃ | CH₃ | 2,4-F(Ph) |
| 2.144 | C₂H₅ | CH₃ | Ph |
| 2.145 | C₂H₅ | CH₃ | 2-Cl(Ph) |
| 2.146 | C₂H₅ | CH₃ | 3-Cl(Ph) |
| 2.147 | C₂H₅ | CH₃ | 4-Cl(Ph) |
| 2.148 | C₂H₅ | CH₃ | 4-Br(Ph) |
| 2.149 | C₂H₅ | CH₃ | 4-F(Ph) |
| 2.150 | C₂H₅ | CH₃ | 4-OCH₃(Ph) |
| 2.151 | C₂H₅ | CH₃ | 4-CH₃(Ph) |
| 2.152 | C₂H₅ | CH₃ | 4-NO₂(Ph) |
| 2.153 | C₂H₅ | CH₃ | 2,4-Cl(Ph) |
| 2.154 | C₂H₅ | CH₃ | 2,4-F(Ph) |
| 2.155 | N-C₃H₇ | CH₃ | Ph |
| 2.156 | N-C₃H₇ | CH₃ | 2-Cl(Ph) |
| 2.157 | N-C₃H₇ | CH₃ | 3-Cl(Ph) |
| 2.158 | N-C₃H₇ | CH₃ | 4-Cl(Ph) |
| 2.159 | N-C₃H₇ | CH₃ | 4-Br(Ph) |
| 2.160 | N-C₃H₇ | CH₃ | 4-F(Ph) |
| 2.161 | N-C₃H₇ | CH₃ | 4-OCH₃(Ph) |
| 2.162 | N-C₃H₇ | CH₃ | 4-CH₃(Ph) |
| 2.163 | N-C₃H₇ | CH₃ | 4-NO₂(Ph) |
| 2.164 | N-C₃H₇ | CH₃ | 2,4-Cl(Ph) |
| 2.165 | N-C₃H₇ | CH₃ | 2,4-F(Ph) |
| 2.166 | iso-C₃H₇ | CH₃ | Ph |
| 2.167 | iso-C₃H₇ | CH₃ | 2-Cl(Ph) |
| 2.168 | iso-C₃H₇ | CH₃ | 3-Cl(Ph) |
| 2.169 | iso-C₃H₇ | CH₃ | 4-Cl(Ph) |
| 2.170 | iso-C₃H₇ | CH₃ | 4-Br(Ph) |
| 2.171 | iso-C₃H₇ | CH₃ | 4-F(Ph) |
| 2.172 | iso-C₃H₇ | CH₃ | 4-OCH₃(Ph) |
| 2.173 | iso-C₃H₇ | CH₃ | 4-CH₃(Ph) |
| 2.174 | iso-C₃H₇ | CH₃ | 4-NO₂(Ph) |
| 2.175 | iso-C₃H₇ | CH₃ | 2,4-Cl(Ph) |
| 2.176 | iso-C₃H₇ | CH₃ | 2,4-F(Ph) |
| 2.177 | n-C₄H₉ | CH₃ | Ph |
| 2.178 | n-C₄H₉ | CH₃ | 2-Cl(Ph) |
| 2.179 | n-C₄H₉ | CH₃ | 3-Cl(Ph) |
| 2.180 | n-C₄H₉ | CH₃ | 4-Cl(Ph) |
| 2.181 | n-C₄H₉ | CH₃ | 4-Br(Ph) |
| 2.182 | n-C₄H₉ | CH₃ | 4-F(Ph) |
| 2.183 | n-C₄H₉ | CH₃ | 4-OCH₃(Ph) |
| 2.184 | n-C₄H₉ | CH₃ | 4-CH₃(Ph) |
| 2.185 | n-C₄H₉ | CH₃ | 4-NO₂(Ph) |
| 2.186 | n-C₄H₉ | CH₃ | 2,4-Cl(Ph) |
| 2.187 | n-C₄H₉ | CH₃ | 2,4-F(Ph) |
| 2.188 | n-C₄H₉ | CH₃ | 4-CF₃(Ph) |
| 2.189 | Ph | H | Ph |
| 2.190 | Ph | H | 2-Cl(Ph) |
| 2.191 | Ph | H | 3-Cl(Ph) |
| 2.192 | Ph | H | 4-Cl(Ph) |
| 2.193 | Ph | H | 4-Br(Ph) |
| 2.194 | Ph | H | 4-F(Ph) |
| 2.195 | Ph | H | 4-OCH₃(Ph) |
| 2.196 | Ph | H | 4-CH₃(Ph) |
| 2.197 | Ph | H | 4-NO₂(Ph) |
| 2.198 | Ph | H | 2,4-Cl(Ph) |
| 2.199 | Ph | H | 2,4-F(Ph) |
| 2.200 | Ph | CH₃ | Ph |
| 2.201 | Ph | CH₃ | 2-Cl(Ph) |
| 2.202 | Ph | CH₃ | 3-Cl(Ph) |
| 2.203 | Ph | CH₃ | 4-Cl(Ph) |
| 2.204 | Ph | CH₃ | 4-Br(Ph) |
| 2.205 | Ph | CH₃ | 4-F(Ph) |
| 2.206 | Ph | CH₃ | 4-OCH₃(Ph) |
| 2.207 | Ph | CH₃ | 4-CH₃(Ph) |
| 2.208 | Ph | CH₃ | 4-NO₂(Ph) |
| 2.209 | Ph | CH₃ | 2,4-Cl(Ph) |
| 2.210 | Ph | CH₃ | 2,4-F(Ph) |
| 2.211 | CN | H | Ph |
| 2.212 | CN | H | 2-Cl(Ph) |
| 2.213 | CN | H | 3-Cl(Ph) |
| 2.214 | CN | H | 4-Cl(Ph) |
| 2.215 | CN | H | 4-Br(Ph) |
| 2.216 | CN | H | 4-F(Ph) |
| 2.217 | CN | H | 4-OCH₃(Ph) |
| 2.218 | CN | H | 4-CH₃(Ph) |
| 2.219 | CN | H | 4-NO₂(Ph) |
| 2.220 | CN | H | 2,4-Cl(Ph) |
| 2.221 | CN | H | 2,4-F(Ph) |
| 2.222 | CN | CH₃ | Ph |
| 2.223 | CN | CH₃ | 2-Cl(Ph) |
| 2.224 | CN | CH₃ | 3-Cl(Ph) |
| 2.225 | CN | CH₃ | 4-Cl(Ph) |
| 2.226 | CN | CH₃ | 4-Br(Ph) |
| 2.227 | CN | CH₃ | 4-F(Ph) |
| 2.228 | CN | CH₃ | 4-OCH₃(Ph) |
| 2.229 | CN | CH₃ | 4-CH₃(Ph) |
| 2.230 | CN | CH₃ | 4-NO₂(Ph) |
| 2.231 | CN | CH₃ | 2,4-Cl(Ph) |
| 2.232 | CN | CH₃ | 2,4-F(Ph) |
| 2.233 | H | H | 1-napthyl |
| 2.234 | CH₃ | H | 1-napthyl |
| 2.235 | C₂H₅ | H | 1-napthyl |
| 2.236 | N-C₃H₇ | H | 1-napthyl |
| 2.237 | iso-C₃H₇ | H | 1-napthyl |
| 2.238 | n-C₄H₉ | H | 1-napthyl |
| 2.239 | iso-C₄H₉ | H | 1-napthyl |
| 2.240 | cyclopropyl | H | 1-napthyl |
| 2.241 | 1-CH₃-cyclopropyl | H | 1-napthyl |
| 2.242 | CN | H | 1-napthyl |
| 2.243 | Ph | H | 1-napthyl |
| 2.244 | H | CH₃ | 1-napthyl |
| 2.245 | CH₃ | CH₃ | 1-napthyl |
| 2.246 | C₂H₅ | CH₃ | 1-napthyl |
| 2.247 | N-C₃H₇ | CH₃ | 1-napthyl |
| 2.248 | iso-C₃H₇ | CH₃ | 1-napthyl |
| 2.249 | n-C₄H₉ | CH₃ | 1-napthyl |
| 2.250 | iso-C₄H₉ | CH₃ | 1-napthyl |
| 2.251 | cyclopropyl | CH₃ | 1-napthyl |
| 2.252 | 1-CH₃-cyclopropyl | CH₃ | 1-napthyl |
| 2.253 | CN | CH₃ | 1-napthyl |
| 2.254 | Ph | CH₃ | 1-napthyl |
| 2.255 | H | H | 2-napthyl |
| 2.256 | CH₃ | H | 2-napthyl |
| 2.257 | C₂H₅ | H | 2-napthyl |
| 2.258 | N-C₃H₇ | H | 2-napthyl |
| 2.259 | iso-C₃H₇ | H | 2-napthyl |
| 2.260 | n-C₄H₉ | H | 2-napthyl |
| 2.261 | iso-C₄H₉ | H | 2-napthyl |
| 2.262 | cyclopropyl | H | 2-napthyl |
| 2.263 | 1-CH₃-cyclopropyl | H | 2-napthyl |
| 2.264 | CN | H | 2-napthyl |
| 2.265 | Ph | H | 2-napthyl |
| 2.266 | H | CH₃ | 2-napthyl |
| 2.267 | CH₃ | CH₃ | 2-napthyl |
| 2.268 | C₂H₅ | CH₃ | 2-napthyl |
| 2.269 | n-C₃H₇ | CH₃ | 2-napthyl |
| 2.270 | iso-C₃H₇ | CH₃ | 2-napthyl |
| 2.271 | n-C₄H₉ | CH₃ | 2-napthyl |
| 2.272 | iso-C₄H₉ | CH₃ | 2-napthyl |
| 2.273 | cyclopropyl | CH₃ | 2-napthyl |
| 2.274 | 1-CH₃-cyclopropyl | CH₃ | 2-napthyl |
| 2.275 | CN | CH₃ | 2-napthyl |
| 2.276 | Ph | CH₃ | 2-napthyl |
| 2.277 | 2-Cl(Ph) | CH₃ | 2-napthyl |
| 2.278 | 3-Cl(Ph) | CH₃ | 2-napthyl |
| 2.279 | 4-Cl(Ph) | CH₃ | 2-napthyl |
| 2.280 | 4-Br(Ph) | CH₃ | 2-napthyl |
| 2.281 | 4-F(Ph) | CH₃ | 2-napthyl |
| 2.282 | 4-OCH₃(Ph) | CH₃ | 2-napthyl |
| 2.283 | 4-CH₃(Ph) | CH₃ | 2-napthyl |
| 2.284 | 3-CF₃(Ph) | CH₃ | 2-napthyl |
| 2.285 | CH₃ | C₂H₅ | Ph |
| 2.286 | CH₃ | C₂H₅ | 2-Cl(Ph) |
| 2.287 | CH₃ | C₂H₅ | 3-Cl(Ph) |
| 2.288 | CH₃ | C2H5 | 4-Cl(Ph) |
| 2.289 | CH₃ | C₂H₅ | 4-Br(Ph) |
| 2.290 | CH₃ | C₂H₅ | 4-F(Ph) |
| 2.291 | CH₃ | C₂H₅ | 4-OCH₃(Ph) |
| 2.292 | CH₃ | C₂H₅ | 4-CH₃(Ph) |

TABLE 2-continued

| Compd. | $R_2$ | $R_3$ | $R_7$ |
|---|---|---|---|
| 2.293 | $CH_3$ | $C_2H_5$ | 4-$NO_2$(Ph) |
| 2.294 | $CH_3$ | $C_2H_5$ | 2,4-Cl(Ph) |
| 2.295 | $CH_3$ | $C_2H_5$ | 2,4-F(Ph) |
| 2.296 | $CH_3$ | n-$C_3H_7$ | Ph |
| 2.297 | $CH_3$ | n-$C_3H_7$ | 2-Cl(Ph) |
| 2.298 | $CH_3$ | n-$C_3H_7$ | 3-Cl(Ph) |
| 2.299 | $CH_3$ | n-$C_3H_7$ | 4-Cl(Ph) |
| 2.300 | $CH_3$ | n-$C_3H_7$ | 4-Br(Ph) |
| 2.301 | $CH_3$ | n-$C_3H_7$ | 4-F(Ph) |
| 2.302 | $CH_3$ | n-$C_3H_7$ | 4-$OCH_3$(Ph) |
| 2.303 | $CH_3$ | n-$C_3H_7$ | 4-$CH_3$(Ph) |
| 2.304 | $CH_3$ | n-$C_3H_7$ | 4-$NO_2$(Ph) |
| 2.305 | $CH_3$ | n-$C_3H_7$ | 2,4-Cl(Ph) |
| 2.306 | $CH_3$ | n-$C_3H_7$ | 2,4-F(Ph) |
| 2.307 | $CH_3$ | iso-$C_3H_7$ | Ph |
| 2.308 | $CH_3$ | iso-$C_3H_7$ | 2-Cl(Ph) |
| 2.309 | $CH_3$ | iso-$C_3H_7$ | 3-Cl(Ph) |
| 2.310 | $CH_3$ | iso-$C_3H_7$ | 4-Cl(Ph) |
| 2.311 | $CH_3$ | iso-$C_3H_7$ | 4-Br(Ph) |
| 2.312 | $CH_3$ | iso-$C_3H_7$ | 4-F(Ph) |
| 2.313 | $CH_3$ | iso-$C_3H_7$ | 4-$OCH_3$(Ph) |
| 2.314 | $CH_3$ | iso-$C_3H_7$ | 4-$CH_3$(Ph) |
| 2.315 | $CH_3$ | iso-$C_3H_7$ | 4-$NO_2$(Ph) |
| 2.316 | $CH_3$ | iso-$C_3H_7$ | 2,4-Cl(Ph) |
| 2.317 | $CH_3$ | iso-$C_3H_7$ | 2,4-F(Ph) |
| 2.318 | $CH_3$ | n-$C_4H_9$ | Ph |
| 2.319 | $CH_3$ | n-$C_4H_9$ | 2-Cl(Ph) |
| 2.320 | $CH_3$ | n-$C_4H_9$ | 3-Cl(Ph) |
| 2.321 | $CH_3$ | n-$C_4H_9$ | 4-Cl(Ph) |
| 2.322 | $CH_3$ | n-$C_4H_9$ | 4-Br(Ph) |
| 2.323 | $CH_3$ | n-$C_4H_9$ | 4-F(Ph) |
| 2.324 | $CH_3$ | n-$C_4H_9$ | 4-$OCH_3$(Ph) |
| 2.325 | $CH_3$ | n-$C_4H_9$ | 4-$CH_3$(Ph) |
| 2.326 | $CH_3$ | n-$C_4H_9$ | 4-$NO_2$(Ph) |
| 2.327 | $CH_3$ | n-$C_4H_9$ | 2,4-Cl(Ph) |
| 2.328 | $CH_3$ | n-$C_4H_9$ | 2,4-F(Ph) |
| 2.329 | $CH_3$ | cyclopropyl | Ph |
| 2.330 | $CH_3$ | cyclopropyl | 2-Cl(Ph) |

Typical compounds encompassed by the present invention of Formula I include those compounds of Formula VI, which is Formula I with $A=R_4=R_5=R_6=H$, $R_1=CH_3$, $X=N$, $Y=NH$, and $Z=O$, and where $R_2$, $R_3$, and $R_7$ are defined in Table 3.

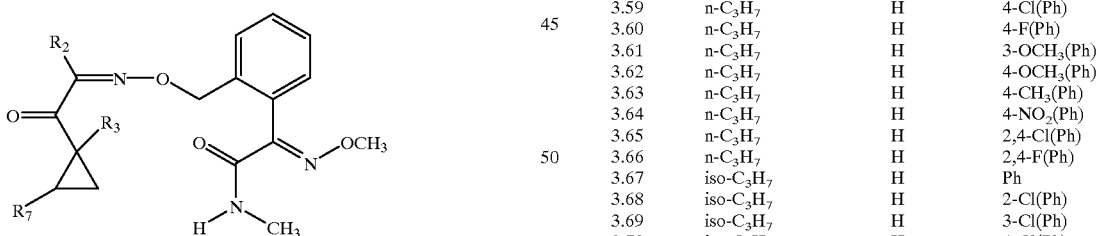

Formula VI

TABLE 3

| Compd. | $R_2$ | $R_3$ | $R_7$ |
|---|---|---|---|
| 3.1 | H | H | Ph |
| 3.2 | H | H | 4-Cl(Ph) |
| 3.3 | H | H | 4-Br(Ph) |
| 3.4 | H | H | 4-F(Ph) |
| 3.5 | H | H | 4-$OCH_3$(Ph) |
| 3.6 | H | H | 4-$CF_3$(Ph) |
| 3.7 | H | H | 4-$NO_2$(Ph) |
| 3.8 | H | H | 2,4-Cl(Ph) |
| 3.9 | H | H | 2,4-F(Ph) |

TABLE 3-continued

| Compd. | $R_2$ | $R_3$ | $R_7$ |
|---|---|---|---|
| 3.10 | H | H | 3,4-F(Ph) |
| 3.11 | $CH_3$ | H | Ph |
| 3.12 | $CH_3$ | H | 2-Cl(Ph) |
| 3.13 | $CH_3$ | H | 3-Cl(Ph) |
| 3.14 | $CH_3$ | H | 4-Cl(Ph) |
| 3.15 | $CH_3$ | H | 2-Br(Ph) |
| 3.16 | $CH_3$ | H | 3-Br(Ph) |
| 3.17 | $CH_3$ | H | 4-Br(Ph) |
| 3.18 | $CH_3$ | H | 2-F(Ph) |
| 3.19 | $CH_3$ | H | 3-F(Ph) |
| 3.20 | $CH_3$ | H | 4-F(Ph) |
| 3.21 | $CH_3$ | H | 2-$OCH_3$(Ph) |
| 3.22 | $CH_3$ | H | 3-$OCH_3$(Ph) |
| 3.23 | $CH_3$ | H | 4-$OCH_3$(Ph) |
| 3.24 | $CH_3$ | H | 2-$CH_3$(Ph) |
| 3.25 | $CH_3$ | H | 3-$CH_3$(Ph) |
| 3.26 | $CH_3$ | H | 4-$CH_3$(Ph) |
| 3.27 | $CH_3$ | H | 2-$CF_3$(Ph) |
| 3.28 | $CH_3$ | H | 3-$CF_3$(Ph) |
| 3.29 | $CH_3$ | H | 4-$CF_3$(Ph) |
| 3.30 | $CH_3$ | H | 2-$NO_2$(Ph) |
| 3.31 | $CH_3$ | H | 3-$NO_2$(Ph) |
| 3.32 | $CH_3$ | H | 4-$NO_2$(Ph) |
| 3.33 | $CH_3$ | H | 2,3-Cl(Ph) |
| 3.34 | $CH_3$ | H | 2,4-Cl(Ph) |
| 3.35 | $CH_3$ | H | 2,5-Cl(Ph) |
| 3.36 | $CH_3$ | H | 2,6-Cl(Ph) |
| 3.37 | $CH_3$ | H | 3,4-Cl(Ph) |
| 3.38 | $CH_3$ | H | 3,5-Cl(Ph) |
| 3.39 | $CH_3$ | H | 2,3-F(Ph) |
| 3.40 | $CH_3$ | H | 2,4-F(Ph) |
| 3.41 | $CH_3$ | H | 2,5-F(Ph) |
| 3.42 | $CH_3$ | H | 2,6-F(Ph) |
| 3.43 | $CH_3$ | H | 3,4-F(Ph) |
| 3.44 | $CH_3$ | H | 3,5-F(Ph) |
| 3.45 | $C_2H_5$ | H | Ph |
| 3.46 | $C_2H_5$ | H | 2-Cl(Ph) |
| 3.47 | $C_2H_5$ | H | 3-Cl(Ph) |
| 3.48 | $C_2H_5$ | H | 4-Cl(Ph) |
| 3.49 | $C_2H_5$ | H | 4-Br(Ph) |
| 3.50 | $C_2H_5$ | H | 4-F(Ph) |
| 3.51 | $C_2H_5$ | H | 4-$OCH_3$(Ph) |
| 3.52 | $C_2H_5$ | H | 4-$CH_3$(Ph) |
| 3.53 | $C_2H_5$ | H | 4-$NO_2$(Ph) |
| 3.54 | $C_2H_5$ | H | 2,4-Cl(Ph) |
| 3.55 | $C_2H_5$ | H | 2,4-F(Ph) |
| 3.56 | n-$C_3H_7$ | H | Ph |
| 3.57 | n-$C_3H_7$ | H | 2-Cl(Ph) |
| 3.58 | n-$C_3H_7$ | H | 3-Cl(Ph) |
| 3.59 | n-$C_3H_7$ | H | 4-Cl(Ph) |
| 3.60 | n-$C_3H_7$ | H | 4-F(Ph) |
| 3.61 | n-$C_3H_7$ | H | 3-$OCH_3$(Ph) |
| 3.62 | n-$C_3H_7$ | H | 4-$OCH_3$(Ph) |
| 3.63 | n-$C_3H_7$ | H | 4-$CH_3$(Ph) |
| 3.64 | n-$C_3H_7$ | H | 4-$NO_2$(Ph) |
| 3.65 | n-$C_3H_7$ | H | 2,4-Cl(Ph) |
| 3.66 | n-$C_3H_7$ | H | 2,4-F(Ph) |
| 3.67 | iso-$C_3H_7$ | H | Ph |
| 3.68 | iso-$C_3H_7$ | H | 2-Cl(Ph) |
| 3.69 | iso-$C_3H_7$ | H | 3-Cl(Ph) |
| 3.70 | iso-$C_3H_7$ | H | 4-Cl(Ph) |
| 3.71 | iso-$C_3H_7$ | H | 4-Br(Ph) |
| 3.72 | iso-$C_3H_7$ | H | 4-F(Ph) |
| 3.73 | iso-$C_3H_7$ | H | 4-$OCH_3$(Ph) |
| 3.74 | iso-$C_3H_7$ | H | 4-$CH_3$(Ph) |
| 3.75 | iso-$C_3H_7$ | H | 4-$NO_2$(Ph) |
| 3.76 | iso-$C_3H_7$ | H | 2,4-Cl(Ph) |
| 3.77 | iso-$C_3H_7$ | H | 2,4-F(Ph) |
| 3.78 | n-$C_4H_9$ | H | Ph |
| 3.79 | n-$C_4H_9$ | H | 2-Cl(Ph) |
| 3.80 | n-$C_4H_9$ | H | 3-Cl(Ph) |
| 3.81 | n-$C_4H_9$ | H | 4-Cl(Ph) |
| 3.82 | n-$C_4H_9$ | H | 4-Br(Ph) |
| 3.83 | n-$C_4H_9$ | H | 4-F(Ph) |
| 3.84 | n-$C_4H_9$ | H | 4-$OCH_3$(Ph) |
| 3.85 | n-$C_4H_9$ | H | 4-$CH_3$(Ph) |
| 3.86 | n-$C_4H_9$ | H | 4-$NO_2$(Ph) |

TABLE 3-continued

| Compd. | R₂ | R₃ | R₇ |
|---|---|---|---|
| 3.87 | n-C₄H₉ | H | 2,4-Cl(Ph) |
| 3.88 | n-C₄H₉ | H | 2,4-F(Ph) |
| 3.89 | iso-C₄H₉ | H | Ph |
| 3.90 | iso-C₄H₉ | H | 2-Cl(Ph) |
| 3.91 | iso-C₄H₉ | H | 3-Cl(Ph) |
| 3.92 | iso-C₄H₉ | H | 4-Cl(Ph) |
| 3.93 | iso-C₄H₉ | H | 4-F(Ph) |
| 3.94 | iso-C₄H₉ | H | 3-OCH₃(Ph) |
| 3.95 | iso-C₄H₉ | H | 4-OCH₃(Ph) |
| 3.96 | iso-C₄H₉ | H | 4-CH₃(Ph) |
| 3.97 | iso-C₄H₉ | H | 4-NO₂(Ph) |
| 3.98 | iso-C₄H₉ | H | 2,4-Cl(Ph) |
| 3.99 | iso-C₄H₉ | H | 2,4-F(Ph) |
| 3.100 | C(CH₃)₃ | H | Ph |
| 3.101 | C(CH₃)₃ | H | 2-Cl(Ph) |
| 3.102 | C(CH₃)₃ | H | 3-Cl(Ph) |
| 3.103 | C(CH₃)₃ | H | 4-Cl(Ph) |
| 3.104 | C(CH₃)₃ | H | 4-F(Ph) |
| 3.105 | C(CH₃)₃ | H | 3-OCH₃(Ph) |
| 3.106 | C(CH₃)₃ | H | 4-OCH₃(Ph) |
| 3.107 | C(CH₃)₃ | H | 4-CH₃(Ph) |
| 3.108 | C(CH₃)₃ | H | 4-NO₂(Ph) |
| 3.109 | C(CH₃)₃ | H | 2,4-Cl(Ph) |
| 3.110 | C(CH₃)₃ | H | 2,4-F(Ph) |
| 3.111 | cyclopropyl | H | Ph |
| 3.112 | cyclopropyl | H | 2-Cl(Ph) |
| 3.113 | cyclopropyl | H | 3-Cl(Ph) |
| 3.114 | cyclopropyl | H | 4-Cl(Ph) |
| 3.115 | cyclopropyl | H | 4-Br(Ph) |
| 3.116 | cyclopropyl | H | 3-OCH₃(Ph) |
| 3.117 | cyclopropyl | H | 4-OCH₃(Ph) |
| 3.118 | cyclopropyl | H | 4-CH₃(Ph) |
| 3.119 | cyclopropyl | H | 4-NO₂(Ph) |
| 3.120 | cyclopropyl | H | 2,4-Cl(Ph) |
| 3.121 | cyclopropyl | H | 2,4-F(Ph) |
| 3.122 | 1-CH₃-cyclopropyl | H | Ph |
| 3.123 | 1-CH₃-cyclopropyl | H | 2-Cl(Ph) |
| 3.124 | 1-CH₃-cyclopropyl | H | 3-Cl(Ph) |
| 3.125 | 1-CH₃-cyclopropyl | H | 4-Cl(Ph) |
| 3.126 | 1-CH₃-cyclopropyl | H | 4-Br(Ph) |
| 3.127 | 1-CH₃-cyclopropyl | H | 4-F(Ph) |
| 3.128 | 1-CH₃-cyclopropyl | H | 4-OCH₃(Ph) |
| 3.129 | 1-CH₃-cyclopropyl | H | 4-CH₃(Ph) |
| 3.130 | 1-CH₃-cyclopropyl | H | 4-NO₂(Ph) |
| 3.131 | 1-CH₃-cyclopropyl | H | 2,4-Cl(Ph) |
| 3.132 | 1-CH₃-cyclopropyl | H | 2,4-F(Ph) |
| 3.133 | CH₃ | CH₃ | Ph |
| 3.134 | CH₃ | CH₃ | 2-Cl(Ph) |
| 3.135 | CH₃ | CH₃ | 3-Cl(Ph) |
| 3.136 | CH₃ | CH₃ | 4-Cl(Ph) |
| 3.137 | CH₃ | CH₃ | 4-Br(Ph) |
| 3.138 | CH₃ | CH₃ | 4-F(Ph) |
| 3.139 | CH₃ | CH₃ | 4-OCH₃(Ph) |
| 3.140 | CH₃ | CH₃ | 4-CH₃(Ph) |
| 3.141 | CH₃ | CH₃ | 4-NO₂(Ph) |
| 3.142 | CH₃ | CH₃ | 2,4-Cl(Ph) |
| 3.143 | CH₃ | CH₃ | 2,4-F(Ph) |
| 3.144 | C₂H₅ | CH₃ | Ph |
| 3.145 | C₂H₅ | CH₃ | 2-Cl(Ph) |
| 3.146 | C₂H₅ | CH₃ | 3-Cl(Ph) |
| 3.147 | C₂H₅ | CH₃ | 4-Cl(Ph) |
| 3.148 | C₂H₅ | CH₃ | 4-Br(Ph) |
| 3.149 | C₂H₅ | CH₃ | 4-F(Ph) |
| 3.150 | C₂H₅ | CH₃ | 4-OCH₃(Ph) |
| 3.151 | C₂H₅ | CH₃ | 4-CH₃(Ph) |
| 3.152 | C₂H₅ | CH₃ | 4-NO₂(Ph) |
| 3.153 | C₂H₅ | CH₃ | 2,4-Cl(Ph) |
| 3.154 | C₂H₅ | CH₃ | 2,4-F(Ph) |
| 3.155 | n-C₃H₇ | CH₃ | Ph |
| 3.156 | n-C₃H₇ | CH₃ | 2-Cl(Ph) |
| 3.157 | n-C₃H₇ | CH₃ | 3-Cl(Ph) |
| 3.158 | n-C₃H₇ | CH₃ | 4-Cl(Ph) |
| 3.159 | n-C₃H₇ | CH₃ | 4-Br(Ph) |
| 3.160 | n-C₃H₇ | CH₃ | 4-F(Ph) |
| 3.161 | n-C₃H₇ | CH₃ | 4-OCH₃(Ph) |
| 3.162 | n-C₃H₇ | CH₃ | 4-CH₃(Ph) |
| 3.163 | n-C₃H₇ | CH₃ | 4-NO₂(Ph) |
| 3.164 | n-C₃H₇ | CH₃ | 2,4-Cl(Ph) |
| 3.165 | n-C₃H₇ | CH₃ | 2,4-F(Ph) |
| 3.166 | iso-C₃H₇ | CH₃ | Ph |
| 3.167 | iso-C₃H₇ | CH₃ | 2-Cl(Ph) |
| 3.168 | iso-C₃H₇ | CH₃ | 3-Cl(Ph) |
| 3.169 | iso-C₃H₇ | CH₃ | 4-Cl(Ph) |
| 3.170 | iso-C₃H₇ | CH₃ | 4-Br(Ph) |
| 3.171 | iso-C₃H₇ | CH₃ | 4-F(Ph) |
| 3.172 | iso-C₃H₇ | CH₃ | 4-OCH₃(Ph) |
| 3.173 | iso-C₃H₇ | CH₃ | 4-CH₃(Ph) |
| 3.174 | iso-C₃H₇ | CH₃ | 4-NO₂(Ph) |
| 3.175 | iso-C₃H₇ | CH₃ | 2,4-Cl(Ph) |
| 3.176 | iso-C₃H₇ | CH₃ | 2,4-F(Ph) |
| 3.177 | n-C₄H₉ | CH₃ | Ph |
| 3.178 | n-C₄H₉ | CH₃ | 2-Cl(Ph) |
| 3.179 | n-C₄H₉ | CH₃ | 3-Cl(Ph) |
| 3.180 | n-C₄H₉ | CH₃ | 4-Cl(Ph) |
| 3.181 | n-C₄H₉ | CH₃ | 4-Br(Ph) |
| 3.182 | n-C₄H₉ | CH₃ | 4-F(Ph) |
| 3.183 | n-C₄H₉ | CH₃ | 4-OCH₃(Ph) |
| 3.184 | n-C₄H₉ | CH₃ | 4-CH₃(Ph) |
| 3.185 | n-C₄H₉ | CH₃ | 4-NO₂(Ph) |
| 3.186 | n-C₄H₉ | CH₃ | 2,4-Cl(Ph) |
| 3.187 | n-C₄H₉ | CH₃ | 2,4-F(Ph) |
| 3.188 | n-C₄H₉ | CH₃ | 4-CF₃(Ph) |
| 3.189 | Ph | H | Ph |
| 3.190 | Ph | H | 2-Cl(Ph) |
| 3.191 | Ph | H | 3-Cl(Ph) |
| 3.192 | Ph | H | 4-Cl(Ph) |
| 3.193 | Ph | H | 4-Br(Ph) |
| 3.194 | Ph | H | 4-F(Ph) |
| 3.195 | Ph | H | 4-OCH₃(Ph) |
| 3.196 | Ph | H | 4-CH₃(Ph) |
| 3.197 | Ph | H | 4-NO₂(Ph) |
| 3.198 | Ph | H | 2,4-Cl(Ph) |
| 3.199 | Ph | H | 2,4-F(Ph) |
| 3.200 | Ph | CH₃ | Ph |
| 3.201 | Ph | CH₃ | 2-Cl(Ph) |
| 3.202 | Ph | CH₃ | 3-Cl(Ph) |
| 3.203 | Ph | CH₃ | 4-Cl(Ph) |
| 3.204 | Ph | CH₃ | 4-Br(Ph) |
| 3.205 | Ph | CH₃ | 4-F(Ph) |
| 3.206 | Ph | CH₃ | 4-OCH₃(Ph) |
| 3.207 | Ph | CH₃ | 4-CH₃(Ph) |
| 3.208 | Ph | CH₃ | 4-NO₂(Ph) |
| 3.209 | Ph | CH₃ | 2,4-Cl(Ph) |
| 3.210 | Ph | CH₃ | 2,4-F(Ph) |
| 3.211 | CN | H | Ph |
| 3.212 | CN | H | 2-Cl(Ph) |
| 3.213 | CN | H | 3-Cl(Ph) |
| 3.214 | CN | H | 4-Cl(Ph) |
| 3.215 | CN | H | 4-Br(Ph) |
| 3.216 | CN | H | 4-F(Ph) |
| 3.217 | CN | H | 4-OCH₃(Ph) |
| 3.218 | CN | H | 4-CH₃(Ph) |
| 3.219 | CN | H | 4-NO₂(Ph) |
| 3.220 | CN | H | 2,4-Cl(Ph) |
| 3.221 | CN | H | 2,4-F(Ph) |
| 3.222 | CN | CH₃ | Ph |
| 3.223 | CN | CH₃ | 2-Cl(Ph) |
| 3.224 | CN | CH₃ | 3-Cl(Ph) |
| 3.225 | CN | CH₃ | 4-Cl(Ph) |
| 3.226 | CN | CH₃ | 4-Br(Ph) |
| 3.227 | CN | CH₃ | 4-F(Ph) |
| 3.228 | CN | CH₃ | 4-OCH₃(Ph) |
| 3.229 | CN | CH₃ | 4-CH₃(Ph) |
| 3.230 | CN | CH₃ | 4-NO₂(Ph) |
| 3.231 | CN | CH₃ | 2,4-Cl(Ph) |
| 3.232 | CN | CH₃ | 2,4-F(Ph) |
| 3.233 | H | H | 1-napthyl |
| 3.234 | CH₃ | H | 1-napthyl |
| 3.235 | C₂H₅ | H | 1-napthyl |
| 3.236 | n-C₃H₇ | H | 1-napthyl |
| 3.237 | iso-C₃H₇ | H | 1-napthyl |
| 3.238 | n-C₄H₉ | H | 1-napthyl |
| 3.239 | iso-C₄H₉ | H | 1-napthyl |
| 3.240 | cyclopropyl | H | 1-napthyl |

TABLE 3-continued

| Compd. | R₂ | R₃ | R₇ |
|---|---|---|---|
| 3.241 | 1-CH₃-cyclopropyl | H | 1-napthyl |
| 3.242 | CN | H | 1-napthyl |
| 3.243 | Ph | H | 1-napthyl |
| 3.244 | H | CH₃ | 1-napthyl |
| 3.245 | CH₃ | CH₃ | 1-napthyl |
| 3.246 | C₂H₅ | CH₃ | 1-napthyl |
| 3.247 | n-C₃H₇ | CH₃ | 1-napthyl |
| 3.248 | iso-C₃H₇ | CH₃ | 1-napthyl |
| 3.249 | n-C₄H₉ | CH₃ | 1-napthyl |
| 3.250 | iso-C₄H₉ | CH₃ | 1-napthyl |
| 3.251 | cyclopropyl | CH₃ | 1-napthyl |
| 3.252 | 1-CH₃-cyclopropyl | CH₃ | 1-napthyl |
| 3.253 | CN | CH₃ | 1-napthyl |
| 3.254 | Ph | CH₃ | 1-napthyl |
| 3.255 | H | H | 2-napthyl |
| 3.256 | CH₃ | H | 2-napthyl |
| 3.257 | C₂H₅ | H | 2-napthyl |
| 3.258 | n-C₃H₇ | H | 2-napthyl |
| 3.259 | iso-C₃H₇ | H | 2-napthyl |
| 3.260 | n-C₄H₉ | H | 2-napthyl |
| 3.261 | iso-C₄H₉ | H | 2-napthyl |
| 3.262 | cyclopropyl | H | 2-napthyl |
| 3.263 | 1-CH₃-cyclopropyl | H | 2-napthyl |
| 3.264 | CN | H | 2-napthyl |
| 3.265 | Ph | H | 2-napthyl |
| 3.266 | H | CH₃ | 2-napthyl |
| 3.267 | CH₃ | CH₃ | 2-napthyl |
| 3.268 | C₂H₅ | CH₃ | 2-napthyl |
| 3.269 | n-C₃H₇ | CH₃ | 2-napthyl |
| 3.270 | iso-C₃H₇ | CH₃ | 2-napthyl |
| 3.271 | n-C₄H₉ | CH₃ | 2-napthyl |
| 3.272 | iso-C₄H₉ | CH₃ | 2-napthyl |
| 3.273 | cyclopropyl | CH₃ | 2-napthyl |
| 3.274 | 1-CH₃-cyclopropyl | CH₃ | 2-napthyl |
| 3.275 | CN | CH₃ | 2-napthyl |
| 3.276 | Ph | CH₃ | 2-napthyl |
| 3.277 | 2-Cl(Ph) | CH₃ | 2-napthyl |
| 3.278 | 3-Cl(Ph) | CH₃ | 2-napthyl |
| 3.279 | 4-Cl(Ph) | CH₃ | 2-napthyl |
| 3.280 | 4-Br(Ph) | CH₃ | 2-napthyl |
| 3.281 | 4-OCH₃(Ph) | CH₃ | 2-napthyl |
| 3.282 | 4-CH₃(Ph) | CH₃ | 2-napthyl |
| 3.283 | 3-CF₃(Ph) | CH₃ | 2-napthyl |
| 3.284 | CH₃ | C₂H₅ | Ph |
| 3.285 | CH₃ | C₂H₅ | 2-Cl(Ph) |
| 3.286 | CH₃ | C₂H₅ | 3-Cl(Ph) |
| 3.287 | CH₃ | C₂H₅ | 4-Cl(Ph) |
| 3.288 | CH₃ | C₂H₅ | 4-Br(Ph) |
| 3.289 | CH₃ | C₂H₅ | 4-F(Ph) |
| 3.290 | CH₃ | C₂H₅ | 4-OCH₃(Ph) |
| 3.291 | CH₃ | C₂H₅ | 4-CH₃(Ph) |
| 3.292 | CH₃ | C₂H₅ | 4-NO₂(Ph) |
| 3.293 | CH₃ | C₂H₅ | 2,4-Cl(Ph) |
| 3.294 | CH₃ | C₂H₅ | 2,4-F(Ph) |
| 3.295 | CH₃ | n-C₃H₇ | Ph |
| 3.296 | CH₃ | n-C₃H₇ | 2-Cl(Ph) |
| 3.297 | CH₃ | n-C₃H₇ | 3-Cl(Ph) |
| 3.298 | CH₃ | n-C₃H₇ | 4-Cl(Ph) |
| 3.299 | CH₃ | n-C₃H₇ | 4-Br(Ph) |
| 3.300 | CH₃ | n-C₃H₇ | 4-F(Ph) |
| 3.301 | CH₃ | n-C₃H₇ | 4-OCH₃(Ph) |
| 3.302 | CH₃ | n-C₃H₇ | 4-CH₃(Ph) |
| 3.303 | CH₃ | n-C₃H₇ | 4-NO₂(Ph) |
| 3.304 | CH₃ | n-C₃H₇ | 2,4-Cl(Ph) |
| 3.305 | CH₃ | n-C₃H₇ | 2,4-F(Ph) |
| 3.306 | CH₃ | iso-C₃H₇ | Ph |
| 3.307 | CH₃ | iso-C₃H₇ | 2-Cl(Ph) |
| 3.308 | CH₃ | iso-C₃H₇ | 3-Cl(Ph) |
| 3.309 | CH₃ | iso-C₃H₇ | 4-Cl(Ph) |
| 3.310 | CH₃ | iso-C₃H₇ | 4-Br(Ph) |
| 3.311 | CH₃ | iso-C₃H₇ | 4-F(Ph) |
| 3.312 | CH₃ | iso-C₃H₇ | 4-OCH₃(Ph) |
| 3.313 | CH₃ | iso-C₃H₇ | 4-CH₃(Ph) |
| 3.314 | CH₃ | iso-C₃H₇ | 4-NO₂(Ph) |
| 3.315 | CH₃ | iso-C₃H₇ | 2,4-Cl(Ph) |
| 3.316 | CH₃ | iso-C₃H₇ | 2,4-F(Ph) |
| 3.317 | CH₃ | n-C₄H₉ | Ph |
| 3.318 | CH₃ | n-C₄H₉ | 2-Cl(Ph) |
| 3.319 | CH₃ | n-C₄H₉ | 3-Cl(Ph) |
| 3.320 | CH₃ | n-C₄H₉ | 4-Cl(Ph) |
| 3.321 | CH₃ | n-C₄H₉ | 4-Br(Ph) |
| 3.322 | CH₃ | n-C₄H₉ | 4-F(Ph) |
| 3.323 | CH₃ | n-C₄H₉ | 4-OCH₃(Ph) |
| 3.324 | CH₃ | n-C₄H₉ | 4-CH₃(Ph) |
| 3.325 | CH₃ | n-C₄H₉ | 4-NO₂(Ph) |
| 3.326 | CH₃ | n-C₄H₉ | 2,4-Cl(Ph) |
| 3.327 | CH₃ | n-C₄H₉ | 2,4-F(Ph) |

Typical compounds encompassed by the present invention of Formula I include those compounds of Formula IV, which is Formula I with $A=R_4=R_5=R_6=H$, $R_1=CH_3$, $X=CH$, $Y=O$, and $Z=O$, and where $R_2$, $R_3$, and $R_7$ are defined in Table 4.

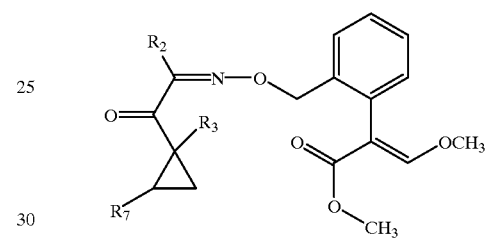

Formula IV

TABLE 4

| Compd. | R₂ | R₃ | R₇ |
|---|---|---|---|
| 4.1 | H | Ph | Ph |
| 4.2 | H | Ph | 2-Cl(Ph) |
| 4.3 | H | Ph | 3-Cl(Ph) |
| 4.4 | H | Ph | 4-Cl(Ph) |
| 4.5 | H | Ph | 2-Br(Ph) |
| 4.6 | H | Ph | 3-Br(Ph) |
| 4.7 | H | Ph | 4-Br(Ph) |
| 4.8 | H | Ph | 2-F(Ph) |
| 4.9 | H | Ph | 3-F(Ph) |
| 4.10 | H | Ph | 4-F(Ph) |
| 4.11 | H | Ph | 2-OCH₃(Ph) |
| 4.12 | H | Ph | 3-OCH₃(Ph) |
| 4.13 | H | Ph | 4-OCH₃(Ph) |
| 4.14 | H | Ph | 2-OC₂H₅(Ph) |
| 4.15 | H | Ph | 3-OC₂H₅(Ph) |
| 4.16 | H | Ph | 4-OC₂H₅(Ph) |
| 4.17 | H | Ph | 4-OPh(Ph) |
| 4.18 | H | Ph | 2-CH₃(Ph) |
| 4.19 | H | Ph | 3-CH₃(Ph) |
| 4.20 | H | Ph | 4-CH₃(Ph) |
| 4.21 | H | Ph | 2-CF₃(Ph) |
| 4.22 | H | Ph | 3-CF₃(Ph) |
| 4.23 | H | Ph | 4-CF₃(Ph) |
| 4.24 | H | Ph | 2-NO₂(Ph) |
| 4.25 | H | Ph | 3-NO₂(Ph) |
| 4.26 | H | Ph | 4-NO₂(Ph) |
| 4.27 | H | Ph | 2,3-Cl(Ph) |
| 4.28 | H | Ph | 2,4-Cl(Ph) |
| 4.29 | H | Ph | 2,5-Cl(Ph) |
| 4.30 | H | Ph | 2,6-Cl(Ph) |
| 4.31 | H | Ph | 3,4-Cl(Ph) |
| 4.32 | H | Ph | 3,5-Cl(Ph) |
| 4.33 | H | Ph | 2,3-F(Ph) |
| 4.34 | H | Ph | 2,4-F(Ph) |
| 4.35 | H | Ph | 2,5-F(Ph) |
| 4.36 | H | Ph | 2,6-F(Ph) |
| 4.37 | H | Ph | 3,4-F(Ph) |

TABLE 4-continued

| Compd. | R$_2$ | R$_3$ | R$_7$ |
|---|---|---|---|
| 4.38 | H | Ph | 3,5-F(Ph) |
| 4.39 | CH$_3$ | Ph | Ph |
| 4.40 | CH$_3$ | Ph | 2-Cl(Ph) |
| 4.41 | CH$_3$ | Ph | 3-Cl(Ph) |
| 4.42 | CH$_3$ | Ph | 4-Cl(Ph) |
| 4.43 | CH$_3$ | Ph | 2-Br(Ph) |
| 4.44 | CH$_3$ | Ph | 3-Br(Ph) |
| 4.45 | CH$_3$ | Ph | 4-Br(Ph) |
| 4.46 | CH$_3$ | Ph | 2-F(Ph) |
| 4.47 | CH$_3$ | Ph | 3-F(Ph) |
| 4.48 | CH$_3$ | Ph | 4-F(Ph) |
| 4.49 | CH$_3$ | Ph | 2-OCH$_3$(Ph) |
| 4.50 | CH$_3$ | Ph | 3-OCH$_3$(Ph) |
| 4.51 | CH$_3$ | Ph | 4-OCH$_3$(Ph) |
| 4.52 | CH$_3$ | Ph | 2-OC$_2$H$_5$(Ph) |
| 4.53 | CH$_3$ | Ph | 3-OC$_2$H$_5$(Ph) |
| 4.54 | CH$_3$ | Ph | 4-OC$_2$H$_5$(Ph) |
| 4.55 | CH$_3$ | Ph | 2-OPh(Ph) |
| 4.56 | CH$_3$ | Ph | 3-OPh(Ph) |
| 4.57 | CH$_3$ | Ph | 4-OPh(Ph) |
| 4.58 | CH$_3$ | Ph | 2-CH$_3$(Ph) |
| 4.59 | CH$_3$ | Ph | 3-CH$_3$(Ph) |
| 4.60 | CH$_3$ | Ph | 4-CH$_3$(Ph) |
| 4.61 | CH$_3$ | Ph | 2-CF$_3$(Ph) |
| 4.62 | CH$_3$ | Ph | 3-CF$_3$(Ph) |
| 4.63 | CH$_3$ | Ph | 4-CF$_3$(Ph) |
| 4.64 | CH$_3$ | Ph | 4-OCF$_3$(Ph) |
| 4.65 | CH$_3$ | Ph | 2-NO$_2$(Ph) |
| 4.66 | CH$_3$ | Ph | 3-NO$_2$(Ph) |
| 4.67 | CH$_3$ | Ph | 4-NO$_2$(Ph) |
| 4.68 | CH$_3$ | Ph | 2,3-Cl(Ph) |
| 4.69 | CH$_3$ | Ph | 2,4-Cl(Ph) |
| 4.70 | CH$_3$ | Ph | 2,5-Cl(Ph) |
| 4.71 | CH$_3$ | Ph | 2,6-Cl(Ph) |
| 4.72 | CH$_3$ | Ph | 3,4-Cl(Ph) |
| 4.73 | CH$_3$ | Ph | 3,5-Cl(Ph) |
| 4.74 | CH$_3$ | Ph | 2,3-F(Ph) |
| 4.75 | CH$_3$ | Ph | 2,4-F(Ph) |
| 4.76 | CH$_3$ | Ph | 2,5-F(Ph) |
| 4.77 | CH$_3$ | Ph | 2,6-F(Ph) |
| 4.78 | CH$_3$ | Ph | 3,4-F(Ph) |
| 4.79 | CH$_3$ | Ph | 3,5-F(Ph) |
| 4.80 | C$_2$H$_5$ | Ph | 2-Cl(Ph) |
| 4.81 | n-C$_3$H$_7$ | Ph | 3-Cl(Ph) |
| 4.82 | iso-C$_3$H$_7$ | Ph | 4-Cl(Ph) |
| 4.83 | n-C$_4$H$_9$ | Ph | 4-Br(Ph) |
| 4.84 | iso-C$_4$H$_9$ | Ph | 4-F(Ph) |
| 4.85 | C(CH$_3$)$_3$ | Ph | 4-OCH$_3$(Ph) |
| 4.86 | n-C$_5$H$_{11}$ | Ph | 4-CH$_3$(Ph) |
| 4.87 | cyclopropyl | Ph | 4-NO$_2$(Ph) |
| 4.88 | 1-CH$_3$-cyclopropyl | Ph | 2,4-Cl(Ph) |
| 4.89 | CN | Ph | 2,4-F(Ph) |
| 4.90 | Ph | Ph | Ph |
| 4.91 | Ph | Ph | 2-Cl(Ph) |
| 4.92 | Ph | Ph | 3-Cl(Ph) |
| 4.93 | Ph | Ph | 4-Cl(Ph) |
| 4.94 | 4-Cl(Ph) | Ph | Ph |
| 4.95 | 4-Cl(Ph) | Ph | 4-Cl(Ph) |
| 4.96 | 4-F(Ph) | Ph | Ph |
| 4.97 | 4-F(Ph) | Ph | 4-F(Ph) |
| 4.98 | 4-CF$_3$(Ph) | Ph | Ph |
| 4.99 | 4-CF$_3$(Ph) | Ph | 4-CF$_3$(Ph) |
| 4.100 | 2,4-Cl(Ph) | Ph | Ph |
| 4.101 | 2,4-Cl(Ph) | Ph | 2,4-Cl(Ph) |
| 4.102 | 2,4-F(Ph) | Ph | Ph |
| 4.103 | H | 2-Cl(Ph) | Ph |
| 4.104 | CH$_3$ | 2-Cl(Ph) | Ph |
| 4.105 | C$_2$H$_5$ | 2-Cl(Ph) | 2-Cl(Ph) |
| 4.106 | n-C$_3$H$_7$ | 2-Cl(Ph) | 3-Cl(Ph) |
| 4.107 | iso-C$_3$H$_7$ | 2-Cl(Ph) | 4-Cl(Ph) |
| 4.108 | n-C$_4$H$_9$ | 2-Cl(Ph) | 4-Br(Ph) |
| 4.109 | iso-C$_4$H$_9$ | 2-Cl(Ph) | 4-F(Ph) |
| 4.110 | C(CH$_3$)$_3$ | 2-Cl(Ph) | 4-OCH$_3$(Ph) |
| 4.111 | n-C$_5$H$_{11}$ | 2-Cl(Ph) | 4-CH$_3$(Ph) |
| 4.112 | cyclopropyl | 2-Cl(Ph) | 4-NO$_2$(Ph) |
| 4.113 | 1-CH$_3$-cyclopropyl | 2-Cl(Ph) | 2,4-Cl(Ph) |
| 4.114 | CN | 2-Cl(Ph) | 2,4-F(Ph) |
| 4.115 | Ph | 2-Cl(Ph) | 2-Cl(Ph) |
| 4.116 | Ph | 2-Cl(Ph) | 3-Cl(Ph) |
| 4.117 | Ph | 2-Cl(Ph) | 4-Cl(Ph) |
| 4.118 | 4-Cl(Ph) | 2-Cl(Ph) | Ph |
| 4.119 | 4-Cl(Ph) | 2-Cl(Ph) | 4-Cl(Ph) |
| 4.120 | 4-F(Ph) | 2-Cl(Ph) | Ph |
| 4.121 | 4-F(Ph) | 2-Cl(Ph) | 4-F(Ph) |
| 4.122 | 4-CF$_3$(Ph) | 2-Cl(Ph) | Ph |
| 4.123 | 4-CF$_3$(Ph) | 2-Cl(Ph) | 4-CF$_3$(Ph) |
| 4.124 | 2,4-Cl(Ph) | 2-Cl(Ph) | Ph |
| 4.125 | 2,4-Cl(Ph) | 2-Cl(Ph) | 2,4-Cl(Ph) |
| 4.126 | 2,4-F(Ph) | 2-Cl(Ph) | Ph |
| 4.127 | H | 4-Cl(Ph) | Ph |
| 4.128 | CH$_3$ | 4-Cl(Ph) | Ph |
| 4.129 | C$_2$H$_5$ | 4-Cl(Ph) | 2-Cl(Ph) |
| 4.130 | n-C$_3$H$_7$ | 4-Cl(Ph) | 3-Cl(Ph) |
| 4.131 | iso-C$_3$H$_7$ | 4-Cl(Ph) | 4-Cl(Ph) |
| 4.132 | n-C$_4$H$_9$ | 4-Cl(Ph) | 4-Br(Ph) |
| 4.133 | iso-C$_4$H$_9$ | 4-Cl(Ph) | 4-F(Ph) |
| 4.134 | C(CH$_3$)$_3$ | 4-Cl(Ph) | 4-OCH$_3$(Ph) |
| 4.135 | n-C$_5$H$_{11}$ | 4-Cl(Ph) | 4-CH$_3$(Ph) |
| 4.136 | cyclopropyl | 4-Cl(Ph) | 4-NO$_2$(Ph) |
| 4.137 | 1-CH$_3$-cyclopropyl | 4-Cl(Ph) | 2,4-Cl(Ph) |
| 4.138 | CN | 4-Cl(Ph) | 2,4-F(Ph) |
| 4.139 | Ph | 4-Cl(Ph) | 2-Cl(Ph) |
| 4.140 | Ph | 4-Cl(Ph) | 3-Cl(Ph) |
| 4.141 | Ph | 4-Cl(Ph) | 4-Cl(Ph) |
| 4.142 | 4-Cl(Ph) | 4-Cl(Ph) | Ph |
| 4.143 | 4-Cl(Ph) | 4-Cl(Ph) | 4-Cl(Ph) |
| 4.144 | 4-F(Ph) | 4-Cl(Ph) | Ph |
| 4.145 | 4-F(Ph) | 4-Cl(Ph) | 4-F(Ph) |
| 4.146 | 4-CF$_3$(Ph) | 4-Cl(Ph) | Ph |
| 4.147 | 4-CF$_3$(Ph) | 4-Cl(Ph) | 4-CF$_3$(Ph) |
| 4.148 | 2,4-Cl(Ph) | 4-Cl(Ph) | Ph |
| 4.149 | 2,4-Cl(Ph) | 4-Cl(Ph) | 2,4-Cl(Ph) |
| 4.150 | 2,4-F(Ph) | 4-Cl(Ph) | Ph |
| 4.151 | H | 4-CF$_3$(Ph) | Ph |
| 4.152 | CH$_3$ | 4-CF$_3$(Ph) | Ph |
| 4.153 | C$_2$H$_5$ | 4-CF$_3$(Ph) | 2-Cl(Ph) |
| 4.154 | n-C$_3$H$_7$ | 4-CF$_3$(Ph) | 3-Cl(Ph) |
| 4.155 | iso-C$_3$H$_7$ | 4-CF$_3$(Ph) | 4-Cl(Ph) |
| 4.156 | n-C$_4$H$_9$ | 4-CF$_3$(Ph) | 4-Br(Ph) |
| 4.157 | iso-C$_4$H$_9$ | 4-CF$_3$(Ph) | 4-F(Ph) |
| 4.158 | C(CH$_3$)$_3$ | 4-CF$_3$(Ph) | 4-OCH$_3$(Ph) |
| 4.159 | n-C$_5$H$_{11}$ | 4-CF$_3$(Ph) | 4-CH$_3$(Ph) |
| 4.160 | cyclopropyl | 4-CF$_3$(Ph) | 4-NO$_2$(Ph) |
| 4.161 | 1-CH$_3$-cyclopropyl | 4-CF$_3$(Ph) | 2,4-Cl(Ph) |
| 4.162 | CN | 4-CF$_3$(Ph) | 2,4-F(Ph) |
| 4.163 | Ph | 4-CF$_3$(Ph) | 2-Cl(Ph) |
| 4.164 | Ph | 4-CF$_3$(Ph) | 3-Cl(Ph) |
| 4.165 | Ph | 4-CF$_3$(Ph) | 4-Cl(Ph) |
| 4.166 | 4-Cl(Ph) | 4-CF$_3$(Ph) | Ph |
| 4.167 | 4-Cl(Ph) | 4-CF$_3$(Ph) | 4-Cl(Ph) |
| 4.168 | 4-F(Ph) | 4-CF$_3$(Ph) | Ph |
| 4.169 | 4-F(Ph) | 4-CF$_3$(Ph) | 4-F(Ph) |
| 4.170 | 4-CF$_3$(Ph) | 4-CF$_3$(Ph) | Ph |
| 4.171 | 4-CF$_3$(Ph) | 4-CF$_3$(Ph) | 4-CF$_3$(Ph) |
| 4.172 | 2,4-Cl(Ph) | 4-CF$_3$(Ph) | Ph |
| 4.173 | 2,4-Cl(Ph) | 4-CF$_3$(Ph) | 2,4-Cl(Ph) |
| 4.174 | 2,4-F(Ph) | 4-CF$_3$(Ph) | Ph |
| 4.175 | H | 1-napthyl | Ph |
| 4.176 | CH$_3$ | 1-napthyl | Ph |
| 4.177 | C$_2$H$_5$ | 1-napthyl | 2-Cl(Ph) |
| 4.178 | n-C$_3$H$_7$ | 1-napthyl | 3-Cl(Ph) |
| 4.179 | iso-C$_3$H$_7$ | 1-napthyl | 4-Cl(Ph) |
| 4.180 | n-C$_4$H$_9$ | 1-napthyl | 4-Br(Ph) |
| 4.181 | iso-C$_4$H$_9$ | 1-napthyl | 4-F(Ph) |
| 4.182 | C(CH$_3$)$_3$ | 1-napthyl | 4-OCH$_3$(Ph) |
| 4.183 | n-C$_5$H$_{11}$ | 1-napthyl | 4-CH$_3$(Ph) |
| 4.184 | cyclopropyl | 1-napthyl | 4-NO$_2$(Ph) |
| 4.185 | 1-CH$_3$-cyclopropyl | 1-napthyl | 2,4-Cl(Ph) |
| 4.186 | CN | 1-napthyl | 2,4-F(Ph) |
| 4.187 | Ph | 1-napthyl | 2-Cl(Ph) |
| 4.188 | Ph | 1-napthyl | 3-Cl(Ph) |
| 4.189 | Ph | 1-napthyl | 4-Cl(Ph) |
| 4.190 | 4-CT(Ph) | 1-napthyl | Ph |
| 4.191 | 4-Cl(Ph) | 1-napthyl | 4-Cl(Ph) |

TABLE 4-continued

| Compd. | R₂ | R₃ | R₇ |
|---|---|---|---|
| 4.192 | 4-F(Ph) | 1-napthyl | Ph |
| 4.193 | 4-F(Ph) | 1-napthyl | 4-F(Ph) |
| 4.194 | 4-CF₃(Ph) | 1-napthyl | Ph |
| 4.195 | 4-CF₃(Ph) | 1-napthyl | 4-CF₃(Ph) |
| 4.196 | 2,4-Cl(Ph) | 1-napthyl | Ph |
| 4.197 | 2,4-Cl(Ph) | 1-napthyl | 2,4-Cl(Ph) |
| 4.198 | 2,4-F(Ph) | 1-napthyl | Ph |
| 4.199 | CH₃ | 2-pyridyl | Ph |
| 4.200 | CH₃ | 3-pyridyl | Ph |
| 4.201 | CH₃ | 4-pyridyl | Ph |
| 4.202 | CH₃ | 2-thienyl | Ph |
| 4.203 | CH₃ | 3-thienyl | Ph |
| 4.204 | CH₃ | 2-furyl | Ph |
| 4.205 | CH₃ | 3-furyl | Ph |
| 4.206 | CH₃ | 5-pyrimidinyl | Ph |
| 4.207 | CH₃ | 2-pyridyl | 4-Cl(Ph) |
| 4.208 | CH₃ | 3-pyridyl | 4-Cl(Ph) |
| 4.209 | CH₃ | 4-pyridyl | 4-Cl(Ph) |
| 4.210 | CH₃ | 2-thienyl | 4-Cl(Ph) |
| 4.211 | CH₃ | 3-thienyl | 4-Cl(Ph) |
| 4.212 | CH₃ | 2-furyl | 4-Cl(Ph) |
| 4.213 | CH₃ | 3-furyl | 4-Cl(Ph) |
| 4.214 | CH₃ | 5-pyrimidinyl | 4-Cl(Ph) |
| 4.215 | CH₃ | 2-pyridyl | 3-CF₃(Ph) |
| 4.216 | CH₃ | 3-pyridyl | 3-CF₃(Ph) |
| 4.217 | CH₃ | 4-pyridyl | 3-CF₃(Ph) |
| 4.218 | CH₃ | 2-thienyl | 3-CF₃(Ph) |
| 4.219 | CH₃ | 3-thienyl | 3-CF₃(Ph) |
| 4.220 | CH₃ | 2-furyl | 3-CF₃(Ph) |
| 4.221 | CH₃ | 3-furyl | 3-CF₃(Ph) |
| 4.222 | CH₃ | 5-pyrimidinyl | 3-CF₃(Ph) |
| 4.223 | CH₃ | 2-pyridyl | 4-CF₃(Ph) |
| 4.224 | CH₃ | 3-pyridyl | 4-CF₃(Ph) |
| 4.225 | CH₃ | 4-pyridyl | 4-CF₃(Ph) |
| 4.226 | CH₃ | 2-thienyl | 4-CF₃(Ph) |

TABLE 5

Compounds 5.1 to 5.226 are compounds of Formula V, which is Formula I with A=R₄=R₅=R₆=H, R₁=CH₃, X=N, Y=O, and Z=O, and where R₂, R₃, and R₇ are defined in Table 4.

TABLE 6

Compounds 6.1 to 6.226 are compounds of Formula VI, which is Formula I with A=R₄=R₅=R₆=H, R₁=CH₃, X=N, Y=NH, and Z=O, and where R₂, R₃, and R₇ are defined in Table 4.

Typical compounds encompassed by the present invention of Formula I include those compounds of Formula IV, which is Formula I with A=R₄=R₅=R₆=H, R₁=CH₃, X=CH, Y=O, and Z=O, and where R₂, R₃, and R₇ are defined in Table 7.

Formula IV

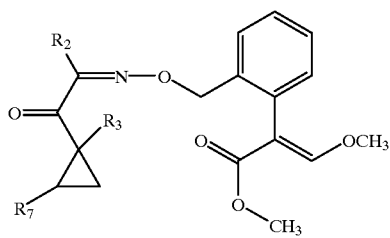

TABLE 7

| Compd. | R₂ | R₃ | R₇ |
|---|---|---|---|
| 7.1 | H | H | 2-pyridyl |
| 7.2 | H | H | 3-pyridyl |
| 7.3 | H | H | 4-pyridyl |
| 7.4 | H | H | 2-thienyl |
| 7.5 | H | H | 3-thienyl |
| 7.6 | H | H | 2-furyl |
| 7.7 | H | H | 3-furyl |
| 7.8 | H | H | 4-pyrimidinyl |
| 7.9 | H | H | 5-pyrimidinyl |
| 7.10 | H | H | pyrazinyl |
| 7.11 | CH₃ | H | 2-pyridyl |
| 7.12 | CH₃ | H | 3-pyridyl |
| 7.13 | CH₃ | H | 4-pyridyl |
| 7.14 | CH₃ | H | 2-thienyl |
| 7.15 | CH₃ | H | 3-thienyl |
| 7.16 | CH₃ | H | 2-furyl |
| 7.17 | CH₃ | H | 3-furyl |
| 7.18 | CH₃ | H | 4-pyrimidinyl |
| 7.19 | CH₃ | H | 5-pyrimidinyl |
| 7.20 | CH₃ | H | pyrazinyl |
| 7.21 | C₂H₅ | H | 2-pyridyl |
| 7.22 | C₂H₅ | H | 3-pyridyl |
| 7.23 | C₂H₅ | H | 4-pyridyl |
| 7.24 | C₂H₅ | H | 2-thienyl |
| 7.25 | C₂H₅ | H | 3-thienyl |
| 7.26 | C₂H₅ | H | 2-furyl |
| 7.27 | C₂H₅ | H | 3-furyl |
| 7.28 | C₂H₅ | H | 4-pyrimidinyl |
| 7.29 | C₂H₅ | H | 5-pyrimidinyl |
| 7.30 | C₂H₅ | H | pyrazinyl |
| 7.31 | n-C₃H₇ | H | 2-pyridyl |
| 7.32 | n-C₃H₇ | H | 3-pyridyl |
| 7.33 | n-C₃H₇ | H | 4-pyridyl |
| 7.34 | n-C₃H₇ | H | 2-thienyl |
| 7.35 | n-C₃H₇ | H | 3-thienyl |
| 7.36 | n-C₃H₇ | H | 2-furyl |
| 7.37 | n-C₃H₇ | H | 3-furyl |
| 7.38 | n-C₃H₇ | H | 4-pyrimidinyl |
| 7.39 | n-C₃H₇ | H | 5-pyrimidinyl |
| 7.40 | n-C₃H₇ | H | pyrazinyl |
| 7.41 | cyclopropyl | H | 2-pyridyl |
| 7.42 | cyclopropyl | H | 3-pyridyl |
| 7.43 | cyclopropyl | H | 4-pyridyl |
| 7.44 | cyclopropyl | H | 2-thienyl |
| 7.45 | cyclopropyl | H | 3-thienyl |
| 7.46 | cyclopropyl | H | 2-furyl |
| 7.47 | cyclopropyl | H | 3-furyl |
| 7.48 | cyclopropyl | H | 4-pyrimidinyl |
| 7.49 | cyclopropyl | H | 5-pyrimidinyl |
| 7.50 | cyclopropyl | H | pyrazinyl |
| 7.51 | CN | H | 2-pyridyl |
| 7.52 | CN | H | 3-pyridyl |
| 7.53 | CN | H | 4-pyridyl |
| 7.54 | CN | H | 2-thienyl |
| 7.55 | CN | H | 3-thienyl |
| 7.56 | CN | H | 2-furyl |
| 7.57 | CN | H | 3-furyl |
| 7.58 | CN | H | 4-pyrimidinyl |
| 7.59 | CN | H | 5-pyrimidinyl |
| 7.60 | CN | H | pyrazinyl |
| 7.61 | CH₃ | CH₃ | 2-pyridyl |
| 7.62 | CH₃ | CH₃ | 3-pyridyl |
| 7.63 | CH₃ | CH₃ | 4-pyridyl |
| 7.64 | CH₃ | CH₃ | 2-thienyl |
| 7.65 | CH₃ | CH₃ | 3-thienyl |
| 7.66 | CH₃ | CH₃ | 2-furyl |
| 7.67 | CH₃ | CH₃ | 3-furyl |
| 7.68 | CH₃ | CH₃ | 4-pyrimidinyl |
| 7.69 | CH₃ | CH₃ | 5-pyrimidinyl |
| 7.70 | CH₃ | CH₃ | pyrazinyl |
| 7.71 | CH₃ | H | 2-pyridylCH₂— |
| 7.71 | CH₃ | H | 3-pyridylCH₂— |
| 7.70 | CH₃ | H | 4-pyridylCH₂— |
| 7.71 | CH₃ | H | 2-thienylCH₂— |
| 7.72 | CH₃ | H | 3-thienylCH₂— |
| 7.73 | CH₃ | H | 2-furylCH₂— |
| 7.74 | CH₃ | H | 3-furylCH₂— |

TABLE 7-continued

| Compd. | R₂ | R₃ | R₇ |
|---|---|---|---|
| 7.75 | CH₃ | CH₃ | 2-pyridylCH₂— |
| 7.76 | CH₃ | CH₃ | 2-thienylCH₂— |
| 7.77 | H | Ph | 2-pyridyl |
| 7.78 | H | Ph | 3-pyridyl |
| 7.79 | H | Ph | 4-pyridyl |
| 7.80 | H | Ph | 2-thienyl |
| 7.81 | H | Ph | 3-thienyl |
| 7.82 | H | Ph | 2-furyl |
| 7.83 | H | Ph | 3-furyl |
| 7.84 | H | Ph | 4-pyrimidinyl |
| 7.85 | H | Ph | 5-pyrimidinyl |
| 7.86 | H | Ph | pyrazinyl |
| 7.87 | CH₃ | Ph | 2-pyridyl |
| 7.88 | CH₃ | Ph | 3-pyridyl |
| 7.89 | CH₃ | Ph | 4-pyridyl |
| 7.90 | CH₃ | Ph | 2-thienyl |
| 7.91 | CH₃ | Ph | 3-thienyl |
| 7.92 | CH₃ | Ph | 2-furyl |
| 7.93 | CH₃ | Ph | 3-furyl |
| 7.94 | CH₃ | Ph | 4-pyrimidinyl |
| 7.95 | CH₃ | Ph | 5-pyrimidinyl |
| 7.96 | CH₃ | Ph | pyrazinyl |
| 7.97 | CH₃ | 2-Cl(Ph) | 2-pyridyl |
| 7.98 | CH₃ | 2-Cl(Ph) | 3-pyridyl |
| 7.99 | CH₃ | 2-Cl(Ph) | 4-pyridyl |
| 7.100 | CH₃ | 2-Cl(Ph) | 2-thienyl |
| 7.101 | CH₃ | 2-Cl(Ph) | 3-thienyl |
| 7.102 | CH₃ | 2-Cl(Ph) | 2-furyl |
| 7.103 | CH₃ | 2-Cl(Ph) | 3-furyl |
| 7.104 | CH₃ | 2-Cl(Ph) | 4-pyrimidinyl |
| 7.105 | CH₃ | 2-Cl(Ph) | 5-pyrimidinyl |
| 7.106 | CH₃ | 2-Cl(Ph) | pyrazinyl |
| 7.107 | CH₃ | 4-Cl(Ph) | 2-pyridyl |
| 7.108 | CH₃ | 4-Cl(Ph) | 3-pyridyl |
| 7.109 | CH₃ | 4-Cl(Ph) | 4-pyridyl |
| 7.110 | CH₃ | 4-Cl(Ph) | 2-thienyl |
| 7.111 | CH₃ | 4-Cl(Ph) | 3-thienyl |
| 7.112 | CH₃ | 4-Cl(Ph) | 2-furyl |
| 7.113 | CH₃ | 4-Cl(Ph) | 3-furyl |
| 7.114 | CH₃ | 4-Cl(Ph) | 4-pyrimidinyl |
| 7.115 | CH₃ | 4-Cl(Ph) | 5-pyrimidinyl |
| 7.116 | CH₃ | 4-Cl(Ph) | pyrazinyl |
| 7.117 | CH₃ | 1-napthyl | 2-pyridyl |
| 7.118 | CH₃ | 1-napthyl | 3-pyridyl |
| 7.119 | CH₃ | 1-napthyl | 4-pyridyl |
| 7.120 | CH₃ | 1-napthyl | 2-thienyl |
| 7.121 | CH₃ | 1-napthyl | 3-thienyl |
| 7.122 | CH₃ | 1-napthyl | 2-furyl |
| 7.123 | CH₃ | 1-napthyl | 3-furyl |
| 7.124 | CH₃ | 1-napthyl | 4-pyrimidinyl |
| 7.125 | CH₃ | 1-napthyl | 5-pyrimidinyl |
| 7.126 | CH₃ | 1-napthyl | pyrazinyl |
| 7.127 | CN | Ph | 2-pyridyl |
| 7.128 | CN | Ph | 3-pyridyl |
| 7.129 | CN | Ph | 4-pyridyl |
| 7.130 | CN | Ph | 2-thienyl |
| 7.131 | CN | Ph | 3-thienyl |
| 7.132 | CN | Ph | 2-furyl |
| 7.133 | CN | Ph | 3-furyl |
| 7.134 | CN | Ph | 4-pyrimidinyl |
| 7.135 | CN | Ph | 5-pyrimidinyl |
| 7.136 | CN | Ph | pyrazinyl |
| 7.127 | CN | 4-Cl(Ph) | 2-pyridyl |
| 7.128 | CN | 4-Cl(Ph) | 3-pyridyl |
| 7.129 | CN | 4-Cl(Ph) | 4-pyridyl |
| 7.130 | CN | 4-Cl(Ph) | 2-thienyl |
| 7.131 | CN | 4-Cl(Ph) | 3-thienyl |
| 7.132 | CN | 4-Cl(Ph) | 2-furyl |
| 7.133 | CN | 4-Cl(Ph) | 3-furyl |
| 7.134 | CN | 4-Cl(Ph) | 4-pyrimidinyl |
| 7.135 | CN | 4-Cl(Ph) | 5-pyrimidinyl |
| 7.136 | CN | 4-Cl(Ph) | pyrazinyl |
| 7.127 | CN | 1-napthyl | 2-pyridyl |
| 7.128 | CN | 1-napthyl | 3-pyridyl |
| 7.129 | CN | 1-napthyl | 4-pyridyl |
| 7.130 | CN | 1-napthyl | 2-thienyl |
| 7.131 | CN | 1-napthyl | 3-thienyl |
| 7.132 | CN | 1-napthyl | 2-furyl |
| 7.133 | CN | 1-napthyl | 3-furyl |
| 7.134 | CN | 1-napthyl | 4-pyrimidinyl |
| 7.135 | CN | 1-napthyl | 5-pyrimidinyl |
| 7.136 | CN | 1-napthyl | pyrazinyl |
| 7.137 | H | 2-pyridyl | 2-pyridyl |
| 7.138 | H | 3-pyridyl | 2-pyridyl |
| 7.139 | H | 4-pyridyl | 2-pyridyl |
| 7.140 | H | 2-thienyl | 2-pyridyl |
| 7.141 | H | 3-thienyl | 2-pyridyl |
| 7.142 | H | 2-furyl | 2-pyridyl |
| 7.143 | H | 3-furyl | 2-pyridyl |
| 7.144 | H | 4-pyrimidinyl | 2-pyridyl |
| 7.145 | H | 5-pyrimidinyl | 2-pyridyl |
| 7.146 | H | pyrazinyl | 2-pyridyl |
| 7.147 | H | 2-pyridyl | 3-pyridyl |
| 7.148 | H | 3-pyridyl | 3-pyridyl |
| 7.149 | H | 4-pyridyl | 3-pyridyl |
| 7.150 | H | 2-thienyl | 3-pyridyl |
| 7.151 | H | 3-thienyl | 3-pyridyl |
| 7.152 | H | 2-furyl | 3-pyridyl |
| 7.153 | H | 3-furyl | 3-pyridyl |
| 7.154 | H | 4-pyrimidinyl | 3-pyridyl |
| 7.155 | H | 5-pyrimidinyl | 3-pyridyl |
| 7.156 | H | pyrazinyl | 3-pyridyl |
| 7.157 | H | 2-pyridyl | 2-thienyl |
| 7.158 | H | 3-pyridyl | 2-thienyl |
| 7.159 | H | 4-pyridyl | 2-thienyl |
| 7.160 | H | 2-thienyl | 2-thienyl |
| 7.161 | H | 3-thienyl | 2-thienyl |
| 7.162 | H | 2-furyl | 2-thienyl |
| 7.163 | H | 3-furyl | 2-thienyl |
| 7.164 | H | 4-pyrimidinyl | 2-thienyl |
| 7.165 | H | 5-pyrimidinyl | 2-thienyl |
| 7.166 | H | pyrazinyl | 2-thienyl |
| 7.167 | CH₃ | 2-pyridyl | 2-pyridyl |
| 7.168 | CH₃ | 3-pyridyl | 2-pyridyl |
| 7.169 | CH₃ | 4-pyridyl | 2-pyridyl |
| 7.170 | CH₃ | 2-thienyl | 2-pyridyl |
| 7.171 | CH₃ | 3-thienyl | 2-pyridyl |
| 7.172 | CH₃ | 2-furyl | 2-pyridyl |
| 7.173 | CH₃ | 3-furyl | 2-pyridyl |
| 7.174 | CH₃ | 4-pyrimidinyl | 2-pyridyl |
| 7.175 | CH₃ | 5-pyrimidinyl | 2-pyridyl |
| 7.176 | CH₃ | pyrazinyl | 2-pyridyl |
| 7.177 | CH₃ | 2-pyridyl | 3-pyridyl |
| 7.178 | CH₃ | 3-pyridyl | 3-pyridyl |
| 7.179 | CH₃ | 4-pyridyl | 3-pyridyl |
| 7.180 | CH₃ | 2-thienyl | 3-pyridyl |
| 7.181 | CH₃ | 3-thienyl | 3-pyridyl |
| 7.182 | CH₃ | 2-furyl | 3-pyridyl |
| 7.183 | CH₃ | 3-furyl | 3-pyridyl |
| 7.184 | CH₃ | 4-pyrimidinyl | 3-pyridyl |
| 7.185 | CH₃ | 5-pyrimidinyl | 3-pyridyl |
| 7.186 | CH₃ | pyrazinyl | 3-pyridyl |
| 7.187 | CH₃ | 2-pyridyl | 2-thienyl |
| 7.188 | CH₃ | 3-pyridyl | 2-thienyl |
| 7.190 | CH₃ | 4-pyridyl | 2-thienyl |
| 7.191 | CH₃ | 2-thienyl | 2-thienyl |
| 7.192 | CH₃ | 3-thienyl | 2-thienyl |
| 7.193 | CH₃ | 2-furyl | 2-thienyl |
| 7.194 | CH₃ | 3-furyl | 2-thienyl |
| 7.195 | CH₃ | 4-pyrimidinyl | 2-thienyl |
| 7.196 | CH₃ | 5-pyrimidinyl | 2-thienyl |
| 7.197 | CH₃ | pyrazinyl | 2-thienyl |
| 7.198 | CN | 2-pyridyl | 2-pyridyl |
| 7.199 | CN | 3-pyridyl | 2-pyridyl |
| 7.200 | CN | 4-pyridyl | 2-pyridyl |
| 7.201 | CN | 2-thienyl | 2-pyridyl |
| 7.202 | CN | 3-thienyl | 2-pyridyl |
| 7.203 | CN | 2-furyl | 2-pyridyl |
| 7.204 | CN | 3-furyl | 2-pyridyl |
| 7.205 | CN | 4-pyrimidinyl | 2-pyridyl |
| 7.206 | CN | 5-pyrimidinyl | 2-pyridyl |
| 7.207 | CN | pyrazinyl | 2-pyridyl |
| 7.208 | CN | 2-pyridyl | 3-pyridyl |
| 7.209 | CN | 3-pyridyl | 3-pyridyl |

TABLE 7-continued

| Compd. | R₂ | R₃ | R₇ |
|---|---|---|---|
| 7.210 | CN | 4-pyridyl | 3-pyridyl |
| 7.211 | CN | 2-thienyl | 3-pyridyl |
| 7.212 | CN | 3-thienyl | 3-pyridyl |
| 7.213 | CN | 2-furyl | 3-pyridyl |
| 7.214 | CN | 3-furyl | 3-pyridyl |
| 7.215 | CN | 4-pyrimidinyl | 3-pyridyl |
| 7.216 | CN | 5-pyrimidinyl | 3-pyridyl |
| 7.217 | CN | pyrazinyl | 3-pyridyl |
| 7.218 | CN | 2-pyridyl | 2-thienyl |
| 7.219 | CN | 3-pyridyl | 2-thienyl |
| 7.220 | CN | 4-pyridyl | 2-thienyl |
| 7.221 | CN | 2-thienyl | 2-thienyl |

TABLE 8

Compounds 8.1 to 8.221 are compounds of Formula V, which is Formula I with A=R₄=R₅=R₆=H, R₁=CH₃, X=N, Y=O, and Z=O, and where R₂, R₃, and R₇ are defined in Table 7.

TABLE 9

Compounds 9.1 to 9.221 are compounds of Formula V, which is Formula I with A=R₄=R₅=R₆=H, R₁=CH₃, X=N, N—H, and Z=O, and where R₂, R₃, and R₇ are defined in Table 7.

Typical compounds encompassed by the present invention of Formula I include those compounds of Formula IV, which is Formula I with A=R₄=R₅=R₆=H, R₁=CH₃, X=CH, Y=O, and Z=O, and where R₂, R₃, and R₇ are defined in Table 10.

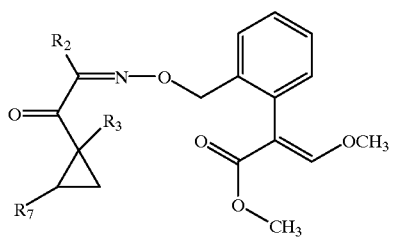

Formula IV

TABLE 10

| Compd. | R₂ | R₃ | R₇ |
|---|---|---|---|
| 10.1 | H | Ph | H |
| 10.2 | H | Ph | CH₃ |
| 10.3 | H | Ph | C₂H₅ |
| 10.4 | H | Ph | n-C₃H₇ |
| 10.5 | H | Ph | iso-C₃H₇ |
| 10.6 | H | Ph | n-C₄H₉ |
| 10.7 | H | Ph | C(CH₃)₃ |
| 10.8 | H | Ph | n-C₅H₁₁ |
| 10.9 | H | Ph | cyclopropyl |
| 10.10 | H | 4-Cl(Ph) | H |
| 10.11 | H | 4-Cl(Ph) | CH₃ |
| 10.12 | H | 4-Cl(Ph) | C₂H₅ |
| 10.13 | H | 4-Cl(Ph) | n-C₃H₇ |
| 10.14 | H | 4-Cl(Ph) | iso-C₃H₇ |
| 10.15 | H | 4-Cl(Ph) | n-C₄H₉ |
| 10.16 | H | 4-Cl(Ph) | C(CH₃)₃ |
| 10.17 | H | 4-Cl(Ph) | n-C₅H₁₁ |
| 10.18 | H | 4-Cl(Ph) | cyclopropyl |
| 10.19 | H | 4-Cl(Ph) | cyclohexyl |
| 10.20 | CH₃ | Ph | H |
| 10.21 | CH₃ | Ph | CH₃ |
| 10.22 | CH₃ | Ph | C₂H₅ |

TABLE 10-continued

| Compd. | R₂ | R₃ | R₇ |
|---|---|---|---|
| 10.23 | CH₃ | Ph | n-C₃H₇ |
| 10.24 | CH₃ | Ph | iso-C₃H₇ |
| 10.25 | CH₃ | Ph | n-C₄H₉ |
| 10.26 | CH₃ | Ph | C(CH₃)₃ |
| 10.27 | CH₃ | Ph | n-C₅H₁₁ |
| 10.28 | CH₃ | Ph | cyclopropyl |
| 10.29 | CH₃ | 4-Cl(Ph) | H |
| 10.30 | CH₃ | 4-Cl(Ph) | CH₃ |
| 10.31 | CH₃ | 4-Cl(Ph) | C₂H₅ |
| 10.32 | CH₃ | 4-Cl(Ph) | n-C₃H₇ |
| 10.33 | CH₃ | 4-Cl(Ph) | iso-C₃H₇ |
| 10.34 | CH₃ | 4-Cl(Ph) | n-C₄H₉ |
| 10.35 | CH₃ | 4-Cl(Ph) | C(CH₃)₃ |
| 10.36 | CH₃ | 4-Cl(Ph) | n-C₅H₁₁ |
| 10.37 | CH₃ | 4-Cl(Ph) | cyclopropyl |
| 10.38 | CH₃ | 4-Cl(Ph) | cyclohexyl |
| 10.39 | H | 1-napthyl | H |
| 10.40 | H | 1-napthyl | CH₃ |
| 10.41 | H | 1-napthyl | C₂H₅ |
| 10.42 | H | 1-napthyl | n-C₃H₇ |
| 10.43 | H | 1-napthyl | iso-C₃H₇ |
| 10.44 | H | 1-napthyl | n-C₄H₉ |
| 10.45 | H | 1-napthyl | C(CH₃)₃ |
| 10.46 | H | 1-napthyl | n-C₅H₁₁ |
| 10.47 | H | 1-napthyl | cyclopropyl |
| 10.48 | H | 1-napthyl | cyclohexyl |
| 10.49 | CH₃ | 1-napthyl | H |
| 10.50 | CH₃ | 1-napthyl | CH₃ |
| 10.51 | CH₃ | 1-napthyl | C₂H₅ |
| 10.52 | CH₃ | 1-napthyl | n-C₃H₇ |
| 10.53 | CH₃ | 1-napthyl | iso-C₃H₇ |
| 10.54 | CH₃ | 1-napthyl | n-C₄H₉ |
| 10.55 | CH₃ | 1-napthyl | C(CH₃)₃ |
| 10.56 | CH₃ | 1-napthyl | n-C₅H₁₁ |
| 10.57 | CH₃ | 1-napthyl | cyclopropyl |
| 10.58 | CH₃ | 1-napthyl | cyclohexyl |
| 10.59 | H | 2-pyridyl | H |
| 10.60 | H | 2-pyridyl | CH₃ |
| 10.61 | H | 2-pyridyl | C₂H₅ |
| 10.62 | H | 2-pyridyl | n-C₃H₇ |
| 10.63 | H | 2-pyridyl | iso-C₃H₇ |
| 10.64 | H | 2-pyridyl | n-C₄H₉ |
| 10.65 | H | 2-pyridyl | C(CH₃)₃ |
| 10.66 | H | 2-pyridyl | n-C₅H₁₁ |
| 10.67 | H | 2-pyridyl | cyclopropyl |
| 10.68 | H | 2-pyridyl | cyclohexyl |
| 10.69 | H | 3-pyridyl | H |
| 10.70 | H | 3-pyridyl | CH₃ |
| 10.71 | H | 3-pyridyl | C₂H₅ |
| 10.72 | H | 3-pyridyl | n-C₃H₇ |
| 10.73 | H | 3-pyridyl | n-C₄H₉ |
| 10.74 | H | 3-pyridyl | iso-C₄H₉ |
| 10.75 | H | 3-pyridyl | C(CH₃)₃ |
| 10.76 | H | 3-pyridyl | n-C₅H₁₁ |
| 10.77 | H | 3-pyridyl | cyclopropyl |
| 10.78 | H | 3-pyridyl | cyclohexyl |
| 10.79 | H | 2-thienyl | H |
| 10.80 | H | 2-thienyl | CH₃ |
| 10.81 | H | 2-thienyl | C₂H₅ |
| 10.82 | H | 2-thienyl | n-C₃H₇ |
| 10.83 | H | 2-thienyl | iso-C₃H₇ |
| 10.84 | H | 2-thienyl | n-C₄H₉ |
| 10.85 | H | 2-thienyl | C(CH₃)₃ |
| 10.86 | H | 2-thienyl | n-C₅H₁₁ |
| 10.87 | H | 2-thienyl | cyclopropyl |
| 10.88 | H | 2-thienyl | cyclohexyl |
| 10.89 | H | 3-thienyl | H |
| 10.90 | H | 3-thienyl | CH₃ |
| 10.91 | H | 3-thienyl | C₂H₅ |
| 10.92 | H | 3-thienyl | n-C₃H₇ |
| 10.93 | H | 3-thienyl | iso-C₃H₇ |
| 10.94 | H | 3-thienyl | n-C₄H₉ |
| 10.95 | H | 3-thienyl | C(CH₃)₃ |
| 10.96 | H | 3-thienyl | n-C₅H₁₁ |
| 10.97 | H | 3-thienyl | cyclopropyl |
| 10.98 | H | 3-thienyl | cyclohexyl |
| 10.99 | H | 2-furyl | H |

TABLE 10-continued

| Compd. | $R_2$ | $R_3$ | $R_7$ |
|---|---|---|---|
| 10.90 | H | 2-furyl | $CH_3$ |
| 10.91 | H | 2-furyl | $C_2H_5$ |
| 10.92 | H | 2-furyl | $n\text{-}C_3H_7$ |
| 10.93 | H | 2-furyl | $iso\text{-}C_3H_7$ |
| 10.94 | H | 2-furyl | $n\text{-}C_4H_9$ |
| 10.95 | H | 2-furyl | $C(CH_3)_3$ |
| 10.96 | H | 2-furyl | $n\text{-}C_5H_{11}$ |
| 10.97 | H | 2-furyl | cyclopropyl |
| 10.98 | H | 2-furyl | cyclohexyl |
| 10.99 | $CH_3$ | 2-pyridyl | H |
| 10.100 | $CH_3$ | 2-pyridyl | $CH_3$ |
| 10.102 | $CH_3$ | 2-pyridyl | $C_2H_5$ |
| 10.103 | $CH_3$ | 2-pyridyl | $n\text{-}C_3H_7$ |
| 10.104 | $CH_3$ | 2-pyridyl | $iso\text{-}C_3H_7$ |
| 10.105 | $CH_3$ | 2-pyridyl | $n\text{-}C_4H_9$ |
| 10.106 | $CH_3$ | 2-pyridyl | $C(CH_3)_3$ |
| 10.107 | $CH_3$ | 2-pyridyl | $n\text{-}C_5H_{11}$ |
| 10.108 | $CH_3$ | 2-pyridyl | cyclopropyl |
| 10.109 | $CH_3$ | 2-pyridyl | cyclohexyl |
| 10.110 | $CH_3$ | 3-pyridyl | H |
| 10.111 | $CH_3$ | 3-pyridyl | $CH_3$ |
| 10.112 | $CH_3$ | 3-pyridyl | $C_2H_5$ |
| 10.113 | $CH_3$ | 3-pyridyl | $n\text{-}C_3H_7$ |
| 10.114 | $CH_3$ | 3-pyridyl | $iso\text{-}C_3H_7$ |
| 10.115 | $CH_3$ | 3-pyridyl | $n\text{-}C_4H_9$ |
| 10.116 | $CH_3$ | 3-pyridyl | $C(CH_3)_3$ |
| 10.117 | $CH_3$ | 3-pyridyl | $n\text{-}C_5H_{11}$ |
| 10.118 | $CH_3$ | 3-pyridyl | cyclopropyl |
| 10.119 | $CH_3$ | 3-pyridyl | cyclohexyl |
| 10.120 | $CH_3$ | 2-thienyl | H |
| 10.121 | $CH_3$ | 2-thienyl | $CH_3$ |
| 10.122 | $CH_3$ | 2-thienyl | $C_2H_5$ |
| 10.123 | $CH_3$ | 2-thienyl | $n\text{-}C_3H_7$ |
| 10.124 | $CH_3$ | 2-thienyl | $iso\text{-}C_3H_7$ |
| 10.125 | $CH_3$ | 2-thienyl | $n\text{-}C_4H_9$ |
| 10.126 | $CH_3$ | 2-thienyl | $C(CH_3)_3$ |
| 10.127 | $CH_3$ | 2-thienyl | $n\text{-}C_5H_{11}$ |
| 10.128 | $CH_3$ | 2-thienyl | cyclopropyl |
| 10.129 | $CH_3$ | 2-thienyl | cyclohexyl |
| 10.130 | $CH_3$ | 3-thienyl | H |
| 10.131 | $CH_3$ | 3-thienyl | $CH_3$ |
| 10.132 | $CH_3$ | 3-thienyl | $C_2H_5$ |
| 10.133 | $CH_3$ | 3-thienyl | $n\text{-}C_3H_7$ |
| 10.134 | $CH_3$ | 3-thienyl | $iso\text{-}C_3H_7$ |
| 10.135 | $CH_3$ | 3-thienyl | $n\text{-}C_4H_9$ |
| 10.136 | $CH_3$ | 3-thienyl | $C(CH_3)_3$ |
| 10.137 | $CH_3$ | 3-thienyl | $n\text{-}C_5H_{11}$ |
| 10.138 | $CH_3$ | 3-thienyl | cyclopropyl |
| 10.139 | $CH_3$ | 3-thienyl | cyclohexyl |

TABLE 11

Compounds 11.1 to 11.139 are compounds of Formula V, which is Formula I with $A=R_4=R_5=R_6=H$, $R_1=CH_3$, $X=N$, $Y=O$, and $Z=O$, and where $R_2$, $R_3$, and $R_7$ are defined in Table 10.

TABLE 12

Compounds 12.1 to 12.139 are compounds of Formula VI, which is Formula I with $A=R_4=R_5=R_6=H$, $R_1=CH_3$, $X=N$, $Y=NH$, and $Z=O$, and where $R_2$, $R_3$, and $R_7$ are defined in Table 10.

Typical compounds encompassed by the present invention of Formula I include those compounds of Formula VII, which is Formula I with $A=R_4=R_5=R_6=H$, $R_1=CH_3$, $X=CH$, $Y=O$, and $Z=NOR_9$, and where $R_2$, $R_3$, $R_7$ and $R_9$ are defined in Table 13.

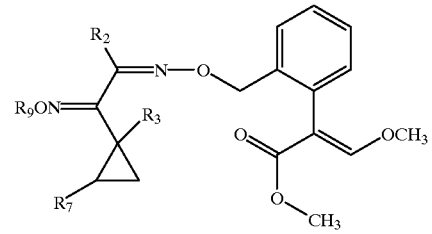

Formula VII

TABLE 13

| Compd | $R_2$ | $R_3$ | $R_7$ | $R_9$ |
|---|---|---|---|---|
| 13.1 | H | H | Ph | H |
| 13.2 | H | H | 4-Cl(Ph) | H |
| 13.3 | H | H | 4-Br(Ph) | H |
| 13.4 | H | H | 4-F(Ph) | H |
| 13.5 | H | H | 4-$OCH_3$(Ph) | H |
| 13.6 | H | H | 4-$CF_3$(Ph) | H |
| 13.7 | H | H | Ph | $CH_3$ |
| 13.8 | H | H | 4-Cl(Ph) | $CH_3$ |
| 13.9 | H | H | 4-Br(Ph) | $CH_3$ |
| 13.10 | H | H | 4-F(Ph) | $CH_3$ |
| 13.11 | $CH_3$ | H | Ph | H |
| 13.12 | $CH_3$ | H | 2-Cl(Ph) | H |
| 13.13 | $CH_3$ | H | 3-Cl(Ph) | H |
| 13.14 | $CH_3$ | H | 4-Cl(Ph) | H |
| 13.15 | $CH_3$ | H | 2-Br(Ph) | H |
| 13.16 | $CH_3$ | H | 3-Br(Ph) | H |
| 13.17 | $CH_3$ | H | 4-Br(Ph) | H |
| 13.18 | $CH_3$ | H | Ph | $CH_3$ |
| 13.19 | $CH_3$ | H | 2-Cl(Ph) | $CH_3$ |
| 13.20 | $CH_3$ | H | 3-Cl(Ph) | $CH_3$ |
| 13.21 | $CH_3$ | H | 4-Cl(Ph) | $CH_3$ |
| 13.22 | $CH_3$ | H | 2-F(Ph) | $CH_3$ |
| 13.23 | $CH_3$ | H | 3-F(Ph) | $CH_3$ |
| 13.24 | $CH_3$ | H | 4-F(Ph) | $CH_3$ |
| 13.25 | $CH_3$ | H | 2-$CH_3$(Ph) | $CH_3$ |
| 13.26 | $CH_3$ | H | 3-$CH_3$(Ph) | $CH_3$ |
| 13.27 | $CH_3$ | H | 2-$CF_3$(Ph) | $CH_3$ |
| 13.28 | $CH_3$ | H | 3-$CF_3$(Ph) | $CH_3$ |
| 13.29 | $CH_3$ | H | 4-$CF_3$(Ph) | $CH_3$ |
| 13.30 | $CH_3$ | H | 2-$OCH_3$(Ph) | $CH_3$ |
| 13.31 | $CH_3$ | H | 3-$OCH_3$(Ph) | $CH_3$ |
| 13.32 | $CH_3$ | H | 2-$OCH_3$(Ph) | $CH_3$ |
| 13.33 | $CH_3$ | H | 2,3-Cl(Ph) | $CH_3$ |
| 13.34 | $CH_3$ | H | 2,4-Cl(Ph) | $CH_3$ |
| 13.35 | $CH_3$ | H | 2,5-Cl(Ph) | $CH_3$ |
| 13.36 | $CH_3$ | H | 2,6-Cl(Ph) | $CH_3$ |
| 13.37 | $CH_3$ | H | 3,4-Cl(Ph) | $CH_3$ |
| 13.38 | $CH_3$ | H | 3,5-Cl(Ph) | $CH_3$ |
| 13.39 | $CH_3$ | H | Ph | $C_2H_5$ |
| 13.40 | $CH_3$ | H | Ph | $n\text{-}C_3H_7$ |
| 13.41 | $CH_3$ | H | Ph | $iso\text{-}C_3H_7$ |
| 13.42 | $CH_3$ | H | Ph | $n\text{-}C_4H_9$ |
| 13.43 | $CH_3$ | H | Ph | $C(CH_3)_3$ |
| 13.44 | $CH_3$ | H | Ph | $CH_2C\equiv CH$ |
| 13.45 | $C_2H_5$ | H | Ph | $CH_3$ |
| 13.46 | $C_2H_5$ | H | 2-Cl(Ph) | $CH_3$ |
| 13.47 | $C_2H_5$ | H | 3-Cl(Ph) | $CH_3$ |
| 13.48 | $C_2H_5$ | H | 4-Cl(Ph) | $CH_3$ |
| 13.49 | $C_2H_5$ | H | 4-Br(Ph) | $CH_3$ |
| 13.50 | $C_2H_5$ | H | 4-F(Ph) | $CH_3$ |
| 13.51 | $C_2H_5$ | H | 4-$OCH_3$(Ph) | $CH_3$ |
| 13.52 | $C_2H_5$ | H | 4-$CH_3$(Ph) | $CH_3$ |
| 13.53 | $C_2H_5$ | H | 4-$NO_2$(Ph) | $CH_3$ |
| 13.54 | $C_2H_5$ | H | 2,4-Cl(Ph) | $CH_3$ |
| 13.55 | $C_2H_5$ | H | 2,4-F(Ph) | $CH_3$ |
| 13.56 | $n\text{-}C_3H_7$ | H | Ph | $CH_3$ |
| 13.57 | $n\text{-}C_3H_7$ | H | 2-Cl(Ph) | $CH_3$ |
| 13.58 | $n\text{-}C_3H_7$ | H | 3-Cl(Ph) | $CH_3$ |
| 13.59 | $n\text{-}C_3H_7$ | H | 4-Cl(Ph) | $CH_3$ |
| 13.60 | $n\text{-}C_3H_7$ | H | 4-F(Ph) | $CH_3$ |
| 13.61 | $n\text{-}C_3H_7$ | H | 3-$OCH_3$(Ph) | $CH_3$ |

TABLE 13-continued

| Compd | R₂ | R₃ | R₇ | R₉ |
|---|---|---|---|---|
| 13.62 | n-C₃H₇ | H | 4-OCH₃(Ph) | CH₃ |
| 13.63 | n-C₃H₇ | H | 4-CH₃(Ph) | CH₃ |
| 13.64 | n-C₃H₇ | H | 4-NO₂(Ph) | CH₃ |
| 13.65 | n-C₃H₇ | H | 2,4-Cl(Ph) | CH₃ |
| 13.66 | n-C₃H₇ | H | 2,4-F(Ph) | CH₃ |
| 13.67 | iso-C₃H₇ | H | Ph | CH₃ |
| 13.68 | iso-C₃H₇ | H | 2-Cl(Ph) | CH₃ |
| 13.69 | iso-C₃H₇ | H | 3-Cl(Ph) | CH₃ |
| 13.70 | iso-C₃H₇ | H | 4-Cl(Ph) | CH₃ |
| 13.71 | iso-C₃H₇ | H | 4-Br(Ph) | CH₃ |
| 13.72 | iso-C₃H₇ | H | 4-F(Ph) | CH₃ |
| 13.73 | iso-C₃H₇ | H | 4-OCH₃(Ph) | CH₃ |
| 13.74 | iso-C₃H₇ | H | 4-CH₃(Ph) | CH₃ |
| 13.75 | iso-C₃H₇ | H | 4-NO₂(Ph) | CH₃ |
| 13.76 | iso-C₃H₇ | H | 2,4-Cl(Ph) | CH₃ |
| 13.77 | iso-C₃H₇ | H | 2,4-F(Ph) | CH₃ |
| 13.78 | n-C₄H₉ | H | Ph | CH₃ |
| 13.79 | n-C₄H₉ | H | 2-Cl(Ph) | CH₃ |
| 13.80 | n-C₄H₉ | H | 3-Cl(Ph) | CH₃ |
| 13.81 | n-C₄H₉ | H | 4-Cl(Ph) | CH₃ |
| 13.82 | n-C₄H₉ | H | 4-Br(Ph) | CH₃ |
| 13.83 | n-C₄H₉ | H | 4-F(Ph) | CH₃ |
| 13.84 | n-C₄H₉ | H | 4-OCH₃(Ph) | CH₃ |
| 13.85 | n-C₄H₉ | H | 4-CH₃(Ph) | CH₃ |
| 13.86 | n-C₄H₉ | H | 4-NO₂(Ph) | CH₃ |
| 13.87 | n-C₄H₉ | H | 2,4-Cl(Ph) | CH₃ |
| 13.88 | n-C₄H₉ | H | 2,4-F(Ph) | CH₃ |
| 13.89 | iso-C₄H₉ | H | Ph | CH₃ |
| 13.90 | iso-C₄H₉ | H | 2-Cl(Ph) | CH₃ |
| 13.91 | iso-C₄H₉ | H | 3-Cl(Ph) | CH₃ |
| 13.92 | iso-C₄H₉ | H | 4-Cl(Ph) | CH₃ |
| 13.93 | iso-C₄H₉ | H | 4-F(Ph) | CH₃ |
| 13.94 | iso-C₄H₉ | H | 3-OCH₃(Ph) | CH₃ |
| 13.95 | iso-C₄H₉ | H | 4-OCH₃(Ph) | CH₃ |
| 13.96 | iso-C₄H₉ | H | 4-CH₃(Ph) | CH₃ |
| 13.97 | iso-C₄H₉ | H | 4-NO₂(Ph) | CH₃ |
| 13.98 | iso-C₄H₉ | H | 2,4-Cl(Ph) | CH₃ |
| 13.99 | iso-C₄H₉ | H | 2,4-F(Ph) | CH₃ |
| 13.100 | C(CH₃)₃ | H | Ph | CH₃ |
| 13.101 | C(CH₃)₃ | H | 2-Cl(Ph) | CH₃ |
| 13.102 | C(CH₃)₃ | H | 3-Cl(Ph) | CH₃ |
| 13.103 | C(CH₃)₃ | H | 4-Cl(Ph) | CH₃ |
| 13.104 | C(CH₃)₃ | H | 4-F(Ph) | CH₃ |
| 13.105 | C(CH₃)₃ | H | 3-OCH₃(Ph) | CH₃ |
| 13.106 | C(CH₃)₃ | H | 4-OCH₃(Ph) | CH₃ |
| 13.107 | C(CH₃)₃ | H | 4-CH₃(Ph) | CH₃ |
| 13.108 | C(CH₃)₃ | H | 4-NO₂(Ph) | CH₃ |
| 13.109 | C(CH₃)₃ | H | 2,4-Cl(Ph) | CH₃ |
| 13.110 | C(CH₃)₃ | H | 2,4-F(Ph) | CH₃ |
| 13.111 | cyclopropyl | H | Ph | CH₃ |
| 13.112 | cyclopropyl | H | 2-Cl(Ph) | CH₃ |
| 13.113 | cyclopropyl | H | 3-Cl(Ph) | CH₃ |
| 13.114 | cyclopropyl | H | 4-Cl(Ph) | CH₃ |
| 13.115 | cyclopropyl | H | 4-Br(Ph) | CH₃ |
| 13.116 | cyclopropyl | H | 3-OCH₃(Ph) | CH₃ |
| 13.117 | cyclopropyl | H | 4-OCH₃(Ph) | CH₃ |
| 13.118 | cyclopropyl | H | 4-CH₃(Ph) | CH₃ |
| 13.119 | cyclopropyl | H | 4-NO₂(Ph) | CH₃ |
| 13.120 | cyclopropyl | H | 2,4-Cl(Ph) | CH₃ |
| 13.121 | cyclopropyl | H | 2,4-F(Ph) | CH₃ |
| 13.122 | 1-CH₃-cyclopropyl | H | Ph | CH₃ |
| 13.123 | 1-CH₃-cyclopropyl | H | 2-Cl(Ph) | CH₃ |
| 13.124 | 1-CH₃-cyclopropyl | H | 3-Cl(Ph) | CH₃ |
| 13.125 | 1-CH₃-cyclopropyl | H | 4-Cl(Ph) | CH₃ |
| 13.126 | 1-CH₃-cyclopropyl | H | 4-Br(Ph) | CH₃ |
| 13.127 | 1-CH₃-cyclopropyl | H | 4-F(Ph) | CH₃ |
| 13.128 | 1-CH₃-cyclopropyl | H | 4-OCH₃(Ph) | CH₃ |
| 13.129 | 1-CH₃-cyclopropyl | H | 4-CH₃(Ph) | CH₃ |
| 13.130 | 1-CH₃-cyclopropyl | H | 4-NO₂(Ph) | CH₃ |
| 13.131 | 1-CH₃-cyclopropyl | H | 2,4-Cl(Ph) | CH₃ |
| 13.132 | 1-CH₃-cyclopropyl | H | 2,4-F(Ph) | CH₃ |
| 13.133 | CH₃ | CH₃ | Ph | H |
| 13.134 | CH₃ | CH₃ | Ph | CH₃ |
| 13.135 | CH₃ | CH₃ | Ph | C₂H₅ |
| 13.136 | CH₃ | CH₃ | Ph | n-C₃H₇ |
| 13.137 | CH₃ | CH₃ | Ph | iso-C₃H₇ |
| 13.138 | CH₃ | CH₃ | Ph | n-C₄H₉ |
| 13.139 | CH₃ | CH₃ | Ph | iso-C₄H₉ |
| 13.140 | CH₃ | CH₃ | Ph | C(CH₃)₃ |
| 13.141 | CH₃ | CH₃ | Ph | CH₂C≡CH |
| 13.142 | CH₃ | CH₃ | 2-Cl(Ph) | CH₃ |
| 13.143 | CH₃ | CH₃ | 3-Cl(Ph) | CH₃ |
| 13.144 | C₂H₅ | CH₃ | Ph | CH₃ |
| 13.145 | C₂H₅ | CH₃ | 2-Cl(Ph) | CH₃ |
| 13.146 | C₂H₅ | CH₃ | 3-Cl(Ph) | CH₃ |
| 13.147 | C₂H₅ | CH₃ | 4-Cl(Ph) | CH₃ |
| 13.148 | C₂H₅ | CH₃ | 4-Br(Ph) | CH₃ |
| 13.149 | C₂H₅ | CH₃ | 4-F(Ph) | CH₃ |
| 13.150 | C₂H₅ | CH₃ | 4-OCH₃(Ph) | CH₃ |
| 13.151 | C₂H₅ | CH₃ | 4-CH₃(Ph) | CH₃ |
| 13.152 | C₂H₅ | CH₃ | 4-NO₂(Ph) | CH₃ |
| 13.153 | C₂H₅ | CH₃ | 2,4-Cl(Ph) | CH₃ |
| 13.154 | C₂H₅ | CH₃ | 2,4-F(Ph) | CH₃ |
| 13.155 | n-C₃H₇ | CH₃ | Ph | CH₃ |
| 13.156 | n-C₃H₇ | CH₃ | 2-Cl(Ph) | CH₃ |
| 13.157 | n-C₃H₇ | CH₃ | 3-Cl(Ph) | CH₃ |
| 13.158 | n-C₃H₇ | CH₃ | 4-Cl(Ph) | CH₃ |
| 13.159 | n-C₃H₇ | CH₃ | 4-Br(Ph) | CH₃ |
| 13.160 | n-C₃H₇ | CH₃ | 4-F(Ph) | CH₃ |
| 13.161 | n-C₃H₇ | CH₃ | 4-OCH₃(Ph) | CH₃ |
| 13.162 | n-C₃H₇ | CH₃ | 4-CH₃(Ph) | CH₃ |
| 13.163 | n-C₃H₇ | CH₃ | 4-NO₂(Ph) | CH₃ |
| 13.164 | n-C₃H₇ | CH₃ | 2,4-Cl(Ph) | CH₃ |
| 13.165 | n-C₃H₇ | CH₃ | 2,4-F(Ph) | CH₃ |
| 13.166 | iso-C₃H₇ | CH₃ | Ph | CH₃ |
| 13.167 | iso-C₃H₇ | CH₃ | 2-Cl(Ph) | CH₃ |
| 13.168 | iso-C₃H₇ | CH₃ | 3-Cl(Ph) | CH₃ |
| 13.169 | iso-C₃H₇ | CH₃ | 4-Cl(Ph) | CH₃ |
| 13.170 | iso-C₃H₇ | CH₃ | 4-Br(Ph) | CH₃ |
| 13.171 | iso-C₃H₇ | CH₃ | 4-F(Ph) | CH₃ |
| 13.172 | iso-C₃H₇ | CH₃ | 4-OCH₃(Ph) | CH₃ |
| 13.173 | iso-C₃H₇ | CH₃ | 4-CH₃(Ph) | CH₃ |
| 13.174 | iso-C₃H₇ | CH₃ | 4-NO₂(Ph) | CH₃ |
| 13.175 | iso-C₃H₇ | CH₃ | 2,4-Cl(Ph) | CH₃ |
| 13.176 | iso-C₃H₇ | CH₃ | 2,4-F(Ph) | CH₃ |
| 13.177 | n-C₄H₉ | CH₃ | Ph | CH₃ |
| 13.178 | n-C₄H₉ | CH₃ | 2-Cl(Ph) | CH₃ |
| 13.179 | n-C₄H₉ | CH₃ | 3-Cl(Ph) | CH₃ |
| 13.180 | n-C₄H₉ | CH₃ | 4-Cl(Ph) | CH₃ |
| 13.181 | n-C₄H₉ | CH₃ | 4-Br(Ph) | CH₃ |
| 13.182 | n-C₄H₉ | CH₃ | 4-F(Ph) | CH₃ |
| 13.183 | n-C₄H₉ | CH₃ | 4-OCH₃(Ph) | CH₃ |
| 13.184 | n-C₄H₉ | CH₃ | 4-CH₃(Ph) | CH₃ |
| 13.185 | n-C₄H₉ | CH₃ | 4-NO₂(Ph) | CH₃ |
| 13.186 | n-C₄H₉ | CH₃ | 2,4-Cl(Ph) | CH₃ |
| 13.187 | n-C₄H₉ | CH₃ | 2,4-F(Ph) | CH₃ |
| 13.188 | n-C₄H₉ | CH₃ | 4-CF₃(Ph) | CH₃ |
| 13.189 | Ph | H | Ph | H |
| 13.190 | Ph | H | Ph | CH₃ |
| 13.191 | Ph | H | Ph | C₂H₅ |
| 13.192 | Ph | H | Ph | n-C₃H₇ |
| 13.193 | Ph | H | Ph | iso-C₃H₇ |
| 13.194 | Ph | H | Ph | n-C₄H₉ |
| 13.195 | Ph | H | Ph | iso-C₄H₉ |
| 13.196 | Ph | H | Ph | C(CH₃)₃ |
| 13.197 | Ph | H | Ph | CH₂C≡CH |
| 13.198 | Ph | H | 2-Cl(Ph) | CH₃ |
| 13.199 | Ph | H | 4-Cl(Ph) | CH₃ |
| 13.200 | Ph | CH₃ | Ph | CH₃ |
| 13.201 | Ph | CH₃ | 2-Cl(Ph) | CH₃ |
| 13.202 | Ph | CH₃ | 3-Cl(Ph) | CH₃ |
| 13.203 | Ph | CH₃ | 4-Cl(Ph) | CH₃ |
| 13.204 | Ph | CH₃ | 4-Br(Ph) | CH₃ |
| 13.205 | Ph | CH₃ | 4-F(Ph) | CH₃ |
| 13.206 | Ph | CH₃ | 4-OCH₃(Ph) | CH₃ |
| 13.207 | Ph | CH₃ | 4-CH₃(Ph) | CH₃ |
| 13.208 | Ph | CH₃ | 4-NO₂(Ph) | CH₃ |
| 13.209 | Ph | CH₃ | 2,4-Cl(Ph) | CH₃ |
| 13.210 | Ph | CH₃ | 2,4-F(Ph) | CH₃ |
| 13.211 | CN | H | Ph | H |
| 13.212 | CN | H | Ph | CH₃ |
| 13.213 | CN | H | Ph | C₂H₅ |
| 13.214 | CN | H | Ph | n-C₃H₇ |
| 13.215 | CN | H | Ph | iso-C₃H₇ |

TABLE 13-continued

| Compd | R2 | R3 | R7 | R9 |
|---|---|---|---|---|
| 13.216 | CN | H | Ph | n-C4H9 |
| 13.217 | CN | H | Ph | iso-C4H9 |
| 13.218 | CN | H | Ph | C(CH3)3 |
| 13.219 | CN | H | Ph | CH2C≡CH |
| 13.220 | CN | H | 2-Cl(Ph) | CH3 |
| 13.221 | CN | H | 4-Cl(Ph) | CH3 |
| 13.222 | CN | CH3 | Ph | H |
| 13.223 | CN | CH3 | 2-Cl(Ph) | CH3 |
| 13.224 | CN | CH3 | 3-Cl(Ph) | CH3 |
| 13.225 | CN | CH3 | 4-Cl(Ph) | CH3 |
| 13.226 | CN | CH3 | 4-Br(Ph) | CH3 |
| 13.227 | CN | CH3 | 4-F(Ph) | CH3 |
| 13.228 | CN | CH3 | 4-OCH3(Ph) | CH3 |
| 13.229 | CN | CH3 | 4-CH3(Ph) | CH3 |
| 13.230 | CN | CH3 | 4-NO2(Ph) | CH3 |
| 13.231 | CN | CH3 | 2,4-Cl(Ph) | CH3 |
| 13.232 | CN | CH3 | 2,4-F(Ph) | CH3 |
| 13.233 | H | H | 1-napthyl | H |
| 13.234 | CH3 | H | 1-napthyl | CH3 |
| 13.235 | C2H5 | H | 1-napthyl | CH3 |
| 13.236 | n-C3H7 | H | 1-napthyl | CH3 |
| 13.237 | iso-C3H7 | H | 1-napthyl | CH3 |
| 13.238 | n-C4H9 | H | 1-napthyl | CH3 |
| 13.239 | iso-C4H9 | H | 1-napthyl | CH3 |
| 13.240 | cyclopropyl | H | 1-napthyl | CH3 |
| 13.241 | 1-CH3-cyclopropyl | H | 1-napthyl | CH3 |
| 13.242 | CN | H | 1-napthyl | CH3 |
| 13.243 | Ph | CH3 | 1-napthyl | CH3 |
| 13.244 | H | CH3 | 1-napthyl | CH3 |
| 13.245 | CH3 | CH3 | 1-napthyl | CH3 |
| 13.246 | C2H5 | CH3 | 1-napthyl | CH3 |
| 13.247 | n-C3H7 | CH3 | 1-napthyl | CH3 |
| 13.248 | iso-C3H7 | CH3 | 1-napthyl | CH3 |
| 13.249 | n-C4H9 | CH3 | 1-napthyl | CH3 |
| 13.250 | iso-C4H9 | CH3 | 1-napthyl | CH3 |
| 13.251 | cyclopropyl | CH3 | 1-napthyl | CH3 |
| 13.252 | 1-CH3-cyclopropyl | CH3 | 1-napthyl | CH3 |
| 13.253 | CN | CH3 | 1-napthyl | CH3 |
| 13.254 | Ph | CH3 | 1-napthyl | CH3 |
| 13.255 | H | H | 2-napthyl | H |
| 13.256 | CH3 | H | 2-napthyl | CH3 |
| 13.257 | C2H5 | H | 2-napthyl | C2H5 |
| 13.258 | n-C3H7 | H | 2-napthyl | n-C3H7 |
| 13.259 | iso-C3H7 | H | 2-napthyl | iso-C3H7 |
| 13.260 | n-C4H9 | H | 2-napthyl | n-C4H9 |
| 13.261 | iso-C4H9 | H | 2-napthyl | iso-C4H9 |
| 13.262 | cyclopropyl | H | 2-napthyl | C(CH3)3 |
| 13.263 | 1-CH3-cyclopropyl | H | 2-napthyl | CH2C≡CH |
| 13.264 | CN | H | 2-napthyl | CH2Ph |
| 13.265 | Ph | H | 2-napthyl | CH2Ph |
| 13.266 | H | CH3 | 2-napthyl | CH3 |
| 13.267 | CH3 | CH3 | 2-napthyl | CH3 |
| 13.268 | C2H5 | CH3 | 2-napthyl | CH3 |
| 13.269 | n-C3H7 | CH3 | 2-napthyl | CH3 |
| 13.270 | iso-C3H7 | CH3 | 2-napthyl | CH3 |
| 13.271 | n-C4H9 | CH3 | 2-napthyl | CH3 |
| 13.272 | iso-C4H9 | CH3 | 2-napthyl | CH3 |
| 13.273 | cyclopropyl | CH3 | 2-napthyl | CH3 |
| 13.274 | 1-CH3-cyclopropyl | CH3 | 2-napthyl | CH3 |
| 13.275 | CN | CH3 | 2-napthyl | CH3 |
| 13.276 | Ph | CH3 | 2-napthyl | CH3 |
| 13.277 | 2-Cl(Ph) | CH3 | 2-napthyl | CH3 |
| 13.278 | 3-Cl(Ph) | CH3 | 2-napthyl | CH3 |
| 13.279 | 4-Cl(Ph) | CH3 | 2-napthyl | CH3 |
| 13.280 | 4-Br(Ph) | CH3 | 2-napthyl | CH3 |
| 13.281 | 4-F(Ph) | CH3 | 2-napthyl | CH3 |
| 13.282 | 4-OCH3(Ph) | CH3 | 2-napthyl | CH3 |
| 13.283 | 4-CH3(Ph) | CH3 | 2-napthyl | CH3 |
| 13.284 | 3-CF3(Ph) | CH3 | 2-napthyl | CH3 |
| 13.285 | CH3 | C2H5 | Ph | CH3 |
| 13.286 | CH3 | C2H5 | 2-Cl(Ph) | CH3 |
| 13.287 | CH3 | C2H5 | 3-Cl(Ph) | CH3 |
| 13.288 | CH3 | C2H5 | 4-Cl(Ph) | CH3 |
| 13.289 | CH3 | C2H5 | 4-Br(Ph) | CH3 |
| 13.290 | CH3 | C2H5 | 4-F(Ph) | CH3 |
| 13.291 | CH3 | C2H5 | 4-OCH3(Ph) | CH3 |
| 13.292 | CH3 | C2H5 | 4-CH3(Ph) | CH3 |

TABLE 13-continued

| Compd | R2 | R3 | R7 | R9 |
|---|---|---|---|---|
| 13.293 | CH3 | C2H5 | 4-NO2(Ph) | CH3 |
| 13.294 | CH3 | C2H5 | 2,4-Cl(Ph) | CH3 |
| 13.295 | CH3 | C2H5 | 2,4-F(Ph) | CH3 |
| 13.296 | CH3 | n-C3H7 | Ph | CH3 |
| 13.297 | CH3 | n-C3H7 | 2-Cl(Ph) | CH3 |
| 13.298 | CH3 | n-C3H7 | 3-Cl(Ph) | CH3 |
| 13.299 | CH3 | n-C3H7 | 4-Cl(Ph) | CH3 |
| 13.300 | CH3 | n-C3H7 | 4-Br(Ph) | CH3 |
| 13.301 | CH3 | n-C3H7 | 4-F(Ph) | CH3 |
| 13.302 | CH3 | n-C3H7 | 4-OCH3(Ph) | CH3 |
| 13.303 | CH3 | n-C3H7 | 4-CH3(Ph) | CH3 |
| 13.304 | CH3 | n-C3H7 | 4-NO2(Ph) | CH3 |
| 13.305 | CH3 | n-C3H7 | 2,4-Cl(Ph) | CH3 |
| 13.306 | CH3 | n-C3H7 | 2,4-F(Ph) | CH3 |
| 13.307 | CH3 | iso-C3H7 | Ph | CH3 |
| 13.308 | CH3 | iso-C3H7 | 2-Cl(Ph) | CH3 |
| 13.309 | CH3 | iso-C3H7 | 3-Cl(Ph) | CH3 |
| 13.310 | CH3 | iso-C3H7 | 4-Cl(Ph) | CH3 |
| 13.311 | CH3 | iso-C3H7 | 4-Br(Ph) | CH3 |
| 13.312 | CH3 | iso-C3H7 | 4-F(Ph) | CH3 |
| 13.313 | CH3 | iso-C3H7 | 4-OCH3(Ph) | CH3 |
| 13.314 | CH3 | iso-C3H7 | 4-CH3(Ph) | CH3 |
| 13.315 | CH3 | iso-C3H7 | 4-NO2(Ph) | CH3 |

Typical compounds encompassed by the present invention of Formula I include those compounds of Formula VIII, which is Formula I with A=R4=R5=R6=H, R1=CH3, X=N, Y=O, and Z=NOR9, and where R2, R3, R7 and R9 are defined in Table 14.

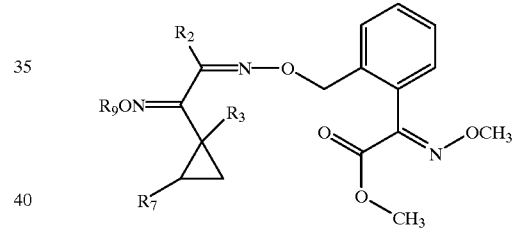

Formula VIII

TABLE 14

| Compd | R2 | R3 | R7 | R9 |
|---|---|---|---|---|
| 14.1 | H | H | Ph | H |
| 14.2 | H | H | 4-Cl(Ph) | H |
| 14.3 | H | H | 4-Br(Ph) | H |
| 14.4 | H | H | 4-F(Ph) | H |
| 14.5 | H | H | 4-OCH3(Ph) | H |
| 14.6 | H | H | 4-CF3(Ph) | H |
| 14.7 | H | H | Ph | CH3 |
| 14.8 | H | H | 4-Cl(Ph) | CH3 |
| 14.9 | H | H | 4-Br(Ph) | CH3 |
| 14.10 | H | H | 4-F(Ph) | CH3 |
| 14.11 | CH3 | H | Ph | H |
| 14.12 | CH3 | H | 2-Cl(Ph) | H |
| 14.13 | CH3 | H | 3-Cl(Ph) | H |
| 14.14 | CH3 | H | 4-Cl(Ph) | H |
| 14.15 | CH3 | H | 2-Br(Ph) | H |
| 14.16 | CH3 | H | 3-Br(Ph) | H |
| 14.17 | CH3 | H | 4-Br(Ph) | H |
| 14.18 | CH3 | H | Ph | CH3 |
| 14.19 | CH3 | H | 2-Cl(Ph) | CH3 |
| 14.20 | CH3 | H | 3-Cl(Ph) | CH3 |
| 14.21 | CH3 | H | 4-Cl(Ph) | CH3 |
| 14.22 | CH3 | H | 2-F(Ph) | CH3 |
| 14.23 | CH3 | H | 3-F(Ph) | CH3 |
| 14.24 | CH3 | H | 4-F(Ph) | CH3 |

TABLE 14-continued

| Compd | $R_2$ | $R_3$ | $R_7$ | $R_9$ |
|---|---|---|---|---|
| 14.25 | $CH_3$ | H | 2-$CH_3$(Ph) | $CH_3$ |
| 14.26 | $CH_3$ | H | 3-$CH_3$(Ph) | $CH_3$ |
| 14.27 | $CH_3$ | H | 2-$CF_3$(Ph) | $CH_3$ |
| 14.28 | $CH_3$ | H | 3-$CF_3$(Ph) | $CH_3$ |
| 14.29 | $CH_3$ | H | 4-$CF_3$(Ph) | $CH_3$ |
| 14.30 | $CH_3$ | H | 2-$OCH_3$(Ph) | $CH_3$ |
| 14.31 | $CH_3$ | H | 3-$OCH_3$(Ph) | $CH_3$ |
| 14.32 | $CH_3$ | H | 4-$OCH_3$(Ph) | $CH_3$ |
| 14.33 | $CH_3$ | H | 2,3-Cl(Ph) | $CH_3$ |
| 14.34 | $CH_3$ | H | 2,4-Cl(Ph) | $CH_3$ |
| 14.35 | $CH_3$ | H | 2,5-Cl(Ph) | $CH_3$ |
| 14.36 | $CH_3$ | H | 2,6-Cl(Ph) | $CH_3$ |
| 14.37 | $CH_3$ | H | 3,4-Cl(Ph) | $CH_3$ |
| 14.38 | $CH_3$ | H | 3,5-Cl(Ph) | $CH_3$ |
| 14.39 | $CH_3$ | H | Ph | $C_2H_5$ |
| 14.40 | $CH_3$ | H | Ph | n-$C_3H_7$ |
| 14.41 | $CH_3$ | H | Ph | iso-$C_3H_7$ |
| 14.42 | $CH_3$ | H | Ph | n-$C_4H_9$ |
| 14.43 | $CH_3$ | H | Ph | $C(CH_3)_3$ |
| 14.44 | $CH_3$ | H | Ph | $CH_2C{\equiv}CH$ |
| 14.45 | $C_2H_5$ | H | Ph | $CH_3$ |
| 14.46 | $C_2H_5$ | H | 2-Cl(Ph) | $CH_3$ |
| 14.47 | $C_2H_5$ | H | 3-Cl(Ph) | $CH_3$ |
| 14.48 | $C_2H_5$ | H | 4-Cl(Ph) | $CH_3$ |
| 14.49 | $C_2H_5$ | H | 4-Br(Ph) | $CH_3$ |
| 14.50 | $C_2H_5$ | H | 4-F(Ph) | $CH_3$ |
| 14.51 | $C_2H_5$ | H | 4-$OCH_3$(Ph) | $CH_3$ |
| 14.52 | $C_2H_5$ | H | 4-$CH_3$(Ph) | $CH_3$ |
| 14.53 | $C_2H_5$ | H | 4-$NO_2$(Ph) | $CH_3$ |
| 14.54 | $C_2H_5$ | H | 2,4-Cl(Ph) | $CH_3$ |
| 14.55 | $C_2H_5$ | H | 2,4-F(Ph) | $CH_3$ |
| 14.56 | n-$C_3H_7$ | H | Ph | $CH_3$ |
| 14.57 | n-$C_3H_7$ | H | 2-Cl(Ph) | $CH_3$ |
| 14.58 | n-$C_3H_7$ | H | 3-Cl(Ph) | $CH_3$ |
| 14.59 | n-$C_3H_7$ | H | 4-Cl(Ph) | $CH_3$ |
| 14.60 | n-$C_3H_7$ | H | 4-F(Ph) | $CH_3$ |
| 14.61 | n-$C_3H_7$ | H | 3-$OCH_3$(Ph) | $CH_3$ |
| 14.62 | n-$C_3H_7$ | H | 4-$OCH_3$(Ph) | $CH_3$ |
| 14.63 | n-$C_3H_7$ | H | 4-$CH_3$(Ph) | $CH_3$ |
| 14.64 | n-$C_3H_7$ | H | 4-$NO_2$(Ph) | $CH_3$ |
| 14.65 | n-$C_3H_7$ | H | 2,4-Cl(Ph) | $CH_3$ |
| 14.66 | n-$C_3H_7$ | H | 2,4-F(Ph) | $CH_3$ |
| 14.67 | iso-$C_3H_7$ | H | Ph | $CH_3$ |
| 14.68 | iso-$C_3H_7$ | H | 2-Cl(Ph) | $CH_3$ |
| 14.69 | iso-$C_3H_7$ | H | 3-Cl(Ph) | $CH_3$ |
| 14.70 | iso-$C_3H_7$ | H | 4-Cl(Ph) | $CH_3$ |
| 14.71 | iso-$C_3H_7$ | H | 4-Br(Ph) | $CH_3$ |
| 14.72 | iso-$C_3H_7$ | H | 4-F(Ph) | $CH_3$ |
| 14.73 | iso-$C_3H_7$ | H | 4-$OCH_3$(Ph) | $CH_3$ |
| 14.74 | iso-$C_3H_7$ | H | 4-$CH_3$(Ph) | $CH_3$ |
| 14.75 | iso-$C_3H_7$ | H | 4-$NO_2$(Ph) | $CH_3$ |
| 14.76 | iso-$C_3H_7$ | H | 2,4-Cl(Ph) | $CH_3$ |
| 14.77 | iso-$C_3H_7$ | H | 2,4-F(Ph) | $CH_3$ |
| 14.78 | n-$C_4H_9$ | H | Ph | $CH_3$ |
| 14.79 | n-$C_4H_9$ | H | 2-Cl(Ph) | $CH_3$ |
| 14.80 | n-$C_4H_9$ | H | 3-Cl(Ph) | $CH_3$ |
| 14.81 | n-$C_4H_9$ | H | 4-Cl(Ph) | $CH_3$ |
| 14.82 | n-$C_4H_9$ | H | 4-Br(Ph) | $CH_3$ |
| 14.83 | n-$C_4H_9$ | H | 4-F(Ph) | $CH_3$ |
| 14.84 | n-$C_4H_9$ | H | 4-$OCH_3$(Ph) | $CH_3$ |
| 14.85 | n-$C_4H_9$ | H | 4-$CH_3$(Ph) | $CH_3$ |
| 14.86 | n-$C_4H_9$ | H | 4-$NO_2$(Ph) | $CH_3$ |
| 14.87 | n-$C_4H_9$ | H | 2,4-Cl(Ph) | $CH_3$ |
| 14.88 | n-$C_4H_9$ | H | 2,4-F(Ph) | $CH_3$ |
| 14.89 | iso-$C_4H_9$ | H | Ph | $CH_3$ |
| 14.90 | iso-$C_4H_9$ | H | 2-Cl(Ph) | $CH_3$ |
| 14.91 | iso-$C_4H_9$ | H | 3-Cl(Ph) | $CH_3$ |
| 14.92 | iso-$C_4H_9$ | H | 4-Cl(Ph) | $CH_3$ |
| 14.93 | iso-$C_4H_9$ | H | 4-F(Ph) | $CH_3$ |
| 14.94 | iso-$C_4H_9$ | H | 3-$OCH_3$(Ph) | $CH_3$ |
| 14.95 | iso-$C_4H_9$ | H | 4-$OCH_3$(Ph) | $CH_3$ |
| 14.96 | iso-$C_4H_9$ | H | 4-$CH_3$(Ph) | $CH_3$ |
| 14.97 | iso-$C_4H_9$ | H | 4-$NO_2$(Ph) | $CH_3$ |
| 14.98 | iso-$C_4H_9$ | H | 2,4-Cl(Ph) | $CH_3$ |
| 14.99 | iso-$C_4H_9$ | H | 2,4-F(Ph) | $CH_3$ |
| 14.100 | $C(CH_3)_3$ | H | Ph | $CH_3$ |
| 14.101 | $C(CH_3)_3$ | H | 2-Cl(Ph) | $CH_3$ |
| 14.102 | $C(CH_3)_3$ | H | 3-Cl(Ph) | $CH_3$ |
| 14.103 | $C(CH_3)_3$ | H | 4-Cl(Ph) | $CH_3$ |
| 14.104 | $C(CH_3)_3$ | H | 4-F(Ph) | $CH_3$ |
| 14.105 | $C(CH_3)_3$ | H | 3-$OCH_3$(Ph) | $CH_3$ |
| 14.106 | $C(CH_3)_3$ | H | 4-$OCH_3$(Ph) | $CH_3$ |
| 14.107 | $C(CH_3)_3$ | H | 4-$CH_3$(Ph) | $CH_3$ |
| 14.108 | $C(CH_3)_3$ | H | 4-$NO_2$(Ph) | $CH_3$ |
| 14.109 | $C(CH_3)_3$ | H | 2,4-Cl(Ph) | $CH_3$ |
| 14.110 | $C(CH_3)_3$ | H | 2,4-F(Ph) | $CH_3$ |
| 14.111 | cyclopropyl | H | Ph | $CH_3$ |
| 14.112 | cyclopropyl | H | 2-Cl(Ph) | $CH_3$ |
| 14.113 | cyclopropyl | H | 3-Cl(Ph) | $CH_3$ |
| 14.114 | cyclopropyl | H | 4-Cl(Ph) | $CH_3$ |
| 14.115 | cyclopropyl | H | 4-Br(Ph) | $CH_3$ |
| 14.116 | cyclopropyl | H | 3-$OCH_3$(Ph) | $CH_3$ |
| 14.117 | cyclopropyl | H | 4-$OCH_3$(Ph) | $CH_3$ |
| 14.118 | cyclopropyl | H | 4-$CH_3$(Ph) | $CH_3$ |
| 14.119 | cyclopropyl | H | 4-$NO_2$(Ph) | $CH_3$ |
| 14.120 | cyclopropyl | H | 2,4-Cl(Ph) | $CH_3$ |
| 14.121 | cyclopropyl | H | 2,4-F(Ph) | $CH_3$ |
| 14.122 | 1-$CH_3$-cyclopropyl | H | Ph | $CH_3$ |
| 14.123 | 1-$CH_3$-cyclopropyl | H | 2-Cl(Ph) | $CH_3$ |
| 14.124 | 1-$CH_3$-cyclopropyl | H | 3-Cl(Ph) | $CH_3$ |
| 14.125 | 1-$CH_3$-cyclopropyl | H | 4-Cl(Ph) | $CH_3$ |
| 14.126 | 1-$CH_3$-cyclopropyl | H | 4-Br(Ph) | $CH_3$ |
| 14.127 | 1-$CH_3$-cyclopropyl | H | 4-F(Ph) | $CH_3$ |
| 14.128 | 1-$CH_3$-cyclopropyl | H | 4-$OCH_3$(Ph) | $CH_3$ |
| 14.129 | 1-$CH_3$-cyclopropyl | H | 4-$CH_3$(Ph) | $CH_3$ |
| 14.130 | 1-$CH_3$-cyclopropyl | H | 4-$NO_2$(Ph) | $CH_3$ |
| 14.131 | 1-$CH_3$-cyclopropyl | H | 2,4-Cl(Ph) | $CH_3$ |
| 14.132 | 1-$CH_3$-cyclopropyl | H | 2,4-F(Ph) | $CH_3$ |
| 14.133 | $CH_3$ | $CH_3$ | Ph | H |
| 14.134 | $CH_3$ | $CH_3$ | Ph | $CH_3$ |
| 14.135 | $CH_3$ | $CH_3$ | Ph | $C_2H_5$ |
| 14.136 | $CH_3$ | $CH_3$ | Ph | n-$C_3H_7$ |
| 14.137 | $CH_3$ | $CH_3$ | Ph | iso-$C_3H_7$ |
| 14.138 | $CH_3$ | $CH_3$ | Ph | n-$C_4H_9$ |
| 14.139 | $CH_3$ | $CH_3$ | Ph | iso-$C_4H_9$ |
| 14.140 | $CH_3$ | $CH_3$ | Ph | $C(CH_3)_3$ |
| 14.141 | $CH_3$ | $CH_3$ | Ph | $CH_2C{\equiv}CH$ |
| 14.142 | $CH_3$ | $CH_3$ | 2-Cl(Ph) | $CH_3$ |
| 14.143 | $CH_3$ | $CH_3$ | 3-Cl(Ph) | $CH_3$ |
| 14.144 | $C_2H_5$ | $CH_3$ | Ph | $CH_3$ |
| 14.145 | $C_2H_5$ | $CH_3$ | 2-Cl(Ph) | $CH_3$ |
| 14.146 | $C_2H_5$ | $CH_3$ | 3-Cl(Ph) | $CH_3$ |
| 14.147 | $C_2H_5$ | $CH_3$ | 4-Cl(Ph) | $CH_3$ |
| 14.148 | $C_2H_5$ | $CH_3$ | 4-Br(Ph) | $CH_3$ |
| 14.149 | $C_2H_5$ | $CH_3$ | 4-F(Ph) | $CH_3$ |
| 14.150 | $C_2H_5$ | $CH_3$ | 4-$OCH_3$(Ph) | $CH_3$ |
| 14.151 | $C_2H_5$ | $CH_3$ | 4-$CH_3$(Ph) | $CH_3$ |
| 14.152 | $C_2H_5$ | $CH_3$ | 4-$NO_2$(Ph) | $CH_3$ |
| 14.153 | $C_2H_5$ | $CH_3$ | 2,4-Cl(Ph) | $CH_3$ |
| 14.154 | $C_2H_5$ | $CH_3$ | 2,4-F(Ph) | $CH_3$ |
| 14.155 | n-$C_3H_7$ | $CH_3$ | Ph | $CH_3$ |
| 14.156 | n-$C_3H_7$ | $CH_3$ | 2-Cl(Ph) | $CH_3$ |
| 14.157 | n-$C_3H_7$ | $CH_3$ | 3-Cl(Ph) | $CH_3$ |
| 14.158 | n-$C_3H_7$ | $CH_3$ | 4-Cl(Ph) | $CH_3$ |
| 14.213 | CN | H | Ph | $C_2H_5$ |
| 14.214 | CN | H | Ph | n-$C_3H_7$ |
| 14.215 | CN | H | Ph | iso-$C_3H_7$ |
| 14.216 | CN | H | Ph | n-$C_4H_9$ |
| 14.217 | CN | H | Ph | iso-$C_4H_9$ |
| 14.218 | CN | H | Ph | $C(CH_3)_3$ |
| 14.219 | CN | H | Ph | $CH_2C{\equiv}CH$ |
| 14.220 | CN | H | 2-Cl(Ph) | $CH_3$ |
| 14.221 | CN | H | 4-Cl(Ph) | $CH_3$ |
| 14.222 | CN | $CH_3$ | Ph | H |
| 14.223 | CN | $CH_3$ | 2-Cl(Ph) | $CH_3$ |
| 14.224 | CN | $CH_3$ | 3-Cl(Ph) | $CH_3$ |
| 14.225 | CN | $CH_3$ | 4-Cl(Ph) | $CH_3$ |
| 14.226 | CN | $CH_3$ | 4-Br(Ph) | $CH_3$ |
| 14.227 | CN | $CH_3$ | 4-F(Ph) | $CH_3$ |
| 14.228 | CN | $CH_3$ | 4-$OCH_3$(Ph) | $CH_3$ |
| 14.229 | CN | $CH_3$ | 4-$CH_3$(Ph) | $CH_3$ |
| 14.230 | CN | $CH_3$ | 4-$NO_2$(Ph) | $CH_3$ |
| 14.231 | CN | $CH_3$ | 2,4-Cl(Ph) | $CH_3$ |
| 14.232 | CN | $CH_3$ | 2,4-F(Ph) | $CH_3$ |

TABLE 14-continued

| Compd | $R_2$ | $R_3$ | $R_7$ | $R_9$ |
|---|---|---|---|---|
| 14.233 | H | H | 1-napthyl | H |
| 14.234 | $CH_3$ | H | 1-napthyl | $CH_3$ |
| 14.235 | $C_2H_5$ | H | 1-napthyl | $CH_3$ |
| 14.236 | $n-C_3H_7$ | H | 1-napthyl | $CH_3$ |
| 14.237 | $iso-C_3H_7$ | H | 1-napthyl | $CH_3$ |
| 14.238 | $n-C_4H_9$ | H | 1-napthyl | $CH_3$ |
| 14.239 | $iso-C_4H_9$ | H | 1-napthyl | $CH_3$ |
| 14.240 | cyclopropyl | H | 1-napthyl | $CH_3$ |
| 14.241 | $1-CH_3$-cyclopropyl | H | 1-napthyl | $CH_3$ |
| 14.242 | CN | H | 1-napthyl | $CH_3$ |
| 14.243 | Ph | $CH_3$ | 1-napthyl | $CH_3$ |
| 14.244 | H | $CH_3$ | 1-napthyl | $CH_3$ |
| 14.245 | $CH_3$ | $CH_3$ | 1-napthyl | $CH_3$ |
| 14.246 | $C_2H_5$ | $CH_3$ | 1-napthyl | $CH_3$ |
| 14.247 | $n-C_3H_7$ | $CH_3$ | 1-napthyl | $CH_3$ |
| 14.248 | $iso-C_3H_7$ | $CH_3$ | 1-napthyl | $CH_3$ |
| 14.249 | $n-C_4H_9$ | $CH_3$ | 1-napthyl | $CH_3$ |
| 14.250 | $iso-C_4H_9$ | $CH_3$ | 1-napthyl | $CH_3$ |
| 14.251 | cyclopropyl | $CH_3$ | 1-napthyl | $CH_3$ |
| 14.252 | $1-CH_3$-cyclopropyl | $CH_3$ | 1-napthyl | $CH_3$ |
| 14.253 | CN | $CH_3$ | 1-napthyl | $CH_3$ |
| 14.254 | Ph | $CH_3$ | 1-napthyl | $CH_3$ |
| 14.255 | H | H | 2-napthyl | H |
| 14.256 | $CH_3$ | H | 2-napthyl | $CH_3$ |
| 14.257 | $C_2H_5$ | H | 2-napthyl | $C_2H_5$ |
| 14.258 | $n-C_3H_7$ | H | 2-napthyl | $n-C_3H_7$ |
| 14.259 | $iso-C_3H_7$ | H | 2-napthyl | $iso-C_3H_7$ |
| 14.260 | $n-C_4H_9$ | H | 2-napthyl | $n-C_4H_9$ |
| 14.261 | $iso-C_4H_9$ | H | 2-napthyl | $iso-C_4H_9$ |
| 14.262 | cyclopropyl | H | 2-napthyl | $C(CH_3)_3$ |
| 14.263 | $1-CH_3$-cyclopropyl | H | 2-napthyl | $CH_2C{\equiv}CH$ |
| 14.264 | CN | H | 2-napthyl | $CH_2Ph$ |
| 14.265 | Ph | H | 2-napthyl | $CH_2Ph$ |
| 14.266 | H | $CH_3$ | 2-napthyl | $CH_3$ |
| 14.267 | $CH_3$ | $CH_3$ | 2-napthyl | $CH_3$ |
| 14.268 | $C_2H_5$ | $CH_3$ | 2-napthyl | $CH_3$ |
| 14.269 | $n-C_3H_7$ | $CH_3$ | 2-napthyl | $CH_3$ |
| 14.270 | $iso-C_3H_7$ | $CH_3$ | 2-napthyl | $CH_3$ |
| 14.271 | $n-C_4H_9$ | $CH_3$ | 2-napthyl | $CH_3$ |
| 14.272 | $iso-C_4H_9$ | $CH_3$ | 2-napthyl | $CH_3$ |
| 14.273 | $cyclo-C_3H_5$ | $CH_3$ | 2-napthyl | $CH_3$ |
| 14.274 | $1-CH_3$-cyclopropyl | $CH_3$ | 2-napthyl | $CH_3$ |
| 14.275 | CN | $CH_3$ | 2-napthyl | $CH_3$ |
| 14.276 | Ph | $CH_3$ | 2-napthyl | $CH_3$ |
| 14.277 | 2-Cl(Ph) | $CH_3$ | 2-napthyl | $CH_3$ |
| 14.278 | 3-Cl(Ph) | $CH_3$ | 2-napthyl | $CH_3$ |
| 14.279 | 4-Cl(Ph) | $CH_3$ | 2-napthyl | $CH_3$ |
| 14.280 | 4-Br(Ph) | $CH_3$ | 2-napthyl | $CH_3$ |
| 14.281 | 4-F(Ph) | $CH_3$ | 2-napthyl | $CH_3$ |
| 14.282 | $4-OCH_3$(Ph) | $CH_3$ | 2-napthyl | $CH_3$ |
| 14.283 | $4-CH_3$(Ph) | $CH_3$ | 2-napthyl | $CH_3$ |
| 14.284 | $3-CF_3$(Ph) | $CH_3$ | 2-napthyl | $CH_3$ |
| 14.285 | $CH_3$ | $C_2H_5$ | Ph | $CH_3$ |
| 14.286 | $CH_3$ | $C_2H_5$ | 2-Cl(Ph) | $CH_3$ |
| 14.287 | $CH_3$ | $C_2H_5$ | 3-Cl(Ph) | $CH_3$ |
| 14.288 | $CH_3$ | $C_2H_5$ | 4-Cl(Ph) | $CH_3$ |
| 14.289 | $CH_3$ | $C_2H_5$ | 4-Br(Ph) | $CH_3$ |
| 14.290 | $CH_3$ | $C_2H_5$ | 4-F(Ph) | $CH_3$ |
| 14.291 | $CH_3$ | $C_2H_5$ | $4-OCH_3$(Ph) | $CH_3$ |
| 14.292 | $CH_3$ | $C_2H_5$ | $4-CH_3$(Ph) | $CH_3$ |
| 14.293 | $CH_3$ | $C_2H_5$ | $4-NO_2$(Ph) | $CH_3$ |
| 14.294 | $CH_3$ | $C_2H_5$ | 2,4-Cl(Ph) | $CH_3$ |
| 14.295 | $CH_3$ | $C_2H_5$ | 2,4-F(Ph) | $CH_3$ |
| 14.296 | $CH_3$ | $n-C_3H_7$ | Ph | $CH_3$ |
| 14.297 | $CH_3$ | $n-C_3H_7$ | 2-Cl(Ph) | $CH_3$ |
| 14.298 | $CH_3$ | $n-C_3H_7$ | 3-Cl(Ph) | $CH_3$ |
| 14.299 | $CH_3$ | $n-C_3H_7$ | 4-Cl(Ph) | $CH_3$ |
| 14.300 | $CH_3$ | $n-C_3H_7$ | 4-Br(Ph) | $CH_3$ |
| 14.301 | $CH_3$ | $n-C_3H_7$ | 4-F(Ph) | $CH_3$ |
| 14.302 | $CH_3$ | $n-C_3H_7$ | $4-OCH_3$(Ph) | $CH_3$ |
| 14.303 | $CH_3$ | $n-C_3H_7$ | $4-CH_3$(Ph) | $CH_3$ |
| 14.304 | $CH_3$ | $n-C_3H_7$ | $4-NO_2$(Ph) | $CH_3$ |
| 14.305 | $CH_3$ | $n-C_3H_7$ | 2,4-Cl(Ph) | $CH_3$ |
| 14.306 | $CH_3$ | $n-C_3H_7$ | 2,4-F(Ph) | $CH_3$ |
| 14.307 | $CH_3$ | $iso-C_3H_7$ | Ph | $CH_3$ |
| 14.308 | $CH_3$ | $iso-C_3H_7$ | 2-Cl(Ph) | $CH_3$ |
| 14.309 | $CH_3$ | $iso-C_3H_7$ | 3-Cl(Ph) | $CH_3$ |
| 14.310 | $CH_3$ | $iso-C_3H_7$ | 4-Cl(Ph) | $CH_3$ |
| 14.311 | $CH_3$ | $iso-C_3H_7$ | 4-Br(Ph) | $CH_3$ |
| 14.312 | $CH_3$ | $iso-C_3H_7$ | 4-F(Ph) | $CH_3$ |
| 14.313 | $CH_3$ | $iso-C_3H_7$ | $4-OCH_3$(Ph) | $CH_3$ |
| 14.314 | $CH_3$ | $iso-C_3H_7$ | $4-CH_3$(Ph) | $CH_3$ |
| 14.315 | $CH_3$ | $iso-C_3H_7$ | $4-NO_2$(Ph) | $CH_3$ |

Typical compounds encompassed by the present invention of Formula I include those compounds of Formula IX, which is Formula I with $A{=}R_4{=}R_5{=}R_6{=}H$, $R_1{=}CH_3$, $X{=}N$, $Y{=}NH$, and $Z{=}NOR_9$, and where $R_2$, $R_3$, $R_7$ and $R_9$ are defined in Table 15.

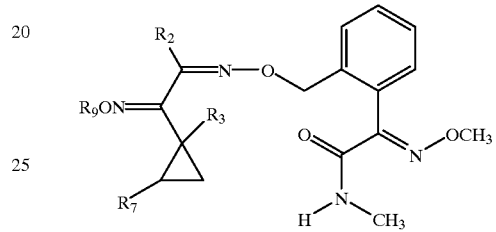

Formula IX

TABLE 15

| Compd | $R_2$ | $R_3$ | $R_7$ | $R_9$ |
|---|---|---|---|---|
| 15.1 | H | H | Ph | H |
| 15.2 | H | H | 4-Cl(Ph) | H |
| 15.3 | H | H | 4-Br(Ph) | H |
| 15.4 | H | H | 4-F(Ph) | H |
| 15.5 | H | H | $4-OCH_3$(Ph) | H |
| 15.6 | H | H | $4-CF_3$(Ph) | H |
| 15.7 | H | H | Ph | $CH_3$ |
| 15.8 | H | H | 4-Cl(Ph) | $CH_3$ |
| 15.9 | H | H | 4-Br(Ph) | $CH_3$ |
| 15.10 | H | H | 4-F(Ph) | $CH_3$ |
| 15.11 | $CH_3$ | H | Ph | H |
| 15.12 | $CH_3$ | H | 2-Cl(Ph) | H |
| 15.13 | $CH_3$ | H | 3-Cl(Ph) | H |
| 15.14 | $CH_3$ | H | 4-Cl(Ph) | H |
| 15.15 | $CH_3$ | H | 2-Br(Ph) | H |
| 15.16 | $CH_3$ | H | 3-Br(Ph) | H |
| 15.17 | $CH_3$ | H | 4-Br(Ph) | H |
| 15.18 | $CH_3$ | H | Ph | $CH_3$ |
| 15.19 | $CH_3$ | H | 2-Cl(Ph) | $CH_3$ |
| 15.20 | $CH_3$ | H | 3-Cl(Ph) | $CH_3$ |
| 15.21 | $CH_3$ | H | 4-Cl(Ph) | $CH_3$ |
| 15.22 | $CH_3$ | H | 2-F(Ph) | $CH_3$ |
| 15.23 | $CH_3$ | H | 3-F(Ph) | $CH_3$ |
| 15.24 | $CH_3$ | H | 4-F(Ph) | $CH_3$ |
| 15.25 | $CH_3$ | H | $2-CH_3$(Ph) | $CH_3$ |
| 15.26 | $CH_3$ | H | $3-CH_3$(Ph) | $CH_3$ |
| 15.27 | $CH_3$ | H | $2-CF_3$(Ph) | $CH_3$ |
| 15.28 | $CH_3$ | H | $3-CF_3$(Ph) | $CH_3$ |
| 15.29 | $CH_3$ | H | $4-CF_3$(Ph) | $CH_3$ |
| 15.30 | $CH_3$ | H | $2-OCH_3$(Ph) | $CH_3$ |
| 15.31 | $CH_3$ | H | $3-OCH_3$(Ph) | $CH_3$ |
| 15.32 | $CH_3$ | H | $4-OCH_3$(Ph) | $CH_3$ |
| 15.33 | $CH_3$ | H | 2,3-Cl(Ph) | $CH_3$ |
| 15.34 | $CH_3$ | H | 2,4-Cl(Ph) | $CH_3$ |
| 15.35 | $CH_3$ | H | 2,5-Cl(Ph) | $CH_3$ |
| 15.36 | $CH_3$ | H | 2,6-Cl(Ph) | $CH_3$ |
| 15.37 | $CH_3$ | H | 3,4-Cl(Ph) | $CH_3$ |
| 15.38 | $CH_3$ | H | 3,5-Cl(Ph) | $CH_3$ |
| 15.39 | $CH_3$ | H | Ph | $C_2H_5$ |
| 15.40 | $CH_3$ | H | Ph | $n-C_3H_7$ |
| 15.41 | $CH_3$ | H | Ph | $iso-C_3H_7$ |

TABLE 15-continued

| Compd | R₂ | R₃ | R₇ | R₉ |
|---|---|---|---|---|
| 15.42 | CH₃ | H | Ph | n-C₄H₉ |
| 15.43 | CH₃ | H | Ph | C(CH₃)₃ |
| 15.44 | CH₃ | H | Ph | CH₂C≡CH |
| 15.45 | C₂H₅ | H | Ph | CH₃ |
| 15.46 | C₂H₅ | H | 2-Cl(Ph) | CH₃ |
| 15.47 | C₂H₅ | H | 3-Cl(Ph) | CH₃ |
| 15.48 | C₂H₅ | H | 4-Cl(Ph) | CH₃ |
| 15.49 | C₂H₅ | H | 4-Br(Ph) | CH₃ |
| 15.50 | C₂H₅ | H | 4-F(Ph) | CH₃ |
| 15.51 | C₂H₅ | H | 4-OCH₃(Ph) | CH₃ |
| 15.52 | C₂H₅ | H | 4-CH₃(Ph) | CH₃ |
| 15.53 | C₂H₅ | H | 4-NO₂(Ph) | CH₃ |
| 15.54 | C₂H₅ | H | 2,4-Cl(Ph) | CH₃ |
| 15.55 | C₂H₅ | H | 2,4-F(Ph) | CH₃ |
| 15.56 | n-C₃H₇ | H | Ph | CH₃ |
| 15.57 | n-C₃H₇ | H | 2-Cl(Ph) | CH₃ |
| 15.58 | n-C₃H₇ | H | 3-Cl(Ph) | CH₃ |
| 15.59 | n-C₃H₇ | H | 4-Cl(Ph) | CH₃ |
| 15.60 | n-C₃H₇ | H | 4-F(Ph) | CH₃ |
| 15.61 | n-C₃H₇ | H | 3-OCH₃(Ph) | CH₃ |
| 15.62 | n-C₃H₇ | H | 4-OCH₃(Ph) | CH₃ |
| 15.63 | n-C₃H₇ | H | 4-CH₃(Ph) | CH₃ |
| 15.64 | n-C₃H₇ | H | 4-NO₂(Ph) | CH₃ |
| 15.65 | n-C₃H₇ | H | 2,4-Cl(Ph) | CH₃ |
| 15.66 | n-C₃H₇ | H | 2,4-F(Ph) | CH₃ |
| 15.67 | iso-C₃H₇ | H | Ph | CH₃ |
| 15.68 | iso-C₃H₇ | H | 2-Cl(Ph) | CH₃ |
| 15.69 | iso-C₃H₇ | H | 3-Cl(Ph) | CH₃ |
| 15.70 | iso-C₃H₇ | H | 4-Cl(Ph) | CH₃ |
| 15.71 | iso-C₃H₇ | H | 4-Br(Ph) | CH₃ |
| 15.72 | iso-C₃H₇ | H | 4-F(Ph) | CH₃ |
| 15.73 | iso-C₃H₇ | H | 4-OCH₃(Ph) | CH₃ |
| 15.74 | iso-C₃H₇ | H | 4-CH₃(Ph) | CH₃ |
| 15.75 | iso-C₃H₇ | H | 4-NO₂(Ph) | CH₃ |
| 15.76 | iso-C₃H₇ | H | 2,4-Cl(Ph) | CH₃ |
| 15.77 | iso-C₃H₇ | H | 2,4-F(Ph) | CH₃ |
| 15.78 | n-C₄H₉ | H | Ph | CH₃ |
| 15.79 | n-C₄H₉ | H | 2-Cl(Ph) | CH₃ |
| 15.80 | n-C₄H₉ | H | 3-Cl(Ph) | CH₃ |
| 15.81 | n-C₄H₉ | H | 4-Cl(Ph) | CH₃ |
| 15.82 | n-C₄H₉ | H | 4-Br(Ph) | CH₃ |
| 15.83 | n-C₄H₉ | H | 4-F(Ph) | CH₃ |
| 15.84 | n-C₄H₉ | H | 4-OCH₃(Ph) | CH₃ |
| 15.85 | n-C₄H₉ | H | 4-CH₃(Ph) | CH₃ |
| 15.86 | n-C₄H₉ | H | 4-NO₂(Ph) | CH₃ |
| 15.87 | n-C₄H₉ | H | 2,4-Cl(Ph) | CH₃ |
| 15.88 | n-C₄H₉ | H | 2,4-F(Ph) | CH₃ |
| 15.89 | iso-C₄H₉ | H | Ph | CH₃ |
| 15.90 | iso-C₄H₉ | H | 2-Cl(Ph) | CH₃ |
| 15.91 | iso-C₄H₉ | H | 3-Cl(Ph) | CH₃ |
| 15.92 | iso-C₄H₉ | H | 4-Cl(Ph) | CH₃ |
| 15.93 | iso-C₄H₉ | H | 4-F(Ph) | CH₃ |
| 15.94 | iso-C₄H₉ | H | 3-OCH₃(Ph) | CH₃ |
| 15.95 | iso-C₄H₉ | H | 4-OCH₃(Ph) | CH₃ |
| 15.96 | iso-C₄H₉ | H | 4-CH₃(Ph) | CH₃ |
| 15.97 | iso-C₄H₉ | H | 4-NO₂(Ph) | CH₃ |
| 15.98 | iso-C₄H₉ | H | 2,4-Cl(Ph) | CH₃ |
| 15.99 | iso-C₄H₉ | H | 2,4-F(Ph) | CH₃ |
| 15.100 | C(CH₃)₃ | H | Ph | CH₃ |
| 15.101 | C(CH₃)₃ | H | 2-Cl(Ph) | CH₃ |
| 15.102 | C(CH₃)₃ | H | 3-Cl(Ph) | CH₃ |
| 15.103 | C(CH₃)₃ | H | 4-Cl(Ph) | CH₃ |
| 15.104 | C(CH₃)₃ | H | 4-F(Ph) | CH₃ |
| 15.105 | C(CH₃)₃ | H | 3-OCH₃(Ph) | CH₃ |
| 15.106 | C(CH₃)₃ | H | 4-OCH₃(Ph) | CH₃ |
| 15.107 | C(CH₃)₃ | H | 4-CH₃(Ph) | CH₃ |
| 15.108 | C(CH₃)₃ | H | 4-NO₂(Ph) | CH₃ |
| 15.109 | C(CH₃)₃ | H | 2,4-Cl(Ph) | CH₃ |
| 15.110 | C(CH₃)₃ | H | 2,4-F(Ph) | CH₃ |
| 15.111 | cyclopropyl | H | Ph | CH₃ |
| 15.112 | cyclopropyl | H | 2-Cl(Ph) | CH₃ |
| 15.113 | cyclopropyl | H | 3-Cl(Ph) | CH₃ |
| 15.114 | cyclopropyl | H | 4-Cl(Ph) | CH₃ |
| 15.115 | cyclopropyl | H | 4-Br(Ph) | CH₃ |
| 15.116 | cyclopropyl | H | 3-OCH₃(Ph) | CH₃ |
| 15.117 | cyclopropyl | H | 4-OCH₃(Ph) | CH₃ |
| 15.118 | cyclopropyl | H | 4-CH₃(Ph) | CH₃ |
| 15.119 | cyclopropyl | H | 4-NO₂(Ph) | CH₃ |
| 15.120 | cyclopropyl | H | 2,4-Cl(Ph) | CH₃ |
| 15.121 | cyclopropyl | H | 2,4-F(Ph) | CH₃ |
| 15.122 | 1-CH₃-cyclopropyl | H | Ph | CH₃ |
| 15.123 | 1-CH₃-cyclopropyl | H | 2-Cl(Ph) | CH₃ |
| 15.124 | 1-CH₃-cyclopropyl | H | 3-Cl(Ph) | CH₃ |
| 15.125 | 1-CH₃-cyclopropyl | H | 4-Cl(Ph) | CH₃ |
| 15.126 | 1-CH₃-cyclopropyl | H | 4-Br(Ph) | CH₃ |
| 15.127 | 1-CH₃-cyclopropyl | H | 4-F(Ph) | CH₃ |
| 15.128 | 1-CH₃-cyclopropyl | H | 4-OCH₃(Ph) | CH₃ |
| 15.129 | 1-CH₃-cyclopropyl | H | 4-CH₃(Ph) | CH₃ |
| 15.130 | 1-CH₃-cyclopropyl | H | 4-NO₂(Ph) | CH₃ |
| 15.131 | 1-CH₃-cyclopropyl | H | 2,4-Cl(Ph) | CH₃ |
| 15.132 | 1-CH₃-cyclopropyl | H | 2,4-F(Ph) | CH₃ |
| 15.133 | CH₃ | CH₃ | Ph | CH₃ |
| 15.134 | CH₃ | CH₃ | Ph | CH₃ |
| 15.135 | CH₃ | CH₃ | Ph | C₂H₅ |
| 15.136 | CH₃ | CH₃ | Ph | n-C₃H₇ |
| 15.137 | CH₃ | CH₃ | Ph | iso-C₅H₇ |
| 15.138 | CH₃ | CH₃ | Ph | n-C₄H₉ |
| 15.139 | CH₃ | CH₃ | Ph | iso-C₄H₉ |
| 15.140 | CH₃ | CH₃ | Ph | C(CH₃)₃ |
| 15.141 | CH₃ | CH₃ | Ph | CH₂C≡CH |
| 15.142 | CH₃ | CH₃ | 2-Cl(Ph) | CH₃ |
| 15.143 | CH₃ | CH₃ | 3-Cl(Ph) | CH₃ |
| 15.144 | C₂H₅ | CH₃ | Ph | CH₃ |
| 15.145 | C₂H₅ | CH₃ | 2-Cl(Ph) | CH₃ |
| 15.146 | C₂H₅ | CH₃ | 3-Cl(Ph) | CH₃ |
| 15.147 | C₂H₅ | CH₃ | 4-Cl(Ph) | CH₃ |
| 15.148 | C₂H₅ | CH₃ | 4-Br(Ph) | CH₃ |
| 15.149 | C₂H₅ | CH₃ | 4-F(Ph) | CH₃ |
| 15.150 | C₂H₅ | CH₃ | 4-OCH₃(Ph) | CH₃ |
| 15.151 | C₂H₅ | CH₃ | 4-CH₃(Ph) | CH₃ |
| 15.152 | C₂H₅ | CH₃ | 4-NO₂(Ph) | CH₃ |
| 15.153 | C₂H₅ | CH₃ | 2,4-Cl(Ph) | CH₃ |
| 15.154 | C₂H₅ | CH₃ | 2,4-F(Ph) | CH₃ |
| 15.155 | n-C₃H₇ | CH₃ | Ph | CH₃ |
| 15.156 | n-C₃H₇ | CH₃ | 2-Cl(Ph) | CH₃ |
| 15.157 | n-C₃H₇ | CH₃ | 3-Cl(Ph) | CH₃ |
| 15.158 | n-C₃H₇ | CH₃ | 4-Cl(Ph) | CH₃ |
| 15.159 | n-C₃H₇ | CH₃ | 4-Br(Ph) | CH₃ |
| 15.160 | n-C₃H₇ | CH₃ | 4-F(Ph) | CH₃ |
| 15.161 | n-C₃H₇ | CH₃ | 4-OCH₃(Ph) | CH₃ |
| 15.162 | n-C₃H₇ | CH₃ | 4-CH₃(Ph) | CH₃ |
| 15.163 | n-C₃H₇ | CH₃ | 4-NO₂(Ph) | CH₃ |
| 15.164 | n-C₃H₇ | CH₃ | 2,4-Cl(Ph) | CH₃ |
| 15.165 | n-C₃H₇ | CH₃ | 2,4-F(Ph) | CH₃ |
| 15.166 | iso-C₃H₇ | CH₃ | Ph | CH₃ |
| 15.167 | iso-C₃H₇ | CH₃ | 2-Cl(Ph) | CH₃ |
| 15.168 | iso-C₃H₇ | CH₃ | 3-Cl(Ph) | CH₃ |
| 15.169 | iso-C₃H₇ | CH₃ | 4-Cl(Ph) | CH₃ |
| 15.170 | iso-C₃H₇ | CH₃ | 4-Br(Ph) | CH₃ |
| 15.171 | iso-C₃H₇ | CH₃ | 4-F(Ph) | CH₃ |
| 15.172 | iso-C₃H₇ | CH₃ | 4-OCH₃(Ph) | CH₃ |
| 15.173 | iso-C₃H₇ | CH₃ | 4-CH₃(Ph) | CH₃ |
| 15.174 | iso-C₃H₇ | CH₃ | 4-NO₂(Ph) | CH₃ |
| 15.175 | iso-C₃H₇ | CH₃ | 2,4-Cl(Ph) | CH₃ |
| 15.176 | iso-C₃H₇ | CH₃ | 2,4-F(Ph) | CH₃ |
| 15.177 | n-C₄H₉ | CH₃ | Ph | CH₃ |
| 15.178 | n-C₄H₉ | CH₃ | 2-Cl(Ph) | CH₃ |
| 15.179 | n-C₄H₉ | CH₃ | 3-Cl(Ph) | CH₃ |
| 15.180 | n-C₄H₉ | CH₃ | 4-Cl(Ph) | CH₃ |
| 15.181 | n-C₄H₉ | CH₃ | 4-Br(Ph) | CH₃ |
| 15.182 | n-C₄H₉ | CH₃ | 4-F(Ph) | CH₃ |
| 15.183 | n-C₄H₉ | CH₃ | 4-OCH₃(Ph) | CH₃ |
| 15.184 | n-C₄H₉ | CH₃ | 4-CH₃(Ph) | CH₃ |
| 15.185 | n-C₄H₉ | CH₃ | 4-NO₃(Ph) | CH₃ |
| 15.186 | n-C₄H₉ | CH₃ | 2,4-Cl(Ph) | CH₃ |
| 15.187 | n-C₄H₉ | CH₃ | 2,4-F(Ph) | CH₃ |
| 15.188 | n-C₄H₉ | CH₃ | 4-CF₃(Ph) | CH₃ |
| 15.189 | Ph | H | Ph | H |
| 15.190 | Ph | H | Ph | CH₃ |
| 15.191 | Ph | H | Ph | C₂H₅ |
| 15.192 | Ph | H | Ph | n-C₃H₇ |
| 15.193 | Ph | H | Ph | iso-C₃H₇ |
| 15.194 | Ph | H | Ph | n-C₄H₉ |
| 15.195 | Ph | H | Ph | iso-C₄H₉ |

TABLE 15-continued

| Compd | R$_2$ | R$_3$ | R$_7$ | R$_9$ |
|---|---|---|---|---|
| 15.196 | Ph | H | Ph | C(CH$_3$)$_3$ |
| 15.197 | Ph | H | Ph | CH$_2$C≡CH |
| 15.198 | Ph | H | 2-Cl(Ph) | CH$_3$ |
| 15.199 | Ph | H | 4-Cl(Ph) | CH$_3$ |
| 15.200 | Ph | CH$_3$ | Ph | CH$_3$ |
| 15.201 | Ph | CH$_3$ | 2-Cl(Ph) | CH$_3$ |
| 15.202 | Ph | CH$_3$ | 3-Cl(Ph) | CH$_3$ |
| 15.203 | Ph | CH$_3$ | 4-Cl(Ph) | CH$_3$ |
| 15.204 | Ph | CH$_3$ | 4-Br(Ph) | CH$_3$ |
| 15.205 | Ph | CH$_3$ | 4-F(Ph) | CH$_3$ |
| 15.206 | Ph | CH$_3$ | 4-OCH$_3$(Ph) | CH$_3$ |
| 15.207 | Ph | CH$_3$ | 4-CH$_3$(Ph) | CH$_3$ |
| 15.208 | Ph | CH$_3$ | 4-NO$_2$(Ph) | CH$_3$ |
| 15.209 | Ph | CH$_3$ | 2,4-Cl(Ph) | CH$_3$ |
| 15.210 | Ph | CH$_3$ | 2,4-F(Ph) | CH$_3$ |
| 15.211 | CN | H | Ph | H |
| 15.212 | CN | H | Ph | CH$_3$ |
| 15.213 | CN | H | Ph | C$_2$H$_5$ |
| 15.214 | CN | H | Ph | n-C$_3$H$_7$ |
| 15.215 | CN | H | Ph | iso-C$_3$H$_7$ |
| 15.216 | CN | H | Ph | n-C$_4$H$_9$ |
| 15.217 | CN | H | Ph | iso-C$_4$H$_9$ |
| 15.218 | CN | H | Ph | C(CH$_3$)$_3$ |
| 15.219 | CN | H | Ph | CH$_2$C≡CH |
| 15.220 | CN | H | 2-Cl(Ph) | CH$_3$ |
| 15.221 | CN | H | 4-Cl(Ph) | CH$_3$ |
| 15.222 | CN | CH$_3$ | Ph | H |
| 15.223 | CN | CH$_3$ | 2-Cl(Ph) | CH$_3$ |
| 15.224 | CN | CH$_3$ | 3-Cl(Ph) | CH$_3$ |
| 15.225 | CN | CH$_3$ | 4-Cl(Ph) | CH$_3$ |
| 15.226 | CN | CH$_3$ | 4-Br(Ph) | CH$_3$ |
| 15.227 | CN | CH$_3$ | 4-F(Ph) | CH$_3$ |
| 15.228 | CN | CH$_3$ | 4-OCH$_3$(Ph) | CH$_3$ |
| 15.229 | CN | CH$_3$ | 4-CH$_3$(Ph) | CH$_3$ |
| 15.230 | CN | CH$_3$ | 4-NO$_2$(Ph) | CH$_3$ |
| 15.231 | CN | CH$_3$ | 2,4-Cl(Ph) | CH$_3$ |
| 15.232 | CN | CH$_3$ | 2,4-F(Ph) | CH$_3$ |
| 15.233 | H | H | 1-napthyl | H |
| 15.234 | CH$_3$ | H | 1-napthyl | CH$_3$ |
| 15.235 | C$_2$H$_5$ | H | 1-napthyl | CH$_3$ |
| 15.236 | n-C$_3$H$_7$ | H | 1-napthyl | CH$_3$ |
| 15.237 | iso-C$_3$H$_7$ | H | 1-napthyl | CH$_3$ |
| 15.238 | n-C$_4$H$_9$ | H | 1-napthyl | CH$_3$ |
| 15.239 | iso-C$_4$H$_9$ | H | 1-napthyl | CH$_3$ |
| 15.240 | cyclopropyl | H | 1-napthyl | CH$_3$ |
| 15.241 | 1-CH$_3$-cyclopropyl | H | 1-napthyl | CH$_3$ |
| 15.242 | CN | H | 1-napthyl | CH$_3$ |
| 15.243 | Ph | CH$_3$ | 1-napthyl | CH$_3$ |
| 15.244 | H | CH$_3$ | 1-napthyl | CH$_3$ |
| 15.245 | CH$_3$ | CH$_3$ | 1-napthyl | CH$_3$ |
| 15.246 | C$_2$H$_5$ | CH$_3$ | 1-napthyl | CH$_3$ |
| 15.247 | n-C$_3$H$_7$ | CH$_3$ | 1-napthyl | CH$_3$ |
| 15.248 | iso-C$_3$H$_7$ | CH$_3$ | 1-napthyl | CH$_3$ |
| 15.249 | n-C$_4$H$_9$ | CH$_3$ | 1-napthyl | CH$_3$ |
| 15.250 | iso-C$_4$H$_9$ | CH$_3$ | 1-napthyl | CH$_3$ |
| 15.251 | cyclopropyl | CH$_3$ | 1-napthyl | CH$_3$ |
| 15.252 | 1-CH$_3$-cyclopropyl | CH$_3$ | 1-napthyl | CH$_3$ |
| 15.253 | CN | CH$_3$ | 1-napthyl | CH$_3$ |
| 15.254 | Ph | CH$_3$ | 1-napthyl | CH$_3$ |
| 15.255 | H | H | 2-napthyl | H |
| 15.256 | CH$_3$ | H | 2-napthyl | CH$_3$ |
| 15.257 | C$_2$H$_5$ | H | 2-napthyl | C$_2$H$_5$ |
| 15.258 | n-C$_3$H$_7$ | H | 2-napthyl | n-C$_3$H$_7$ |
| 15.259 | iso-C$_3$H$_7$ | H | 2-napthyl | iso-C$_3$H$_7$ |
| 15.260 | n-C$_4$H$_9$ | H | 2-napthyl | n-C$_4$H$_9$ |
| 15.261 | iso-C$_4$H$_9$ | H | 2-napthyl | iso-C$_4$H$_9$ |
| 15.262 | cyclopropyl | H | 2-napthyl | C(CH$_3$)$_3$ |
| 15.263 | 1-CH$_3$-cyclopropyl | H | 2-napthyl | CH$_2$C≡CH |
| 15.264 | CN | H | 2-napthyl | CH$_2$Ph |
| 15.265 | Ph | H | 2-napthyl | CH$_2$Ph |
| 15.266 | H | CH$_3$ | 2-napthyl | CH$_3$ |
| 15.267 | CH$_3$ | CH$_3$ | 2-napthyl | CH$_3$ |
| 15.268 | C$_2$H$_5$ | CH$_3$ | 2-napthyl | CH$_3$ |
| 15.269 | n-C$_3$H$_7$ | CH$_3$ | 2-napthyl | CH$_3$ |
| 15.270 | iso-C$_3$H$_7$ | CH$_3$ | 2-napthyl | CH$_3$ |
| 15.271 | n-C$_4$H$_9$ | CH$_3$ | 2-napthyl | CH$_3$ |
| 15.272 | iso-C$_4$H$_9$ | CH$_3$ | 2-napthyl | CH$_3$ |
| 15.273 | cyclopropyl | CH$_3$ | 2-napthyl | CH$_3$ |
| 15.274 | 1-CH$_3$-cyclopropyl | CH$_3$ | 2-napthyl | CH$_3$ |
| 15.275 | CN | CH$_3$ | 2-napthyl | CH$_3$ |
| 15.276 | Ph | CH$_3$ | 2-napthyl | CH$_3$ |
| 15.277 | | 2-Cl(Ph) | CH$_3$ | 2-napthyl | CH$_3$ |
| 15.278 | | 3-Cl(Ph) | CH$_3$ | 2-napthyl | CH$_3$ |
| 15.279 | | 4-Cl(Ph) | CH$_3$ | 2-napthyl | CH$_3$ |
| 15.280 | | 4-Br(Ph) | CH$_3$ | 2-napthyl | CH$_3$ |
| 15.281 | | 4-F(Ph) | CH$_3$ | 2-napthyl | CH$_3$ |
| 15.282 | | 4-OCH$_3$(Ph) | CH$_3$ | 2-napthyl | CH$_3$ |
| 15.283 | | 4-CH$_3$(Ph) | CH$_3$ | 2-napthyl | CH$_3$ |
| 15.284 | | 3-CF$_3$(Ph) | CH$_3$ | 2-napthyl | CH$_3$ |
| 15.285 | CH$_3$ | C$_2$H$_5$ | Ph | CH$_3$ |
| 15.286 | CH$_3$ | C$_2$H$_5$ | 2-Cl(Ph) | CH$_3$ |
| 15.287 | CH$_3$ | C$_2$H$_5$ | 3-Cl(Ph) | CH$_3$ |
| 15.288 | CH$_3$ | C$_2$H$_5$ | 4-Cl(Ph) | CH$_3$ |
| 15.289 | CH$_3$ | C$_2$H$_5$ | 4-Br(Ph) | CH$_3$ |
| 15.290 | CH$_3$ | C$_2$H$_5$ | 4-F(Ph) | CH$_3$ |
| 15.291 | CH$_3$ | C$_2$H$_5$ | 4-OCH$_3$(Ph) | CH$_3$ |
| 15.292 | CH$_3$ | C$_2$H$_5$ | 4-CH$_3$(Ph) | CH$_3$ |
| 15.293 | CH$_3$ | C$_2$H$_5$ | 4-NO$_2$(Ph) | CH$_3$ |
| 15.294 | CH$_3$ | C$_2$H$_5$ | 2,4-Cl(Ph) | CH$_3$ |
| 15.295 | CH$_3$ | C$_2$H$_5$ | 2,4-F(Ph) | CH$_3$ |
| 15.296 | CH$_3$ | n-C$_3$H$_7$ | Ph | CH$_3$ |
| 15.297 | CH$_3$ | n-C$_3$H$_7$ | 2-Cl(Ph) | CH$_3$ |
| 15.298 | CH$_3$ | n-C$_3$H$_7$ | 3-Cl(Ph) | CH$_3$ |
| 15.299 | CH$_3$ | n-C$_3$H$_7$ | 4-Cl(Ph) | CH$_3$ |
| 15.300 | CH$_3$ | n-C$_3$H$_7$ | 4-Br(Ph) | CH$_3$ |
| 15.301 | CH$_3$ | n-C$_3$H$_7$ | 4-F(Ph) | CH$_3$ |
| 15.302 | CH$_3$ | n-C$_3$H$_7$ | 4-OCH$_3$(Ph) | CH$_3$ |
| 15.303 | CH$_3$ | n-C$_3$H$_7$ | 4-CH$_3$(Ph) | CH$_3$ |
| 15.304 | CH$_3$ | n-C$_3$H$_7$ | 4-NO$_2$(Ph) | CH$_3$ |
| 15.305 | CH$_3$ | n-C$_3$H$_7$ | 2,4-Cl(Ph) | CH$_3$ |
| 15.306 | CH$_3$ | n-C$_3$H$_7$ | 2,4-F(Ph) | CH$_3$ |
| 15.307 | CH$_3$ | iso-C$_3$H$_7$ | Ph | CH$_3$ |
| 15.308 | CH$_3$ | iso-C$_3$H$_7$ | 2-Cl(Ph) | CH$_3$ |
| 15.309 | CH$_3$ | iso-C$_3$H$_7$ | 3-Cl(Ph) | CH$_3$ |
| 15.310 | CH$_3$ | iso-C$_3$H$_7$ | 4-Cl(Ph) | CH$_3$ |
| 15.311 | CH$_3$ | iso-C$_3$H$_7$ | 4-Br(Ph) | CH$_3$ |
| 15.312 | CH$_3$ | iso-C$_3$H$_7$ | 4-F(Ph) | CH$_3$ |
| 15.313 | CH$_3$ | iso-C$_3$H$_7$ | 4-OCH$_3$(Ph) | CH$_3$ |
| 15.314 | CH$_3$ | iso-C$_3$H$_7$ | 4-CH$_3$(Ph) | CH$_3$ |
| 15.315 | CH$_3$ | iso-C$_3$H$_7$ | 4-NO$_2$(Ph) | CH$_3$ |

TABLE 16

Compounds 16.1 to 16.226 are compounds of Formula VII which is Formula I with A=R$_4$=R$_5$=R$_6$=H, R$_1$=CH$_3$, X=CH, Y=O, and Z=NOR$_9$, where R$_9$ is CH$_3$ and R$_2$, R$_3$, and R$_7$ are defined in Table 4.

TABLE 17

Compounds 17.1 to 17.226 are compounds of Formula VIII which is Formula I with A=R$_4$=R$_5$=R$_6$=H, R$_1$=CH$_3$, X=N, Y=O, and Z=NOR$_9$, where R$_9$ is CH$_3$ and R$_2$, R$_3$, and R$_7$ are defined in Table 4.

TABLE 18

Compounds 18.1 to 18.226 are compounds of Formula IX which is Formula I with A=R$_4$=R$_5$=R$_6$=H, R$_1$=CH$_3$, X=N, Y=NH, and Z=NOR$_9$, where R$_9$ is CH$_3$ and R$_2$, R$_3$, and R$_7$ are defined in Table 4.

TABLE 19

Compounds 19.1 to 19.221 are compounds of Formula VII which is Formula I with A=R$_4$=R$_5$=R$_6$=H, R$_1$=CH$_3$, X=CH, Y=O, and Z=NOR$_9$, where R$_9$ is C$_2$H$_5$ and R$_2$, R$_3$, and R$_7$ are defined in Table 7.

TABLE 20

Compounds 20.1 to 20.221 are compounds of Formula VIII which is Formula I with A=R$_4$=R$_5$=R$_6$=H, $R_1$=CH$_3$, X=N, Y=O, and Z=NOR$_9$, where R$_9$ is C$_2$H$_5$ and R$_2$, R$_3$, and R$_7$ are defined in Table 7.

TABLE 21

Compounds 21.1 to 21.221 are compounds of Formula IX which is Formula I with A=R$_4$=R$_5$=R$_6$=H, R$_1$=CH$_3$, X=N, Y=NH, and Z=NOR$_9$, where R$_9$ is C$_2$H$_5$ and R$_2$, R$_3$, and R$_7$ are defined in Table 7.

TABLE 22

Compounds 22.1 to 23.139 are compounds of Formula VII which is Formula I with A=R$_4$=R$_5$=R$_6$=H, R$_1$=CH$_3$, X=CH, Y=O, and Z=NOR$_9$, where R$_9$ is CH$_2$Ph and R$_2$, R$_3$, and R$_7$ are defined in Table 10.

TABLE 23

Compounds 23.1 to 23.139 are compounds of Formula VIII which is Formula I with A=R$_4$=R$_5$=R$_6$=H, R$_1$=CH$_3$, X=N, Y=O, and Z=NOR$_9$, where R$_9$ is CH$_2$Ph and R$_2$, R$_3$, and R$_7$ are defined in Table 10.

TABLE 24

Compounds 24.1 to 24.139 are compounds of Formula IX which is Formula I with A=R$_4$=R$_5$=R$_6$=H, R$_1$=CH$_3$, X=N, Y=NH, and Z=NOR$_9$, where R$_9$ is CH$_2$Ph and R$_2$, R$_3$, and R$_7$ are defined in Table 10.

Typical compounds encompassed by the present invention of Formula I include those compounds of Formula X, which is Formula I with A=R$_4$=R$_5$=R$_6$=H, R$_1$=CH$_3$, X=CH, Y=O, Z=NR$_{10}$ and R$_{10}$ is NR$_8$R$_9$, and where R$_2$, R$_3$, R$_7$, R$_8$ and R$_9$ are defined in Table 25.

Formula X

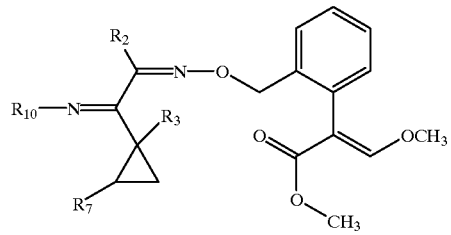

TABLE 25

| Compd | R$_2$ | R$_3$ | R$_7$ | R$_8$ | R$_9$ |
|---|---|---|---|---|---|
| 25.1 | H | H | Ph | CH$_3$ | H |
| 25.2 | H | H | 4-Cl(Ph) | CH$_3$ | H |
| 25.3 | H | H | 4-Br(Ph) | CH$_3$ | H |
| 25.4 | H | H | 4-F(Ph) | CH$_3$ | H |
| 25.5 | H | H | 4-OCH$_3$(Ph) | CH$_3$ | H |
| 25.6 | H | H | 4-CF$_3$(Ph) | CH$_3$ | H |
| 25.7 | H | H | Ph | CH$_3$ | CH$_3$ |
| 25.8 | H | H | 4-Cl(Ph) | CH$_3$ | CH$_3$ |
| 25.9 | H | H | 4-Br(Ph) | CH$_3$ | CH$_3$ |
| 25.10 | H | H | 4-F(Ph) | CH$_3$ | CH$_3$ |
| 25.11 | CH$_3$ | H | Ph | CH$_3$ | H |
| 25.12 | CH$_3$ | H | 2-Cl(Ph) | CH$_3$ | H |
| 25.13 | CH$_3$ | H | 3-Cl(Ph) | CH$_3$ | H |
| 25.14 | CH$_3$ | H | 4-Cl(Ph) | CH$_3$ | H |
| 25.15 | CH$_3$ | H | 2-Br(Ph) | CH$_3$ | H |
| 25.16 | CH$_3$ | H | 3-Br(Ph) | CH$_3$ | H |
| 25.17 | CH$_3$ | H | 4-Br(Ph) | CH$_3$ | H |
| 25.18 | CH$_3$ | H | Ph | CH$_3$ | CH$_3$ |
| 25.19 | CH$_3$ | H | 2-Cl(Ph) | CH$_3$ | CH$_3$ |

TABLE 25-continued

| Compd | R$_2$ | R$_3$ | R$_7$ | R$_8$ | R$_9$ |
|---|---|---|---|---|---|
| 25.20 | CH$_3$ | H | 3-Cl(Ph) | CH$_3$ | CH$_3$ |
| 25.21 | CH$_3$ | H | 4-Cl(Ph) | CH$_3$ | CH$_3$ |
| 25.22 | CH$_3$ | H | 2-Br(Ph) | CH$_3$ | CH$_3$ |
| 25.23 | CH$_3$ | H | 3-Br(Ph) | CH$_3$ | CH$_3$ |
| 25.24 | CH$_3$ | H | 4-Br(Ph) | CH$_3$ | CH$_3$ |
| 25.25 | CH$_3$ | H | 2-CH$_3$(Ph) | CH$_3$ | CH$_3$ |
| 25.26 | CH$_3$ | H | 3-CH$_3$(Ph) | CH$_3$ | CH$_3$ |
| 25.27 | CH$_3$ | H | 2-CF$_3$(Ph) | CH$_3$ | CH$_3$ |
| 25.28 | CH$_3$ | H | 3-CF$_3$(Ph) | CH$_3$ | CH$_3$ |
| 25.29 | CH$_3$ | H | 4-CF$_3$(Ph) | CH$_3$ | CH$_3$ |
| 25.30 | CH$_3$ | H | 2-NO$_2$(Ph) | CH$_3$ | CH$_3$ |
| 25.31 | CH$_3$ | H | 3-NO$_2$(Ph) | CH$_3$ | CH$_3$ |
| 25.32 | CH$_3$ | H | 4-NO$_2$(Ph) | CH$_3$ | CH$_3$ |
| 25.33 | CH$_3$ | H | 2,3-Cl(Ph) | CH$_3$ | CH$_3$ |
| 25.34 | CH$_3$ | H | 2,4-Cl(Ph) | CH$_3$ | CH$_3$ |
| 25.35 | CH$_3$ | H | 2,5-Cl(Ph) | CH$_3$ | CH$_3$ |
| 25.36 | CH$_3$ | H | 2,6-Cl(Ph) | CH$_3$ | CH$_3$ |
| 25.37 | CH$_3$ | H | 3,4-Cl(Ph) | CH$_3$ | CH$_3$ |
| 25.38 | CH$_3$ | H | 3,5-Cl(Ph) | CH$_3$ | CH$_3$ |
| 25.39 | CH$_3$ | H | Ph | C$_2$H$_5$ | CH$_3$ |
| 25.40 | CH$_3$ | H | Ph | n-C$_3$H$_7$ | CH$_3$ |
| 25.41 | CH$_3$ | H | Ph | iso-C$_3$H$_7$ | CH$_3$ |
| 25.42 | CH$_3$ | H | Ph | n-C$_4$H$_9$ | CH$_3$ |
| 25.43 | CH$_3$ | H | Ph | iso-C$_4$H$_9$ | CH$_3$ |
| 25.44 | CH$_3$ | H | Ph | C(CH$_3$)$_3$ | CH$_3$ |
| 25.45 | CH$_3$ | H | Ph | H | COCH$_3$ |
| 25.46 | CH$_3$ | H | 2-Cl(Ph) | H | COCH$_3$ |
| 25.47 | CH$_3$ | H | 3-Cl(Ph) | H | COCH$_3$ |
| 25.48 | CH$_3$ | H | 4-Cl(Ph) | H | COCH$_3$ |
| 25.49 | CH$_3$ | H | 4-Br(Ph) | H | COCH$_3$ |
| 25.50 | CH$_3$ | H | 4-F(Ph) | H | COCH$_3$ |
| 25.51 | CH$_3$ | H | 4-OCH$_3$(Ph) | H | COCH$_3$ |
| 25.52 | CH$_3$ | H | 4-CH$_3$(Ph) | H | COCH$_3$ |
| 25.53 | CH$_3$ | H | 4-NO$_2$(Ph) | H | COCH$_3$ |
| 25.54 | CH$_3$ | H | 2,4-Cl(Ph) | H | COCH$_3$ |
| 25.55 | CH$_3$ | H | 2,4-F(Ph) | H | COCH$_3$ |
| 25.56 | CH$_3$ | H | Ph | CH$_3$ | COCH$_3$ |
| 25.57 | CH$_3$ | H | 2-Cl(Ph) | CH$_3$ | COCH$_3$ |
| 25.58 | CH$_3$ | H | 3-Cl(Ph) | CH$_3$ | COCH$_3$ |
| 25.59 | CH$_3$ | H | 4-Cl(Ph) | CH$_3$ | COCH$_3$ |
| 25.60 | CH$_3$ | H | 4-F(Ph) | CH$_3$ | COCH$_3$ |
| 25.61 | CH$_3$ | H | 3-OCH$_3$(Ph) | CH$_3$ | COCH$_3$ |
| 25.62 | CH$_3$ | H | 4-OCH$_3$(Ph) | CH$_3$ | COCH$_3$ |
| 25.63 | CH$_3$ | H | 4-CH$_3$(Ph) | CH$_3$ | COCH$_3$ |
| 25.64 | CH$_3$ | H | 4-NO$_2$(Ph) | CH$_3$ | COCH$_3$ |
| 25.65 | CH$_3$ | H | 2,4-Cl(Ph) | CH$_3$ | COCH$_3$ |
| 25.66 | CH$_3$ | H | 2,4-F(Ph) | CH$_3$ | COCH$_3$ |
| 25.67 | CH$_3$ | H | Ph | H | COPh |
| 25.68 | CH$_3$ | H | 2-Cl(Ph) | H | COPh |
| 25.69 | CH$_3$ | H | 3-Cl(Ph) | H | COPh |
| 25.70 | CH$_3$ | H | 4-Cl(Ph) | H | COPh |
| 25.71 | CH$_3$ | H | 4-Br(Ph) | H | COPh |
| 25.72 | CH$_3$ | H | 4-F(Ph) | H | COPh |
| 25.73 | CH$_3$ | H | 4-OCH$_3$(Ph) | H | COPh |
| 25.74 | CH$_3$ | H | 4-CH$_3$(Ph) | H | COPh |
| 25.75 | CH$_3$ | H | 4-NO$_2$(Ph) | H | COPh |
| 25.76 | CH$_3$ | H | 2,4-Cl(Ph) | H | COPh |
| 25.77 | CH$_3$ | H | 2,4-F(Ph) | H | COPh |
| 25.78 | CH$_3$ | H | Ph | CH$_3$ | COPh |
| 25.79 | CH$_3$ | H | 2-Cl(Ph) | CH$_3$ | COPh |
| 25.80 | CH$_3$ | H | 3-Cl(Ph) | CH$_3$ | COPh |
| 25.81 | CH$_3$ | H | 4-Cl(Ph) | CH$_3$ | COPh |
| 25.82 | CH$_3$ | H | 4-Br(Ph) | CH$_3$ | COPh |
| 25.83 | CH$_3$ | H | 4-F(Ph) | CH$_3$ | COPh |
| 25.84 | CH$_3$ | H | 4-OCH$_3$(Ph) | CH$_3$ | COPh |
| 25.85 | CH$_3$ | H | 4-CH$_3$(Ph) | CH$_3$ | COPh |
| 25.86 | CH$_3$ | H | 4-NO$_2$(Ph) | CH$_3$ | COPh |
| 25.87 | CH$_3$ | H | 2,4-Cl(Ph) | CH$_3$ | COPh |
| 25.88 | CH$_3$ | H | 2,4-F(Ph) | CH$_3$ | COPh |
| 25.89 | C$_2$H$_5$ | H | Ph | H | COCH$_3$ |
| 25.90 | C$_2$H$_5$ | H | 2-Cl(Ph) | H | COCH$_3$ |
| 25.91 | C$_2$H$_5$ | H | 3-Cl(Ph) | H | COCH$_3$ |
| 25.92 | C$_2$H$_5$ | H | 4-Cl(Ph) | H | COCH$_3$ |
| 25.93 | C$_2$H$_5$ | H | 4-F(Ph) | H | COCH$_3$ |
| 25.94 | C$_2$H$_5$ | H | 3-OCH$_3$(Ph) | H | COCH$_3$ |
| 25.95 | C$_2$H$_5$ | H | 4-OCH$_3$(Ph) | H | COCH$_3$ |
| 25.96 | C$_2$H$_5$ | H | 4-CH$_3$(Ph) | H | COCH$_3$ |

TABLE 25-continued

| Compd | R₂ | R₃ | R₇ | R₈ | R₉ |
|---|---|---|---|---|---|
| 25.97 | C₂H₅ | H | 4-NO₂(Ph) | H | COCH₃ |
| 25.98 | C₂H₅ | H | 2,4-Cl(Ph) | H | COCH₃ |
| 25.99 | C₂H₅ | H | 2,4-F(Ph) | H | COCH₃ |
| 25.100 | C₂H₅ | H | Ph | CH₃ | COCH₃ |
| 25.101 | C₂H₅ | H | 2-Cl(Ph) | CH₃ | COCH₃ |
| 25.102 | C₂H₅ | H | 3-Cl(Ph) | CH₃ | COCH₃ |
| 25.103 | C₂H₅ | H | 4-Cl(Ph) | CH₃ | COCH₃ |
| 25.104 | C₂H₅ | H | 4-F(Ph) | CH₃ | COCH₃ |
| 25.105 | C₂H₅ | H | 3-OCH₃(Ph) | CH₃ | COCH₃ |
| 25.106 | C₂H₅ | H | 4-OCH₃(Ph) | CH₃ | COCH₃ |
| 25.107 | C₂H₅ | H | 4-CH₃(Ph) | CH₃ | COCH₃ |
| 25.108 | C₂H₅ | H | 4-NO₂(Ph) | CH₃ | COCH₃ |
| 25.109 | C₂H₅ | H | 2,4-Cl(Ph) | CH₃ | COCH₃ |
| 25.110 | C₂H₅ | H | 2,4-F(Ph) | CH₃ | COCH₃ |
| 25.111 | C₂H₅ | H | Ph | H | COPh |
| 25.112 | C₂H₅ | H | 2-Cl(Ph) | H | COPh |
| 25.113 | C₂H₅ | H | 3-Cl(Ph) | H | COPh |
| 25.114 | C₂H₅ | H | 4-Cl(Ph) | H | COPh |
| 25.115 | C₂H₅ | H | 4-Br(Ph) | H | COPh |
| 25.116 | C₂H₅ | H | 3-OCH₃(Ph) | H | COPh |
| 25.117 | C₂H₅ | H | 4-OCH₃(Ph) | H | COPh |
| 25.118 | C₂H₅ | H | 4-CH₃(Ph) | H | COPh |
| 25.119 | C₂H₅ | H | 4-NO₂(Ph) | H | COPh |
| 25.120 | C₂H₅ | H | 2,4-Cl(Ph) | H | COPh |
| 25.121 | C₂H₅ | H | 2,4-F(Ph) | H | COPh |
| 25.122 | C₂H₅ | H | Ph | CH₃ | COPh |
| 25.123 | C₂H₅ | H | 2-Cl(Ph) | CH₃ | COPh |
| 25.124 | C₂H₅ | H | 3-Cl(Ph) | CH₃ | COPh |
| 25.125 | C₂H₅ | H | 4-Cl(Ph) | CH₃ | COPh |
| 25.126 | C₂H₅ | H | 4-Br(Ph) | CH₃ | COPh |
| 25.127 | C₂H₅ | H | 4-F(Ph) | CH₃ | COPh |
| 25.128 | C₂H₅ | H | 4-OCH₃(Ph) | CH₃ | COPh |
| 25.129 | C₂H₅ | H | 4-CH₃(Ph) | CH₃ | COPh |
| 25.130 | C₂H₅ | H | 4-NO₂(Ph) | CH₃ | COPh |
| 25.131 | C₂H₅ | H | 2,4-Cl(Ph) | CH₃ | COPh |
| 25.132 | C₂H₅ | H | 2,4-F(Ph) | CH₃ | COPh |
| 25.133 | CH₃ | H | Ph | C₂H₅ | COCH₃ |
| 25.134 | CH₃ | H | Ph | n-C₃H₇ | COCH₃ |
| 25.135 | CH₃ | H | Ph | iso-C₃H₇ | COCH₃ |
| 25.136 | CH₃ | H | Ph | n-C₄H₉ | COCH₃ |
| 25.137 | CH₃ | H | Ph | iso-C₄H₉ | COCH₃ |
| 25.138 | CH₃ | H | Ph | C(CH₃)₃ | COCH₃ |
| 25.139 | CH₃ | H | 4-Cl(Ph) | C₂H₅ | COCH₃ |
| 25.140 | CH₃ | H | 4-Cl(Ph) | n-C₃H₇ | COCH₃ |
| 25.141 | CH₃ | H | 4-Cl(Ph) | iso-C₃H₇ | COCH₃ |
| 25.142 | CH₃ | H | 4-Cl(Ph) | n-C₄H₉ | COCH₃ |
| 25.143 | CH₃ | H | 4-Cl(Ph) | iso-C₄H₉ | COCH₃ |
| 25.144 | CH₃ | H | 4-Cl(Ph) | C(CH₃)₃ | COCH₃ |
| 25.145 | CH₃ | H | Ph | C₂H₅ | COPh |
| 25.146 | CH₃ | H | Ph | n-C₃H₇ | COPh |
| 25.147 | CH₃ | H | Ph | iso-C₃H₇ | COPh |
| 25.148 | CH₃ | H | Ph | n-C₄H₉ | COPh |
| 25.149 | CH₃ | H | Ph | C(CH₃)₃ | COPh |
| 25.150 | CH₃ | H | 4-Cl(Ph) | CH₃ | COCH₂Ph |
| 25.151 | CH₃ | H | 4-Br(Ph) | CH₃ | COCH₂Ph |
| 25.152 | CH₃ | H | 4-F(Ph) | CH₃ | COCH₂Ph |
| 25.153 | CH₃ | H | 4-OCH₃(Ph) | CH₃ | COCH₂Ph |
| 25.154 | CH₃ | H | 4-CH₃(Ph) | CH₃ | COCH₂Ph |
| 25.155 | CH₃ | H | 4-NO₂(Ph) | CH₃ | COCH₂Ph |
| 25.156 | CH₃ | H | 2,4-Cl(Ph) | CH₃ | COCH₂Ph |
| 25.157 | CH₃ | H | 2,4-F(Ph) | CH₃ | COCH₂Ph |
| 25.158 | CH₃ | H | 4-Cl(Ph) | C₂H₅ | COCH₂Ph |
| 25.159 | CH₃ | H | 4-Br(Ph) | n-C₃H₇ | COCH₂Ph |
| 25.160 | CH₃ | H | 4-F(Ph) | iso-C₃H₇ | COCH₂Ph |
| 25.161 | CH₃ | H | 4-OCH₃(Ph) | n-C₄H₉ | COCH₂Ph |
| 25.162 | CH₃ | H | 4-CH₃(Ph) | iso-C₄H₉ | COCH₂Ph |
| 25.163 | CH₃ | H | 4-NO₂(Ph) | C(CH₃)₃ | COCH₂Ph |
| 25.164 | Ph | H | Ph | CH₃ | H |
| 25.165 | Ph | H | 2-Cl(Ph) | CH₃ | H |
| 25.166 | Ph | H | 3-Cl(Ph) | CH₃ | H |
| 25.167 | Ph | H | 4-Cl(Ph) | CH₃ | H |
| 25.168 | Ph | H | 4-Br(Ph) | CH₃ | H |
| 25.169 | Ph | H | 4-F(Ph) | CH₃ | H |
| 25.170 | Ph | H | 4-OCH₃(Ph) | CH₃ | H |
| 25.171 | Ph | H | 4-CH₃(Ph) | CH₃ | H |
| 25.172 | Ph | H | 4-NO₂(Ph) | CH₃ | H |
| 25.173 | Ph | H | 2,4-Cl(Ph) | CH₃ | H |
| 25.174 | Ph | H | Ph | CH₃ | CH₃ |
| 25.175 | Ph | H | 2-Cl(Ph) | CH₃ | CH₃ |
| 25.176 | Ph | H | 3-Cl(Ph) | CH₃ | CH₃ |
| 25.177 | Ph | H | 4-Cl(Ph) | CH₃ | CH₃ |
| 25.178 | Ph | H | 4-Br(Ph) | CH₃ | CH₃ |
| 25.179 | Ph | H | 4-F(Ph) | CH₃ | CH₃ |
| 25.180 | CN | H | 4-Cl(Ph) | CH₃ | H |
| 25.181 | CN | H | 4-Br(Ph) | CH₃ | H |
| 25.182 | CN | H | 4-F(Ph) | CH₃ | H |
| 25.183 | CN | H | 4-OCH₃(Ph) | CH₃ | H |
| 25.184 | CN | H | 4-CH₃(Ph) | CH₃ | H |
| 25.185 | CN | H | 4-NO₂(Ph) | CH₃ | H |
| 25.186 | CN | H | 2,4-Cl(Ph) | CH₃ | H |
| 25.187 | CN | H | 2,4-F(Ph) | CH₃ | H |
| 25.188 | CN | H | 4-CF₃(Ph) | CH₃ | H |
| 25.189 | CN | H | Ph | CH₃ | CH₃ |
| 25.190 | CN | H | Ph | CH₃ | COCH₃ |
| 25.191 | H | H | 1-napthyl | CH₃ | H |
| 25.192 | H | H | 1-napthyl | CH₃ | CH₃ |
| 25.193 | H | H | 1-napthyl | CH₃ | COCH₃ |
| 25.194 | H | H | 1-napthyl | CH₃ | COPh |
| 25.195 | CH₃ | H | 1-napthyl | CH₃ | H |
| 25.196 | CH₃ | H | 1-napthyl | CH₃ | CH₃ |
| 25.197 | CH₃ | H | 1-napthyl | CH₃ | COCH₃ |
| 25.198 | CH₃ | H | 1-napthyl | CH₃ | COPh |
| 25.199 | CH₃ | H | 1-napthyl | CH₃ | COCH₂Ph |
| 25.200 | H | H | 1-napthyl | CH₃ | CO₂CH₃ |
| 25.201 | CH₃ | H | 1-napthyl | CH₃ | CO₂CH₃ |
| 25.202 | H | H | 2-napthyl | CH₃ | H |
| 25.203 | H | H | 2-napthyl | CH₃ | CH₃ |
| 25.204 | H | H | 2-napthyl | CH₃ | COCH₃ |
| 25.205 | H | H | 2-napthyl | CH₃ | COPh |
| 25.206 | CH₃ | H | 2-napthyl | CH₃ | H |
| 25.207 | CH₃ | H | 2-napthyl | CH₃ | CH₃ |
| 25.208 | CH₃ | H | 2-napthyl | CH₃ | COCH₃ |
| 25.209 | CH₃ | H | 2-napthyl | CH₃ | COPh |
| 25.210 | CH₃ | H | 2-napthyl | CH₃ | COCH₂Ph |
| 25.211 | H | H | 2-napthyl | CH₃ | CO₂CH₃ |
| 25.212 | CH₃ | H | 2-napthyl | CH₃ | CO₂CH₃ |
| 25.213 | H | CH₃ | Ph | CH₃ | H |
| 25.214 | H | CH₃ | 4-Cl(Ph) | CH₃ | H |
| 25.215 | H | CH₃ | 4-Br(Ph) | CH₃ | H |
| 25.216 | H | CH₃ | 4-F(Ph) | CH₃ | H |
| 25.217 | H | CH₃ | 4-OCH₃(Ph) | CH₃ | H |
| 25.218 | H | CH₃ | 4-CF₃(Ph) | CH₃ | H |
| 25.219 | H | CH₃ | Ph | CH₃ | CH₃ |
| 25.220 | H | CH₃ | 4-Cl(Ph) | CH₃ | CH₃ |
| 25.221 | H | CH₃ | 4-Br(Ph) | CH₃ | CH₃ |
| 25.222 | H | CH₃ | 4-F(Ph) | CH₃ | CH₃ |
| 25.223 | H | CH₃ | 4-OCH₃(Ph) | CH₃ | CH₃ |
| 25.224 | H | CH₃ | 4-CF₃(Ph) | CH₃ | CH₃ |
| 25.225 | H | CH₃ | Ph | CH₃ | C₂H₅ |
| 25.226 | H | CH₃ | 4-Cl(Ph) | CH₃ | n-C₃H₇ |
| 25.227 | H | CH₃ | 4-Br(Ph) | CH₃ | iso-C₃H₇ |
| 25.228 | H | CH₃ | 4-F(Ph) | CH₃ | n-C₄H₉ |
| 25.229 | H | CH₃ | 4-OCH₃(Ph) | CH₃ | iso-C₄H₉ |
| 25.230 | H | CH₃ | 4-CH₃(Ph) | CH₃ | C(CH₃)₃ |
| 25.231 | H | CH₃ | 4-NO₂(Ph) | CH₃ | CH₃ |
| 25.232 | H | CH₃ | 2,4-Cl(Ph) | CH₃ | CH₃ |
| 25.233 | H | CH₃ | Ph | CH₃ | COCH₃ |
| 25.234 | H | CH₃ | 4-Cl(Ph) | CH₃ | COCH₃ |
| 25.235 | H | CH₃ | 4-Br(Ph) | CH₃ | COCH₃ |
| 25.236 | H | CH₃ | 4-F(Ph) | CH₃ | COCH₃ |
| 25.237 | H | CH₃ | 4-OCH₃(Ph) | CH₃ | COCH₃ |
| 25.238 | H | CH₃ | 4-CH₃(Ph) | CH₃ | COCH₃ |
| 25.239 | H | CH₃ | 4-NO₂(Ph) | CH₃ | COCH₃ |
| 25.240 | H | CH₃ | 2,4-Cl(Ph) | CH₃ | COCH₃ |
| 25.241 | H | CH₃ | Ph | CH₃ | COPh |
| 25.242 | H | CH₃ | 4-Cl(Ph) | CH₃ | COPh |
| 25.243 | H | CH₃ | 4-Br(Ph) | CH₃ | COPh |
| 25.244 | H | CH₃ | 4-F(Ph) | CH₃ | COPh |
| 25.245 | H | CH₃ | 4-OCH₃(Ph) | CH₃ | COPh |
| 25.246 | H | CH₃ | 4-CH₃(Ph) | CH₃ | COPh |
| 25.247 | H | CH₃ | 4-NO₂(Ph) | CH₃ | COPh |
| 25.248 | H | CH₃ | 2,4-Cl(Ph) | CH₃ | COPh |
| 25.249 | CH₃ | CH₃ | Ph | CH₃ | H |
| 25.250 | CH₃ | CH₃ | 4-Cl(Ph) | CH₃ | H |

TABLE 25-continued

| Compd | R2 | R3 | R7 | R8 | R9 |
|---|---|---|---|---|---|
| 25.251 | $CH_3$ | $CH_3$ | 4-Br(Ph) | $CH_3$ | H |
| 25.252 | $CH_3$ | $CH_3$ | 4-F(Ph) | $CH_3$ | H |
| 25.253 | $CH_3$ | $CH_3$ | 4-$OCH_3$(Ph) | $CH_3$ | H |
| 25.254 | $CH_3$ | $CH_3$ | 4-$CH_3$(Ph) | $CH_3$ | H |
| 25.255 | $CH_3$ | $CH_3$ | 4-$NO_2$(Ph) | $CH_3$ | H |
| 25.256 | $CH_3$ | $CH_3$ | 2,4-Cl(Ph) | $CH_3$ | H |
| 25.257 | $CH_3$ | $CH_3$ | Ph | $CH_3$ | $COCH_3$ |
| 25.258 | $CH_3$ | $CH_3$ | 4-Cl(Ph) | $CH_3$ | $COCH_3$ |
| 25.259 | $CH_3$ | $CH_3$ | 4-Br(Ph) | $CH_3$ | $COCH_3$ |
| 25.260 | $CH_3$ | $CH_3$ | 4-F(Ph) | $CH_3$ | $COCH_3$ |
| 25.261 | $CH_3$ | $CH_3$ | 4-$OCH_3$(Ph) | $CH_3$ | $COCH_3$ |
| 25.262 | $CH_3$ | $CH_3$ | 4-$CH_3$(Ph) | $CH_3$ | $COCH_3$ |
| 25.263 | $CH_3$ | $CH_3$ | 4-$NO_2$(Ph) | $CH_3$ | $COCH_3$ |
| 25.264 | $CH_3$ | $CH_3$ | 2,4-Cl(Ph) | $CH_3$ | $COCH_3$ |
| 25.265 | CN | $CH_3$ | Ph | $CH_3$ | H |
| 25.266 | CN | $CH_3$ | 4-Cl(Ph) | $CH_3$ | H |
| 25.267 | CN | $CH_3$ | 4-Br(Ph) | $CH_3$ | H |
| 25.268 | CN | $CH_3$ | 4-F(Ph) | $CH_3$ | H |
| 25.269 | CN | $CH_3$ | 4-$OCH_3$(Ph) | $CH_3$ | H |
| 25.270 | CN | $CH_3$ | 4-$CH_3$(Ph) | $CH_3$ | H |
| 25.271 | CN | $CH_3$ | 4-$NO_2$(Ph) | $CH_3$ | H |
| 25.272 | CN | $CH_3$ | 2,4-Cl(Ph) | $CH_3$ | H |
| 25.273 | CN | $CH_3$ | Ph | $CH_3$ | $CH_3$ |
| 25.274 | CN | $CH_3$ | 4-Cl(Ph) | $CH_3$ | $CH_3$ |
| 25.275 | CN | $CH_3$ | 4-Br(Ph) | $CH_3$ | $CH_3$ |
| 25.276 | CN | $CH_3$ | 4-F(Ph) | $CH_3$ | $CH_3$ |
| 25.277 | CN | $CH_3$ | 4-$OCH_3$(Ph) | $CH_3$ | $CH_3$ |
| 25.278 | CN | $CH_3$ | 4-$CH_3$(Ph) | $CH_3$ | $CH_3$ |
| 25.279 | CN | $CH_3$ | 4-$NO_2$(Ph) | $CH_3$ | $CH_3$ |
| 25.280 | CN | $CH_3$ | 2,4-Cl(Ph) | $CH_3$ | $CH_3$ |
| 25.281 | CN | $CH_3$ | Ph | $CH_3$ | $COCH_3$ |
| 25.282 | CN | $CH_3$ | 4-Cl(Ph) | $CH_3$ | $COCH_3$ |
| 25.283 | CN | $CH_3$ | 4-Br(Ph) | $CH_3$ | $COCH_3$ |
| 25.284 | CN | $CH_3$ | 4-F(Ph) | $CH_3$ | $COCH_3$ |
| 25.285 | CN | $CH_3$ | 4-$OCH_3$(Ph) | $CH_3$ | $COCH_3$ |
| 25.286 | CN | $CH_3$ | 4-$CH_3$(Ph) | $CH_3$ | $COCH_3$ |
| 25.287 | CN | $CH_3$ | 4-$NO_2$(Ph) | $CH_3$ | $COCH_3$ |
| 25.288 | CN | $CH_3$ | 2,4-Cl(Ph) | $CH_3$ | $COCH_3$ |
| 25.289 | CN | $CH_3$ | Ph | $CH_3$ | COPh |
| 25.290 | CN | $CH_3$ | 4-Cl(Ph) | $CH_3$ | COPh |
| 25.291 | CN | $CH_3$ | 4-Br(Ph) | $CH_3$ | COPh |
| 25.292 | CN | $CH_3$ | 4-F(Ph) | $CH_3$ | COPh |
| 25.293 | CN | $CH_3$ | 4-$NO_2$(Ph) | $CH_3$ | COPh |
| 25.294 | CN | $CH_3$ | 2,4-Cl(Ph) | $CH_3$ | COPh |
| 25.295 | CN | $CH_3$ | 2,4-F(Ph) | $CH_3$ | COPh |
| 25.296 | CN | H | Ph | $C_2H_5$ | H |
| 25.297 | CN | H | 2-Cl(Ph) | n-$C_3H_7$ | H |
| 25.298 | CN | H | 3-Cl(Ph) | iso-$C_3H_7$ | H |
| 25.299 | CN | H | 4-Cl(Ph) | n-$C_4H_9$ | H |
| 25.300 | CN | H | 4-Br(Ph) | iso-$C_4H_9$ | H |
| 25.301 | CN | H | 4-F(Ph) | $C(CH_3)_3$ | H |
| 25.302 | CN | H | 4-$OCH_3$(Ph) | $C_2H_5$ | $COCH_3$ |
| 25.303 | CN | H | 4-$CH_3$(Ph) | n-$C_3H_7$ | $COCH_3$ |
| 25.304 | CN | H | 4-$NO_2$(Ph) | iso-$C_3H_7$ | $COCH_3$ |
| 25.305 | CN | H | 2,4-Cl(Ph) | n-$C_4H_9$ | $COCH_3$ |
| 25.306 | CN | H | 2,4-F(Ph) | iso-$C_4H_9$ | $COCH_3$ |
| 25.307 | CN | H | Ph | $C(CH_3)_3$ | $COCH_3$ |
| 25.308 | CN | H | 2-Cl(Ph) | $C_2H_5$ | COPh |
| 25.309 | CN | H | 3-Cl(Ph) | n-$C_3H_7$ | COPh |
| 25.310 | CN | H | 4-Cl(Ph) | iso-$C_3H_7$ | COPh |
| 25.311 | $CH_3$ | H | 4-Br(Ph) | n-$C_4H_9$ | COPh |
| 25.312 | $CH_3$ | H | 4-F(Ph) | iso-$C_4H_9$ | COPh |
| 25.313 | $CH_3$ | H | 4-$OCH_3$(Ph) | $C(CH_3)_3$ | COPh |

Typical compounds encompassed by the present invention of Formula I include those compounds of Formula XI, which is Formula I with A=$R_4$=$R_5$=$R_6$=H, $R_1$=$CH_3$, X=N, Y=O, Z=$NR_{10}$ and $R_{10}$ is $NR_8R_9$, and where $R_2$, $R_3$, $R_7$, $R_8$ and $R_9$ are defined in Table 26.

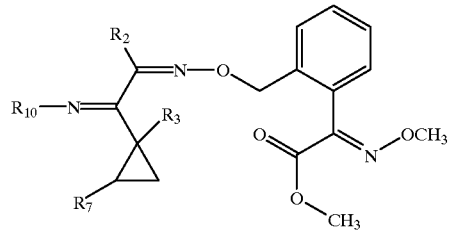

Formula XI

TABLE 26

| Compd | R2 | R3 | R7 | R8 | R9 |
|---|---|---|---|---|---|
| 26.1 | H | H | Ph | $CH_3$ | H |
| 26.2 | H | H | 4-Cl(Ph) | $CH_3$ | H |
| 26.3 | H | H | 4-Br(Ph) | $CH_3$ | H |
| 26.4 | H | H | 4-F(Ph) | $CH_3$ | H |
| 26.5 | H | H | 4-$OCH_3$(Ph) | $CH_3$ | H |
| 26.6 | H | H | 4-$CF_3$(Ph) | $CH_3$ | H |
| 26.7 | H | H | Ph | $CH_3$ | $CH_3$ |
| 26.8 | H | H | 4-Cl(Ph) | $CH_3$ | $CH_3$ |
| 26.9 | H | H | 4-Br(Ph) | $CH_3$ | $CH_3$ |
| 26.10 | H | H | 4-F(Ph) | $CH_3$ | $CH_3$ |
| 26.11 | $CH_3$ | H | Ph | $CH_3$ | H |
| 26.12 | $CH_3$ | H | 2-Cl(Ph) | $CH_3$ | H |
| 26.13 | $CH_3$ | H | 3-Cl(Ph) | $CH_3$ | H |
| 26.14 | $CH_3$ | H | 4-Cl(Ph) | $CH_3$ | H |
| 26.15 | $CH_3$ | H | 2-Br(Ph) | $CH_3$ | H |
| 26.16 | $CH_3$ | H | 3-Br(Ph) | $CH_3$ | H |
| 26.17 | $CH_3$ | H | 4-Br(Ph) | $CH_3$ | H |
| 26.18 | $CH_3$ | H | Ph | $CH_3$ | $CH_3$ |
| 26.19 | $CH_3$ | H | 2-Cl(Ph) | $CH_3$ | $CH_3$ |
| 26.20 | $CH_3$ | H | 3-Cl(Ph) | $CH_3$ | $CH_3$ |
| 26.21 | $CH_3$ | H | 4-Cl(Ph) | $CH_3$ | $CH_3$ |
| 26.22 | $CH_3$ | H | 2-Br(Ph) | $CH_3$ | $CH_3$ |
| 26.23 | $CH_3$ | H | 3-Br(Ph) | $CH_3$ | $CH_3$ |
| 26.24 | $CH_3$ | H | 4-Br(Ph) | $CH_3$ | $CH_3$ |
| 26.25 | $CH_3$ | H | 2-$CH_3$(Ph) | $CH_3$ | $CH_3$ |
| 26.26 | $CH_3$ | H | 3-$CH_3$(Ph) | $CH_3$ | $CH_3$ |
| 26.27 | $CH_3$ | H | 2-$CF_3$(Ph) | $CH_3$ | $CH_3$ |
| 26.28 | $CH_3$ | H | 3-$CF_3$(Ph) | $CH_3$ | $CH_3$ |
| 26.29 | $CH_3$ | H | 4-$CF_3$(Ph) | $CH_3$ | $CH_3$ |
| 26.30 | $CH_3$ | H | 2-$NO_2$(Ph) | $CH_3$ | $CH_3$ |
| 26.31 | $CH_3$ | H | 3-$NO_2$(Ph) | $CH_3$ | $CH_3$ |
| 26.32 | $CH_3$ | H | 4-$NO_2$(Ph) | $CH_3$ | $CH_3$ |
| 26.33 | $CH_3$ | H | 2,3-Cl(Ph) | $CH_3$ | $CH_3$ |
| 26.34 | $CH_3$ | H | 2,4-Cl(Ph) | $CH_3$ | $CH_3$ |
| 26.35 | $CH_3$ | H | 2,5-Cl(Ph) | $CH_3$ | $CH_3$ |
| 26.36 | $CH_3$ | H | 2,6-Cl(Ph) | $CH_3$ | $CH_3$ |
| 26.37 | $CH_3$ | H | 3,4-Cl(Ph) | $CH_3$ | $CH_3$ |
| 26.38 | $CH_3$ | H | 3,5-Cl(Ph) | $CH_3$ | $CH_3$ |
| 26.39 | $CH_3$ | H | Ph | $C_2H_5$ | $CH_3$ |
| 26.40 | $CH_3$ | H | Ph | n-$C_3H_7$ | $CH_3$ |
| 26.41 | $CH_3$ | H | Ph | iso-$C_3H_7$ | $CH_3$ |
| 26.42 | $CH_3$ | H | Ph | n-$C_4H_9$ | $CH_3$ |
| 26.43 | $CH_3$ | H | Ph | iSO-$C_4H_9$ | $CH_3$ |
| 26.44 | $CH_3$ | H | Ph | $C(CH_3)_3$ | $CH_3$ |
| 26.45 | $CH_3$ | H | Ph | H | $COCH_3$ |
| 26.46 | $CH_3$ | H | 2-Cl(Ph) | H | $COCH_3$ |
| 26.47 | $CH_3$ | H | 3-Cl(Ph) | H | $COCH_3$ |
| 26.48 | $CH_3$ | H | 4-Cl(Ph) | H | $COCH_3$ |
| 26.49 | $CH_3$ | H | 4-Br(Ph) | H | $COCH_3$ |
| 26.50 | $CH_3$ | H | 4-F(Ph) | H | $COCH_3$ |
| 26.51 | $CH_3$ | H | 4-$OCH_3$(Ph) | H | $COCH_3$ |
| 26.52 | $CH_3$ | H | 4-$CH_3$(Ph) | H | $COCH_3$ |
| 26.53 | $CH_3$ | H | 4-$NO_2$(Ph) | H | $COCH_3$ |
| 26.54 | $CH_3$ | H | 2,4-Cl(Ph) | H | $COCH_3$ |
| 26.55 | $CH_3$ | H | 2,4-F(Ph) | H | $COCH_3$ |
| 26.56 | $CH_3$ | H | Ph | $CH_3$ | $COCH_3$ |
| 26.57 | $CH_3$ | H | 2-Cl(Ph) | $CH_3$ | $COCH_3$ |
| 26.58 | $CH_3$ | H | 3-Cl(Ph) | $CH_3$ | $COCH_3$ |
| 26.59 | $CH_3$ | H | 4-Cl(Ph) | $CH_3$ | $COCH_3$ |
| 26.60 | $CH_3$ | H | 4-F(Ph) | $CH_3$ | $COCH_3$ |
| 26.61 | $CH_3$ | H | 3-$OCH_3$(Ph) | $CH_3$ | $COCH_3$ |

TABLE 26-continued

| Compd | R$_2$ | R$_3$ | R$_7$ | R$_8$ | R$_9$ |
|---|---|---|---|---|---|
| 26.62 | CH$_3$ | H | 4-OCH$_3$(Ph) | CH$_3$ | COCH$_3$ |
| 26.63 | CH$_3$ | H | 4-CH$_3$(Ph) | CH$_3$ | COCH$_3$ |
| 26.64 | CH$_3$ | H | 4-NO$_2$(Ph) | CH$_3$ | COCH$_3$ |
| 26.65 | CH$_3$ | H | 2,4-Cl(Ph) | CH$_3$ | COCH$_3$ |
| 26.66 | CH$_3$ | H | 2,4-F(Ph) | CH$_3$ | COCH$_3$ |
| 26.67 | CH$_3$ | H | Ph | H | COPh |
| 26.68 | CH$_3$ | H | 2-Cl(Ph) | H | COPh |
| 26.69 | CH$_3$ | H | 3-Cl(Ph) | H | COPh |
| 26.70 | CH$_3$ | H | 4-Cl(Ph) | H | COPh |
| 26.71 | CH$_3$ | H | 4-Br(Ph) | H | COPh |
| 26.72 | CH$_3$ | H | 4-F(Ph) | H | COPh |
| 26.73 | CH$_3$ | H | 4-OCH$_3$(Ph) | H | COPh |
| 26.74 | CH$_3$ | H | 4-CH$_3$(Ph) | H | COPh |
| 26.75 | CH$_3$ | H | 4-NO$_2$(Ph) | H | COPh |
| 26.76 | CH$_3$ | H | 2,4-Cl(Ph) | H | COPh |
| 26.77 | CH$_3$ | H | 2,4-F(Ph) | H | COPh |
| 26.78 | CH$_3$ | H | Ph | CH$_3$ | COPh |
| 26.79 | CH$_3$ | H | 2-Cl(Ph) | CH$_3$ | COPh |
| 26.80 | CH$_3$ | H | 3-Cl(Ph) | CH$_3$ | COPh |
| 26.81 | CH$_3$ | H | 4-Cl(Ph) | CH$_3$ | COPh |
| 26.82 | CH$_3$ | H | 4-Br(Ph) | CH$_3$ | COPh |
| 26.83 | CH$_3$ | H | 4-F(Ph) | CH$_3$ | COPh |
| 26.84 | CH$_3$ | H | 4-OCH$_3$(Ph) | CH$_3$ | COPh |
| 26.85 | CH$_3$ | H | 4-CH$_3$(Ph) | CH$_3$ | COPh |
| 26.86 | CH$_3$ | H | 4-NO$_2$(Ph) | CH$_3$ | COPh |
| 26.87 | CH$_3$ | H | 2,4-Cl(Ph) | CH$_3$ | COPh |
| 26.88 | CH$_3$ | H | 2,4-F(Ph) | CH$_3$ | COPh |
| 26.89 | C$_2$H$_5$ | H | Ph | H | COCH$_3$ |
| 26.90 | C$_2$H$_5$ | H | 2-Cl(Ph) | H | COCH$_3$ |
| 26.91 | C$_2$H$_5$ | H | 3-Cl(Ph) | H | COCH$_3$ |
| 26.92 | C$_2$H$_5$ | H | 4-Cl(Ph) | H | COCH$_3$ |
| 26.93 | C$_2$H$_5$ | H | 4-F(Ph) | H | COCH$_3$ |
| 26.94 | C$_2$H$_5$ | H | 3-OCH$_3$(Ph) | H | COCH$_3$ |
| 26.95 | C$_2$H$_5$ | H | 4-OCH$_3$(Ph) | H | COCH$_3$ |
| 26.96 | C$_2$H$_5$ | H | 4-CH$_3$(Ph) | H | COCH$_3$ |
| 26.97 | C$_2$H$_5$ | H | 4-NO$_2$(Ph) | H | COCH$_3$ |
| 26.98 | C$_2$H$_5$ | H | 2,4-Cl(Ph) | H | COCH$_3$ |
| 26.99 | C$_2$H$_5$ | H | 2,4-F(Ph) | H | COCH$_3$ |
| 26.100 | C$_2$H$_5$ | H | Ph | CH$_3$ | COCH$_3$ |
| 26.101 | C$_2$H$_5$ | H | 2-Cl(Ph) | CH$_3$ | COCH$_3$ |
| 26.102 | C$_2$H$_5$ | H | 3-Cl(Ph) | CH$_3$ | COCH$_3$ |
| 26.103 | C$_2$H$_5$ | H | 4-Cl(Ph) | CH$_3$ | COCH$_3$ |
| 26.104 | C$_2$H$_5$ | H | 4-F(Ph) | CH$_3$ | COCH$_3$ |
| 26.105 | C$_2$H$_5$ | H | 3-OCH$_3$(Ph) | CH$_3$ | COCH$_3$ |
| 26.106 | C$_2$H$_5$ | H | 4-OCH$_3$(Ph) | CH$_3$ | COCH$_3$ |
| 26.107 | C$_2$H$_5$ | H | 4-CH$_3$(Ph) | CH$_3$ | COCH$_3$ |
| 26.108 | C$_2$H$_5$ | H | 4-NO$_2$(Ph) | CH$_3$ | COCH$_3$ |
| 26.109 | C$_2$H$_5$ | H | 2,4-Cl(Ph) | CH$_3$ | COCH$_3$ |
| 26.110 | C$_2$H$_5$ | H | 2,4-F(Ph) | CH$_3$ | COCH$_3$ |
| 26.111 | C$_2$H$_5$ | H | Ph | H | COPh |
| 26.112 | C$_2$H$_5$ | H | 2-Cl(Ph) | H | COPh |
| 26.113 | C$_2$H$_5$ | H | 3-Cl(Ph) | H | COPh |
| 26.114 | C$_2$H$_5$ | H | 4-Cl(Ph) | H | COPh |
| 26.115 | C$_2$H$_5$ | H | 4-Br(Ph) | H | COPh |
| 26.116 | C$_2$H$_5$ | H | 3-OCH$_3$(Ph) | H | COPh |
| 26.117 | C$_2$H$_5$ | H | 4-OCH$_3$(Ph) | H | COPh |
| 26.118 | C$_2$H$_5$ | H | 4-CH$_3$(Ph) | H | COPh |
| 26.119 | C$_2$H$_5$ | H | 4-NO$_2$(Ph) | H | COPh |
| 26.120 | C$_2$H$_5$ | H | 2,4-Cl(Ph) | H | COPh |
| 26.121 | C$_2$H$_5$ | H | 2,4-F(Ph) | H | COPh |
| 26.122 | C$_2$H$_5$ | H | Ph | CH$_3$ | COPh |
| 26.123 | C$_2$H$_5$ | H | 2-Cl(Ph) | CH$_3$ | COPh |
| 26.124 | C$_2$H$_5$ | H | 3-Cl(Ph) | CH$_3$ | COPh |
| 26.125 | C$_2$H$_5$ | H | 4-Cl(Ph) | CH$_3$ | COPh |
| 26.126 | C$_2$H$_5$ | H | 4-Br(Ph) | CH$_3$ | COPh |
| 26.127 | C$_2$H$_5$ | H | 4-F(Ph) | CH$_3$ | COPh |
| 26.128 | C$_2$H$_5$ | H | 4-OCH$_3$(Ph) | CH$_3$ | COPh |
| 26.129 | C$_2$H$_5$ | H | 4-CH$_3$(Ph) | CH$_3$ | COPh |
| 26.130 | C$_2$H$_5$ | H | 4-NO$_2$(Ph) | CH$_3$ | COPh |
| 26.131 | C$_2$H$_5$ | H | 2,4-Cl(Ph) | CH$_3$ | COPh |
| 26.132 | C$_2$H$_5$ | H | 2,4-F(Ph) | CH$_3$ | COPh |
| 26.133 | CH$_3$ | H | Ph | C$_2$H$_5$ | COCH$_3$ |
| 26.134 | CH$_3$ | H | Ph | n-C$_3$H$_7$ | COCH$_3$ |
| 26.135 | CH$_3$ | H | Ph | iso-C$_3$H$_7$ | COCH$_3$ |
| 26.136 | CH$_3$ | H | Ph | n-C$_4$H$_9$ | COCH$_3$ |
| 26.137 | CH$_3$ | H | Ph | iso-C$_4$H$_9$ | COCH$_3$ |
| 26.138 | CH$_3$ | H | Ph | C(CH$_3$)$_3$ | COCH$_3$ |
| 26.139 | CH$_3$ | H | 4-Cl(Ph) | C$_2$H$_5$ | COCH$_3$ |
| 26.140 | CH$_3$ | H | 4-Cl(Ph) | n-C$_3$H$_7$ | COCH$_3$ |
| 26.141 | CH$_3$ | H | 4-Cl(Ph) | iso-C$_3$H$_7$ | COCH$_3$ |
| 26.142 | CH$_3$ | H | 4-Cl(Ph) | n-C$_4$H$_9$ | COCH$_3$ |
| 26.143 | CH$_3$ | H | 4-Cl(Ph) | iso-C$_4$H$_9$ | COCH$_3$ |
| 26.144 | CH$_3$ | H | 4-Cl(Ph) | C(CH$_3$)$_3$ | COCH$_3$ |
| 26.145 | CH$_3$ | H | Ph | C$_2$H$_5$ | COPh |
| 26.146 | CH$_3$ | H | Ph | n-C$_3$H$_7$ | COPh |
| 26.147 | CH$_3$ | H | Ph | iso-C$_3$H$_7$ | COPh |
| 26.148 | CH$_3$ | H | Ph | n-C$_4$H$_9$ | COPh |
| 26.149 | CH$_3$ | H | Ph | C(CH$_3$)$_3$ | COPh |
| 26.150 | CH$_3$ | H | 4-Cl(Ph) | CH$_3$ | COCH$_2$Ph |
| 26.151 | CH$_3$ | H | 4-Br(Ph) | CH$_3$ | COCH$_2$Ph |
| 26.152 | CH$_3$ | H | 4-F(Ph) | CH$_3$ | COCH$_2$Ph |
| 26.153 | CH$_3$ | H | 4-OCH$_3$(Ph) | CH$_3$ | COCH$_2$Ph |
| 26.154 | CH$_3$ | H | 4-CH$_3$(Ph) | CH$_3$ | COCH$_2$Ph |
| 26.155 | CH$_3$ | H | 4-NO$_2$(Ph) | CH$_3$ | COCH$_2$Ph |
| 26.156 | CH$_3$ | H | 2,4-Cl(Ph) | CH$_3$ | COCH$_2$Ph |
| 26.157 | CH$_3$ | H | 2,4-F(Ph) | CH$_3$ | COCH$_2$Ph |
| 26.158 | CH$_3$ | H | 4-Cl(Ph) | C$_2$H$_5$ | COCH$_2$Ph |
| 26.159 | CH$_3$ | H | 4-Br(Ph) | n-C$_3$H$_7$ | COCH$_2$Ph |
| 26.160 | CH$_3$ | H | 4-F(Ph) | iso-C$_3$H$_7$ | COCH$_2$Ph |
| 26.161 | CH$_3$ | H | 4-OCH$_3$(Ph) | n-C$_4$H$_9$ | COCH$_2$Ph |
| 26.162 | CH$_3$ | H | 4-CH$_3$(Ph) | iso-C$_4$H$_9$ | COCH$_2$Ph |
| 26.163 | CH$_3$ | H | 4-NO$_2$(Ph) | C(CH$_3$)$_3$ | COCH$_2$Ph |
| 26.164 | Ph | H | Ph | CH$_3$ | H |
| 26.165 | Ph | H | 2-Cl(Ph) | CH$_3$ | H |
| 26.166 | Ph | H | 3-Cl(Ph) | CH$_3$ | H |
| 26.167 | Ph | H | 4-Cl(Ph) | CH$_3$ | H |
| 26.168 | Ph | H | 4-Br(Ph) | CH$_3$ | H |
| 26.169 | Ph | H | 4-F(Ph) | CH$_3$ | H |
| 26.170 | Ph | H | 4-OCH$_3$(Ph) | CH$_3$ | H |
| 26.171 | Ph | H | 4-CH$_3$(Ph) | CH$_3$ | H |
| 26.172 | Ph | H | 4-NO$_2$(Ph) | CH$_3$ | H |
| 26.173 | Ph | H | 2,4-Cl(Ph) | CH$_3$ | H |
| 26.174 | Ph | H | Ph | CH$_3$ | CH$_3$ |
| 26.175 | Ph | H | 2-Cl(Ph) | CH$_3$ | CH$_3$ |
| 26.176 | Ph | H | 3-Cl(Ph) | CH$_3$ | CH$_3$ |
| 26.177 | Ph | H | 4-Cl(Ph) | CH$_3$ | CH$_3$ |
| 26.178 | Ph | H | 4-Br(Ph) | CH$_3$ | CH$_3$ |
| 26.179 | Ph | H | 4-F(Ph) | CH$_3$ | CH$_3$ |
| 26.180 | CN | H | 4-Cl(Ph) | CH$_3$ | H |
| 26.181 | CN | H | 4-Br(Ph) | CH$_3$ | H |
| 26.182 | CN | H | 4-F(Ph) | CH$_3$ | H |
| 26.183 | CN | H | 4-OCH$_3$(Ph) | CH$_3$ | H |
| 26.184 | CN | H | 4-CH$_3$(Ph) | CH$_3$ | H |
| 26.185 | CN | H | 4-NO$_2$(Ph) | CH$_3$ | H |
| 26.186 | CN | H | 2,4-Cl(Ph) | CH$_3$ | H |
| 26.187 | CN | H | 2,4-F(Ph) | CH$_3$ | H |
| 26.188 | CN | H | 4-CF$_3$(Ph) | CH$_3$ | H |
| 26.189 | CN | H | Ph | CH$_3$ | CH$_3$ |
| 26.190 | CN | H | Ph | CH$_3$ | COCH$_3$ |
| 26.191 | H | H | 1-napthyl | CH$_3$ | H |
| 26.192 | H | H | 1-napthyl | CH$_3$ | CH$_3$ |
| 26.193 | H | H | 1-napthyl | CH$_3$ | COCH$_3$ |
| 26.194 | H | H | 1-napthyl | CH$_3$ | COPh |
| 26.195 | CH$_3$ | H | 1-napthyl | CH$_3$ | H |
| 26.196 | CH$_3$ | H | 1-napthyl | CH$_3$ | CH$_3$ |
| 26.197 | CH$_3$ | H | 1-napthyl | CH$_3$ | COCH$_3$ |
| 26.198 | CH$_3$ | H | 1-napthyl | CH$_3$ | COPh |
| 26.199 | CH$_3$ | H | 1-napthyl | CH$_3$ | COCH$_2$Ph |
| 26.200 | H | H | 1-napthyl | CH$_3$ | CO$_2$CH$_3$ |
| 26.201 | CH$_3$ | H | 1-napthyl | CH$_3$ | CO$_2$CH$_3$ |
| 26.202 | H | H | 2-napthyl | CH$_3$ | H |
| 26.203 | H | H | 2-napthyl | CH$_3$ | CH$_3$ |
| 26.204 | H | H | 2-napthyl | CH$_3$ | COCH$_3$ |
| 26.205 | H | H | 2-napthyl | CH$_3$ | COPh |
| 26.206 | CH$_3$ | H | 2-napthyl | CH$_3$ | H |
| 26.207 | CH$_3$ | H | 2-napthyl | CH$_3$ | CH$_3$ |
| 26.208 | CH$_3$ | H | 2-napthyl | CH$_3$ | COCH$_3$ |
| 26.209 | CH$_3$ | H | 2-napthyl | CH$_3$ | COPh |
| 26.210 | CH$_3$ | H | 2-napthyl | CH$_3$ | COCH$_2$Ph |
| 26.211 | H | H | 2-napthyl | CH$_3$ | CO$_2$CH$_3$ |
| 26.212 | CH$_3$ | H | 2-napthyl | CH$_3$ | CO$_2$CH$_3$ |
| 26.213 | H | CH$_3$ | Ph | CH$_3$ | H |
| 26.214 | H | CH$_3$ | 4-Cl(Ph) | CH$_3$ | H |
| 26.215 | H | CH$_3$ | 4-Br(Ph) | CH$_3$ | H |

TABLE 26-continued

| Compd | R2 | R3 | R7 | R8 | R9 |
|---|---|---|---|---|---|
| 26.216 | H | CH3 | 4-F(Ph) | CH3 | H |
| 26.217 | H | CH3 | 4-OCH3(Ph) | CH3 | H |
| 26.218 | H | CH3 | 4-CF3(Ph) | CH3 | H |
| 26.219 | H | CH3 | Ph | CH3 | CH3 |
| 26.220 | H | CH3 | 4-Cl(Ph) | CH3 | CH3 |
| 26.221 | H | CH3 | 4-Br(Ph) | CH3 | CH3 |
| 26.222 | H | CH3 | 4-F(Ph) | CH3 | CH3 |
| 26.223 | H | CH3 | 4-OCH3(Ph) | CH3 | CH3 |
| 26.224 | H | CH3 | 4-CF3(Ph) | CH3 | CH3 |
| 26.225 | H | CH3 | Ph | CH3 | C2H5 |
| 26.226 | H | CH3 | 4-Cl(Ph) | CH3 | n-C3H7 |
| 26.227 | H | CH3 | 4-Br(Ph) | CH3 | iso-C3H7 |
| 26.228 | H | CH3 | 4-F(Ph) | CH3 | n-C4H9 |
| 26.229 | H | CH3 | 4-OCH3(Ph) | CH3 | iso-C4H9 |
| 26.230 | H | CH3 | 4-CH3(Ph) | CH3 | C(CH3)3 |
| 26.231 | H | CH3 | 4-NO2(Ph) | CH3 | CH3 |
| 26.232 | H | CH3 | 2,4-Cl(Ph) | CH3 | CH3 |
| 26.233 | H | CH3 | Ph | CH3 | COCH3 |
| 26.234 | H | CH3 | 4-Cl(Ph) | CH3 | COCH3 |
| 26.235 | H | CH3 | 4-Br(Ph) | CH3 | COCH3 |
| 26.236 | H | CH3 | 4-F(Ph) | CH3 | COCH3 |
| 26.237 | H | CH3 | 4-OCH3(Ph) | CH3 | COCH3 |
| 26.238 | H | CH3 | 4-CH3(Ph) | CH3 | COCH3 |
| 26.239 | H | CH3 | 4-NO2(Ph) | CH3 | COCH3 |
| 26.240 | H | CH3 | 2,4-Cl(Ph) | CH3 | COCH3 |
| 26.241 | H | CH3 | Ph | CH3 | COPh |
| 26.242 | H | CH3 | 4-Cl(Ph) | CH3 | COPh |
| 26.243 | H | CH3 | 4-Br(Ph) | CH3 | COPh |
| 26.244 | H | CH3 | 4-F(Ph) | CH3 | COPh |
| 26.245 | H | CH3 | 4-OCH3(Ph) | CH3 | COPh |
| 26.246 | H | CH3 | 4-CH3(Ph) | CH3 | COPh |
| 26.247 | H | CH3 | 4-NO2(Ph) | CH3 | COPh |
| 26.248 | H | CH3 | 2,4-Cl(Ph) | CH3 | COPh |
| 26.249 | CH3 | CH3 | Ph | CH3 | H |
| 26.250 | CH3 | CH3 | 4-Cl(Ph) | CH3 | H |
| 26.251 | CH3 | CH3 | 4-Br(Ph) | CH3 | H |
| 26.252 | CH3 | CH3 | 4-F(Ph) | CH3 | H |
| 26.253 | CH3 | CH3 | 4-OCH3(Ph) | CH3 | H |
| 26.254 | CH3 | CH3 | 4-CH3(Ph) | CH3 | H |
| 26.255 | CH3 | CH3 | 4-NO2(Ph) | CH3 | H |
| 26.256 | CH3 | CH3 | 2,4-Cl(Ph) | CH3 | R |
| 26.257 | CH3 | CH3 | Ph | CH3 | COCH3 |
| 26.258 | CH3 | CH3 | 4-Cl(Ph) | CH3 | COCH3 |
| 26.259 | CH3 | CH3 | 4-Br(Ph) | CH3 | COCH3 |
| 26.260 | CH3 | CH3 | 4-F(Ph) | CH3 | COCH3 |
| 26.261 | CH3 | CH3 | 4-OCH3(Ph) | CH3 | COCH3 |
| 26.262 | CH3 | CH3 | 4-CH3(Ph) | CH3 | COCH3 |
| 26.263 | CH3 | CH3 | 4-NO2(Ph) | CH3 | COCH3 |
| 26.264 | CH3 | CH3 | 2,4-Cl(Ph) | CH3 | COCH3 |
| 26.265 | CN | CH3 | Ph | CH3 | H |
| 26.266 | CN | CH3 | 4-Cl(Ph) | CH3 | H |
| 26.267 | CN | CH3 | 4-Br(Ph) | CH3 | H |
| 26.268 | CN | CH3 | 4-F(Ph) | CH3 | H |
| 26.269 | CN | CH3 | 4-OCH3(Ph) | CH3 | H |
| 26.270 | CN | CH3 | 4-CH3(Ph) | CH3 | H |
| 26.271 | CN | CH3 | 4-NO2(Ph) | CH3 | H |
| 26.272 | CN | CH3 | 2,4-Cl(Ph) | CH3 | H |
| 26.273 | CN | CH3 | Ph | CH3 | CH3 |
| 26.274 | CN | CH3 | 4-Cl(Ph) | CH3 | CH3 |
| 26.275 | CN | CH3 | 4-Br(Ph) | CH3 | CH3 |
| 26.276 | CN | CH3 | 4-F(Ph) | CH3 | CH3 |
| 26.277 | CN | CH3 | 4-OCH3(Ph) | CH3 | CH3 |
| 26.278 | CN | CH3 | 4-CH3(Ph) | CH3 | CH3 |
| 26.279 | CN | CH3 | 4-NO2(Ph) | CH3 | CH3 |
| 26.280 | CN | CH3 | 2,4-Cl(Ph) | CH3 | CH3 |
| 26.281 | CN | CH3 | Ph | CH3 | COCH3 |
| 26.282 | CN | CH3 | 4-Cl(Ph) | CH3 | COCH3 |
| 26.283 | CN | CH3 | 4-Br(Ph) | CH3 | COCH3 |
| 26.284 | CN | CH3 | 4-F(Ph) | CH3 | COCH3 |
| 26.285 | CN | CH3 | 4-OCH3(Ph) | CH3 | COCH3 |
| 26.286 | CN | CH3 | 4-CH3(Ph) | CH3 | COCH3 |
| 26.287 | CN | CH3 | 4-NO2(Ph) | CH3 | COCH3 |
| 26.288 | CN | CH3 | 2,4-Cl(Ph) | CH3 | COCH3 |
| 26.289 | CN | CH3 | Ph | CH3 | COPh |
| 26.290 | CN | CH3 | 4-Cl(Ph) | CH3 | C()Ph |
| 26.291 | CN | CH3 | 4-Br(Ph) | CH3 | COPh |
| 26.292 | CN | CH3 | 4-F(Ph) | CH3 | COPh |
| 26.293 | CN | CH3 | 4-NO2(Ph) | CH3 | COPh |
| 26.294 | CN | CH3 | 2,4-Cl(Ph) | CH3 | COPh |
| 26.295 | CN | CH3 | 2,4-F(Ph) | CH3 | COPh |
| 26.296 | CN | H | Ph | C2H5 | H |
| 26.297 | CN | H | 2-Cl(Ph) | n-CsH7 | H |
| 26.298 | CN | H | 3-Cl(Ph) | iso-C3H7 | H |
| 26.299 | CN | H | 4-Cl(Ph) | n-C4H9 | H |
| 26.300 | CN | H | 4-Br(Ph) | iso-C4H9 | H |
| 26.301 | CN | H | 4-F(Ph) | C(CH3)3 | H |
| 26.302 | CN | H | 4-OCH3(Ph) | C2H5 | COCH3 |
| 26.303 | CN | H | 4-CH3(Ph) | n-C3H7 | COCH3 |
| 26.304 | CN | H | 4-NO2(Ph) | iso-C3H7 | COCH3 |
| 26.305 | CN | H | 2,4-Cl(Ph) | n-C4H9 | COCH3 |
| 26.306 | CN | H | 2,4-F(Ph) | iso-C4H9 | COCH3 |
| 26.307 | CN | H | Ph | C(CH3)3 | COCH3 |
| 26.308 | CN | H | 2-Cl(Ph) | C2H5 | COPh |
| 26.309 | CN | H | 3-Cl(Ph) | n-C3H7 | COPh |
| 26.310 | CN | H | 4-Cl(Ph) | iso-C3H7 | COPh |
| 26.311 | CH3 | H | 4-Br(Ph) | n-C4H9 | COPh |
| 26.312 | CH3 | H | 4-F(Ph) | iso-C4H9 | COPh |
| 26.313 | CH3 | H | 4-OCH3(Ph) | C(CH3)3 | COPh |

Typical compounds encompassed by the present invention of Formula I include those compounds of Formula XII, which is Formula I with A=R4=R5=R6=H, R1=CH3, X=N, Y=NH, Z=NR10 and R10 is NR8R9, and where R2, R3, R7, R8 and R9 are defined in Table 27.

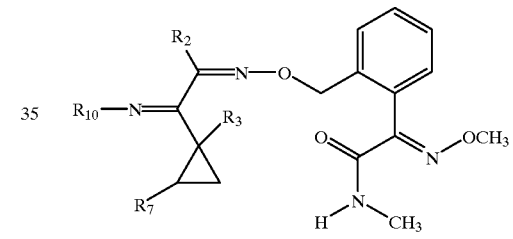

Formula XII

TABLE 27

| Compd | R2 | R3 | R7 | R8 | R9 |
|---|---|---|---|---|---|
| 27.1 | H | H | Ph | CH3 | H |
| 27.2 | H | H | 4-Cl(Ph) | CH3 | H |
| 27.3 | H | H | 4-Br(Ph) | CH3 | H |
| 27.4 | H | H | 4-F(Ph) | CH3 | H |
| 27.5 | H | H | 4-OCH3(Ph) | CH3 | H |
| 27.6 | H | H | 4-CF3(Ph) | CH3 | H |
| 27.7 | H | H | Ph | CH3 | CH3 |
| 27.8 | H | H | 4-Cl(Ph) | CH3 | CH3 |
| 27.9 | H | H | 4-Br(Ph) | CH3 | CH3 |
| 27.10 | H | H | 4-F(Ph) | CH3 | CH3 |
| 27.11 | CH3 | H | Ph | CH3 | H |
| 27.12 | CH3 | H | 2-Cl(Ph) | CH3 | H |
| 27.13 | CH3 | H | 3-Cl(Ph) | CH3 | H |
| 27.14 | CH3 | H | 4-Cl(Ph) | CH3 | H |
| 27.15 | CH3 | H | 2-Br(Ph) | CH3 | H |
| 27.16 | CH3 | H | 3-Br(Ph) | CH3 | H |
| 27.17 | CH3 | H | 4-Br(Ph) | CH3 | H |
| 27.18 | CH3 | H | Ph | CH3 | CH3 |
| 27.19 | CH3 | H | 2-Cl(Ph) | CH3 | CH3 |
| 27.20 | CH3 | H | 3-Cl(Ph) | CH3 | CH3 |
| 27.21 | CH3 | H | 4-Cl(Ph) | CH3 | CH3 |
| 27.22 | CH3 | H | 2-Br(Ph) | CH3 | CH3 |
| 27.23 | CH3 | H | 3-Br(Ph) | CH3 | CH3 |
| 27.24 | CH3 | H | 4-Br(Ph) | CH3 | CH3 |
| 27.25 | CH3 | H | 2-CH3(Ph) | CH3 | CH3 |
| 27.26 | CH3 | H | 3-CH3(Ph) | CH3 | CH3 |

TABLE 27-continued

| Compd | R₂ | R₃ | R₇ | R₈ | R₉ |
|---|---|---|---|---|---|
| 27.27 | CH₃ | H | 2-CF₃(Ph) | CH₃ | CH₃ |
| 27.28 | CH₃ | H | 3-CF₃(Ph) | CH₃ | CH₃ |
| 27.29 | CH₃ | H | 4-CF₃(Ph) | CH₃ | CH₃ |
| 27.30 | CH₃ | H | 2-NO₂(Ph) | CH₃ | CH₃ |
| 27.31 | CH₃ | H | 3-NO₂(Ph) | CH₃ | CH₃ |
| 27.32 | CH₃ | H | 4-NO₂(Ph) | CH₃ | CH₃ |
| 27.33 | CH₃ | H | 2,3-Cl(Ph) | CH₃ | CH₃ |
| 27.34 | CH₃ | H | 2,4-Cl(Ph) | CH₃ | CH₃ |
| 27.35 | CH₃ | H | 2,5-Cl(Ph) | CH₃ | CH₃ |
| 27.36 | CH₃ | H | 2,6-Cl(Ph) | CH₃ | CH₃ |
| 27.37 | CH₃ | H | 3,4-Cl(Ph) | CH₃ | CH₃ |
| 27.38 | CH₃ | H | 3,5-Cl(Ph) | CH₃ | CH₃ |
| 27.39 | CH₃ | H | Ph | C₂H₅ | CH₃ |
| 27.40 | CH₃ | H | Ph | n-C₃H₇ | CH₃ |
| 27.41 | CH₃ | H | Ph | iso-C₃H₇ | CH₃ |
| 27.42 | CH₃ | H | Ph | n-C₄H₉ | CH₃ |
| 27.43 | CH₃ | H | Ph | iso-C₄H₉ | CH₃ |
| 27.44 | CH₃ | H | Pb | C(CH₃)₃ | CH₃ |
| 27.45 | CH₃ | H | Ph | H | COCH₃ |
| 27.46 | CH₃ | H | 2-Cl(Ph) | H | COCH₃ |
| 27.47 | CH₃ | H | 3-Cl(Ph) | H | COCH₃ |
| 27.48 | CH₃ | H | 4-Cl(Ph) | H | COCH₃ |
| 27.49 | CH₃ | H | 4-Br(Ph) | H | COCH₃ |
| 27.50 | CH₃ | H | 4-F(Ph) | H | COCH₃ |
| 27.51 | CH₃ | H | 4-OCH₃(Ph) | H | COCH₃ |
| 27.52 | CH₃ | H | 4-CH₃(Ph) | H | COCH₃ |
| 27.53 | CH₃ | H | 4-NO₂(Ph) | H | COCH₃ |
| 27.54 | CH₃ | H | 2,4-Cl(Ph) | H | COCH₃ |
| 27.55 | CH₃ | H | 2,4-F(Ph) | H | COCH₃ |
| 27.56 | CH₃ | H | Ph | CH₃ | COCH₃ |
| 27.57 | CH₃ | H | 2-Cl(Ph) | CH₃ | COCH₃ |
| 27.58 | CH₃ | H | 3-Cl(Ph) | CH₃ | COCH₃ |
| 27.59 | CH₃ | H | 4-Cl(Ph) | CH₃ | COCH₃ |
| 27.60 | CH₃ | H | 4-F(Ph) | CH₃ | COCH₃ |
| 27.61 | CH₃ | H | 3-OCH₃(Ph) | CH₃ | COCH₃ |
| 27.62 | CH₃ | H | 4-OCH₃(Ph) | CH₃ | COCH₃ |
| 27.63 | CH₃ | H | 4-CH₃(Ph) | CH₃ | COCH₃ |
| 27.64 | CH₃ | H | 4-NO₂(Ph) | CH₃ | COCH₃ |
| 27.65 | CH₃ | H | 2,4-Cl(Ph) | CH₃ | COCH₃ |
| 27.66 | CH₃ | H | 2,4-F(Ph) | CH₃ | COCH₃ |
| 27.67 | CH₃ | H | Ph | H | COPh |
| 27.68 | CH₃ | H | 2-Cl(Ph) | H | COPh |
| 27.69 | CH₃ | H | 3-Cl(Ph) | H | COPh |
| 27.70 | CH₃ | H | 4-Cl(Ph) | H | COPh |
| 27.71 | CH₃ | H | 4-Br(Ph) | H | COPh |
| 27.72 | CH₃ | H | 4-F(Ph) | H | COPh |
| 27.73 | CH₃ | H | 4-OCH₃(Ph) | H | COPh |
| 27.74 | CH₃ | H | 4-CH₃(Ph) | H | COPh |
| 27.75 | CH₃ | H | 4-NO₂(Ph) | H | COPh |
| 27.76 | CH₃ | H | 2,4-Cl(Ph) | H | COPh |
| 27.77 | CH₃ | H | 2,4-F(Ph) | H | COPh |
| 27.78 | CH₃ | H | Ph | CH₃ | COPh |
| 27.79 | CH₃ | H | 2-Cl(Ph) | CH₃ | COPh |
| 27.80 | CH₃ | H | 3-Cl(Ph) | CH₃ | COPh |
| 27.81 | CH₃ | H | 4-Cl(Ph) | CH₃ | COPh |
| 27.82 | CH₃ | H | 4-Br(Ph) | CH₃ | COPh |
| 27.83 | CH₃ | H | 4-F(Ph) | CH₃ | COPh |
| 27.84 | CH₃ | H | 4-OCH₃(Ph) | CH₃ | COPh |
| 27.85 | CH₃ | H | 4-CH₃(Ph) | CH₃ | COPh |
| 27.86 | CH₃ | H | 4-NO₂(Ph) | CH₃ | COPh |
| 27.87 | CH₃ | H | 2,4-Cl(Ph) | CH₃ | COPh |
| 27.88 | CH₃ | H | 2,4-F(Ph) | CH₃ | COPh |
| 27.89 | C₂H₅ | H | Ph | H | COCH₃ |
| 27.90 | C₂H₅ | H | 2-Cl(Ph) | H | COCH₃ |
| 27.91 | C₂H₅ | H | 3-Cl(Ph) | H | COCH₃ |
| 27.92 | C₂H₅ | H | 4-Cl(Ph) | H | COCH₃ |
| 27.93 | C₂H₅ | H | 4-F(Ph) | H | COCH₃ |
| 27.94 | C₂H₅ | H | 3-OCH₃(Ph) | H | COCH₃ |
| 27.95 | C₂H₅ | H | 4-OCH₃(Ph) | H | COCH₃ |
| 27.96 | C₂H₅ | H | 4-CH₃(Ph) | H | COCH₃ |
| 27.97 | C₂H₅ | H | 4-NO₂(Ph) | H | COCH₃ |
| 27.98 | C₂H₅ | H | 2,4-Cl(Ph) | H | COCH₃ |
| 27.99 | C₂H₅ | H | 2,4-F(Ph) | H | COCH₃ |
| 27.100 | C₂H₅ | H | Ph | CH₃ | COCH₃ |
| 27.101 | C₂H₅ | H | 2-Cl(Ph) | CH₃ | COCH₃ |
| 27.102 | C₂H₅ | H | 3-Cl(Ph) | CH₃ | COCH₃ |
| 27.103 | C₂H₅ | H | 4-Cl(Ph) | CH₃ | COCH₃ |
| 27.104 | C₂H₅ | H | 4-F(Ph) | CH₃ | COCH₃ |
| 27.105 | C₂H₅ | H | 3-OCH₃(Ph) | CH₃ | COCH₃ |
| 27.106 | C₂H₅ | H | 4-OCH₃(Ph) | CH₃ | COCH₃ |
| 27.107 | C₂H₅ | H | 4-CH₃(Ph) | CH₃ | COCH₃ |
| 27.108 | C₂H₅ | H | 4-NO₂(Ph) | CH₃ | COCH₃ |
| 27.109 | C₂H₅ | H | 2,4-Cl(Ph) | CH₃ | COCH₃ |
| 27.110 | C₂H₅ | H | 2,4-F(Ph) | CH₃ | COCH₃ |
| 27.111 | C₂H₅ | H | Ph | H | COPh |
| 27.112 | C₂H₅ | H | 2-Cl(Ph) | H | COPh |
| 27.113 | C₂H₅ | H | 3-Cl(Ph) | H | COPh |
| 27.114 | C₂H₅ | H | 4-Cl(Ph) | H | COPh |
| 27.115 | C₂H₅ | H | 4-Br(Ph) | H | COPh |
| 27.116 | C₂H₅ | H | 3-OCH₃(Ph) | H | COPh |
| 27.117 | C₂H₅ | H | 4-OCH₃(Ph) | H | COPh |
| 27.118 | C₂H₅ | H | 4-CH₃(Ph) | H | COPh |
| 27.119 | C₂H₅ | H | 4-NO₂(Ph) | H | COPh |
| 27.120 | C₂H₅ | H | 2,4-Cl(Ph) | H | COPh |
| 27.121 | C₂H₅ | H | 2,4-F(Ph) | H | COPh |
| 27.122 | C₂H₅ | H | Ph | CH₃ | COPh |
| 27.123 | C₂H₅ | H | 2-Cl(Ph) | CH₃ | COPh |
| 27.124 | C₂H₅ | H | 3-Cl(Ph) | CH₃ | COPh |
| 27.125 | C₂H₅ | H | 4-Cl(Ph) | CH₃ | COPh |
| 27.126 | C₂H₅ | H | 4-Br(Ph) | CH₃ | COPh |
| 27.127 | C₂H₅ | H | 4-F(Ph) | CH₃ | COPh |
| 27.128 | C₂H₅ | H | 4-OCH₃(Ph) | CH₃ | COPh |
| 27.129 | C₂H₅ | H | 4-CH₃(Ph) | CH₃ | COPh |
| 27.130 | C₂H₅ | H | 4-NO₂(Ph) | CH₃ | COPh |
| 27.131 | C₂H₅ | H | 2,4-Cl(Ph) | CH₃ | COPh |
| 27.132 | C₂H₅ | H | 2,4-F(Ph) | CH₃ | COPh |
| 27.133 | CH₃ | H | Ph | C₂H₅ | COCH₃ |
| 27.134 | CH₃ | H | Ph | n-C₃H₇ | COCH₃ |
| 27.135 | CH₃ | H | Ph | iso-C₃H₇ | COCH₃ |
| 27.136 | CH₃ | H | Ph | n-C₄H₉ | COCH₃ |
| 27.137 | CH₃ | H | Ph | iso-C₄H₉ | COCH₃ |
| 27.138 | CH₃ | H | Ph | C(CH₃)₃ | COCH₃ |
| 27.139 | CH₃ | H | 4-Cl(Ph) | C₂H₅ | COCH₃ |
| 27.140 | CH₃ | H | 4-Cl(Ph) | n-C₃H₇ | COCH₃ |
| 27.141 | CH₃ | H | 4-Cl(Ph) | iso-C₃H₇ | COCH₃ |
| 27.142 | CH₃ | H | 4-Cl(Ph) | n-C₄H₉ | COCH₃ |
| 27.143 | CH₃ | H | 4-Cl(Ph) | iso-C₄H₉ | COCH₃ |
| 27.144 | CH₃ | H | 4-Cl(Ph) | C(CH₃)₃ | COCH₃ |
| 27.145 | CH₃ | H | Ph | C₂H₅ | COPh |
| 27.146 | CH₃ | H | Ph | n-C₃H₇ | COPh |
| 27.147 | CH₃ | H | Ph | iso-C₃H₇ | COPh |
| 27.148 | CH₃ | H | Ph | n-C₄H₉ | COPh |
| 27.149 | CH₃ | H | Ph | C(CH₃)₃ | COPh |
| 27.150 | CH₃ | H | 4-Cl(Ph) | CH₃ | COCH₂Ph |
| 27.151 | CH₃ | H | 4-Br(Ph) | CH₃ | COCH₂Ph |
| 27.152 | CH₃ | H | 4-F(Ph) | CH₃ | COCH₂Ph |
| 27.153 | CH₃ | H | 4-OCH₃(Ph) | CH₃ | COCH₂Ph |
| 27.154 | CH₃ | H | 4-CH₃(Ph) | CH₃ | COCH₂Ph |
| 27.155 | CH₃ | H | 4-NO₂(Ph) | CH₃ | COCH₂Ph |
| 27.156 | CH₃ | H | 2,4-Cl(Ph) | CH₃ | COCH₂Ph |
| 27.157 | CH₃ | H | 2,4-F(Ph) | CH₃ | COCH₂Ph |
| 27.158 | CH₃ | H | 4-Cl(Ph) | C₂H₅ | COCH₂Ph |
| 27.159 | CH₃ | H | 4-Br(Ph) | n-C₃H₇ | COCH₂Ph |
| 27.160 | CH₃ | H | 4-F(Ph) | iso-C₃H₇ | COCH₂Ph |
| 27.161 | CH₃ | H | 4-OCH₃(Ph) | n-C₄H₉ | COCH₂Ph |
| 27.162 | CH₃ | H | 4-CH₃(Ph) | iso-C₄H₉ | COCH₂Ph |
| 27.163 | CH₃ | H | 4-NO₂(Ph) | C(CH₃)₃ | COCH₂Ph |
| 27.164 | Ph | H | Ph | CH₃ | H |
| 27.165 | Ph | H | 2-Cl(Ph) | CH₃ | H |
| 27.166 | Ph | H | 3-Cl(Ph) | CH₃ | H |
| 27.167 | Ph | H | 4-Cl(Ph) | CH₃ | H |
| 27.168 | Ph | H | 4-Br(Ph) | CH₃ | H |
| 27.169 | Ph | H | 4-F(Ph) | CH₃ | H |
| 27.170 | Ph | H | 4-OCH₃(Ph) | CH₃ | H |
| 27.171 | Ph | H | 4-CH₃(Ph) | CH₃ | H |
| 27.172 | Ph | H | 4-NO₂(Ph) | CH₃ | H |
| 27.173 | Ph | H | 2,4-Cl(Ph) | CH₃ | H |
| 27.174 | Ph | H | Ph | CH₃ | CH₃ |
| 27.175 | Ph | H | 2-Cl(Ph) | CH₃ | CH₃ |
| 27.176 | Ph | H | 3-Cl(Ph) | CH₃ | CH₃ |
| 27.177 | Ph | H | 4-Cl(Ph) | CH₃ | CH₃ |
| 27.178 | Ph | H | 4-Br(Ph) | CH₃ | CH₃ |
| 27.179 | Ph | H | 4-F(Ph) | CH₃ | CH₃ |
| 27.180 | CN | H | 4-Cl(Ph) | CH₃ | H |

TABLE 27-continued

| Compd | R₂ | R₃ | R₇ | R₈ | R₉ |
|---|---|---|---|---|---|
| 27.181 | CN | H | 4-Br(Ph) | CH₃ | H |
| 27.182 | CN | H | 4-F(Ph) | CH₃ | H |
| 27.183 | CN | H | 4-OCH₃(Ph) | CH₃ | H |
| 27.184 | CN | H | 4-CH₃(Ph) | CH₃ | H |
| 27.185 | CN | H | 4-NO₂(Ph) | CH₃ | H |
| 27.186 | CN | H | 2,4-Cl(Ph) | CH₃ | H |
| 27.187 | CN | H | 2,4-F(Ph) | CH₃ | H |
| 27.188 | CN | H | 4-CF₃(Ph) | CH₃ | H |
| 27.189 | CN | H | Ph | CH₃ | CH₃ |
| 27.190 | CN | H | Ph | CH₃ | COCH₃ |
| 27.191 | H | H | 1-napthyl | CH₃ | H |
| 27.192 | H | H | 1-napthyl | CH₃ | CH₃ |
| 27.193 | H | H | 1-napthyl | CH₃ | COCH₃ |
| 27.194 | H | H | 1-napthyl | CH₃ | COPh |
| 27.195 | CH₃ | H | 1-napthyl | CH₃ | H |
| 27.196 | CH₃ | H | 1-napthyl | CH₃ | CH₃ |
| 27.197 | CH₃ | H | 1-napthyl | CH₃ | COCH₃ |
| 27.198 | CH₃ | H | 1-napthyl | CH₃ | COPh |
| 27.199 | CH₃ | H | 1-napthyl | CH₃ | COCH₂Ph |
| 27.200 | H | H | 1-napthyl | CH₃ | CO₂CH₃ |
| 27.201 | CH₃ | H | 1-napthyl | CH₃ | CO₂CH₃ |
| 27.202 | H | H | 2-napthyl | CH₃ | H |
| 27.203 | H | H | 2-napthyl | CH₃ | CH₃ |
| 27.204 | H | H | 2-napthyl | CH₃ | COCH₃ |
| 27.205 | H | H | 2-napthyl | CH₃ | COPh |
| 27.206 | CH₃ | H | 2-napthyl | CH₃ | H |
| 27.207 | CH₃ | H | 2-napthyl | CH₃ | CH₃ |
| 27.208 | CH₃ | H | 2-napthyl | CH₃ | COCH₃ |
| 27.209 | CH₃ | H | 2-napthyl | CH₃ | COPh |
| 27.210 | CH₃ | H | 2-napthyl | CH₃ | COCH₂Ph |
| 27.211 | H | H | 2-napthyl | CH₃ | CO₂CH₃ |
| 27.212 | CH₃ | H | 2-napthyl | CH₃ | CO₂CH₃ |
| 27.213 | H | CH₃ | Ph | CH₃ | H |
| 27.214 | H | CH₃ | 4-Cl(Ph) | CH₃ | H |
| 27.215 | H | CH₃ | 4-Br(Ph) | CH₃ | H |
| 27.216 | H | CH₃ | 4-F(Ph) | CH₃ | H |
| 27.217 | H | CH₃ | 4-OCH₃(Ph) | CH₃ | H |
| 27.218 | H | CH₃ | 4-CF₃(Ph) | CH₃ | H |
| 27.219 | H | CH₃ | Ph | CH₃ | CH₃ |
| 27.220 | H | CH₃ | 4-Cl(Ph) | CH₃ | CH₃ |
| 27.221 | H | CH₃ | 4-Br(Ph) | CH₃ | CH₃ |
| 27.222 | H | CH₃ | 4-F(Ph) | CH₃ | CH₃ |
| 27.223 | H | CH₃ | 4-OCH₃(Ph) | CH₃ | CH₃ |
| 27.224 | H | CH₃ | 4-CF₃(Ph) | CH₃ | CH₃ |
| 27.225 | H | CH₃ | Ph | CH₃ | C₂H₅ |
| 27.226 | H | CH₃ | 4-Cl(Ph) | CH₃ | n-C₃H₇ |
| 27.227 | H | CH₃ | 4-Br(Ph) | CH₃ | iso-C₃H₇ |
| 27.228 | H | CH₃ | 4-F(Ph) | CH₃ | n-C₄H₉ |
| 27.229 | H | CH₃ | 4-OCH₃(Ph) | CH₃ | iso-C₄H₉ |
| 27.230 | H | CH₃ | 4-CH₃(Ph) | CH₃ | C(CH₃)₃ |
| 27.231 | H | CH₃ | 4-NO₂(Ph) | CH₃ | CH₃ |
| 27.232 | H | CH₃ | 2,4-Cl(Ph) | CH₃ | CH₃ |
| 27.233 | H | CH₃ | Ph | CH₃ | COCH₃ |
| 27.234 | H | CH₃ | 4-Cl(Ph) | CH₃ | COCH₃ |
| 27.235 | H | CH₃ | 4-Br(Ph) | CH₃ | COCH₃ |
| 27.236 | H | CH₃ | 4-F(Ph) | CH₃ | COCH₃ |
| 27.237 | H | CH₃ | 4-OCH₃(Ph) | CH₃ | COCH₃ |
| 27.238 | H | CH₃ | 4-CH₃(Ph) | CH₃ | COCH₃ |
| 27.239 | H | CH₃ | 4-NO₂(Ph) | CH₃ | COCH₃ |
| 27.240 | H | CH₃ | 2,4-Cl(Ph) | CH₃ | COCH₃ |
| 27.241 | H | CH₃ | Ph | CH₃ | COPh |
| 27.242 | H | CH₃ | 4-Cl(Ph) | CH₃ | COPh |
| 27.243 | H | CH₃ | 4-Br(Ph) | CH₃ | COPh |
| 27.244 | H | CH₃ | 4-F(Ph) | CH₃ | COPh |
| 27.245 | H | CH₃ | 4-OCH₃(Ph) | CH₃ | COPh |
| 27.246 | H | CH₃ | 4-CH₃(Ph) | CH₃ | COPh |
| 27.247 | H | CH₃ | 4-NO₂(Ph) | CH₃ | COPh |
| 27.248 | H | CH₃ | 2,4-Cl(Ph) | CH₃ | COPh |
| 27.249 | CH₃ | CH₃ | Ph | CH₃ | H |
| 27.250 | CH₃ | CH₃ | 4-Cl(Ph) | CH₃ | H |
| 27.251 | CH₃ | CH₃ | 4-Br(Ph) | CH₃ | H |
| 27.252 | CH₃ | CH₃ | 4-F(Ph) | CH₃ | H |
| 27.253 | CH₃ | CH₃ | 4-OCH₃(Ph) | CH₃ | H |
| 27.254 | CH₃ | CH₃ | 4-CH₃(Ph) | CH₃ | H |
| 27.255 | CH₃ | CH₃ | 4-NO₂(Ph) | CH₃ | H |
| 27.256 | CH₃ | CH₃ | 2,4-Cl(Ph) | CH₃ | H |
| 27.257 | CH₃ | CH₃ | Ph | CH₃ | COCH₃ |
| 27.258 | CH₃ | CH₃ | 4-Cl(Ph) | CH₃ | COCH₃ |
| 27.259 | CH₃ | CH₃ | 4-Br(Ph) | CH₃ | COCH₃ |
| 27.260 | CH₃ | CH₃ | 4-F(Ph) | CH₃ | COCH₃ |
| 27.261 | CH₃ | CH₃ | 4-OCH₃(Ph) | CH₃ | COCH₃ |
| 27.262 | CH₃ | CH₃ | 4-CH₃(Ph) | CH₃ | COCH₃ |
| 27.263 | CH₃ | CH₃ | 4-NO₂(Ph) | CH₃ | COCH₃ |
| 27.264 | CH₃ | CH₃ | 2,4-Cl(Ph) | CH₃ | COCH₃ |
| 27.265 | CN | CH₃ | Ph | CH₃ | H |
| 27.266 | CN | CH₃ | 4-Cl(Ph) | CH₃ | H |
| 27.267 | CN | CH₃ | 4-Br(Ph) | CH₃ | H |
| 27.268 | CN | CH₃ | 4-F(Ph) | CH₃ | H |
| 27.269 | CN | CH₃ | 4-OCH₃(Ph) | CH₃ | H |
| 27.270 | CN | CH₃ | 4-CH₃(Ph) | CH₃ | H |
| 27.271 | CN | CH₃ | 4-NO₂(Ph) | CH₃ | H |
| 27.272 | CN | CH₃ | 2,4-Cl(Ph) | CH₃ | H |
| 27.273 | CN | CH₃ | Ph | CH₃ | CH₃ |
| 27.274 | CN | CH₃ | 4-Cl(Ph) | CH₃ | CH₃ |
| 27.275 | CN | CH₃ | 4-Br(Ph) | CH₃ | CH₃ |
| 27.276 | CN | CH₃ | 4-F(Ph) | CH₃ | CH₃ |
| 27.277 | CN | CH₃ | 4-OCH₃(Ph) | CH₃ | CH₃ |
| 27.278 | CN | CH₃ | 4-CH₃(Ph) | CH₃ | CH₃ |
| 27.279 | CN | CH₃ | 4-NO₂(Ph) | CH₃ | CH₃ |
| 27.280 | CN | CH₃ | 2,4-Cl(Ph) | CH₃ | CH₃ |
| 27.281 | CN | CH₃ | Ph | CH₃ | COCH₃ |
| 27.282 | CN | CH₃ | 4-Cl(Ph) | CH₃ | COCH₃ |
| 27.283 | CN | CH₃ | 4-Br(Ph) | CH₃ | COCH₃ |
| 27.284 | CN | CH₃ | 4-F(Ph) | CH₃ | COCH₃ |
| 27.285 | CN | CH₃ | 4-OCH₃(Ph) | CH₃ | COCH₃ |
| 27.286 | CN | CH₃ | 4-CH₃(Ph) | CH₃ | COCH₃ |
| 27.287 | CN | CH₃ | 4-NO₂(Ph) | CH₃ | COCH₃ |
| 27.288 | CN | CH₃ | 2,4-Cl(Ph) | CH₃ | COCH₃ |
| 27.289 | CN | CH₃ | Ph | CH₃ | COPh |
| 27.290 | CN | CH₃ | 4-Cl(Ph) | CH₃ | COPh |
| 27.291 | CN | CH₃ | 4-Br(Ph) | CH₃ | COPh |
| 27.292 | CN | CH₃ | 4-F(Ph) | CH₃ | COPh |
| 27.293 | CN | CH₃ | 4-NO₂(Ph) | CH₃ | COPh |
| 27.294 | CN | CH₃ | 2,4-Cl(Ph) | CH₃ | COPh |
| 27.295 | CN | CH₃ | 2,4-F(Ph) | CH₃ | COPh |
| 27.296 | CN | H | Ph | C₂H₅ | H |
| 27.297 | CN | H | 2-Cl(Ph) | n-C₃H₇ | H |
| 27.298 | CN | H | 3-Cl(Ph) | iso-C₃H₇ | H |
| 27.299 | CN | H | 4-Cl(Ph) | n-C₄H₉ | H |
| 27.300 | CN | H | 4-Br(Ph) | iso-C₄H₉ | H |
| 27.301 | CN | H | 4-F(Ph) | C(CH₃)₃ | H |
| 27.302 | CN | H | 4-OCH₃(Ph) | C₂H₅ | COCH₃ |
| 27.303 | CN | H | 4-CH₃(Ph) | n-C₃H₇ | COCH₃ |
| 27.304 | CN | H | 4-NO₂(Ph) | iso-C₃H₇ | COCH₃ |
| 27.305 | CN | H | 2,4-Cl(Ph) | n-C₄H₉ | COCH₃ |
| 27.306 | CN | H | 2,4-F(Ph) | iso-C₄H₉ | COCH₃ |
| 27.307 | CN | H | Ph | C(CH₃)₃ | COCH₃ |
| 27.308 | CN | H | 2-Cl(Ph) | C₂H₅ | COPh |
| 27.309 | CN | H | 3-Cl(Ph) | n-C₃H₇ | COPh |
| 27.310 | CN | H | 4-Cl(Ph) | iso-C₃H₇ | COPh |
| 27.311 | CH₃ | H | 4-Br(Ph) | n-C₄H₉ | COPh |
| 27.312 | CH₃ | H | 4-F(Ph) | iso-C₄H₉ | COPh |
| 27.313 | CH₃ | H | 4-OCH₃(Ph) | C(CH₃)₃ | COPh |

TABLE 28

Compounds 28.1 to 28.226 are compounds of Formula X which is Formula I with A=R₄=R₅=R₆=H, R₁=CH₃, X=CH, Y=O, and Z=NR₁₀, R₁₀ is NHCOCH₃ and where R₂, R₃, and R₇ are defined in Table 4.

TABLE 29

Compounds 29.1 to 29.226 are compounds of Formula XI which is Formula I with A=R₄=R₅=R₆=H, R₁=CH₃, X=N, Y=O, and Z=NR₁₀, R₁₀ is NHCOCH₃ and where R₂, R₃, and R₇ are defined in Table 4.

TABLE 30

Compounds 30.1 to 30.226 are compounds of Formula XII which is Formula I with A=R₄=R₅=R₆=H, $R_1=CH_3$, $X=N$, $Y=NH$, and $Z=NR_{10}$, $R_{10}$ is $NHCOCH_3$ and where $R_2$, $R_3$, and $R_7$ are defined in Table 4.

TABLE 31

Compounds 31.1 to 31.221 are compounds of Formula X which is Formula I with $A=R_4R_5=R_6=H$, $R_1=CH_3$, $X=CH$, $Y=O$, and $Z=NR_{10}$, $R_{10}$ is $NHCOC_2H_5$ and where $R_2$, $R_3$, and $R_7$ are defined in Table 7.

TABLE 32

Compounds 32.1 to 32.221 are compounds of Formula XI which is Formula I with $A=R_4=R_5=R_6=H$, $R_1=CH_3$, $X=N$, $Y=O$, and $Z=NR_{10}$, $R_{10}$ is $NHCOC_2H_5$ and where $R_2$, $R_3$, and $R_7$ are defined in Table 7.

TABLE 33

Compounds 33.1 to 33.221 are compounds of Formula XII which is Formula I with $A=R_4=R_5=R_6=H$, $R_1=CH_3$, $X=N$, $Y=NH$, and $Z=NR_{10}$, $R_{10}$ is $NHCOC_2H_5$ and where $R_2$, $R_3$ and $R_7$ are defined in Table 7.

TABLE 34

Compounds 34.1 to 34.139 are compounds of Formula X which is Formula I with $A=R_4=R_5=R_6=H$, $R_1=CH_3$, $X=CH$, $Y=O$, and $Z=NR_{10}$, $R_{10}$ is NHCOPh and where $R_2$, $R_3$, and $R_7$ are defined in Table 10.

TABLE 35

Compounds 35.1 to 35.139 are compounds of Formula XI which is Formula I with $A=R_4=R_5=R_6=H$, $R_1=CH_3$, $X=N$, $Y=O$, and $Z=NR_{10}$, $R_{10}$ is NHCOPh and where $R_2$, $R_3$, and $R_7$ are defined in Table 10.

TABLE 36

Compounds 36.1 to 36.139 are compounds of Formula XII which is Formula I with $A=R_4=R_5=R_6=H$, $R_1=CH_3$, $X=N$, $Y=NH$, and $Z=NR_{10}$, $R_{10}$ is NHCOPh and where $R_2$, $R_3$, and $R_7$ are defined in Table 10.

Typical compounds encompassed by the present invention of Formula I include those compounds of Formula X, which is Formula I with $A=R_4=R_5=R_6=H$, $R_1=CH_3$, $X=CH$, $Y=O$, $Z=NR_{10}$, and where $R_2$, $R_3$, $R_7$, and $R_{10}$ are defined in Table 37.

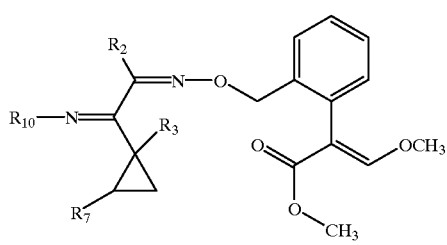

Formula X

TABLE 37

| Compd. | $R_2$ | $R_3$ | $R_7$ | $R_{10}$ |
|---|---|---|---|---|
| 37.1 | H | H | Ph | $CH_3$ |
| 37.2 | H | H | 4-Cl(Ph) | $CH_3$ |
| 37.3 | H | H | 4-Br(Ph) | $CH_3$ |
| 37.4 | H | H | 4-F(Ph) | $CH_3$ |
| 37.5 | H | H | 4-OCH$_3$(Ph) | $CH_3$ |
| 37.6 | H | H | 4-CF$_3$(Ph) | $CH_3$ |
| 37.7 | H | H | Ph | $CH_3$ |
| 37.8 | H | H | 4-Cl(Ph) | $CH_3$ |
| 37.9 | H | H | 4-Br(Ph) | $CH_3$ |
| 37.10 | H | H | 4-F(Ph) | $CH_3$ |
| 37.11 | $CH_3$ | H | Ph | $CH_3$ |
| 37.12 | $CH_3$ | H | 2-Cl(Ph) | $CH_3$ |
| 37.13 | $CH_3$ | H | 3-Cl(Ph) | $CH_3$ |
| 37.14 | $CH_3$ | H | 4-Cl(Ph) | $CH_3$ |
| 37.15 | $CH_3$ | H | 2-Br(Ph) | $CH_3$ |
| 37.16 | $CH_3$ | H | 3-Br(Ph) | $CH_3$ |
| 37.17 | $CH_3$ | H | 4-Br(Ph) | $CH_3$ |
| 37.18 | $CH_3$ | H | Ph | $C_2H_5$ |
| 37.19 | $CH_3$ | H | 2-Cl(Ph) | $C_2H_5$ |
| 37.20 | $CH_3$ | H | 3-Cl(Ph) | $C_2H_5$ |
| 37.21 | $CH_3$ | H | 4-Cl(Ph) | $C_2H_5$ |
| 37.22 | $CH_3$ | H | 2-Br(Ph) | $C_2H_5$ |
| 37.23 | $CH_3$ | H | 3-Br(Ph) | $C_2H_5$ |
| 37.24 | $CH_3$ | H | 4-Br(Ph) | $C_2H_5$ |
| 37.25 | $CH_3$ | H | 2-CH$_3$(Ph) | $C_2H_5$ |
| 37.26 | $CH_3$ | H | 3-CH$_3$(Ph) | $C_2H_5$ |
| 37.27 | $CH_3$ | H | 2-CF$_3$(Ph) | $C_2H_5$ |
| 37.28 | $CH_3$ | H | 3-CF$_3$(Ph) | $C_2H_5$ |
| 37.29 | $CH_3$ | H | 4-CF$_3$(Ph) | $C_2H_5$ |
| 37.30 | $CH_3$ | H | 2-NO$_2$(Ph) | $C_2H_5$ |
| 37.31 | $CH_3$ | H | 3-NO$_2$(Ph) | $C_2H_5$ |
| 37.32 | $CH_3$ | H | 4-NO$_2$(Ph) | $C_2H_5$ |
| 37.33 | $CH_3$ | H | 2,3-Cl(Ph) | $C_2H_5$ |
| 37.34 | $CH_3$ | H | 2,4-Cl(Ph) | $C_2H_5$ |
| 37.35 | $CH_3$ | H | 2,5-Cl(Ph) | $C_2H_5$ |
| 37.36 | $CH_3$ | H | 2,6-Cl(Ph) | $C_2H_5$ |
| 37.37 | $CH_3$ | H | 3,4-Cl(Ph) | $C_2H_5$ |
| 37.38 | $CH_3$ | H | 3,5-Cl(Ph) | $C_2H_5$ |
| 37.39 | $CH_3$ | H | Ph | n-$C_3H_7$ |
| 37.40 | $CH_3$ | H | Ph | iso-$C_3H_7$ |
| 37.41 | $CH_3$ | H | Ph | n-$C_4H_9$ |
| 37.42 | $CH_3$ | H | Ph | iso-$C_4H_9$ |
| 37.43 | $CH_3$ | H | Ph | $C(CH_3)_3$ |
| 37.44 | $CH_3$ | H | Ph | $CH_2CH=CH_2$ |
| 37.45 | $CH_3$ | H | Ph | $CH_2C\equiv CH$ |
| 37.46 | $CH_3$ | H | Ph | $PhCH_2$ |
| 37.47 | $CH_3$ | $CH_3$ | Ph | $CH_3$ |
| 37.48 | $CH_3$ | $CH_3$ | 4-Cl(Ph) | $CH_3$ |
| 37.49 | $CH_3$ | $CH_3$ | 4-Br(Ph) | $CH_3$ |
| 37.50 | $CH_3$ | $CH_3$ | 4-F(Ph) | $CH_3$ |
| 37.51 | $CH_3$ | $CH_3$ | 4-OCH$_3$(Ph) | $CH_3$ |
| 37.52 | $CH_3$ | $CH_3$ | 4-CH$_3$(Ph) | $CH_3$ |
| 37.53 | $CH_3$ | $CH_3$ | 4-NO$_2$(Ph) | $CH_3$ |
| 37.54 | $CH_3$ | $CH_3$ | 2,4-Cl(Ph) | $CH_3$ |
| 37.55 | $CH_3$ | $CH_3$ | 2,4-F(Ph) | $CH_3$ |
| 37.56 | $CH_3$ | $CH_3$ | Ph | $C_2H_5$ |
| 37.57 | $CH_3$ | $CH_3$ | 2-Cl(Ph) | $C_2H_5$ |
| 37.58 | $CH_3$ | $CH_3$ | 3-Cl(Ph) | $C_2H_5$ |
| 37.59 | $CH_3$ | $CH_3$ | 4-Cl(Ph) | $C_2H_5$ |
| 37.60 | $CH_3$ | $CH_3$ | 4-F(Ph) | $C_2H_5$ |
| 37.61 | $CH_3$ | $CH_3$ | 3-OCH$_3$(Ph) | $C_2H_5$ |
| 37.62 | $CH_3$ | $CH_3$ | 4-OCH$_3$(Ph) | $C_2H_5$ |
| 37.63 | $CH_3$ | $CH_3$ | 4-CH$_3$(Ph) | $C_2H_5$ |
| 37.64 | $CH_3$ | $CH_3$ | 4-NO$_2$(Ph) | $C_2H_5$ |
| 37.65 | $CH_3$ | $CH_3$ | 2,4-Cl(Ph) | $C_2H_5$ |
| 37.66 | $CH_3$ | $CH_3$ | 2,4-Fh | $C_2H_5$ |
| 37.67 | $CH_3$ | $CH_3$ | Ph | n-$C_3H_7$ |
| 37.68 | $CH_3$ | $CH_3$ | 2-Cl(Ph) | iso-$C_3H_7$ |
| 37.69 | $CH_3$ | $CH_3$ | 3-Cl(Ph) | n-$C_4H_9$ |
| 37.70 | $CH_3$ | $CH_3$ | 4-Cl(Ph) | iso-$C_4H_9$ |
| 37.71 | $CH_3$ | $CH_3$ | 4-Br(Ph) | sec-$C_4H_9$ |
| 37.72 | $CH_3$ | $CH_3$ | 4-F(Ph) | $C(CH_3)_3$ |
| 37.73 | $CH_3$ | $CH_3$ | 4-OCH$_3$(ph) | $CH_2CH=CH_2$ |
| 37.74 | $CH_3$ | $CH_3$ | 4-CH$_3$(Ph) | $CH_2C\equiv CH$ |
| 37.75 | $CH_3$ | $CH_3$ | 4-NO$_2$(Ph) | $PhCH_2$ |
| 37.76 | $CH_3$ | $CH_3$ | 2,4-Cl(Ph) | $PhCH_2CH_2$ |
| 37.77 | $CH_3$ | $CH_3$ | 2,4-F(Ph) | $PhCH_2CH_2$ |
| 37.78 | $C_2H_5$ | H | Ph | $CH_3$ |
| 37.79 | $C_2H_5$ | H | 2-Cl(Ph) | $CH_3$ |

TABLE 37-continued

| Compd. | R$_2$ | R$_3$ | R$_7$ | R$_{10}$ |
|---|---|---|---|---|
| 37.80 | C$_2$H$_5$ | H | 3-Cl(Ph) | CH$_3$ |
| 37.81 | C$_2$H$_5$ | H | 4-Cl(Ph) | CH$_3$ |
| 37.82 | C$_2$H$_5$ | H | 4-Br(Ph) | CH$_3$ |
| 37.83 | C$_2$H$_5$ | H | 4-F(Ph) | CH$_3$ |
| 37.84 | C$_2$H$_5$ | H | 4-OCH$_3$(Ph) | CH$_3$ |
| 37.85 | C$_2$H$_5$ | H | 4-CH$_3$(Ph) | CH$_3$ |
| 37.86 | C$_2$H$_5$ | H | 4-NO$_2$(Ph) | CH$_3$ |
| 37.87 | C$_2$H$_5$ | H | 2,4-Cl(Ph) | CH$_3$ |
| 37.88 | C$_2$H$_5$ | H | 2,4-F(Ph) | CH$_3$ |
| 37.89 | C$_2$H$_5$ | H | Ph | C$_2$H$_5$ |
| 37.90 | C$_2$H$_5$ | H | 2-Cl(Ph) | C$_2$H$_5$ |
| 37.91 | C$_2$H$_5$ | H | 3-Cl(Ph) | C$_2$H$_5$ |
| 37.92 | C$_2$H$_5$ | H | 4-Cl(Ph) | C$_2$H$_5$ |
| 37.93 | C$_2$H$_5$ | H | 4-F(Ph) | C$_2$H$_5$ |
| 37.94 | C$_2$H$_5$ | H | 3-OCH$_3$(Ph) | C$_2$H$_5$ |
| 37.95 | C$_2$H$_5$ | H | 4-OCH$_3$(Ph) | C$_2$H$_5$ |
| 37.96 | C$_2$H$_5$ | H | 4-CH$_3$(Ph) | C$_2$H$_5$ |
| 37.97 | C$_2$H$_5$ | H | 4-NO$_2$h) | C$_2$H$_5$ |
| 37.98 | C$_2$H$_5$ | H | 2,4-Cl(Ph) | C$_2$H$_5$ |
| 37.99 | C$_2$H$_5$ | H | 2,4-F(Ph) | C$_2$H$_5$ |
| 37.100 | C$_2$H$_5$ | H | Ph | n-C$_3$H$_7$ |
| 37.101 | C$_2$H$_5$ | H | 2-Cl(Ph) | iso-C$_3$H$_7$ |
| 37.102 | C$_2$H$_5$ | H | 3-Cl(Ph) | n-C$_4$H$_9$ |
| 37.103 | C$_2$H$_5$ | H | 4-Cl(Ph) | iso-C$_4$H$_9$ |
| 37.104 | C$_2$H$_5$ | H | 4-F(Ph) | sec-C$_4$H$_9$ |
| 37.105 | C$_2$H$_5$ | H | 3-OCH$_3$(Ph) | C(CH$_3$)$_3$ |
| 37.106 | C$_2$H$_5$ | H | 4-OCH$_3$(Ph) | CH$_2$CH=CH$_2$ |
| 37.107 | C$_2$H$_5$ | H | 4-CH$_3$(Ph) | CH$_2$C≡CH |
| 37.108 | C$_2$H$_5$ | H | 4-NO$_2$(Ph) | PhCH$_2$ |
| 37.109 | C$_2$H$_5$ | H | 2,4-Cl(Ph) | PhCH$_2$CH$_2$ |
| 37.110 | C$_2$H$_5$ | H | 2,4-F(Ph) | CH$_3$ |
| 37.111 | n-C$_3$H$_7$ | H | Ph | CH$_3$ |
| 37.112 | n-C$_3$H$_7$ | H | 2-Cl(Ph) | CH$_3$ |
| 37.113 | n-C$_3$H$_7$ | H | 3-Cl(Ph) | CH$_3$ |
| 37.114 | n-C$_3$H$_7$ | H | 4-Cl(Ph) | CH$_3$ |
| 37.115 | n-C$_3$H$_7$ | H | 4-Br(Ph) | CH$_3$ |
| 37.116 | n-C$_3$H$_7$ | H | 3-OCH$_3$(Ph) | CH$_3$ |
| 37.117 | n-C$_3$H$_7$ | H | 4-OCH$_3$(Ph) | CH$_3$ |
| 37.118 | n-C$_3$H$_7$ | H | 4-CH$_3$(Ph) | CH$_3$ |
| 37.119 | n-C$_3$H$_7$ | H | 4-NO$_2$(Ph) | CH$_3$ |
| 37.120 | n-C$_3$H$_7$ | H | 2,4-Cl(Ph) | CH$_3$ |
| 37.121 | n-C$_3$H$_7$ | H | 2,4-F(Ph) | CH$_3$ |
| 37.122 | n-C$_3$H$_7$ | H | Ph | C$_2$H$_5$ |
| 37.123 | n-C$_3$H$_7$ | H | 2-Cl(Ph) | C$_2$H$_5$ |
| 37.124 | n-C$_3$H$_7$ | H | 3-Cl(Ph) | C$_2$H$_5$ |
| 37.125 | n-C$_3$H$_7$ | H | 4-Cl(Ph) | C$_2$H$_5$ |
| 37.126 | n-C$_3$H$_7$ | H | 4-Br(Ph) | C$_2$H$_5$ |
| 37.127 | n-C$_3$H$_7$ | H | 4-F(Ph) | C$_2$H$_5$ |
| 37.128 | n-C$_3$H$_7$ | H | 4-OCH$_3$(Ph) | C$_2$H$_5$ |
| 37.129 | n-C$_3$H$_7$ | H | 4-CH$_3$(Ph) | C$_2$H$_5$ |
| 37.130 | n-C$_3$H$_7$ | H | 4-NO$_2$(Ph) | C$_2$H$_5$ |
| 37.131 | n-C$_3$H$_7$ | H | 2,4-Cl(Ph) | C$_2$H$_5$ |
| 37.132 | n-C$_3$H$_7$ | H | 2,4-F(Ph) | C$_2$H$_5$ |
| 37.133 | n-C$_3$H$_7$ | H | Ph | n-C$_3$H$_7$ |
| 37.134 | n-C$_3$H$_7$ | H | Ph | iso-C$_3$H$_7$ |
| 37.135 | n-C$_3$H$_7$ | H | Ph | n-C$_4$H$_9$ |
| 37.136 | n-C$_3$H$_7$ | H | Ph | iso-C$_4$H$_9$ |
| 37.137 | n-C$_3$H$_7$ | H | Ph | C(CH$_3$)$_3$ |
| 37.138 | n-C$_3$H$_7$ | H | Ph | CH$_2$CH=CH$_2$ |
| 37.139 | n-C$_3$H$_7$ | H | Ph | CH$_2$C≡CH |
| 37.140 | n-C$_3$H$_7$ | H | Ph | PhCH$_2$ |
| 37.141 | n-C$_3$H$_7$ | H | Ph | PhCH$_2$CH$_2$ |
| 37.142 | iso-C$_3$H$_7$ | H | Ph | C$_2$H$_5$ |
| 37.143 | iso-C$_3$H$_7$ | H | Ph | n-C$_3$H$_7$ |
| 37.144 | iso-C$_3$H$_7$ | H | Ph | iso-C$_3$H$_7$ |
| 37.145 | iso-C$_3$H$_7$ | H | Ph | n-C$_4$H$_9$ |
| 37.146 | iso-C$_3$H$_7$ | H | Ph | iso-C$_4$H$_9$ |
| 37.147 | iso-C$_3$H$_7$ | H | Ph | C(CH$_3$)$_3$ |
| 37.148 | iso-C$_3$H$_7$ | H | Ph | CH$_2$CH=CH$_2$ |
| 37.149 | iso-C$_3$H$_7$ | H | Ph | CH$_2$C≡CH |
| 37.150 | iso-C$_3$H$_7$ | H | Ph | PhCH$_2$ |
| 37.151 | iso-C$_3$H$_7$ | H | Ph | PhCH$_2$CH$_2$ |
| 37.152 | cyclopropyl | H | Ph | CH$_3$ |
| 37.153 | cyclopropyl | H | 2-Cl(Ph) | CH$_3$ |
| 37.154 | cyclopropyl | H | 3-Cl(Ph) | CH$_3$ |
| 37.155 | cyclopropyl | H | 4-Cl(Ph) | CH$_3$ |
| 37.156 | cyclopropyl | H | 4-Br(Ph) | CH$_3$ |
| 37.157 | cyclopropyl | H | 4-F(Ph) | CH$_3$ |
| 37.158 | cyclopropyl | H | 4-OCH$_3$(Ph) | CH$_3$ |
| 37.159 | cyclopropyl | H | 4-CH$_3$(Ph) | CH$_3$ |
| 37.160 | cyclopropyl | H | 4-NO$_2$(Ph) | CH$_3$ |
| 37.161 | cyclopropyl | H | 2,4-Cl(Ph) | CH$_3$ |
| 37.162 | cyclopropyl | H | 2,4-F(Ph) | CH$_3$ |
| 37.163 | cyclopropyl | H | 3,4-F(Ph) | CH$_3$ |
| 37.164 | Ph | H | Ph | CH$_3$ |
| 37.165 | Ph | H | 2-Cl(Ph) | C$_2$H$_5$ |
| 37.166 | Ph | H | 3-Cl(Ph) | n-C$_3$H$_7$ |
| 37.167 | Ph | H | 4-Cl(Ph) | iso-C$_3$H$_7$ |
| 37.168 | Ph | H | 4-Br(Ph) | n-C$_4$H$_9$ |
| 37.169 | Ph | H | 4-F(Ph) | iso-C$_4$H$_9$ |
| 37.170 | Ph | H | 4-OCH$_3$(Ph) | C(CH$_3$)$_3$ |
| 37.171 | Ph | H | 4-CH$_3$(Ph) | CH$_2$CH=CH$_2$ |
| 37.172 | Ph | H | 4-NO$_2$(Ph) | CH$_2$C≡CH |
| 37.173 | Ph | H | 2,4-Cl(Ph) | PhCH$_2$ |
| 37.174 | CN | H | Ph | CH$_3$ |
| 37.175 | CN | H | 2-Cl(Ph) | CH$_3$ |
| 37.176 | CN | H | 3-Cl(Ph) | CH$_3$ |
| 37.177 | CN | H | 4-Cl(Ph) | CH$_3$ |
| 37.178 | CN | H | 4-Br(Ph) | CH$_3$ |
| 37.179 | CN | H | 4-F(Ph) | CH$_3$ |
| 37.180 | CN | H | 4-Cl(Ph) | CH$_3$ |
| 37.181 | CN | H | 4-Br(Ph) | CH$_3$ |
| 37.182 | CN | H | 4-F(Ph) | CH$_3$ |
| 37.183 | CN | H | 4-OCH$_3$(Ph) | CH$_3$ |
| 37.184 | CN | H | 4-CH$_3$(Ph) | CH$_3$ |
| 37.185 | CN | H | 4-NO$_2$(Ph) | CH$_3$ |
| 37.186 | CN | H | 2,4-Cl(Ph) | CH$_3$ |
| 37.187 | CN | H | 2,4-F(Ph) | CH$_3$ |
| 37.188 | CN | H | 4-CF$_3$(Ph) | CH$_3$ |
| 37.189 | CN | H | Ph | C$_2$H$_5$ |
| 37.190 | CN | H | Ph | n-C$_3$H$_7$ |
| 37.191 | CN | H | Ph | iso-C$_3$H$_7$ |
| 37.192 | CN | H | Ph | n-C$_4$H$_9$ |
| 37.193 | CN | H | Ph | iso-C$_4$H$_9$ |
| 37.194 | CN | H | Ph | C(CH$_3$)$_3$ |
| 37.195 | CN | H | Ph | CH$_2$CH=CH$_2$ |
| 37.196 | CN | H | Ph | CH$_2$C≡CH |
| 37.197 | CN | H | Ph | PhCH$_2$ |
| 37.198 | CH$_3$ | H | 1-napthyl | CH$_3$ |
| 37.199 | CH$_3$ | H | 1-napthyl | C$_2$H$_5$ |
| 37.200 | CH$_3$ | H | 1-napthyl | n-C$_3$H$_7$ |
| 37.201 | CH$_3$ | H | 1-napthyl | iso-C$_3$H$_7$ |
| 37.202 | CH$_3$ | H | 1-napthyl | n-C$_4$H$_9$ |
| 37.203 | CH$_3$ | H | 1-napthyl | iso-C$_4$H$_9$ |
| 37.204 | CH$_3$ | H | 1-napthyl | C(CH$_3$)$_3$ |
| 37.205 | CH$_3$ | H | 1-napthyl | CH$_2$CH=CH$_2$ |
| 37.206 | CH$_3$ | H | 1-napthyl | CH$_2$C≡CH |
| 37.207 | CH$_3$ | H | 1-napthyl | PhCH$_2$ |
| 37.208 | CH$_3$ | H | 2-napthyl | CH$_3$ |
| 37.209 | CH$_3$ | H | 2-napthyl | C$_2$H$_5$ |
| 37.210 | CH$_3$ | H | 2-napthyl | n-C$_3$H$_7$ |
| 37.211 | CH$_3$ | H | 2-napthyl | iso-C$_3$H$_7$ |
| 37.212 | CH$_3$ | H | 2-napthyl | n-C$_4$H$_9$ |
| 37.213 | CH$_3$ | H | 2-napthyl | iso-C$_4$H$_9$ |
| 37.214 | CH$_3$ | H | 2-napthyl | C(CH$_3$)$_3$ |
| 37.215 | CH$_3$ | H | 2-napthyl | CH$_2$CH=CH$_2$ |
| 37.216 | CH$_3$ | H | 2-napthyl | CH$_2$C≡CH |
| 37.217 | CH$_3$ | H | 2-napthyl | PhCH$_2$ |
| 37.218 | CN | H | 1-napthyl | CH$_3$ |
| 37.219 | CN | H | 1-napthyl | C$_2$H$_5$ |
| 37.220 | CN | H | 1-napthyl | n-C$_3$H$_7$ |
| 37.221 | CN | H | 1-napthyl | iso-C$_3$H$_7$ |
| 37.222 | CN | H | 1-napthyl | n-C$_4$H$_9$ |
| 37.223 | CN | H | 1-napthyl | iso-C$_4$H$_9$ |
| 37.224 | CN | H | 1-napthyl | C(CH$_3$)$_3$ |
| 37.225 | CN | H | 1-napthyl | CH$_2$CH=CH$_2$ |
| 37.226 | CN | H | 1-napthyl | CH$_2$C≡CH |
| 37.227 | CN | H | 1-napthyl | PhCH$_2$ |
| 37.228 | CN | H | 2-napthyl | CH$_3$ |
| 37.229 | CN | H | 2-napthyl | C$_2$H$_5$ |
| 37.230 | CN | H | 2-napthyl | n-C$_3$H$_7$ |
| 37.231 | CN | H | 2-napthyl | iso-C$_3$H$_7$ |
| 37.232 | CN | H | 2-napthyl | n-C$_4$H$_9$ |
| 37.233 | CN | H | 2-napthyl | iso-C$_4$H$_9$ |

TABLE 37-continued

| Compd. | R$_2$ | R$_3$ | R$_7$ | R$_{10}$ |
|---|---|---|---|---|
| 37.234 | CN | H | 2-napthyl | C(CH$_3$)$_3$ |
| 37.235 | CN | H | 2-napthyl | CH$_2$CH=CH$_2$ |
| 37.236 | CN | H | 2-napthyl | CH$_2$C≡CH |
| 37.237 | CN | H | 2-napthyl | PhCH$_2$ |
| 37.238 | CH$_3$ | CH$_3$ | 1-napthyl | CH$_3$ |
| 37.239 | CH$_3$ | CH$_3$ | 1-napthyl | C$_2$H$_5$ |
| 37.240 | CH$_3$ | CH$_3$ | 1-napthyl | n-C$_3$H$_7$ |
| 37.241 | CH$_3$ | CH$_3$ | 1-napthyl | iso-C$_3$H$_7$ |
| 37.242 | CH$_3$ | CH$_3$ | 1-napthyl | n-C$_4$H$_9$ |
| 37.243 | CH$_3$ | CH$_3$ | 1-napthyl | iso-C$_4$H$_9$ |
| 37.244 | CH$_3$ | CH$_3$ | 1-napthyl | C(CH$_3$)$_3$ |
| 37.245 | CH$_3$ | CH$_3$ | 1-napthyl | CH$_2$CH=CH$_2$ |
| 37.246 | CH$_3$ | CH$_3$ | 1-napthyl | CH$_2$C≡CH |
| 37.247 | CH$_3$ | CH$_s$ | 1-napthyl | PhCH$_2$ |
| 37.248 | CH$_3$ | CH$_3$ | 2-napthyl | CH$_3$ |
| 37.249 | CH$_3$ | CH$_3$ | 2-napthyl | C$_2$H$_5$ |
| 37.250 | CH$_3$ | CH$_3$ | 2-napthyl | n-C$_3$H$_7$ |
| 37.251 | CH$_3$ | CH$_3$ | 2-napthyl | iso-C$_3$H$_7$ |
| 37.252 | CH$_3$ | CH$_3$ | 2-napthyl | n-C$_4$H$_9$ |
| 37.253 | CH$_3$ | CH$_3$ | 2-napthyl | iso-C$_4$H$_9$ |
| 37.254 | CH$_3$ | CH$_3$ | 2-napthyl | C(CH$_3$)$_3$ |
| 37.255 | CH$_3$ | CH$_3$ | 2-napthyl | CH$_2$CH=CH$_2$ |
| 37.256 | CH$_3$ | CH$_3$ | 2-napthyl | CH$_2$C≡CH |
| 37.257 | CH$_3$ | CH$_3$ | 2-napthyl | PhCH$_2$ |
| 37.258 | CN | CH$_3$ | 1-napthyl | CH$_3$ |
| 37.259 | CN | CH$_3$ | 1-napthyl | C$_2$H$_5$ |
| 37.260 | CN | CH$_3$ | 1-napthyl | n-C$_3$H$_7$ |
| 37.261 | CN | CH$_3$ | 1-napthyl | iso-C$_3$H$_7$ |
| 37.262 | CN | CH$_3$ | 1-napthyl | n-C$_4$H$_9$ |
| 37.263 | CN | CH$_3$ | 1-napthyl | iso-C$_4$H$_9$ |
| 37.264 | CN | CH$_3$ | 1-napthyl | C(CH$_3$)$_3$ |
| 37.265 | CN | CH$_3$ | 1-napthyl | CH$_2$CH=CH$_2$ |
| 37.266 | CN | CH$_3$ | 1-napthyl | CH$_2$C≡CH |
| 37.267 | CN | CH$_3$ | 1-napthyl | PhCH$_2$ |
| 37.268 | CN | CH$_3$ | 2-napthyl | CH$_3$ |
| 37.269 | CN | CH$_3$ | 2-napthyl | C$_2$H$_5$ |
| 37.270 | CN | CH$_3$ | 2-napthyl | n-C$_3$H$_7$ |
| 37.271 | CN | CH$_3$ | 2-napthyl | iso-C$_3$H$_7$ |
| 37.272 | CN | CH$_3$ | 2-napthyl | n-C$_4$H$_9$ |

Typical compounds encompassed by the present invention of Formula I include those compounds of Formula XI, which is Formula I with A=R$_4$=R$_5$=R$_6$=H, R$_1$=CH$_3$, X=N, Y=O, Z=NR$_{10}$, and where R$_2$, R$_3$, R$_7$, and R$_{10}$ are defined in Table 38.

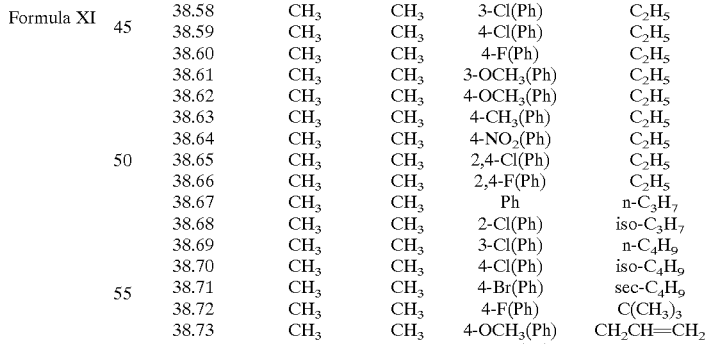

Formula XI

TABLE 38

| Compd. | R$_2$ | R$_3$ | R$_7$ | R$_{10}$ |
|---|---|---|---|---|
| 38.1 | H | H | Ph | CH$_3$ |
| 38.2 | H | H | 4-Cl(Ph) | CH$_3$ |
| 38.3 | H | H | 4-Br(Ph) | CH$_3$ |
| 38.4 | H | H | 4-F(Ph) | CH$_3$ |
| 38.5 | H | H | 4-OCH$_3$(Ph) | CH$_3$ |
| 38.6 | H | H | 4-CF$_3$(Ph) | CH$_3$ |
| 38.7 | H | H | Ph | CH$_3$ |
| 38.8 | H | H | 4-Cl(Ph) | CH$_3$ |
| 38.9 | H | H | 4-Br(Ph) | CH$_3$ |
| 38.10 | H | H | 4-F(Ph) | CH$_3$ |
| 38.11 | CH$_3$ | H | Ph | CH$_3$ |
| 38.12 | CH$_3$ | H | 2-Cl(Ph) | CH$_3$ |
| 38.13 | CH$_3$ | H | 3-Cl(Ph) | CH$_3$ |
| 38.14 | CH$_3$ | H | 4-Cl(Ph) | CH$_3$ |
| 38.15 | CH$_3$ | H | 2-Br(Ph) | CH$_3$ |
| 38.16 | CH$_3$ | H | 3-Br(Ph) | CH$_3$ |
| 38.17 | CH$_3$ | H | 4-Br(Ph) | CH$_3$ |
| 38.18 | CH$_3$ | H | Ph | C$_2$H$_5$ |
| 38.19 | CH$_3$ | H | 2-Cl(Ph) | C$_2$H$_5$ |
| 38.20 | CH$_3$ | H | 3-Cl(Ph) | C$_2$H$_5$ |
| 38.21 | CH$_3$ | H | 4-Cl(Ph) | C$_2$H$_5$ |
| 38.22 | CH$_3$ | H | 2-Br(Ph) | C$_2$H$_5$ |
| 38.23 | CH$_3$ | H | 3-Br(Ph) | C$_2$H$_5$ |
| 38.24 | CH$_3$ | H | 4-Br(Ph) | C$_2$H$_5$ |
| 38.25 | CH$_3$ | H | 2-CH$_3$(Ph) | C$_2$H$_5$ |
| 38.26 | CH$_3$ | H | 3-CH$_3$(Ph) | C$_2$H$_5$ |
| 38.27 | CH$_3$ | H | 2-CF$_3$(Ph) | C$_2$H$_5$ |
| 38.28 | CH$_3$ | H | 3-CF$_3$(Ph) | C$_2$H$_5$ |
| 38.29 | CH$_3$ | H | 4-CF$_3$(Ph) | C$_2$H$_5$ |
| 38.30 | CH$_3$ | H | 2-NO$_2$(Ph) | C$_2$H$_5$ |
| 38.31 | CH$_3$ | H | 3-NO$_2$(Ph) | C$_2$H$_5$ |
| 38.32 | CH$_3$ | H | 4-NO$_2$(Ph) | C$_2$H$_5$ |
| 38.33 | CH$_3$ | H | 2,3-Cl(Ph) | C$_2$H$_5$ |
| 38.34 | CH$_3$ | H | 2,4-Cl(Ph) | C$_2$H$_5$ |
| 38.35 | CH$_3$ | H | 2,5-Cl(Ph) | C$_2$H$_5$ |
| 38.36 | CH$_3$ | H | 2,6-Cl(Ph) | C$_2$H$_5$ |
| 38.37 | CH$_3$ | H | 3,4-Cl(Ph) | C$_2$H$_5$ |
| 38.38 | CH$_3$ | H | 3,5-Cl(Ph) | C$_2$H$_5$ |
| 38.39 | CH$_3$ | H | Ph | n-C$_3$H$_7$ |
| 38.40 | CH$_3$ | H | Ph | iso-C$_3$H$_7$ |
| 38.41 | CH$_3$ | H | Ph | n-C$_4$H$_9$ |
| 38.42 | CH$_3$ | H | Ph | iso-C$_4$H$_9$ |
| 38.43 | CH$_3$ | H | Ph | C(CH$_3$)$_3$ |
| 38.44 | CH$_3$ | H | Ph | CH$_2$CH=CH$_2$ |
| 38.45 | CH$_3$ | H | Ph | CH$_2$C≡CH |
| 38.46 | CH$_3$ | H | Ph | PhCH$_2$ |
| 38.47 | CH$_3$ | CH$_3$ | Ph | CH$_3$ |
| 38.48 | CH$_3$ | CH$_3$ | 4-Cl(Ph) | CH$_3$ |
| 38.49 | CH$_3$ | CH$_3$ | 4-Br(Ph) | CH$_3$ |
| 38.50 | CH$_3$ | CH$_3$ | 4-F(Ph) | CH$_3$ |
| 38.51 | CH$_3$ | CH$_3$ | 4-OCH$_3$(Ph) | CH$_3$ |
| 38.52 | CH$_3$ | CH$_3$ | 4-CH$_3$(Ph) | CH$_3$ |
| 38.53 | CH$_3$ | CH$_3$ | 4-NO$_2$(Ph) | CH$_3$ |
| 38.54 | CH$_3$ | CH$_3$ | 2,4-Cl(Ph) | CH$_3$ |
| 38.55 | CH$_3$ | CH$_3$ | 2,4-F(Ph) | CH$_3$ |
| 38.56 | CH$_3$ | CH$_3$ | Ph | C$_2$H$_5$ |
| 38.57 | CH$_3$ | CH$_3$ | 2-Cl(Ph) | C$_2$H$_5$ |
| 38.58 | CH$_3$ | CH$_3$ | 3-Cl(Ph) | C$_2$H$_5$ |
| 38.59 | CH$_3$ | CH$_3$ | 4-Cl(Ph) | C$_2$H$_5$ |
| 38.60 | CH$_3$ | CH$_3$ | 4-F(Ph) | C$_2$H$_5$ |
| 38.61 | CH$_3$ | CH$_3$ | 3-OCH$_3$(Ph) | C$_2$H$_5$ |
| 38.62 | CH$_3$ | CH$_3$ | 4-OCH$_3$(Ph) | C$_2$H$_5$ |
| 38.63 | CH$_3$ | CH$_3$ | 4-CH$_3$(Ph) | C$_2$H$_5$ |
| 38.64 | CH$_3$ | CH$_3$ | 4-NO$_2$(Ph) | C$_2$H$_5$ |
| 38.65 | CH$_3$ | CH$_3$ | 2,4-Cl(Ph) | C$_2$H$_5$ |
| 38.66 | CH$_3$ | CH$_3$ | 2,4-F(Ph) | C$_2$H$_5$ |
| 38.67 | CH$_3$ | CH$_3$ | Ph | n-C$_3$H$_7$ |
| 38.68 | CH$_3$ | CH$_3$ | 2-Cl(Ph) | iso-C$_3$H$_7$ |
| 38.69 | CH$_3$ | CH$_3$ | 3-Cl(Ph) | n-C$_4$H$_9$ |
| 38.70 | CH$_3$ | CH$_3$ | 4-Cl(Ph) | iso-C$_4$H$_9$ |
| 38.71 | CH$_3$ | CH$_3$ | 4-Br(Ph) | sec-C$_4$H$_9$ |
| 38.72 | CH$_3$ | CH$_3$ | 4-F(Ph) | C(CH$_3$)$_3$ |
| 38.73 | CH$_3$ | CH$_3$ | 4-OCH$_3$(Ph) | CH$_2$CH=CH$_2$ |
| 38.74 | CH$_3$ | CH$_3$ | 4-CH$_3$(Ph) | CH$_2$C≡CH |
| 38.75 | CH$_3$ | CH3 | 4-NO$_2$(Ph) | PhCH$_2$ |
| 38.76 | CH$_3$ | CH3 | 2,4-Cl(Ph) | PhCH$_2$CH$_2$ |
| 38.77 | CH$_3$ | CH3 | 2,4-F(Ph) | PhCH$_2$CH$_2$ |
| 38.78 | C$_2$H$_5$ | H | Ph | CH$_3$ |
| 38.79 | C$_2$H$_5$ | H | 2-Cl(Ph) | CH$_3$ |
| 38.80 | C$_2$H$_5$ | H | 3-Cl(Ph) | CH$_3$ |
| 38.81 | C$_2$H$_5$ | H | 4-Cl(Ph) | CH$_3$ |
| 38.82 | C$_2$H$_5$ | H | 4-Br(Ph) | CH$_3$ |
| 38.83 | C$_2$H$_5$ | H | 4-F(Ph) | CH$_3$ |
| 38.84 | C$_2$H$_5$ | H | 4-OCH$_3$(Ph) | CH$_3$ |
| 38.85 | C$_2$H$_5$ | H | 4-CH$_3$(Ph) | CH$_3$ |

TABLE 38-continued

| Compd. | R₂ | R₃ | R₇ | R₁₀ |
|---|---|---|---|---|
| 38.86 | C₂H₅ | H | 4-NO₂(Ph) | CH₃ |
| 38.87 | C₂H₅ | H | 2,4-Cl(Ph) | CH₃ |
| 38.88 | C₂H₅ | H | 2,4-F(Ph) | CH₃ |
| 38.89 | C₂H₅ | H | Ph | C₂H₅ |
| 38.90 | C₂H₅ | H | 2-Cl(Ph) | C₂H₅ |
| 38.91 | C₂H₅ | H | 3-Cl(Ph) | C₂H₅ |
| 38.92 | C₂H₅ | H | 4-Cl(Ph) | C₂H₅ |
| 38.93 | C₂H₅ | H | 4-F(Ph) | C₂H₅ |
| 38.94 | C₂H₅ | H | 3-OCH₃(Ph) | C₂H₅ |
| 38.95 | C₂H₅ | H | 4-OCH₃(Ph) | C₂H₅ |
| 38.96 | C₂H₅ | H | 4-CH₃(Ph) | C₂H₅ |
| 38.97 | C₂H₅ | H | 4-NO₂(Ph) | C₂H₅ |
| 38.98 | C₂H₅ | H | 2,4-Cl(Ph) | C₂H₅ |
| 38.99 | C₂H₅ | H | 2,4-F(Ph) | C₂H₅ |
| 38.100 | C₂H₅ | H | Ph | n-C₃H₇ |
| 38.101 | C₂H₅ | H | 2-Cl(Ph) | iso-C₃H₇ |
| 38.102 | C₂H₅ | H | 3-Cl(Ph) | n-C₄H₉ |
| 38.103 | C₂H₅ | H | 4-Cl(Ph) | iso-C₄H₉ |
| 38.104 | C₂H₅ | H | 4-F(Ph) | sec-C₄H₉ |
| 38.105 | C₂H₅ | H | 3-OCH₃(Ph) | C(CH₃)₃ |
| 38.106 | C₂H₅ | H | 4-OCH₃(Ph) | CH₂CH=CH₂ |
| 38.107 | C₂H₅ | H | 4-CH₃(Ph) | CH₂C≡CH |
| 38.108 | C₂H₅ | H | 4-NO₂(Ph) | PhCH₂ |
| 38.109 | C₂H₅ | H | 2,4-Cl(Ph) | PhCH₂CH₂ |
| 38.110 | C₂H₅ | H | 2,4-F(Ph) | CH₃ |
| 38.111 | n-C₃H₇ | H | Ph | CH₃ |
| 38.112 | n-C₃H₇ | H | 2-Cl(Ph) | CH₃ |
| 38.113 | n-C₃H₇ | H | 3-Cl(Ph) | CH₃ |
| 38.114 | n-C₃H₇ | H | 4-Cl(Ph) | CH₃ |
| 38.115 | n-C₃H₇ | H | 4-Br(Ph) | CH₃ |
| 38.116 | n-C₃H₇ | H | 3-OCH₃(Ph) | CH₃ |
| 38.117 | n-C₃H₇ | H | 4-OCH₃(Ph) | CH₃ |
| 38.118 | n-C₃H₇ | H | 4-CH₃(Ph) | CH₃ |
| 38.119 | n-C₃H₇ | H | 4-NO₂(Ph) | CH₃ |
| 38.120 | n-C₃H₇ | H | 2,4-Cl(Ph) | CH₃ |
| 38.121 | n-C₃H₇ | H | 2,4-F(Ph) | CH₃ |
| 38.122 | n-C₃H₇ | H | Ph | C₂H₅ |
| 38.123 | n-C₃H₇ | H | 2-Cl(Ph) | C₂H₅ |
| 38.124 | n-C₃H₇ | H | 3-Cl(Ph) | C₂H₅ |
| 38.125 | n-C₃H₇ | H | 4-Cl(Ph) | C₂H₅ |
| 38.126 | n-C₃H₇ | H | 4-Br(Ph) | C₂H₅ |
| 38.127 | n-C₃H₇ | H | 4-F(Ph) | C₂H₅ |
| 38.128 | n-C₃H₇ | H | 4-OCH₃(Ph) | C₂H₅ |
| 38.129 | n-C₃H₇ | H | 4-CH₃(Ph) | C₂H₅ |
| 38.130 | n-C₃H₇ | H | 4-NO₂(Ph) | C₂H₅ |
| 38.131 | n-C₃H₇ | H | 2,4-Cl(Ph) | C₂H₅ |
| 38.132 | n-C₃H₇ | H | 2,4-F(Ph) | C₂H₅ |
| 38.133 | n-C₃H₇ | H | Ph | n-C₃H₇ |
| 38.134 | n-C₃H₇ | H | Ph | iso-C₃H₇ |
| 38.135 | n-C₃H₇ | H | Ph | n-C₄H₉ |
| 38.136 | n-C₃H₇ | H | Ph | iso-C₄H₉ |
| 38.137 | n-C₃H₇ | H | Ph | C(CH₃)₃ |
| 38.138 | n-C₃H₇ | H | Ph | CH₂CH=CH₂ |
| 38.139 | n-C₃H₇ | H | Ph | CH₂C≡CH |
| 38.140 | n-C₃H₇ | H | Ph | PhCH₂ |
| 38.141 | n-C₃H₇ | H | Ph | PhCH₂CH₂ |
| 38.142 | iso-C₃H₇ | H | Ph | C₂H₅ |
| 38.143 | iso-C₃H₇ | H | Ph | n-C₃H₇ |
| 38.144 | iso-C₃H₇ | H | Ph | iso-C₃H₇ |
| 38.145 | iso-C₃H₇ | H | Ph | n-C₄H₉ |
| 38.146 | iso-C₃H₇ | H | Ph | iso-C₄H₉ |
| 38.147 | iso-C₃H₇ | H | Ph | C(CH₃)₃ |
| 38.148 | iso-C₃H₇ | H | Ph | CH₂CH=CH₂ |
| 38.149 | iso-C₃H₇ | H | Ph | CH₂C≡CH |
| 38.150 | iso-C₃H₇ | H | Ph | PhCH₂ |
| 38.151 | iso-C₃H₇ | H | Ph | PhCH₂CH₂ |
| 38.152 | cyClopropyl | H | 4-F(Ph) | CH₃ |
| 38.153 | cyclopropyl | H | 4-OCH₃(Ph) | CH₃ |
| 38.154 | cyclopropyl | H | 4-CH₃(Ph) | CH₃ |
| 38.155 | cyclopropyl | H | 4-NO₂(Ph) | CH₃ |
| 38.156 | cyclopropyl | H | 2,4-Cl(Ph) | CH₃ |
| 38.157 | cyclopropyl | H | 2,4-F(Ph) | CH₃ |
| 38.158 | cyclopropyl | H | 4-Cl(Ph) | CH₃ |
| 38.159 | cyclopropyl | H | 4-Br(Ph) | CH₃ |
| 38.160 | cyclopropyl | H | 4-F(Ph) | CH₃ |
| 38.161 | cyclopropyl | H | 4-OCH₃(Ph) | CH₃ |
| 38.162 | cyclopropyl | H | 4-CH₃(Ph) | CH₃ |
| 38.163 | cyclopropyl | H | 4-NO₂(Ph) | CH₃ |
| 38.164 | Ph | H | Ph | CH₃ |
| 38.165 | Ph | H | 2-Cl(Ph) | C₂H₅ |
| 38.166 | Ph | H | 3-Cl(Ph) | n-C₃H₇ |
| 38.167 | Ph | H | 4-Cl(Ph) | iso-C₃H₇ |
| 38.168 | Ph | H | 4-Br(Ph) | n-C₄H₉ |
| 38.169 | Ph | H | 4-F(Ph) | iso-C₄H₉ |
| 38.170 | Ph | H | 4-OCH₃(Ph) | C(CH₃)₃ |
| 38.171 | Ph | H | 4-CH₃(Ph) | CH₂CH=CH₂ |
| 38.172 | Ph | H | 4-NO₂(Ph) | CH₂C≡CH |
| 38.173 | Ph | H | 2,4-Cl(Ph) | PhCH₂ |
| 38.174 | CN | H | Ph | CH₃ |
| 38.175 | CN | H | 2-Cl(Ph) | CH₃ |
| 38.176 | CN | H | 3-Cl(Ph) | CH₃ |
| 38.177 | CN | H | 4-Cl(Ph) | CH₃ |
| 38.178 | CN | H | 4-Br(Ph) | CH₃ |
| 38.179 | CN | H | 4-F(Ph) | CH₃ |
| 38.180 | CN | H | 4-Cl(Ph) | CH₃ |
| 38.181 | CN | H | 4-Br(Ph) | CH₃ |
| 38.182 | CN | H | 4-F(Ph) | CH₃ |
| 38.183 | CN | H | 4-OCH₃(Ph) | CH₃ |
| 38.184 | CN | H | 4-CH₃(Ph) | CH₃ |
| 38.185 | CN | H | 4-NO₂(Ph) | CH₃ |
| 38.186 | CN | H | 2,4-Cl(Ph) | CH₃ |
| 38.187 | CN | H | 2,4-F(Ph) | CH₃ |
| 38.188 | CN | H | 4-CF₃(Ph) | CH₃ |
| 38.189 | CN | H | Ph | C₂H₅ |
| 38.190 | CN | H | Ph | n-C₃H₇ |
| 38.191 | CN | H | Ph | iso-C₃H₇ |
| 38.192 | CN | H | Ph | n-C₄H₉ |
| 38.193 | CN | H | Ph | iso-C₄H₉ |
| 38.194 | CN | H | Ph | C(CH₃)₃ |
| 38.195 | CN | H | Ph | CH₂CH=CH₂ |
| 38.196 | CN | H | Ph | CH₂C≡CH |
| 38.197 | CN | H | Ph | PhCH₂ |
| 38.198 | CH₃ | H | 1-napthyl | CH₃ |
| 38.199 | CH₃ | H | 1-napthyl | C₂H₅ |
| 38.200 | CH₃ | H | 1-napthyl | n-C₃H₇ |
| 38.201 | CH₃ | H | 1-napthyl | iso-C₃H₇ |
| 38.202 | CH₃ | H | 1-napthyl | n-C₄H₉ |
| 38.203 | CH₃ | H | 1-napthyl | iso-C₄H₉ |
| 38.204 | CH₃ | H | 1-napthyl | C(CH₃)₃ |
| 38.205 | CH₃ | H | 1-napthyl | CH₂CH=CH₂ |
| 38.206 | CH₃ | H | 1-napthyl | CH₂C≡CH |
| 38.207 | CH₃ | H | 1-napthyl | PhCH₂ |
| 38.208 | CH₃ | H | 2-napthyl | CH₃ |
| 38.209 | CH₃ | H | 2-napthyl | C₂H₅ |
| 38.210 | CH₃ | H | 2-napthyl | n-C₃H₇ |
| 38.211 | CH₃ | H | 2-napthyl | iso-C₃H₇ |
| 38.212 | CH₃ | H | 2-napthyl | n-C₄H₉ |
| 38.213 | CH₃ | H | 2-napthyl | iso-C₄H₉ |
| 38.214 | CH₃ | H | 2-napthyl | C(CH₃)₃ |
| 38.215 | CH₃ | H | 2-napthyl | CH₂CH=CH₂ |
| 38.216 | CH₃ | H | 2-napthyl | CH₂C≡CH |
| 38.217 | CH₃ | H | 2-napthyl | PhCH₂ |
| 38.218 | CN | H | 1-napthyl | CH₃ |
| 38.219 | CN | H | 1-napthyl | C₂H₅ |
| 38.220 | CN | H | 1-napthyl | n-C₃H₇ |
| 38.221 | CN | H | 1-napthyl | iso-C₃H₇ |
| 38.222 | CN | H | 1-napthyl | n-C₄H₉ |
| 38.223 | CN | H | 1-napthyl | iso-C₄H₉ |
| 38.224 | CN | H | 1-napthyl | C(CH₃)₃ |
| 38.225 | CN | H | 1-napthyl | CH₂CH=CH₂ |
| 38.226 | CN | H | 1-napthyl | CH₂C≡CH |
| 38.227 | CN | H | 1-napthyl | PhCH₂ |
| 38.228 | CN | H | 2-napthyl | CH₃ |
| 38.229 | CN | H | 2-napthyl | C₂H₅ |
| 38.230 | CN | H | 2-napthyl | n-C₃H₇ |
| 38.231 | CN | H | 2-napthyl | iso-C₃H₇ |
| 38.232 | CN | H | 2-napthyl | n-C₄H₉ |
| 38.233 | CN | H | 2-napthyl | iso-C₄H₉ |
| 38.234 | CN | H | 2-napthyl | C(CH₃)₃ |
| 38.235 | CN | H | 2-napthyl | CH₂CH=CH₂ |
| 38.236 | CN | H | 2-napthyl | CH₂C≡CH |
| 38.237 | CN | H | 2-napthyl | PhCH₂ |
| 38.238 | CH₃ | CH₃ | 1-napthyl | CH₃ |
| 38.239 | CH₃ | CH₃ | 1-napthyl | C₂H₅ |

TABLE 38-continued

| Compd. | R$_2$ | R$_3$ | R$_7$ | R$_{10}$ |
|---|---|---|---|---|
| 38.240 | CH$_3$ | CH$_3$ | 1-napthyl | n-C$_3$H$_7$ |
| 38.241 | CH$_3$ | CH$_3$ | 1-napthyl | iso-C$_3$H$_7$ |
| 38.242 | CH$_3$ | CH$_3$ | 1-napthyl | n-C$_4$H$_9$ |
| 38.243 | CH$_3$ | CH$_3$ | 1-napthyl | iso-C$_4$H$_9$ |
| 38.244 | CH$_3$ | CH$_3$ | 1-napthyl | C(CH$_3$)$_3$ |
| 38.245 | CH$_3$ | CH$_3$ | 1-napthyl | CH$_2$CH=CH$_2$ |
| 38.246 | CH$_3$ | CH$_3$ | 1-napthyl | CH$_2$C≡CH |
| 38.247 | CH$_3$ | CH$_3$ | 1-napthyl | PhCH$_2$ |
| 38.248 | CH$_3$ | CH$_3$ | 2-napthyl | CH$_3$ |
| 38.249 | CH$_3$ | CH$_3$ | 2-napthyl | C$_2$H$_5$ |
| 38.250 | CH$_3$ | CH$_3$ | 2-napthyl | n-C$_3$H$_7$ |
| 38.251 | CH$_3$ | CH$_3$ | 2-napthyl | iso-C$_3$H$_7$ |
| 38.252 | CH$_3$ | CH$_3$ | 2-napthyl | n-C$_4$H$_9$ |
| 38.253 | CH$_3$ | CH$_3$ | 2-napthyl | iso-C$_4$H$_9$ |
| 38.254 | CH$_3$ | CH$_3$ | 2-napthyl | C(CH$_3$)$_3$ |
| 38.255 | CH$_3$ | CH$_3$ | 2-napthyl | CH$_2$CH=CH$_2$ |
| 38.256 | CH$_3$ | CH$_3$ | 2-napthyl | CH$_2$C≡CH |
| 38.257 | CH$_3$ | CH$_3$ | 2-napthyl | PhCH$_2$ |
| 38.258 | CN | CH$_3$ | 1-napthyl | CH$_3$ |
| 38.259 | CN | CH$_3$ | 1-napthyl | C$_2$H$_5$ |
| 38.260 | CN | CH$_3$ | 1-napthyl | n-C$_3$H$_7$ |
| 38.261 | CN | CH$_3$ | 1-napthyl | iso-C$_3$H$_7$ |
| 38.262 | CN | CH$_3$ | 1-napthyl | n-C$_4$H$_9$ |
| 38.263 | CN | CH$_3$ | 1-napthyl | iso-C$_4$H$_9$ |
| 38.264 | CN | CH$_3$ | 1-napthyl | C(CH$_3$)$_3$ |
| 38.265 | CN | CH$_3$ | 1-napthyl | CH$_2$CH=CH$_2$ |
| 38.266 | CN | CH$_3$ | 1-napthyl | CH$_2$C≡CH |
| 38.267 | CN | CH$_3$ | 1-napthyl | PhCH$_2$ |
| 38.268 | CN | CH$_3$ | 2-napthyl | CH$_3$ |
| 38.269 | CN | CH$_3$ | 2-napthyl | C$_2$H$_5$ |
| 38.270 | CN | CH$_3$ | 2-napthyl | n-C$_3$H$_7$ |
| 38.271 | CN | CH$_3$ | 2-napthyl | iso-C$_3$H$_7$ |
| 38.272 | CN | CH$_3$ | 2-napthyl | n-C$_4$H$_9$ |

Typical compounds encompassed by the present invention of Formula I include those compounds of Formula XII, which is Formula I with A=R$_4$=R$_5$=R$_6$=H, R$_1$=CH$_3$, X=N, Y=NH, Z=NR$_{10}$, and where R$_2$, R$_3$, R$_7$, and R$_{10}$ are defined in Table 39.

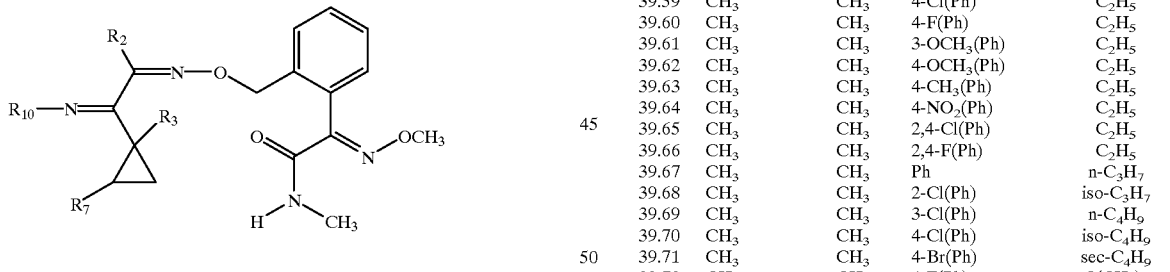

Formula XII

TABLE 39

| Compd. | R$_2$ | R$_3$ | R$_7$ | R$_{10}$ |
|---|---|---|---|---|
| 39.1 | H | H | Ph | CH$_3$ |
| 39.2 | H | H | 4-Cl(Ph) | CH$_3$ |
| 39.3 | H | H | 4-Br(Ph) | CH$_3$ |
| 39.4 | H | H | 4-F(Ph) | CH$_3$ |
| 39.5 | H | H | 4-OCH$_3$(Ph) | CH$_3$ |
| 39.6 | H | H | 4-CF$_3$(Ph) | CH$_3$ |
| 39.7 | H | H | Ph | CH$_3$ |
| 39.8 | H | H | 4-Cl(Ph) | CH$_3$ |
| 39.9 | H | H | 4-Br(Ph) | CH$_3$ |
| 39.10 | H | H | 4-F(Ph) | CH$_3$ |
| 39.11 | CH$_3$ | H | Ph | CH$_3$ |
| 39.12 | CH$_3$ | H | 2-Cl(Ph) | CH$_3$ |
| 39.13 | CH$_3$ | H | 3-Cl(Ph) | CH$_3$ |
| 39.14 | CH$_3$ | H | 4-Cl(Ph) | CH$_3$ |
| 39.15 | CH$_3$ | H | 2-Br(Ph) | CH$_3$ |
| 39.16 | CH$_3$ | H | 3-Br(Ph) | CH$_3$ |
| 39.17 | CH$_3$ | H | 4-Br(Ph) | CH$_3$ |
| 39.18 | CH$_3$ | H | Ph | C$_2$H$_5$ |
| 39.19 | CH$_3$ | H | 2-Cl(Ph) | C$_2$H$_5$ |
| 39.20 | CH$_3$ | H | 3-Cl(Ph) | C$_2$H$_5$ |
| 39.21 | CH$_3$ | H | 4-Cl(Ph) | C$_2$H$_5$ |
| 39.22 | CH$_3$ | H | 2-Br(Ph) | C$_2$H$_5$ |
| 39.23 | CH$_3$ | H | 3-Br(Ph) | C$_2$H$_5$ |
| 39.24 | CH$_3$ | H | 4-Br(Ph) | C$_2$H$_5$ |
| 39.25 | CH$_3$ | H | 2-CH$_3$(Ph) | C$_2$H$_5$ |
| 39.26 | CH$_3$ | H | 3-CH$_3$(Ph) | C$_2$H$_5$ |
| 39.27 | CH$_3$ | H | 2-CF$_3$(Ph) | C$_2$H$_5$ |
| 39.28 | CH$_3$ | H | 3-CF$_3$(Ph) | C$_2$H$_5$ |
| 39.29 | CH$_3$ | H | 4-CF$_3$(Ph) | C$_2$H$_5$ |
| 39.30 | CH$_3$ | H | 2-NO$_2$(Ph) | C$_2$H$_5$ |
| 39.31 | CH$_3$ | H | 3-NO$_2$(Ph) | C$_2$H$_5$ |
| 39.32 | CH$_3$ | H | 4-NO$_2$(Ph) | C$_2$H$_5$ |
| 39.33 | CH$_3$ | H | 2,3-Cl(Ph) | C$_2$H$_5$ |
| 39.34 | CH$_3$ | H | 2,4-Cl(Ph) | C$_2$H$_5$ |
| 39.35 | CH$_3$ | H | 2,5-Cl(Ph) | C$_2$H$_5$ |
| 39.36 | CH$_3$ | H | 2,6-Cl(Ph) | C$_2$H$_5$ |
| 39.37 | CH$_3$ | H | 3,4-Cl(Ph) | C$_2$H$_5$ |
| 39.38 | CH$_3$ | H | 3,5-Cl(Ph) | C$_2$H$_5$ |
| 39.39 | CH$_3$ | H | Ph | n-C$_3$H$_7$ |
| 39.40 | CH$_3$ | H | Ph | iso-C$_3$H$_7$ |
| 39.41 | CH$_3$ | H | Ph | n-C$_4$H$_9$ |
| 39.42 | CH$_3$ | H | Ph | iso-C$_4$H$_9$ |
| 39.43 | CH$_3$ | H | Ph | C(CH$_3$)$_3$ |
| 39.44 | CH$_3$ | H | Ph | CH$_2$CH=CH$_2$ |
| 39.45 | CH$_3$ | H | Ph | CH$_2$C≡CH |
| 39.46 | CH$_3$ | H | Ph | PhCH$_2$ |
| 39.47 | CH$_3$ | CH$_3$ | Ph | CH$_3$ |
| 39.48 | CH$_3$ | CH$_3$ | 4-Cl(Ph) | CH$_3$ |
| 39.49 | CH$_3$ | CH$_3$ | 4-Br(Ph) | CH$_3$ |
| 39.50 | CH$_3$ | CH$_3$ | 4-F(Ph) | CH$_3$ |
| 39.51 | CH$_3$ | CH$_3$ | 4-OCH$_3$(Ph) | CH$_3$ |
| 39.52 | CH$_3$ | CH$_3$ | 4-CH$_3$(Ph) | CH$_3$ |
| 39.53 | CH$_3$ | CH$_3$ | 4-NO$_2$(Ph) | CH$_3$ |
| 39.54 | CH$_3$ | CH$_3$ | 2,4-Cl(Ph) | CH$_3$ |
| 39.55 | CH$_3$ | CH$_3$ | 2,4-F(Ph) | CH$_3$ |
| 39.56 | CH$_3$ | CH$_3$ | Ph | C$_2$H$_5$ |
| 39.57 | CH$_3$ | CH$_3$ | 2-Cl(Ph) | C$_2$H$_5$ |
| 39.58 | CH$_3$ | CH$_3$ | 3-Cl(Ph) | C$_2$H$_5$ |
| 39.59 | CH$_3$ | CH$_3$ | 4-Cl(Ph) | C$_2$H$_5$ |
| 39.60 | CH$_3$ | CH$_3$ | 4-F(Ph) | C$_2$H$_5$ |
| 39.61 | CH$_3$ | CH$_3$ | 3-OCH$_3$(Ph) | C$_2$H$_5$ |
| 39.62 | CH$_3$ | CH$_3$ | 4-OCH$_3$(Ph) | C$_2$H$_5$ |
| 39.63 | CH$_3$ | CH$_3$ | 4-CH$_3$(Ph) | C$_2$H$_5$ |
| 39.64 | CH$_3$ | CH$_3$ | 4-NO$_2$(Ph) | C$_2$H$_5$ |
| 39.65 | CH$_3$ | CH$_3$ | 2,4-Cl(Ph) | C$_2$H$_5$ |
| 39.66 | CH$_3$ | CH$_3$ | 2,4-F(Ph) | C$_2$H$_5$ |
| 39.67 | CH$_3$ | CH$_3$ | Ph | n-C$_3$H$_7$ |
| 39.68 | CH$_3$ | CH$_3$ | 2-Cl(Ph) | iso-C$_3$H$_7$ |
| 39.69 | CH$_3$ | CH$_3$ | 3-Cl(Ph) | n-C$_4$H$_9$ |
| 39.70 | CH$_3$ | CH$_3$ | 4-Cl(Ph) | iso-C$_4$H$_9$ |
| 39.71 | CH$_3$ | CH$_3$ | 4-Br(Ph) | sec-C$_4$H$_9$ |
| 39.72 | CH$_3$ | CH$_3$ | 4-F(Ph) | C(CH$_3$)$_3$ |
| 39.73 | CH$_3$ | CH$_3$ | 4-OCH$_3$(Ph) | CH$_2$CH=CH$_2$ |
| 39.74 | CH$_3$ | CH$_3$ | 4-CH$_3$(Ph) | CH$_2$C≡CH |
| 39.75 | CH$_3$ | CH$_3$ | 4-NO$_2$(Ph) | PhCH$_2$ |
| 39.76 | CH$_3$ | CH$_3$ | 2,4-Cl(Ph) | PhCH$_2$CH$_2$ |
| 39.77 | CH$_3$ | CH$_3$ | 2,4-F(Ph) | PhCH$_2$CH$_2$ |
| 39.78 | C$_2$H$_5$ | H | Ph | CH$_3$ |
| 39.79 | C$_2$H$_5$ | H | 2-Cl(Ph) | CH$_3$ |
| 39.80 | C$_2$H$_5$ | H | 3-Cl(Ph) | CH$_3$ |
| 39.81 | C$_2$H$_5$ | H | 4-Cl(Ph) | CH$_3$ |
| 39.82 | C$_2$H$_5$ | H | 4-Br(Ph) | CH$_3$ |
| 39.83 | C$_2$H$_5$ | H | 4-F(Ph) | CH$_3$ |
| 39.84 | C$_2$H$_5$ | H | 4-OCH$_3$(Ph) | CH$_3$ |
| 39.85 | C$_2$H$_5$ | H | 4-CH$_3$(Ph) | CH$_3$ |
| 39.86 | C$_2$H$_5$ | H | 4-NO$_2$(Ph) | CH$_3$ |
| 39.87 | C$_2$H$_5$ | H | 2,4-Cl(Ph) | CH$_3$ |
| 39.88 | C$_2$H$_5$ | H | 2,4-F(Ph) | CH$_3$ |
| 39.89 | C$_2$H$_5$ | H | Ph | C$_2$H$_5$ |
| 39.90 | C$_2$H$_5$ | H | 2-Cl(Ph) | C$_2$H$_5$ |
| 39.91 | C$_2$H$_5$ | H | 3-Cl(Ph) | C$_2$H$_5$ |

TABLE 39-continued

| Compd. | R₂ | R₃ | R₇ | R₁₀ |
|---|---|---|---|---|
| 39.92 | C₂H₅ | H | 4-Cl(Ph) | C₂H₅ |
| 39.93 | C₂H₅ | H | 4-F(Ph) | C₂H₅ |
| 39.94 | C₂H₅ | H | 3-OCH₃(Ph) | C₂H₅ |
| 39.95 | C₂H₅ | H | 4-OCH₃(Ph) | C₂H₅ |
| 39.96 | C₂H₅ | H | 4-CH₃(Ph) | C₂H₅ |
| 39.97 | C₂H₅ | H | 4-NO₂(Ph) | C₂H₅ |
| 39.98 | C₂H₅ | H | 2,4-Cl(Ph) | C₂H₅ |
| 39.99 | C₂H₅ | H | 2,4-F(Ph) | C₂H₅ |
| 39.100 | C₂H₅ | H | Ph | n-C₃H₇ |
| 39.101 | C₂H₅ | H | 2-Cl(Ph) | iso-C₃H₇ |
| 39.102 | C₂H₅ | H | 3-Cl(Ph) | n-C₄H₉ |
| 39.103 | C₂H₅ | H | 4-Cl(Ph) | iso-C₄H₉ |
| 39.104 | C₂H₅ | H | 4-F(Ph) | sec-C₄H₉ |
| 39.105 | C₂H₅ | H | 3-OCH₃(Ph) | C(CH₃)₃ |
| 39.106 | C₂H₅ | H | 4-OCH₃(Ph) | CH₂CH=CH₂ |
| 39.107 | C₂H₅ | H | 4-CH₃(Ph) | CH₂C≡CH |
| 39.108 | C₂H₅ | H | 4-NO₂(Ph) | PhCH₂ |
| 39.109 | C₂H₅ | H | 2,4-Cl(Ph) | PhCH₂CH₂ |
| 39.110 | C₂H₅ | H | 2,4-F(Ph) | CH₃ |
| 39.111 | n-C₃H₇ | H | Ph | CH₃ |
| 39.112 | n-C₃H₇ | H | 2-Cl(Ph) | CH₃ |
| 39.113 | n-C₃H₇ | H | 3-Cl(Ph) | CH₃ |
| 39.114 | n-C₃H₇ | H | 4-Cl(Ph) | CH₃ |
| 39.115 | n-C₃H₇ | H | 4-Br(Ph) | CH₃ |
| 39.116 | n-C₃H₇ | H | 3-OCH₃(Ph) | CH₃ |
| 39.117 | n-C₃H₇ | H | 4-OCH₃(Ph) | CH₃ |
| 39.118 | n-C₃H₇ | H | 4-CH₃(Ph) | CH₃ |
| 39.119 | n-C₃H₇ | H | 4-NO₂(Ph) | CH₃ |
| 39.120 | n-C₃H₇ | H | 2,4-Cl(Ph) | CH₃ |
| 39.121 | n-C₃H₇ | H | 2,4-F(Ph) | CH₃ |
| 39.122 | n-C₃H₇ | H | Ph | C₂H₅ |
| 39.123 | n-C₃H₇ | H | 2-Cl(Ph) | C₂H₅ |
| 39.124 | n-C₃H₇ | H | 3-Cl(Ph) | C₂H₅ |
| 39.125 | n-C₃H₇ | H | 4-Cl(Ph) | C₂H₅ |
| 39.126 | n-C₃H₇ | H | 4-Br(Ph) | C₂H₅ |
| 39.127 | n-C₃H₇ | H | 4-F(Ph) | C₂H₅ |
| 39.128 | n-C₃H₇ | H | 4-OCH₃(Ph) | C₂H₅ |
| 39.129 | n-C₃H₇ | H | 4-CH₃(Ph) | C₂H₅ |
| 39.130 | n-C₃H₇ | H | 4-NO₂(Ph) | C₂H₅ |
| 39.131 | n-C₃H₇ | H | 2,4-Cl(Ph) | C₂H₅ |
| 39.132 | n-C₃H₇ | H | 2,4-F(Ph) | C₂H₅ |
| 39.133 | n-C₃H₇ | H | Ph | n-C₃H₇ |
| 39.134 | n-C₃H₇ | H | Ph | iso-C₃H₇ |
| 39.135 | n-C₃H₇ | H | Ph | n-C₄H₉ |
| 39.136 | n-C₃H₇ | H | Ph | iso-C₄H₉ |
| 39.137 | n-C₃H₇ | H | Ph | C(CH₃)₃ |
| 39.138 | n-C₃H₇ | H | Ph | CH₂CH=CH₂ |
| 39.139 | n-C₃H₇ | H | Ph | CH₂C≡CH |
| 39.140 | n-C₃H₇ | H | Ph | PhCH₂ |
| 39.141 | n-C₃H₇ | H | Ph | PhCH₂CH₂ |
| 39.142 | iso-C₃H₇ | H | Ph | C₂H₅ |
| 39.143 | iso-C₃H₇ | H | Ph | n-C₃H₇ |
| 39.144 | iso-C₃H₇ | H | Ph | iso-C₃H₇ |
| 39.145 | iso-C₃H₇ | H | Ph | n-C₄H₉ |
| 39.146 | iso-C₃H₇ | H | Ph | iso-C₄H₉ |
| 39.147 | iso-C₃H₇ | H | Ph | C(CH₃)₃ |
| 39.148 | iso-C₃H₇ | H | Ph | CH₂CH=CH₂ |
| 39.149 | iso-C₃H₇ | H | Ph | CH₂C≡CH |
| 39.150 | iso-C₃H₇ | H | Ph | PhCH₂ |
| 39.151 | iso-C₃H₇ | H | Ph | PhCH₂CH₂ |
| 39.152 | cyclopropyl | H | 4-F(Ph) | CH₃ |
| 39.153 | cyclopropyl | H | 4-OCH₃(Ph) | CH₃ |
| 39.154 | cyclopropyl | H | 4-CH₃(Ph) | CH₃ |
| 39.155 | cyclopropyl | H | 4-NO₂(Ph) | CH₃ |
| 39.156 | cyclopropyl | H | 2,4-Cl(Ph) | CH₃ |
| 39.157 | cyclopropyl | H | 2,4-F(Ph) | CH₃ |
| 39.158 | cyclopropyl | H | 4-Cl(Ph) | CH₃ |
| 39.159 | cyclopropyl | H | 4-Br(Ph) | CH₃ |
| 39.160 | cyclopropyl | H | 4-F(Ph) | CH₃ |
| 39.161 | cyclopropyl | H | 4-OCH₃(Ph) | CH₃ |
| 39.162 | cyclopropyl | H | 4-CH₃(Ph) | CH₃ |
| 39.163 | cyclopropyl | H | 4-NO₂(Ph) | CH₃ |
| 39.164 | Ph | H | Ph | CH₃ |
| 39.165 | Ph | H | 2-Cl(Ph) | C₂H₅ |
| 39.166 | Ph | H | 3-Cl(Ph) | n-C₃H₇ |
| 39.167 | Ph | H | 4-Cl(Ph) | iso-C₃H₇ |
| 39.168 | Ph | H | 4-Br(Ph) | n-C₄H₉ |
| 39.169 | Ph | H | 4-F(Ph) | iso-C₄H₉ |
| 39.170 | Ph | H | 4-OCH₃(Ph) | C(CH₃)₃ |
| 39.171 | Ph | H | 4-CH₃(Ph) | CH₂CH=CH₂ |
| 39.172 | Ph | H | 4-NO₂(Ph) | CH₂C≡CH |
| 39.173 | Ph | H | 2,4-Cl(Ph) | PhCH₂ |
| 39.174 | CN | H | Ph | CH₃ |
| 39.175 | CN | H | 2-Cl(Ph) | CH₃ |
| 39.176 | CN | H | 3-Cl(Ph) | CH₃ |
| 39.177 | CN | H | 4-Cl(Ph) | CH₃ |
| 39.178 | CN | H | 4-Br(Ph) | CH₃ |
| 39.179 | CN | H | 4-F(Ph) | CH₃ |
| 39.180 | CN | H | 4-Cl(Ph) | CH₃ |
| 39.181 | CN | H | 4-Br(Ph) | CH₃ |
| 39.182 | CN | H | 4-F(Ph) | CH₃ |
| 39.183 | CN | H | 4-OCH₃(Ph) | CH₃ |
| 39.184 | CN | H | 4-CH₃(Ph) | CH₃ |
| 39.185 | CN | H | 4-NO₂(Ph) | CH₃ |
| 39.186 | CN | H | 2,4-Cl(Ph) | CH₃ |
| 39.187 | CN | H | 2,4-F(Ph) | CH₃ |
| 39.188 | CN | H | 4-CF₃(Ph) | CH₃ |
| 39.189 | CN | H | Ph | C₂H₅ |
| 39.190 | CN | H | Ph | n-C₃H₇ |
| 39.191 | CN | H | Ph | iso-C₃H₇ |
| 39.192 | CN | H | Ph | n-C₄H₉ |
| 39.193 | CN | H | Ph | iso-C₄H₉ |
| 39.194 | CN | H | Ph | C(CH₃)₃ |
| 39.195 | CN | H | Ph | CH₂CH=CH₂ |
| 39.196 | CN | H | Ph | CH₂C≡CH |
| 39.197 | CN | H | Ph | PhCH₂ |
| 39.198 | CH₃ | H | 1-napthyl | CH₃ |
| 39.199 | CH₃ | H | 1-napthyl | C₂H₅ |
| 39.200 | CH₃ | H | 1-napthyl | n-C₃H₇ |
| 39.201 | CH₃ | H | 1-napthyl | iso-C₃H₇ |
| 39.202 | CH₃ | H | 1-napthyl | n-C₄H₉ |
| 39.203 | CH₃ | H | 1-napthyl | iso-C₄H₉ |
| 39.204 | CH₃ | H | 1-napthyl | C(CH₃)₃ |
| 39.205 | CH₃ | H | 1-napthyl | CH₂CH=CH₂ |
| 39.206 | CH₃ | H | 1-napthyl | CH₂C≡CH |
| 39.207 | CH₃ | H | 1-napthyl | PhCH₂ |
| 39.208 | CH₃ | H | 2-napthyl | CH₃ |
| 39.209 | CH₃ | H | 2-napthyl | C₂H₅ |
| 39.210 | CH₃ | H | 2-napthyl | n-C₃H₇ |
| 39.211 | CH₃ | H | 2-napthyl | iso-C₃H₇ |
| 39.212 | CH₃ | H | 2-napthyl | n-C₄H₉ |
| 39.213 | CH₃ | H | 2-napthyl | iso-C₄H₉ |
| 39.214 | CH₃ | H | 2-napthyl | C(CH₃)₃ |
| 39.215 | CH₃ | H | 2-napthyl | CH₂CH=CH₂ |
| 39.216 | CH₃ | H | 2-napthyl | CH₂C≡CH |
| 39.217 | CH₃ | H | 2-napthyl | PhCH₂ |
| 39.218 | CN | H | 1-napthyl | CH₃ |
| 39.219 | CN | H | 1-napthyl | C₂H₅ |
| 39.220 | CN | H | 1-napthyl | n-C₃H₇ |
| 39.221 | CN | H | 1-napthyl | iso-C₃H₇ |
| 39.222 | CN | H | 1-napthyl | n-C₄H₉ |
| 39.223 | CN | H | 1-napthyl | iso-C₄H₉ |
| 39.224 | CN | H | 1-napthyl | C(CH₃)₃ |
| 39.225 | CN | H | 1-napthyl | CH₂CH=CH₂ |
| 39.226 | CN | H | 1-napthyl | CH₂C≡CH |
| 39.227 | CN | H | 1-napthyl | PhCH₂ |
| 39.228 | CN | H | 2-napthyl | CH₃ |
| 39.229 | CN | H | 2-napthyl | C₂H₅ |
| 39.230 | CN | H | 2-napthyl | n-C₃H₇ |
| 39.231 | CN | H | 2-napthyl | iso-C₃H₇ |
| 39.232 | CN | H | 2-napthyl | n-C₄H₉ |
| 39.233 | CN | H | 2-napthyl | iso-C₄H₉ |
| 39.234 | CN | H | 2-napthyl | C(CH₃)₃ |
| 39.235 | CN | H | 2-napthyl | CH₂CH=CH₂ |
| 39.236 | CN | H | 2-napthyl | CH₂C≡CH |
| 39.237 | CN | H | 2-napthyl | PhCH₂ |
| 39.238 | CH₃ | CH₃ | 1-napthyl | CH₃ |
| 39.239 | CH₃ | CH₃ | 1-napthyl | C₂H₅ |
| 39.240 | CH₃ | CH₃ | 1-napthyl | n-C₃H₇ |
| 39.241 | CH₃ | CH₃ | 1-napthyl | iso-C₃H₇ |
| 39.242 | CH₃ | CH₃ | 1-napthyl | n-C₄H₉ |
| 39.243 | CH₃ | CH₃ | 1-napthyl | iso-C₄H₉ |
| 39.244 | CH₃ | CH₃ | 1-napthyl | C(CH₃)₃ |
| 39.245 | CH₃ | CH₃ | 1-napthyl | CH₂CH=CH₂ |

TABLE 39-continued

| Compd. | R$_2$ | R$_3$ | R$_7$ | R$_{10}$ |
|---|---|---|---|---|
| 39.246 | CH$_3$ | CH$_3$ | 1-napthyl | CH$_2$C≡CH |
| 39.247 | CH$_3$ | CH$_3$ | 1-napthyl | PhCH$_2$ |
| 39.248 | CH$_3$ | CH$_3$ | 2-napthyl | CH$_3$ |
| 39.249 | CH$_3$ | CH$_3$ | 2-napthyl | C$_2$H$_5$ |
| 39.250 | CH$_3$ | CH$_3$ | 2-napthyl | n-C$_3$H$_7$ |
| 39.251 | CH$_3$ | CH$_3$ | 2-napthyl | iso-C$_3$H$_7$ |
| 39.252 | CH$_3$ | CH$_3$ | 2-napthyl | n-C$_4$H$_9$ |
| 39.253 | CH$_3$ | CH$_3$ | 2-napthyl | iso-C$_4$H$_9$ |
| 39.254 | CH$_3$ | CH$_3$ | 2-napthyl | C(CH$_3$)$_3$ |
| 39.255 | CH$_3$ | CH$_3$ | 2-napthyl | CH$_2$CH=CH$_2$ |
| 39.256 | CH$_3$ | CH$_3$ | 2-napthyl | CH$_2$C≡CH |
| 39.257 | CH$_3$ | CH$_3$ | 2-napthyl | PhCH$_2$ |
| 39.258 | CN | CH$_3$ | 1-napthyl | CH$_3$ |
| 39.259 | CN | CH$_3$ | 1-napthyl | C$_2$H$_5$ |
| 39.260 | CN | CH$_3$ | 1-napthyl | n-C$_3$H$_7$ |
| 39.261 | CN | CH$_3$ | 1-napthyl | iso-C$_3$H$_7$ |
| 39.262 | CN | CH$_3$ | 1-napthyl | n-C$_4$H$_9$ |
| 39.263 | CN | CH$_3$ | 1-napthyl | iso-C$_4$H$_9$ |
| 39.264 | CN | CH$_3$ | 1-napthyl | C(CH$_3$)$_3$ |
| 39.265 | CN | CH$_3$ | 1-napthyl | CH$_2$CH=CH$_2$ |
| 39.266 | CN | CH$_3$ | 1-napthyl | CH$_2$C≡CH |
| 39.267 | CN | CH$_3$ | 1-napthyl | PhCH$_2$ |
| 39.268 | CN | CH$_3$ | 2-napthyl | CH$_3$ |
| 39.269 | CN | CH$_3$ | 2-napthyl | C$_2$H$_5$ |
| 39.270 | CN | CH$_3$ | 2-napthyl | n-C$_3$H$_7$ |
| 39.271 | CN | CH$_3$ | 2-napthyl | iso-C$_3$H$_7$ |
| 39.272 | CN | CH$_3$ | 2-napthyl | n-C$_4$H$_9$ |

TABLE 40

Compounds 40.1 to 40.226 are compounds of Formula X which is Formula I with A=R$_4$=R$_5$=R$_6$=H, R$_1$=CH$_3$, X=CH, Y=O, Z=NR$_{10}$, where R$_{10}$ is CH$_3$ and the substituents R$_2$, R$_3$, and R$_7$ are defined in Table 4.

TABLE 41

Compounds 41.1 to 41.226 are compounds of Formula XI which is Formula I with A=R$_4$=R$_5$=R$_6$=H, R$_1$=CH$_3$, X=N, Y=O, Z=NR$_{10}$, where R$_{10}$ is CH$_3$ and the substituents R$_2$, R$_3$, and R$_7$ are defined in Table 4.

TABLE 42

Compounds 42.1 to 42.226 are compounds of Formula XII which is Formula I with A=R$_4$=R$_5$=R$_6$=H, R$_1$=CH$_3$, X=N, Y=NH, Z=NR$_{10}$, where R$_{10}$ is CH$_3$ and the substituents R$_2$, R$_3$, and R$_7$ are defined in Table 4.

TABLE 43

Compounds 43.1 to 43.221 are compounds of Formula X which is Formula with A=R$_4$=R$_5$=R$_6$=H, R$_1$=CH$_3$, X=CH, Y=O, Z=NR$_{10}$, where R$_{10}$ is C$_2$H$_5$ and the substituents R$_2$, R$_3$, and R$_7$ are defined in Table 7.

TABLE 44

Compounds 44.1 to 44.221 are compounds of Formula XI which is Formula I with A=R$_4$=R$_5$=R$_6$=H, R$_1$=CH$_3$, X=N, Y=O, Z=NR$_{10}$, where R$_{10}$ is C$_2$H$_5$ and the substituents R$_2$, R$_3$, and R$_7$ are defined in Table 7.

TABLE 45

Compounds 45.1 to 45.221 are compounds of Formula XII which is Formula I with A=R$_4$=R$_5$=R$_6$=H, R$_1$=CH$_3$, X=N, Y=NH, Z=NR$_{10}$, where R$_{10}$ is C$_2$H$_5$ and the substituents R$_2$, R$_3$, and R$_7$ are defined in Table 7.

TABLE 46

Compounds 46.1 to 46.139 are compounds of Formula X which is Formula I with A=R$_4$=R$_5$=R$_6$=H, R$_1$=CH$_3$, X=CH, Y=O, Z=NR$_{10}$, where R$_{10}$ is Ph and the substituents R$_2$, R$_3$, and R$_7$ are defined in Table 10.

TABLE 47

Compounds 47.1 to 47.139 are compounds of Formula XI which is Formula I with A=R$_4$=R$_5$=R$_6$=H, R$_1$=CH$_3$, X=N, Y=O, Z=NR$_{10}$, where R$_{10}$ is Ph and the substituents R$_2$, R$_3$, and R$_7$ are defined in Table 10.

TABLE 48

Compounds 48.1 to 48.139 are compounds of Formula XII which is Formula I with A=R$_4$=R$_5$=R$_6$=H, R$_1$=CH$_3$, X=N, Y=NH, Z=NR$_{10}$, where R$_{10}$ is Ph and the substituents R$_2$, R$_3$, and R$_7$ are defined in Table 10.

Typical compounds encompassed by the present invention of Formula I include those compounds of Formula X, which is Formula I with A=R$_4$=R$_5$=R$_6$=H, R$_1$=CH$_3$, X=CH, Y=O, Z=NR$_{10}$, and where R$_2$, R$_3$, R$_7$, R$_{10}$, R$_{11}$ and R$_{12}$ are defined in Table 49.

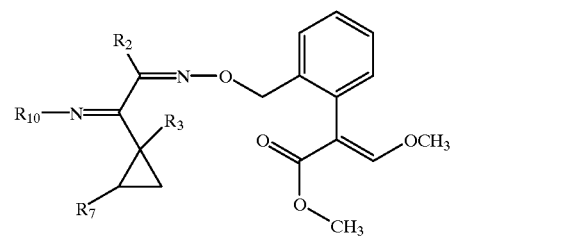

Formula X

TABLE 49

| Compd | R$_2$ | R$_3$ | R$_7$ | R$_{10}$ | R$_{11}$ | R$_{12}$ |
|---|---|---|---|---|---|---|
| 49.1 | H | H | Ph | N=CR$_{11}$R$_{12}$ | CH$_3$ | CH$_3$ |
| 49.2 | H | H | 4-Cl(Ph) | N=CR$_{11}$R$_{12}$ | CH$_3$ | CH$_3$ |
| 49.3 | H | H | 4-Br(Ph) | N=CR$_{11}$R$_{12}$ | CH$_3$ | CH$_3$ |
| 49.4 | H | H | 4-F(Ph) | N=CR$_{11}$R$_{12}$ | CH$_3$ | CH$_3$ |
| 49.5 | H | H | 4-OCH$_3$(Ph) | N=CR$_{11}$R$_{12}$ | CH$_3$ | CH$_3$ |
| 49.6 | H | H | 4-CF$_3$(Ph) | N=CR$_{11}$R$_{12}$ | CH$_3$ | CH$_3$ |
| 49.7 | H | H | Ph | N=CR$_{11}$R$_{12}$ | CH$_3$ | CH$_3$ |
| 49.8 | H | H | 4-Cl(Ph) | N=CR$_{11}$R$_{12}$ | CH$_3$ | CH$_3$ |
| 49.9 | H | H | 4-Br(Ph) | N=CR$_{11}$R$_{12}$ | CH$_3$ | CH$_3$ |
| 49.10 | H | H | 4-F(Ph) | N=CR$_{11}$R$_{12}$ | CH$_3$ | CH$_3$ |

TABLE 49-continued

| Compd | R$_2$ | R$_3$ | R$_7$ | R$_{10}$ | R$_{11}$ | R$_{12}$ |
|---|---|---|---|---|---|---|
| 49.11 | CH$_3$ | H | Ph | N=CR$_{11}$R$_{12}$ | CH$_3$ | CH$_3$ |
| 49.12 | CH$_3$ | H | 2-Cl(Ph) | N=CR$_{11}$R$_{12}$ | CH$_3$ | CH$_3$ |
| 49.13 | CH$_3$ | H | 3-Cl(Ph) | N=CR$_{11}$R$_{12}$ | CH$_3$ | CH$_3$ |
| 49.14 | CH$_3$ | H | 4-Cl(Ph) | N=CR$_{11}$R$_{12}$ | CH$_3$ | CH$_3$ |
| 49.15 | CH$_3$ | H | 2-Br(Ph) | N=CR$_{11}$R$_{12}$ | CH$_3$ | CH$_3$ |
| 49.16 | CH$_3$ | H | 3-Br(Ph) | N=CR$_{11}$R$_{12}$ | CH$_3$ | CH$_3$ |
| 49.17 | CH$_3$ | H | 4-Br(Ph) | N=CR$_{11}$R$_{12}$ | CH$_3$ | CH$_3$ |
| 49.18 | CH$_3$ | H | Ph | N=CR$_{11}$R$_{12}$ | H | Ph |
| 49.19 | CH$_3$ | H | 2-Cl(Ph) | N=CR$_{11}$R$_{12}$ | H | Ph |
| 49.20 | CH$_3$ | H | 3-Cl(Ph) | N=CR$_{11}$R$_{12}$ | H | Ph |
| 49.21 | CH$_3$ | H | 4-Cl(Ph) | N=CR$_{11}$R$_{12}$ | H | Ph |
| 49.22 | CH$_3$ | H | 2-Br(Ph) | N=CR$_{11}$R$_{12}$ | H | Ph |
| 49.23 | CH$_3$ | H | 3-Br(Ph) | N=CR$_{11}$R$_{12}$ | H | Ph |
| 49.24 | CH$_3$ | H | 4-Br(Ph) | N=CR$_{11}$R$_{12}$ | H | Ph |
| 49.25 | CH$_3$ | H | 2-CH$_3$(Ph) | N=CR$_{11}$R$_{12}$ | H | Ph |
| 49.26 | CH$_3$ | H | 3-CH$_3$(Ph) | N=CR$_{11}$R$_{12}$ | H | Ph |
| 49.27 | CH$_3$ | H | 2-CF$_3$(Ph) | N=CR$_{11}$R$_{12}$ | H | Ph |
| 49.28 | CH$_3$ | H | 3-CF$_3$(Ph) | N=CR$_{11}$R$_{12}$ | H | Ph |
| 49.29 | CH$_3$ | H | 4-CF$_3$(Ph) | N=CR$_{11}$R$_{12}$ | H | Ph |
| 49.30 | CH$_3$ | H | 2-NO$_2$(Ph) | N=CR$_{11}$R$_{12}$ | H | Ph |
| 49.31 | CH$_3$ | H | 3-NO$_2$(Ph) | N=CR$_{11}$R$_{12}$ | H | Ph |
| 49.32 | CH$_3$ | H | 4-NO$_2$(Ph) | N=CR$_{11}$R$_{12}$ | H | Ph |
| 49.33 | CH$_3$ | H | 2,3-Cl(Ph) | N=CR$_{11}$R$_{12}$ | H | Ph |
| 49.34 | CH$_3$ | H | 2,4-Cl(Ph) | N=CR$_{11}$R$_{12}$ | H | Ph |
| 49.35 | CH$_3$ | H | 2,5-Cl(Ph) | N=CR$_{11}$R$_{12}$ | H | Ph |
| 49.36 | CH$_3$ | H | 2,6-Cl(Ph) | N=CR$_{11}$R$_{12}$ | H | Ph |
| 49.37 | CH$_3$ | H | 3,4-Cl(Ph) | N=CR$_{11}$R$_{12}$ | H | Ph |
| 49.38 | CH$_3$ | H | 3,5-Cl(Ph) | N=CR$_{11}$R$_{12}$ | H | Ph |
| 49.39 | CH$_3$ | H | Ph | N=CR$_{11}$R$_{12}$ | CH$_3$ | Ph |
| 49.40 | CH$_3$ | H | 2-Cl(Ph) | N=CR$_{11}$R$_{12}$ | CH$_3$ | Ph |
| 49.41 | CH$_3$ | H | 3-Cl(Ph) | N=CR$_{11}$R$_{12}$ | CH$_3$ | Ph |
| 49.42 | CH$_3$ | H | 4-Cl(Ph) | N=CR$_{11}$R$_{12}$ | CH$_3$ | Ph |
| 49.43 | CH$_3$ | H | 2-Br(Ph) | N=CR$_{11}$R$_{12}$ | CH$_3$ | Ph |
| 49.44 | CH$_3$ | H | 3-Br(Ph) | N=CR$_{11}$R$_{12}$ | CH$_3$ | Ph |
| 49.45 | CH$_3$ | H | 4-Br(Ph) | N=CR$_{11}$R$_{12}$ | CH$_3$ | Ph |
| 49.46 | CH$_3$ | H | 2-CH$_3$(Ph) | N=CR$_{11}$R$_{12}$ | CH$_3$ | Ph |
| 49.47 | CH$_3$ | H | 3-CH$_3$(Ph) | N=CR$_{11}$R$_{12}$ | CH$_3$ | Ph |
| 49.48 | CH$_3$ | H | 2-CF$_3$(Ph) | N=CR$_{11}$R$_{12}$ | CH$_3$ | Ph |
| 49.49 | CH$_3$ | H | 3-CF$_3$(Ph) | N=CR$_{11}$R$_{12}$ | CH$_3$ | Ph |
| 49.50 | CH$_3$ | H | 4-F(Ph) | N=CR$_{11}$R$_{12}$ | CH$_3$ | Ph |
| 49.51 | CH$_3$ | H | 4-OCH$_3$(Ph) | N=CR$_{11}$R$_{12}$ | CH$_3$ | Ph |
| 49.52 | CH$_3$ | H | 4-CH$_3$(Ph) | N=CR$_{11}$R$_{12}$ | CH$_3$ | Ph |
| 49.53 | CH$_3$ | H | 4-NO$_2$(Ph) | N=CR$_{11}$R$_{12}$ | CH$_3$ | Ph |
| 49.54 | CH$_3$ | H | 2,4-Cl(Ph) | N=CR$_{11}$R$_{12}$ | CH$_3$ | Ph |
| 49.55 | CH$_3$ | H | 2,4-F(Ph) | N=CR$_{11}$R$_{12}$ | CH$_3$ | Ph |
| 49.56 | CH$_3$ | H | Ph | N=CR$_{11}$R$_{12}$ | Ph | Ph |
| 49.57 | CH$_3$ | H | 2-Cl(Ph) | N=CR$_{11}$R$_{12}$ | Ph | Ph |
| 49.58 | CH$_3$ | H | 3-Cl(Ph) | N=CR$_{11}$R$_{12}$ | Ph | Ph |
| 49.59 | CH$_3$ | H | 4-Cl(Ph) | N=CR$_{11}$R$_{12}$ | Ph | Ph |
| 49.60 | CH$_3$ | H | 4-F(Ph) | N=CR$_{11}$R$_{12}$ | Ph | Ph |
| 49.61 | CH$_3$ | H | 3-OCH$_3$(Ph) | N=CR$_{11}$R$_{12}$ | Ph | Ph |
| 49.62 | CH$_3$ | H | 4-OCH$_3$(Ph) | N=CR$_{11}$R$_{12}$ | Ph | Ph |
| 49.63 | CH$_3$ | H | 4-CH$_3$(Ph) | N=CR$_{11}$R$_{12}$ | Ph | Ph |
| 49.64 | CH$_3$ | H | 4-NO$_2$(Ph) | N=CR$_{11}$R$_{12}$ | Ph | Ph |
| 49.65 | CH$_3$ | H | 2,4-Cl(Ph) | N=CR$_{11}$R$_{12}$ | Ph | Ph |
| 49.66 | CH$_3$ | H | 2,4-F(Ph) | N=CR$_{11}$R$_{12}$ | Ph | Ph |
| 49.67 | C$_2$H$_5$ | H | Ph | N=CR$_{11}$R$_{12}$ | CH$_3$ | CH$_3$ |
| 49.68 | C$_2$H$_5$ | H | 2-Cl(Ph) | N=CR$_{11}$R$_{12}$ | CH$_3$ | CH$_3$ |
| 49.69 | C$_2$H$_5$ | H | 3-Cl(Ph) | N=CR$_{11}$R$_{12}$ | CH$_3$ | CH$_3$ |
| 49.70 | C$_2$H$_5$ | H | 4-Cl(Ph) | N=CR$_{11}$R$_{12}$ | CH$_3$ | CH$_3$ |
| 49.71 | C$_2$H$_5$ | H | 4-Br(Ph) | N=CR$_{11}$R$_{12}$ | CH$_3$ | CH$_3$ |
| 49.72 | C$_2$H$_5$ | H | 4-F(Ph) | N=CR$_{11}$R$_{12}$ | CH$_3$ | CH$_3$ |
| 49.73 | C$_2$H$_5$ | H | 4-OCH$_3$(Ph) | N=CR$_{11}$R$_{12}$ | CH$_3$ | CH$_3$ |
| 49.74 | C$_2$H$_5$ | H | 4-CH$_3$(Ph) | N=CR$_{11}$R$_{12}$ | CH$_3$ | CH$_3$ |
| 49.75 | C$_2$H$_5$ | H | 4-NO$_2$(Ph) | N=CR$_{11}$R$_{12}$ | CH$_3$ | CH$_3$ |
| 49.76 | C$_2$H$_5$ | H | 2,4-Cl(Ph) | N=CR$_{11}$R$_{12}$ | CH$_3$ | CH$_3$ |
| 49.77 | C$_2$H$_5$ | H | 2,4-F(Ph) | N=CR$_{11}$R$_{12}$ | CH$_3$ | CH$_3$ |
| 49.78 | C$_2$H$_5$ | H | Ph | N=CR$_{11}$R$_{12}$ | CH$_3$ | CH$_3$ |
| 49.79 | C$_2$H$_5$ | H | 2-Cl(Ph) | N=CR$_{11}$R$_{12}$ | H | Ph |
| 49.80 | C$_2$H$_5$ | H | 3-Cl(Ph) | N=CR$_{11}$R$_{12}$ | H | Ph |
| 49.81 | C$_2$H$_5$ | H | 4-Cl(Ph) | N=CR$_{11}$R$_{12}$ | H | Ph |
| 49.82 | C$_2$H$_5$ | H | 4-Br(Ph) | N=CR$_{11}$R$_{12}$ | H | Ph |
| 49.83 | C$_2$H$_5$ | H | 4-F(Ph) | N=CR$_{11}$R$_{12}$ | H | Ph |
| 49.84 | C$_2$H$_5$ | H | 4-OCH$_3$(Ph) | N=CR$_{11}$R$_{12}$ | H | Ph |
| 49.85 | C$_2$H$_5$ | H | 4-CH$_3$(Ph) | N=CR$_{11}$R$_{12}$ | H | Ph |
| 49.86 | C$_2$H$_5$ | H | 4-NO$_2$(Ph) | N=CR$_{11}$R$_{12}$ | H | Ph |
| 49.87 | C$_2$H$_5$ | H | 2,4-Cl(Ph) | N=CR$_{11}$R$_{12}$ | H | Ph |

TABLE 49-continued

| Compd | R$_2$ | R$_3$ | R$_7$ | R$_{10}$ | R$_{11}$ | R$_{12}$ |
|---|---|---|---|---|---|---|
| 49.88 | C$_2$H$_5$ | H | 2,4-F(Ph) | N=CR$_{11}$R$_{12}$ | H | Ph |
| 49.89 | C$_2$H$_5$ | H | Ph | N=CR$_{11}$R$_{12}$ | CH$_3$ | Ph |
| 49.90 | C$_2$H$_5$ | H | 2-Cl(Ph) | N=CR$_{11}$R$_{12}$ | CH$_3$ | Ph |
| 49.91 | C$_2$H$_5$ | H | 3-Cl(Ph) | N=CR$_{11}$R$_{12}$ | CH$_3$ | Ph |
| 49.92 | C$_2$H$_5$ | H | 4-Cl(Ph) | N=CR$_{11}$R$_{12}$ | CH$_3$ | Ph |
| 49.93 | C$_2$H$_5$ | H | 4-F(Ph) | N=CR$_{11}$R$_{12}$ | CH$_3$ | Ph |
| 49.94 | C$_2$H$_5$ | H | 3-OCH$_3$(Ph) | N=CR$_{11}$R$_{12}$ | CH$_3$ | Ph |
| 49.95 | C$_2$H$_5$ | H | 4-OCH$_3$(Ph) | N=CR$_{11}$R$_{12}$ | CH$_3$ | Ph |
| 49.96 | C$_2$H$_5$ | H | 4-CH$_3$(Ph) | N=CR$_{11}$R$_{12}$ | CH$_3$ | Ph |
| 49.97 | C$_2$H$_5$ | H | 4-NO$_2$(Ph) | N=CR$_{11}$R$_{12}$ | CH$_3$ | Ph |
| 49.98 | C$_2$H$_5$ | H | 2,4-Cl(Ph) | N=CR$_{11}$R$_{12}$ | CH$_3$ | Ph |
| 49.99 | C$_2$H$_5$ | H | 2,4-F(Ph) | N=CR$_{11}$R$_{12}$ | CH$_3$ | Ph |
| 49.100 | C$_2$H$_5$ | H | Ph | N=CR$_{11}$R$_{12}$ | Ph | Ph |
| 49.101 | C$_2$H$_5$ | H | 2-Cl(Ph) | N=CR$_{11}$R$_{12}$ | Ph | Ph |
| 49.102 | C$_2$H$_5$ | H | 3-Cl(Ph) | N=CR$_{11}$R$_{12}$ | Ph | Ph |
| 49.103 | C$_2$H$_5$ | H | 4-Cl(Ph) | N=CR$_{11}$R$_{12}$ | Ph | Ph |
| 49.104 | C$_2$H$_5$ | H | 4-F(Ph) | N=CR$_{11}$R$_{12}$ | Ph | Ph |
| 49.105 | C$_2$H$_5$ | H | 3-OCH$_3$(Ph) | N=CR$_{11}$R$_{12}$ | Ph | Ph |
| 49.106 | C$_2$H$_5$ | H | 4-OCH$_3$(Ph) | N=CR$_{11}$R$_{12}$ | Ph | Ph |
| 49.107 | C$_2$H$_5$ | H | 4-CH$_3$(Ph) | N=CR$_{11}$R$_{12}$ | Ph | Ph |
| 49.108 | C$_2$H$_5$ | H | 4-NO$_2$(Ph) | N=CR$_{11}$R$_{12}$ | Ph | Ph |
| 49.109 | C$_2$H$_5$ | H | 2,4-Cl(Ph) | N=CR$_{11}$R$_{12}$ | Ph | Ph |
| 49.110 | C$_2$H$_5$ | H | 2,4-F(Ph) | N=CR$_{11}$R$_{12}$ | Ph | Ph |
| 49.111 | iso-C$_3$H$_7$ | H | Ph | N=CR$_{11}$R$_{12}$ | CH$_3$ | CH$_3$ |
| 49.112 | iso-C$_3$H$_7$ | H | 2-Cl(Ph) | N=CR$_{11}$R$_{12}$ | CH$_3$ | CH$_3$ |
| 49.113 | iso-C$_3$H$_7$ | H | 3-Cl(Ph) | N=CR$_{11}$R$_{12}$ | CH$_3$ | CH$_3$ |
| 49.114 | iso-C$_3$H$_7$ | H | 4-Cl(Ph) | N=CR$_{11}$R$_{12}$ | CH$_3$ | CH$_3$ |
| 49.115 | iso-C$_3$H$_7$ | H | 4-Br(Ph) | N=CR$_{11}$R$_{12}$ | H | Ph |
| 49.116 | iso-C$_3$H$_7$ | H | 3-OCH$_3$(Ph) | N=CR$_{11}$R$_{12}$ | H | Ph |
| 49.117 | iso-C$_3$H$_7$ | H | 4-OCH$_3$(Ph) | N=CR$_{11}$R$_{12}$ | H | Ph |
| 49.118 | iso-C$_3$H$_7$ | H | 4-CH$_3$(Ph) | N=CR$_{11}$R$_{12}$ | H | Ph |
| 49.119 | iso-C$_3$H$_7$ | H | 4-NO$_2$(Ph) | N=CR$_{11}$R$_{12}$ | CH$_3$ | Ph |
| 49.120 | iso-C$_3$H$_7$ | H | 2,4-Cl(Ph) | N=CR$_{11}$R$_{12}$ | CH$_3$ | Ph |
| 49.121 | iso-C$_3$H$_7$ | H | 2,4-F(Ph) | N=CR$_{11}$R$_{12}$ | CH$_3$ | Ph |
| 49.122 | cyclopropyl | H | Ph | N=CR$_{11}$R$_{12}$ | Ph | 4-Cl(Ph) |
| 49.123 | cyclopropyl | H | 2-Cl(Ph) | N=CR$_{11}$R$_{12}$ | Ph | 4-Cl(Ph) |
| 49.124 | cyclopropyl | H | 3-Cl(Ph) | N=CR$_{11}$R$_{12}$ | Ph | 4-Cl(Ph) |
| 49.125 | cyclopropyl | H | 4-Cl(Ph) | N=CR$_{11}$R$_{12}$ | Ph | 4-Cl(Ph) |
| 49.126 | cyclopropyl | H | 4-Br(Ph) | N=CR$_{11}$R$_{12}$ | Ph | 4-Cl(Ph) |
| 49.127 | cyclopropyl | H | 4-F(Ph) | N=CR$_{11}$R$_{12}$ | Ph | 4-Cl(Ph) |
| 49.128 | cyclopropyl | H | 4-OCH$_3$(Ph) | N=CR$_{11}$R$_{12}$ | Ph | 4-pyridyl |
| 49.129 | cyclopropyl | H | 4-CH$_3$(Ph) | N=CR$_{11}$R$_{12}$ | Ph | 4-pyridyl |
| 49.130 | cyclopropyl | H | 4-NO$_2$(Ph) | N=CR$_{11}$R$_{12}$ | Ph | 4-pyridyl |
| 49.131 | cyclopropyl | H | 2,4-Cl(Ph) | N=CR$_{11}$R$_{12}$ | Ph | 4-pyridyl |
| 49.132 | cyclopropyl | H | 2,4-F(Ph) | N=CR$_{11}$R$_{12}$ | Ph | 4-pyridyl |
| 49.133 | CH$_3$ | H | 1-napthyl | N=CR$_{11}$R$_{12}$ | CH$_3$ | CH$_3$ |
| 49.134 | C$_2$H$_5$ | H | 1-napthyl | N=CR$_{11}$R$_{12}$ | CH$_3$ | CH$_3$ |
| 49.135 | n-C$_3$H$_7$ | H | 1-napthyl | N=CR$_{11}$R$_{12}$ | CH$_3$ | CH$_3$ |
| 49.136 | iso-C$_3$H$_7$ | H | 1-napthyl | N=CR$_{11}$R$_{12}$ | CH$_3$ | CH$_3$ |
| 49.137 | cyclopropyl | H | 1-napthyl | N=CR$_{11}$R$_{12}$ | CH$_3$ | CH$_3$ |
| 49.138 | CH$_3$ | H | 1-napthyl | N=CR$_{11}$R$_{12}$ | H | Ph |
| 49.139 | C$_2$H$_5$ | H | 1-napthyl | N=CR$_{11}$R$_{12}$ | H | Ph |
| 49.140 | n-C$_3$H$_7$ | H | 1-napthyl | N=CR$_{11}$R$_{12}$ | H | Ph |
| 49.141 | iso-C$_3$H$_7$ | H | 1-napthyl | N=CR$_{11}$R$_{12}$ | H | Ph |
| 49.142 | cyclopropyl | H | 1-napthyl | N=CR$_{11}$R$_{12}$ | H | Ph |
| 49.143 | CH$_3$ | H | 1-napthyl | N=CR$_{11}$R$_{12}$ | CH$_3$ | Ph |
| 49.144 | C$_2$H$_5$ | H | 1-napthyl | N=CR$_{11}$R$_{12}$ | CH$_3$ | Ph |
| 49.145 | n-C$_3$H$_7$ | H | 1-napthyl | N=CR$_{11}$R$_{12}$ | CH$_3$ | Ph |
| 49.146 | iso-C$_3$H$_7$ | H | 1-napthyl | N=CR$_{11}$R$_{12}$ | CH$_3$ | Ph |
| 49.147 | cyclopropyl | H | 1-napthyl | N=CR$_{11}$R$_{12}$ | CH$_3$ | Ph |
| 49.148 | CH$_3$ | H | 1-napthyl | N=CR$_{11}$R$_{12}$ | Ph | Ph |
| 49.149 | C$_2$H$_5$ | H | 1-napthyl | N=CR$_{11}$R$_{12}$ | Ph | Ph |
| 49.150 | n-C$_3$H$_7$ | H | 1-napthyl | N=CR$_{11}$R$_{12}$ | Ph | Ph |
| 49.151 | iso-C$_3$H$_7$ | H | 1-napthyl | N=CR$_{11}$R$_{12}$ | Ph | Ph |
| 49.152 | cyclopropyl | H | 1-napthyl | N=CR$_{11}$R$_{12}$ | Ph | Ph |
| 49.153 | CH$_3$ | H | 2-napthyl | N=CR$_{11}$R$_{12}$ | CH$_3$ | CH$_3$ |
| 49.154 | C$_2$H$_5$ | H | 2-napthyl | N=CR$_{11}$R$_{12}$ | CH$_3$ | CH$_3$ |
| 49.155 | n-C$_3$H$_7$ | H | 2-napthyl | N=CR$_{11}$R$_{12}$ | CH$_3$ | CH$_3$ |
| 49.156 | iso-C$_3$H$_7$ | H | 2-napthyl | N=CR$_{11}$R$_{12}$ | CH$_3$ | CH$_3$ |
| 49.157 | cyclopropyl | H | 2-napthyl | N=CR$_{11}$R$_{12}$ | CH$_3$ | CH$_3$ |
| 49.158 | CH$_3$ | H | 2-napthyl | N=CR$_{11}$R$_{12}$ | H | Ph |
| 49.159 | C$_2$H$_5$ | H | 2-napthyl | N=CR$_{11}$R$_{12}$ | H | Ph |
| 49.160 | n-C$_3$H$_7$ | H | 2-napthyl | N=CR$_{11}$R$_{12}$ | H | Ph |
| 49.161 | iso-C$_3$H$_7$ | H | 2-napthyl | N=CR$_{11}$R$_{12}$ | H | Ph |
| 49.162 | cyclopropyl | H | 2-napthyl | N=CR$_{11}$R$_{12}$ | H | Ph |
| 49.163 | CH$_3$ | H | 2-napthyl | N=CR$_{11}$R$_{12}$ | CH$_3$ | Ph |
| 49.164 | C$_2$H$_5$ | H | 2-napthyl | N=CR$_{11}$R$_{12}$ | CH$_3$ | Ph |

TABLE 49-continued

| Compd | R$_2$ | R$_3$ | R$_7$ | R$_{10}$ | R$_{11}$ | R$_{12}$ |
|---|---|---|---|---|---|---|
| 49.165 | n-C$_3$H$_7$ | H | 2-napthyl | N=CR$_{11}$R$_{12}$ | CH$_3$ | Ph |
| 49.166 | iso-C$_3$H$_7$ | H | 2-napthyl | N=CR$_{11}$R$_{12}$ | CH$_3$ | Ph |
| 49.167 | cyclopropyl | H | 2-napthyl | N=CR$_{11}$R$_{12}$ | CH$_3$ | Ph |
| 49.168 | CH$_3$ | H | 2-napthyl | N=CR$_{11}$R$_{12}$ | Ph | Ph |
| 49.169 | C$_2$H$_5$ | H | 2-napthyl | N=CR$_{11}$R$_{12}$ | Ph | Ph |
| 49.170 | n-C$_3$H$_7$ | H | 2-napthyl | N=CR$_{11}$R$_{12}$ | Ph | Ph |
| 49.171 | iso-C$_3$H$_7$ | H | 2-napthyl | N=CR$_{11}$R$_{12}$ | Ph | Ph |
| 49.172 | cyclopropyl | H | 2-napthyl | N=CR$_{11}$R$_{12}$ | Ph | Ph |
| 49.173 | CH$_3$ | H | Ph | N=CR$_{11}$R$_{12}$ | Ph | 4-Cl(Ph) |
| 49.174 | CH$_3$ | H | 2-Cl(Ph) | N=CR$_{11}$R$_{12}$ | Ph | 4-Cl(Ph) |
| 49.175 | CH$_3$ | H | 3-Cl(Ph) | N=CR$_{11}$R$_{12}$ | Ph | 4-Cl(Ph) |
| 49.176 | CH$_3$ | H | 4-Cl(Ph) | N=CR$_{11}$R$_{12}$ | Ph | 4-Cl(Ph) |
| 49.177 | CH$_3$ | H | 4-Br(Ph) | N=CR$_{11}$R$_{12}$ | Ph | 4-Cl(Ph) |
| 49.178 | CH$_3$ | H | 4-F(Ph) | N=CR$_{11}$R$_{12}$ | Ph | 4-Cl(Ph) |
| 49.179 | CH$_3$ | H | 4-OCH$_3$(Ph) | N=CR$_{11}$R$_{12}$ | Ph | 4-Cl(Ph) |
| 49.180 | CH$_3$ | H | 4-CH$_3$(Ph) | N=CR$_{11}$R$_{12}$ | Ph | 4-Cl(Ph) |
| 49.181 | CH$_3$ | H | 4-NO$_2$(Ph) | N=CR$_{11}$R$_{12}$ | Ph | 4-Cl(Ph) |
| 49.182 | CH$_3$ | H | 2,4-Cl(Ph) | N=CR$_{11}$R$_{12}$ | Ph | 4-Cl(Ph) |
| 49.183 | CH$_3$ | H | 2,4-F(Ph) | N=CR$_{11}$R$_{12}$ | Ph | 4-Cl(Ph) |
| 49.184 | CH$_3$ | H | 4-CH$_3$(Ph) | N=CR$_{11}$R$_{12}$ | Ph | 4-Cl(Ph) |
| 49.185 | CH$_3$ | H | 4-NO$_2$(Ph) | N=CR$_{11}$R$_{12}$ | Ph | 4-Cl(Ph) |
| 49.186 | CH$_3$ | H | 2,4-Cl(Ph) | N=CR$_{11}$R$_{12}$ | Ph | 4-Cl(Ph) |
| 49.187 | CH$_3$ | H | 2,4-F(Ph) | N=CR$_{11}$R$_{12}$ | Ph | 4-Cl(Ph) |
| 49.188 | CH$_3$ | H | 4-CF$_3$(Ph) | N=CR$_{11}$R$_{12}$ | Ph | 4-Cl(Ph) |
| 49.189 | CH$_3$ | H | Ph | N=CR$_{11}$R$_{12}$ | Ph | 4-pyridyl |
| 49.190 | CH$_3$ | H | 4-Cl(Ph) | N=CR$_{11}$R$_{12}$ | Ph | 4-pyridyl |
| 49.191 | CH$_3$ | H | 4-Br(Ph) | N=CR$_{11}$R$_{12}$ | Ph | 4-pyridyl |
| 49.192 | CH$_3$ | H | 4-F(Ph) | N=CR$_{11}$R$_{12}$ | Ph | 4-pyridyl |
| 49.193 | CH$_3$ | H | 4-OCH$_3$(Ph) | N=CR$_{11}$R$_{12}$ | Ph | 4-pyridyl |
| 49.194 | CH$_3$ | H | 4-CH$_3$(Ph) | N=CR$_{11}$R$_{12}$ | Ph | 4-pyridyl |
| 49.195 | CH$_3$ | H | 4-NO$_2$(Ph) | N=CR$_{11}$R$_{12}$ | Ph | 4-pyridyl |
| 49.196 | CH$_3$ | H | 2,4-Cl(Ph) | N=CR$_{11}$R$_{12}$ | Ph | 4-pyridyl |
| 49.197 | CH$_3$ | H | 2,4-F(Ph) | N=CR$_{11}$R$_{12}$ | Ph | 4-pyridyl |
| 49.198 | CH$_3$ | H | 4-CF$_3$(Ph) | N=CR$_{11}$R$_{12}$ | Ph | 4-pyridyl |
| 49.199 | CH$_3$ | H | Ph | N=CR$_{11}$R$_{12}$ | CH$_3$ | N(CH$_3$)$_2$ |
| 49.200 | CH$_3$ | H | 4-Cl(Ph) | N=CR$_{11}$R$_{12}$ | CH$_3$ | N(CH$_3$)$_2$ |
| 49.201 | CH$_3$ | H | 4-Br(Ph) | N=CR$_{11}$R$_{12}$ | CH$_3$ | N(CH$_3$)$_2$ |
| 49.202 | CH$_3$ | H | 4-F(Ph) | N=CR$_{11}$R$_{12}$ | CH$_3$ | N(CH$_3$)$_2$ |
| 49.203 | CH$_3$ | H | 4-OCH$_3$(Ph) | N=CR$_{11}$R$_{12}$ | CH$_3$ | N(CH$_3$)$_2$ |
| 49.204 | CH$_3$ | H | 4-CH$_3$(Ph) | N=CR$_{11}$R$_{12}$ | CH$_3$ | N(CH$_3$)$_2$ |
| 49.205 | CH$_3$ | H | 4-NO$_2$(Ph) | N=CR$_{11}$R$_{12}$ | CH$_3$ | N(CH$_3$)$_2$ |
| 49.206 | CH$_3$ | H | 2,4-Cl(Ph) | N=CR$_{11}$R$_{12}$ | CH$_3$ | N(CH$_3$)$_2$ |
| 49.207 | CH$_3$ | H | 2,4-F(Ph) | N=CR$_{11}$R$_{12}$ | CH$_3$ | N(CH$_3$)$_2$ |
| 49.208 | CH$_3$ | H | 4-CF$_3$(Ph) | N=CR$_{11}$R$_{12}$ | CH$_3$ | N(CH$_3$)$_2$ |
| 49.209 | CH$_3$ | H | Ph | N=cyclopentyl | | |
| 49.210 | CH$_3$ | H | 4-Cl(Ph) | N=cyclopentyl | | |
| 49.211 | CH$_3$ | H | 4-Br(Ph) | N=cyclopentyl | | |
| 49.212 | CH$_3$ | H | 4-F(Ph) | N=cyclopentyl | | |
| 49.213 | CH$_3$ | H | 4-OCH$_3$(Ph) | N=cyclopentyl | | |
| 49.214 | CH$_3$ | H | 4-CH$_3$(Ph) | N=cyclopentyl | | |
| 49.215 | CH$_3$ | H | 4-NO$_2$(Ph) | N=cyclopentyl | | |
| 49.216 | CH$_3$ | H | 2,4-Cl(Ph) | N=cyclopentyl | | |
| 49.217 | CH$_3$ | H | 2,4-F(Ph) | N=cyclopentyl | | |
| 49.218 | CH$_3$ | H | 4-CF$_3$(Ph) | N=cyclopentyl | | |
| 49.219 | CH$_3$ | H | Ph | N=cyclohexyl | | |
| 49.220 | CH$_3$ | H | 4-Cl(Ph) | N=cyclohexyl | | |
| 49.221 | CH$_3$ | H | 4-Br(Ph) | N=cyclohexyl | | |
| 49.222 | CH$_3$ | H | 4-F(Ph) | N=cyclohexyl | | |
| 49.223 | CH$_3$ | H | 4-OCH$_3$(Ph) | N=cyclohexyl | | |
| 49.224 | CH$_3$ | H | 4-CH$_3$(Ph) | N=cyclohexyl | | |
| 49.225 | CH$_3$ | H | 4-NO$_2$(Ph) | N=cyclohexyl | | |
| 49.226 | CH$_3$ | H | 2,4-Cl(Ph) | N=cyclohexyl | | |
| 49.227 | CH$_3$ | H | 2,4-F(Ph) | N=cyclohexyl | | |
| 49.228 | CH$_3$ | H | 4-CF$_3$(Ph) | N=cyclohexyl | | |
| 49.229 | CH$_3$ | H | 1-napthyl | N=cyclopentyl | | |
| 49.230 | C$_2$H$_5$ | H | 1-napthyl | N=cyclopentyl | | |
| 49.231 | n-C$_3$H$_7$ | H | 1-napthyl | N=cyclopentyl | | |
| 49.232 | iso-C$_3$H$_7$ | H | 1-napthyl | N=cyclopentyl | | |
| 49.233 | cyclopropyl | H | 1-napthyl | N=cyclopentyl | | |
| 49.234 | CH$_3$ | H | 1-napthyl | N=cyclohexyl | | |
| 49.235 | C$_2$H$_5$ | H | 1-napthyl | N=cyclohexyl | | |
| 49.236 | n-C$_3$H$_7$ | H | 1-napthyl | N=cyclohexyl | | |
| 49.237 | iso-C$_3$H$_7$ | H | 1-napthyl | N=cyclohexyl | | |
| 49.238 | cyclopropyl | H | 1-napthyl | N=cyclohexyl | | |
| 49.239 | CH$_3$ | H | 2-napthyl | N=cyclopentyl | | |
| 49.240 | C$_2$H$_5$ | H | 2-napthyl | N=cyclopentyl | | |
| 49.241 | n-C$_3$H$_7$ | H | 2-napthyl | N=cyclopentyl | | |

TABLE 49-continued

| Compd | $R_2$ | $R_3$ | $R_7$ | $R_{10}$ | $R_{11}$ | $R_{12}$ |
|---|---|---|---|---|---|---|
| 49.242 | iso-$C_3H_7$ | H | 2-napthyl | N=cyclopentyl | | |
| 49.243 | cyclopropyl | H | 2-napthyl | N=cyclopentyl | | |
| 49.244 | $CH_3$ | H | 2-napthyl | N=cyclohexyl | | |
| 49.245 | $C_2H_5$ | H | 2-napthyl | N=cyclohexyl | | |
| 49.246 | n-$C_3H_7$ | H | 2-napthyl | N=cyclohexyl | | |
| 49.247 | iso-$C_3H_7$ | H | 2-napthyl | N=cyclohexyl | | |
| 49.248 | cyclopropyl | H | 2-napthyl | N=cyclohexyl | | |
| 49.249 | $CH_3$ | H | 1-napthyl | N=$CR_{11}R_{12}$ | $CH_3$ | $N(CH_3)_2$ |
| 49.250 | $C_2H_5$ | H | 1-napthyl | N=$CR_{11}R_{12}$ | $CH_3$ | $N(CH_3)_2$ |
| 49.251 | n-$C_3H_7$ | H | 1-napthyl | N=$CR_{11}R_{12}$ | $CH_3$ | $N(CH_3)_2$ |
| 49.252 | iso-$C_3H_7$ | H | 1-napthyl | N=$CR_{11}R_{12}$ | $CH_3$ | $N(CH_3)_2$ |
| 49.253 | cyclopropyl | H | 1-napthyl | N=$CR_{11}R_{12}$ | $CH_3$ | $N(CH_3)_2$ |
| 49.254 | $CH_3$ | H | 2-napthyl | N=$CR_{11}R_{12}$ | $CH_3$ | $N(CH_3)_2$ |
| 49.255 | $C_2H_5$ | H | 2-napthyl | N=$CR_{11}R_{12}$ | $CH_3$ | $N(CH_3)_2$ |
| 49.256 | n-$C_3H_7$ | H | 2-napthyl | N=$CR_{11}R_{12}$ | $CH_3$ | $N(CH_3)_2$ |
| 49.257 | iso-$C_3H_7$ | H | 2-napthyl | N=$CR_{11}R_{12}$ | $CH_3$ | $N(CH_3)_2$ |
| 49.258 | cyclopropyl | H | 2-napthyl | N=$CR_{11}R_{12}$ | $CH_3$ | $N(CH_3)_2$ |
| 49.259 | $CH_3$ | $CH_3$ | Ph | N=$CR_{11}R_{12}$ | H | Ph |
| 49.260 | $C_2H_5$ | $CH_3$ | 4-Cl(Ph) | N=$CR_{11}R_{12}$ | H | Ph |
| 49.261 | n-$C_3H_7$ | $CH_3$ | 4-Br(Ph) | N=$CR_{11}R_{12}$ | H | Ph |
| 49.262 | iso-$C_2H_7$ | $CH_3$ | 4-F(Ph) | N=$CR_{11}R_{12}$ | H | Ph |
| 49.263 | $CH_3$ | $CH_3$ | Ph | N=$CR_{11}R_{12}$ | $CH_3$ | Ph |
| 49.264 | $C_2H_5$ | $CH_3$ | 4-Cl(Ph) | N=$CR_{11}R_{12}$ | $CH_3$ | Ph |
| 49.265 | n-$C_3H_7$ | $CH_3$ | 4-Br(Ph) | N=$CR_{11}R_{12}$ | $CH_3$ | Ph |
| 49.266 | iso-$C_3H_7$ | $CH_3$ | 4-F(Ph) | N=$CR_{11}R_{12}$ | $CH_3$ | Ph |
| 49.267 | $CH_3$ | $CH_3$ | Ph | N=$CR_{11}R_{12}$ | Ph | Ph |
| 49.268 | $C_2H_5$ | $CH_3$ | 4-Cl(Ph) | N=$CR_{11}R_{12}$ | Ph | Ph |
| 49.269 | n-$C_3H_7$ | $CH_3$ | 4-Br(Ph) | N=$CR_{11}R_{12}$ | Ph | Ph |
| 49.270 | iso-$C_3H_7$ | $CH_3$ | 4-F(Ph) | N=$CR_{11}R_{12}$ | Ph | Ph |
| 49.271 | $CH_3$ | $CH_3$ | Ph | N=$CR_{11}R_{12}$ | Ph | 4-Cl(Ph) |
| 49.272 | $C_2H_5$ | $CH_3$ | 4-Cl(Ph) | N=$CR_{11}R_{12}$ | Ph | 4-Cl(Ph) |

Typical compounds encompassed by the present invention of Formula I include those compounds of Formula XI, which is Formula I with A=$R_4$=$R_5$=$R_6$=H, $R_1$=$CH_3$, X=N, Y=O, Z=$NR_{10}$, and where $R_2$, $R_3$, $R_7$, $R_{10}$, $R_{11}$ and $R_{12}$ are defined in Table 50.

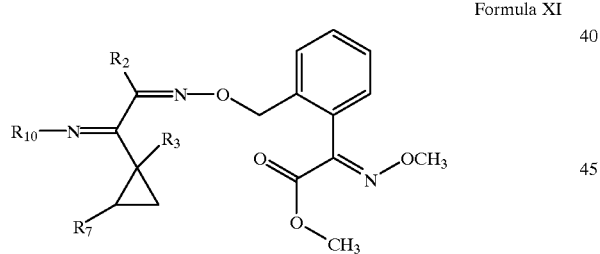

Formula XI

TABLE 50

| Compd. | $R_2$ | $R_3$ | $R_7$ | $R_{10}$ | $R_{11}$ | $R_{12}$ |
|---|---|---|---|---|---|---|
| 50.1 | H | H | Ph | N=$CR_{11}R_{12}$ | $CH_3$ | $CH_3$ |
| 50.2 | H | H | 4-Cl(Ph) | N=$CR_{11}R_{12}$ | $CH_3$ | $CH_3$ |
| 50.3 | H | H | 4-Br(Ph) | N=$CR_{11}R_{12}$ | $CH_3$ | $CH_3$ |
| 50.4 | H | H | 4-F(Ph) | N=$CR_{11}R_{12}$ | $CH_3$ | $CH_3$ |
| 50.5 | H | H | 4-$OCH_3$(Ph) | N=$CR_{11}R_{12}$ | $CH_3$ | $CH_3$ |
| 50.6 | H | H | 4-$CF_3$(Ph) | N=$CR_{11}R_{12}$ | $CH_3$ | $CH_3$ |
| 50.7 | H | H | Ph | N=$CR_{11}R_{12}$ | $CH_3$ | $CH_3$ |
| 50.8 | H | H | 4-Cl(Ph) | N=$CR_{11}R_{12}$ | $CH_3$ | $CH_3$ |
| 50.9 | H | H | 4-Br(Ph) | N=$CR_{11}R_{12}$ | $CH_3$ | $CH_3$ |
| 50.10 | H | H | 4-F(Ph) | N=$CR_{11}R_{12}$ | $CH_3$ | $CH_3$ |
| 50.11 | $CH_3$ | H | Ph | N=$CR_{11}R_{12}$ | $CH_3$ | $CH_3$ |
| 50.12 | $CH_3$ | H | 2-Cl(Ph) | N=$CR_{11}R_{12}$ | $CH_3$ | $CH_3$ |
| 50.13 | $CH_3$ | H | 3-Cl(Ph) | N=$CR_{11}R_{12}$ | $CH_3$ | $CH_3$ |

TABLE 50-continued

| Compd. | R$_2$ | R$_3$ | R$_7$ | R$_{10}$ | R$_{11}$ | R$_{12}$ |
|---|---|---|---|---|---|---|
| 50.14 | CH$_3$ | H | 4-Cl(Ph) | N=CR$_{11}$R$_{12}$ | CH$_3$ | CH$_3$ |
| 50.15 | CH$_3$ | H | 2-Br(Ph) | N=CR$_{11}$R$_{12}$ | CH$_3$ | CH$_3$ |
| 50.16 | CH$_3$ | H | 3-Br(Ph) | N=CR$_{11}$R$_{12}$ | CH$_3$ | CH$_3$ |
| 50.17 | CH$_3$ | H | 4-Br(Ph) | N=CR$_{11}$R$_{12}$ | CH$_3$ | CH$_3$ |
| 50.18 | CH$_3$ | H | Ph | N=CR$_{11}$R$_{12}$ | H | Ph |
| 50.19 | CH$_3$ | H | 2-Cl(Ph) | N=CR$_{11}$R$_{12}$ | H | Ph |
| 50.20 | CH$_3$ | H | 3-Cl(Ph) | N=CR$_{11}$R$_{12}$ | H | Ph |
| 50.21 | CH$_3$ | H | 4-Cl(Ph) | N=CR$_{11}$R$_{12}$ | H | Ph |
| 50.22 | CH$_3$ | H | 2-Br(Ph) | N=CR$_{11}$R$_{12}$ | H | Ph |
| 50.23 | CH$_3$ | H | 3-Br(Ph) | N=CR$_{11}$R$_{12}$ | H | Ph |
| 50.24 | CH$_3$ | H | 4-Br(Ph) | N=CR$_{11}$R$_{12}$ | H | Ph |
| 50.25 | CH$_3$ | H | 2-CH$_3$(Ph) | N=CR$_{11}$R$_{12}$ | H | Ph |
| 50.26 | CH$_3$ | H | 3-CH$_3$(Ph) | N=CR$_{11}$R$_{12}$ | H | Ph |
| 50.27 | CH$_3$ | H | 2-CF$_3$(Ph) | N=CR$_{11}$R$_{12}$ | H | Ph |
| 50.28 | CH$_3$ | H | 3-CF$_3$(Ph) | N=CR$_{11}$R$_{12}$ | H | Ph |
| 50.29 | CH$_3$ | H | 4-CF$_3$(Ph) | N=CR$_{11}$R$_{12}$ | H | Ph |
| 50.30 | CH$_3$ | H | 2-NO$_2$(Ph) | N=CR$_{11}$R$_{12}$ | H | Ph |
| 50.31 | CH$_3$ | H | 3-NO$_2$(Ph) | N=CR$_{11}$R$_{12}$ | H | Ph |
| 50.32 | CH$_3$ | H | 4-NO$_2$(Ph) | N=CR$_{11}$R$_{12}$ | H | Ph |
| 50.33 | CH$_3$ | H | 2,3-Cl(Ph) | N=CR$_{11}$R$_{12}$ | H | Ph |
| 50.34 | CH$_3$ | H | 2,4-Cl(Ph) | N=CR$_{11}$R$_{12}$ | H | Ph |
| 50.35 | CH$_3$ | H | 2,5-Cl(Ph) | N=CR$_{11}$R$_{12}$ | H | Ph |
| 50.36 | CH$_3$ | H | 2,6-Cl(Ph) | N=CR$_{11}$R$_{12}$ | H | Ph |
| 50.37 | CH$_3$ | H | 3,4-Cl(Ph) | N=CR$_{11}$R$_{12}$ | H | Ph |
| 50.38 | CH$_3$ | H | 3,5-Cl(Ph) | N=CR$_{11}$R$_{12}$ | H | Ph |
| 50.39 | CH$_3$ | H | Ph | N=CR$_{11}$R$_{12}$ | CH$_3$ | Ph |
| 50.40 | CH$_3$ | H | 2-Cl(Ph) | N=CR$_{11}$R$_{12}$ | CH$_3$ | Ph |
| 50.41 | CH$_3$ | H | 3-Cl(Ph) | N=CR$_{11}$R$_{12}$ | CH$_3$ | Ph |
| 50.42 | CH$_3$ | H | 4-Cl(Ph) | N=CR$_{11}$R$_{12}$ | CH$_3$ | Ph |
| 50.43 | CH$_3$ | H | 2-Br(Ph) | N=CR$_{11}$R$_{12}$ | CH$_3$ | Ph |
| 50.44 | CH$_3$ | H | 3-Br(Ph) | N=CR$_{11}$R$_{12}$ | CH$_3$ | Ph |
| 50.45 | CH$_3$ | H | 4-Br(Ph) | N=CR$_{11}$R$_{12}$ | CH$_3$ | Ph |
| 50.46 | CH$_3$ | H | 2-CH$_3$(Ph) | N=CR$_{11}$R$_{12}$ | CH$_3$ | Ph |
| 50.47 | CH$_3$ | H | 3-CH$_3$(Ph) | N=CR$_{11}$R$_{12}$ | CH$_3$ | Ph |
| 50.48 | CH$_3$ | H | 2-CF$_3$(Ph) | N=CR$_{11}$R$_{12}$ | CH$_3$ | Ph |
| 50.49 | CH$_3$ | H | 3-CF$_3$(Ph) | N=CR$_{11}$R$_{12}$ | CH$_3$ | Ph |
| 50.50 | CH$_3$ | H | 4-F(Ph) | N=CR$_{11}$R$_{12}$ | CH$_3$ | Ph |
| 50.51 | CH$_3$ | H | 4-OCH$_3$(Ph) | N=CR$_{11}$R$_{12}$ | CH$_3$ | Ph |
| 50.52 | CH$_3$ | H | 4-CH$_3$(Ph) | N=CR$_{11}$R$_{12}$ | CH$_3$ | Ph |
| 50.53 | CH$_3$ | H | 4-NO$_2$(Ph) | N=CR$_{11}$R$_{12}$ | CH$_3$ | Ph |
| 50.54 | CH$_3$ | H | 2,4-Cl(Ph) | N=CR$_{11}$R$_{12}$ | CH$_3$ | Ph |
| 50.55 | CH$_3$ | H | 2,4-F(Ph) | N=CR$_{11}$R$_{12}$ | CH$_3$ | Ph |
| 50.56 | CH$_3$ | H | Ph | N=CR$_{11}$R$_{12}$ | Ph | Ph |
| 50.57 | CH$_3$ | H | 2-Cl(Ph) | N=CR$_{11}$R$_{12}$ | Ph | Ph |
| 50.58 | CH$_3$ | H | 3-Cl(Ph) | N=CR$_{11}$R$_{12}$ | Ph | Ph |
| 50.59 | CH$_3$ | H | 4-Cl(Ph) | N=CR$_{11}$R$_{12}$ | Ph | Ph |
| 50.60 | CH$_3$ | H | 4-F(Ph) | N=CR$_{11}$R$_{12}$ | Ph | Ph |
| 50.61 | CH$_3$ | H | 3-OCH$_3$(Ph) | N=CR$_{11}$R$_{12}$ | Ph | Ph |
| 50.62 | CH$_3$ | H | 4-OCH$_3$(Ph) | N=CR$_{11}$R$_{12}$ | Ph | Ph |
| 50.63 | CH$_3$ | H | 4-CH$_3$(Ph) | N=CR$_{11}$R$_{12}$ | Ph | Ph |
| 50.64 | CH$_3$ | H | 4-NO$_2$(Ph) | N=CR$_{11}$R$_{12}$ | Ph | Ph |
| 50.65 | CH$_3$ | H | 2,4-Cl(Ph) | N=CR$_{11}$R$_{12}$ | Ph | Ph |
| 50.66 | CH$_3$ | H | 2,4-F(Ph) | N=CR$_{11}$R$_{12}$ | Ph | Ph |
| 50.67 | C$_2$H$_5$ | H | Ph | N=CR$_{11}$R$_{12}$ | CH$_3$ | CH$_3$ |
| 50.68 | C$_2$H$_5$ | H | 2-Cl(Ph) | N=CR$_{11}$R$_{12}$ | CH$_3$ | CH$_3$ |
| 50.69 | C$_2$H$_5$ | H | 3-Cl(Ph) | N=CR$_{11}$R$_{12}$ | CH$_3$ | CH$_3$ |
| 50.70 | C$_2$H$_5$ | H | 4-Cl(Ph) | N=CR$_{11}$R$_{12}$ | CH$_3$ | CH$_3$ |
| 50.71 | C$_2$H$_5$ | H | 4-Br(Ph) | N=CR$_{11}$R$_{12}$ | CH$_3$ | CH$_3$ |
| 50.72 | C$_2$H$_5$ | H | 4-F(Ph) | N=CR$_{11}$R$_{12}$ | CH$_3$ | CH$_3$ |
| 50.73 | C$_2$H$_5$ | H | 4-OCH$_3$(Ph) | N=CR$_{11}$R$_{12}$ | CH$_3$ | CH$_3$ |
| 50.74 | C$_2$H$_5$ | H | 4-CH$_3$(Ph) | N=CR$_{11}$R$_{12}$ | CH$_3$ | CH$_3$ |
| 50.75 | C$_2$H$_5$ | H | 4-NO$_2$(Ph) | N=CR$_{11}$R$_{12}$ | CH$_3$ | CH$_3$ |
| 50.76 | C$_2$H$_5$ | H | 2,4-Cl(Ph) | N=CR$_{11}$R$_{12}$ | CH$_3$ | CH$_3$ |
| 50.77 | C$_2$H$_5$ | H | 2,4-F(Ph) | N=CR$_{11}$R$_{12}$ | CH$_3$ | CH$_3$ |
| 50.78 | C$_2$H$_5$ | H | Ph | N=CR$_{11}$R$_{12}$ | CH$_3$ | CH$_3$ |
| 50.79 | C$_2$H$_5$ | H | 2-Cl(Ph) | N=CR$_{11}$R$_{12}$ | H | Ph |
| 50.80 | C$_2$H$_5$ | H | 3-Cl(Ph) | N=CR$_{11}$R$_{12}$ | H | Ph |
| 50.81 | C$_2$H$_5$ | H | 4-Cl(Ph) | N=CR$_{11}$R$_{12}$ | H | Ph |
| 50.82 | C$_2$H$_5$ | H | 4-Br(Ph) | N=CR$_{11}$R$_{12}$ | H | Ph |
| 50.83 | C$_2$H$_5$ | H | 4-F(Ph) | N=CR$_{11}$R$_{12}$ | H | Ph |
| 50.84 | C$_2$H$_5$ | H | 4-OCH$_3$(Ph) | N=CR$_{11}$R$_{12}$ | H | Ph |
| 50.85 | C$_2$H$_5$ | H | 4-CH$_3$(Ph) | N=CR$_{11}$R$_{12}$ | H | Ph |
| 50.86 | C$_2$H$_5$ | H | 4-NO$_2$(Ph) | N=CR$_{11}$R$_{12}$ | H | Ph |
| 50.87 | C$_2$H$_5$ | H | 2,4-Cl(Ph) | N=CR$_{11}$R$_{12}$ | H | Ph |
| 50.88 | C$_2$H$_5$ | H | 2,4-F(Ph) | N=CR$_{11}$R$_{12}$ | H | Ph |
| 50.89 | C$_2$H$_5$ | H | Ph | N=CR$_{11}$R$_{12}$ | CH$_3$ | Ph |
| 50.90 | C$_2$H$_5$ | H | 2-Cl(Ph) | N=CR$_{11}$R$_{12}$ | CH$_3$ | Ph |

TABLE 50-continued

| Compd. | R$_2$ | R$_3$ | R$_7$ | R$_{10}$ | R$_{11}$ | R$_{12}$ |
|---|---|---|---|---|---|---|
| 50.91 | C$_2$H$_5$ | H | 3-Cl(Ph) | N=CR$_{11}$R$_{12}$ | CH$_3$ | Ph |
| 50.92 | C$_2$H$_5$ | H | 4-Cl(Ph) | N=CR$_{11}$R$_{12}$ | CH$_3$ | Ph |
| 50.93 | C$_2$H$_5$ | H | 4-F(Ph) | N=CR$_{11}$R$_{12}$ | CH$_3$ | Ph |
| 50.94 | C$_2$H$_5$ | H | 3-OCH$_3$(Ph) | N=CR$_{11}$R$_{12}$ | CH$_3$ | Ph |
| 50.95 | C$_2$H$_5$ | H | 4-OCH$_3$(Ph) | N=CR$_{11}$R$_{12}$ | CH$_3$ | Ph |
| 50.96 | C$_2$H$_5$ | H | 4-CH$_3$(Ph) | N=CR$_{11}$R$_{12}$ | CH$_3$ | Ph |
| 50.97 | C$_2$H$_5$ | H | 4-NO$_2$(Ph) | N=CR$_{11}$R$_{12}$ | CH$_3$ | Ph |
| 50.98 | C$_2$H$_5$ | H | 2,4-Cl(Ph) | N=CR$_{11}$R$_{12}$ | CH$_3$ | Ph |
| 50.99 | C$_2$H$_5$ | H | 2,4-F(Ph) | N=CR$_{11}$R$_{12}$ | CH$_3$ | Ph |
| 50.100 | C$_2$H$_5$ | H | Ph | N=CR$_{11}$R$_{12}$ | Ph | Ph |
| 50.101 | C$_2$H$_5$ | H | 2-Cl(Ph) | N=CR$_{11}$R$_{12}$ | Ph | Ph |
| 50.102 | C$_2$H$_5$ | H | 3-Cl(Ph) | N=CR$_{11}$R$_{12}$ | Ph | Ph |
| 50.103 | C$_2$H$_5$ | H | 4-Cl(Ph) | N=CR$_{11}$R$_{12}$ | Ph | Ph |
| 50.104 | C$_2$H$_5$ | H | 4-F(Ph) | N=CR$_{11}$R$_{12}$ | Ph | Ph |
| 50.105 | C$_2$H$_5$ | H | 3-OCH$_3$(Ph) | N=CR$_{11}$R$_{12}$ | Ph | Ph |
| 50.106 | C$_2$H$_5$ | H | 4-OCH$_3$(Ph) | N=CR$_{11}$R$_{12}$ | Ph | Ph |
| 50.107 | C$_2$H$_5$ | H | 4-CH$_3$(Ph) | N=CR$_{11}$R$_{12}$ | Ph | Ph |
| 50.108 | C$_2$H$_5$ | H | 4-NO$_2$(Ph) | N=CR$_{11}$R$_{12}$ | Ph | Ph |
| 50.109 | C$_2$H$_5$ | H | 2,4-Cl(Ph) | N=CR$_{11}$R$_{12}$ | Ph | Ph |
| 50.110 | C$_2$H$_5$ | H | 2,4-F(Ph) | N=CR$_{11}$R$_{12}$ | Ph | Ph |
| 50.111 | iso-C$_3$H$_7$ | H | Ph | N=CR$_{11}$R$_{12}$ | CH$_3$ | CH$_3$ |
| 50.112 | iso-C$_3$H$_7$ | H | 2-Cl(Ph) | N=CR$_{11}$R$_{12}$ | CH$_3$ | CH$_3$ |
| 50.113 | iSO-C$_3$H$_7$ | H | 3-Cl(Ph) | N=CR$_{11}$R$_{12}$ | CH$_3$ | CH$_3$ |
| 50.114 | iSO-C$_3$H$_7$ | H | 4-Cl(Ph) | N=CR$_{11}$R$_{12}$ | CH$_3$ | CH$_3$ |
| 50.115 | iso-C$_3$H$_7$ | H | 4-Br(Ph) | N=CR$_{11}$R$_{12}$ | H | Ph |
| 50.116 | iso-C$_3$H$_7$ | H | 3-OCH$_3$(Ph) | N=CR$_{11}$R$_{12}$ | H | Ph |
| 50.117 | iso-C$_3$H$_7$ | H | 4-OCH$_3$(Ph) | N=CR$_{11}$R$_{12}$ | H | Ph |
| 50.118 | iso-C$_3$H$_7$ | H | 4-CH$_3$(Ph) | N=CR$_{11}$R$_{12}$ | H | Ph |
| 50.119 | iso-C$_3$H$_7$ | H | 4-NO$_2$(Ph) | N=CR$_{11}$R$_{12}$ | CH$_3$ | Ph |
| 50.120 | iso-C$_3$H$_7$ | H | 2,4-Cl(Ph) | N=CR$_{11}$R$_{12}$ | CH$_3$ | Ph |
| 50.121 | iso-C$_3$H$_7$ | H | 2,4-F(Ph) | N=CR$_{11}$R$_{12}$ | CH$_3$ | Ph |
| 50.122 | cyclopropyl | H | Ph | N=CR$_{11}$R$_{12}$ | Ph | 4-Cl(Ph) |
| 50.123 | cyclopropyl | H | 2-Cl(Ph) | N=CR$_{11}$R$_{12}$ | Ph | 4-Cl(Ph) |
| 50.124 | cyclopropyl | H | 3-Cl(Ph) | N=CR$_{11}$R$_{12}$ | Ph | 4-Cl(Ph) |
| 50.125 | cyclopropyl | H | 4-Cl(Ph) | N=CR$_{11}$R$_{12}$ | Ph | 4-Cl(Ph) |
| 50.126 | cyclopropyl | H | 4-Br(Ph) | N=CR$_{11}$R$_{12}$ | Ph | 4-Cl(Ph) |
| 50.127 | cyclopropyl | H | 4-F(Ph) | N=CR$_{11}$R$_{12}$ | Ph | 4-Cl(Ph) |
| 50.128 | cyclopropyl | H | 4-OCH$_3$(Ph) | N=CR$_{11}$R$_{12}$ | Ph | 4-pyridyl |
| 50.129 | cyclopropyl | H | 4-CH$_3$(Ph) | N=CR$_{11}$R$_{12}$ | Ph | 4-pyridyl |
| 50.130 | cyclopropyl | H | 4-NO$_2$(Ph) | N=CR$_{11}$R$_{12}$ | Ph | 4-pyridyl |
| 50.131 | cyclopropyl | H | 2,4-Cl(Ph) | N=CR$_{11}$R$_{12}$ | Ph | 4-pyridyl |
| 50.132 | cyclopropyl | H | 2,4-F(Ph) | N=CR$_{11}$R$_{12}$ | Ph | 4-pyridyl |
| 50.133 | CH$_3$ | H | 1-napthyl | N=CR$_{11}$R$_{12}$ | CH$_3$ | CH$_3$ |
| 50.134 | C$_2$H$_5$ | H | 1-napthyl | N=CR$_{11}$R$_{12}$ | CH$_3$ | CH$_3$ |
| 50.135 | n-C$_3$H$_7$ | H | 1-napthyl | N=CR$_{11}$R$_{12}$ | CH$_3$ | CH$_3$ |
| 50.136 | iso-C$_3$H$_7$ | H | 1-napthyl | N=CR$_{11}$R$_{12}$ | CH$_3$ | CH$_3$ |
| 50.137 | cyclopropyl | H | 1-napthyl | N=CR$_{11}$R$_{12}$ | CH$_3$ | CH$_3$ |
| 50.138 | CH$_3$ | H | 1-napthyl | N=CR$_{11}$R$_{12}$ | H | Ph |
| 50.139 | C$_2$H$_5$ | H | 1-napthyl | N=CR$_{11}$R$_{12}$ | H | Ph |
| 50.140 | n-C$_3$H$_7$ | H | 1-napthyl | N=CR$_{11}$R$_{12}$ | H | Ph |
| 50.141 | iso-C$_3$H$_7$ | H | 1-napthyl | N=CR$_{11}$R$_{12}$ | H | Ph |
| 50.142 | cyclopropyl | H | 1-napthyl | N=CR$_{11}$R$_{12}$ | H | Ph |
| 50.143 | CH$_3$ | H | 1-napthyl | N=CR$_{11}$R$_{12}$ | CH$_3$ | Ph |
| 50.144 | C$_2$H$_5$ | H | 1-napthyl | N=CR$_{11}$R$_{12}$ | CH$_3$ | Ph |
| 50.145 | n-C$_3$H$_7$ | H | 1-napthyl | N=CR$_{11}$R$_{12}$ | CH$_3$ | Ph |
| 50.146 | iso-C$_3$H$_7$ | H | 1-napthyl | N=CR$_{11}$R$_{12}$ | CH$_3$ | Ph |
| 50.147 | cyclopropyl | H | 1-napthyl | N=CR$_{11}$R$_{12}$ | CH$_3$ | Ph |
| 50.148 | CH$_3$ | H | 1-napthyl | N=CR$_{11}$R$_{12}$ | Ph | Ph |
| 50.149 | C$_2$H$_5$ | H | 1-napthyl | N=CR$_{11}$R$_{12}$ | Ph | Ph |
| 50.150 | n-C$_3$H$_7$ | H | 1-napthyl | N=CR$_{11}$R$_{12}$ | Ph | Ph |
| 50.151 | iso-C$_3$H$_7$ | H | 1-napthyl | N=CR$_{11}$R$_{12}$ | Ph | Ph |
| 50.152 | cyclopropyl | H | 1-napthyl | N=CR$_{11}$R$_{12}$ | Ph | Ph |
| 50.153 | CH$_3$ | H | 2-napthyl | N=CR$_{11}$R$_{12}$ | CH$_3$ | CH$_3$ |
| 50.154 | C$_2$H$_5$ | H | 2-napthyl | N=CR$_{11}$R$_{12}$ | CH$_3$ | CH$_3$ |
| 50.155 | n-C$_3$H$_7$ | H | 2-napthyl | N=CR$_{11}$R$_{12}$ | CH$_3$ | CH$_3$ |
| 50.156 | iso-C$_3$H$_7$ | H | 2-napthyl | N=CR$_{11}$R$_{12}$ | CH$_3$ | CH$_3$ |
| 50.157 | cyclopropyl | H | 2-napthyl | N=CR$_{11}$R$_{12}$ | CH$_3$ | CH$_3$ |
| 50.158 | CH$_3$ | H | 2-napthyl | N=CR$_{11}$R$_{12}$ | H | Ph |
| 50.159 | C$_2$H$_5$ | H | 2-napthyl | N=CR$_{11}$R$_{12}$ | H | Ph |
| 50.160 | n-C$_3$H$_7$ | H | 2-napthyl | N=CR$_{11}$R$_{12}$ | H | Ph |
| 50.161 | iso-C$_3$H$_7$ | H | 2-napthyl | N=CR$_{11}$R$_{12}$ | H | Ph |
| 50.162 | cyclopropyl | H | 2-napthyl | N=CR$_{11}$R$_{12}$ | H | Ph |
| 50.163 | CH$_3$ | H | 2-napthyl | N=CR$_{11}$R$_{12}$ | CH$_3$ | Ph |
| 50.164 | C$_2$H$_5$ | H | 2-napthyl | N=CR$_{11}$R$_{12}$ | CH$_3$ | Ph |
| 50.165 | n-C$_3$H$_7$ | H | 2-napthyl | N=CR$_{11}$R$_{12}$ | CH$_3$ | Ph |
| 50.166 | iso-C$_3$H$_7$ | H | 2-napthyl | N=CR$_{11}$R$_{12}$ | CH$_3$ | Ph |
| 50.167 | cyclopropyl | H | 2-napthyl | N=CR$_{11}$R$_{12}$ | CH$_3$ | Ph |

TABLE 50-continued

| Compd. | R$_2$ | R$_3$ | R$_7$ | R$_{10}$ | R$_{11}$ | R$_{12}$ |
|---|---|---|---|---|---|---|
| 50.168 | CH$_3$ | H | 2-napthyl | N=CR$_{11}$R$_{12}$ | Ph | Ph |
| 50.169 | C$_2$H$_5$ | H | 2-napthyl | N=CR$_{11}$R$_{12}$ | Ph | Ph |
| 50.170 | n-C$_3$H$_7$ | H | 2-napthyl | N=CR$_{11}$R$_{12}$ | Ph | Ph |
| 50.171 | iso-C$_3$H$_7$ | H | 2-napthyl | N=CR$_{11}$R$_{12}$ | Ph | Ph |
| 50.172 | cyclopropyl | H | 2-napthyl | N=CR$_{11}$R$_{12}$ | Ph | Ph |
| 50.173 | CH$_3$ | H | Ph | N=CR$_{11}$R$_{12}$ | Ph | 4-Cl(Ph) |
| 50.174 | CH$_3$ | H | 2-Cl(Ph) | N=CR$_{11}$R$_{12}$ | Ph | 4-Cl(Ph) |
| 50.175 | CH$_3$ | H | 3-Cl(Ph) | N=CR$_{11}$R$_{12}$ | Ph | 4-Cl(Ph) |
| 50.176 | CH$_3$ | H | 4-Cl(Ph) | N=CR$_{11}$R$_{12}$ | Ph | 4-Cl(Ph) |
| 50.177 | CH$_3$ | H | 4-Br(Ph) | N=CR$_{11}$R$_{12}$ | Ph | 4-Cl(Ph) |
| 50.178 | CH$_3$ | H | 4-F(Ph) | N=CR$_{11}$R$_{12}$ | Ph | 4-Cl(Ph) |
| 50.179 | CH$_3$ | H | 4-OCH$_3$(Ph) | N=CR$_{11}$R$_{12}$ | Ph | 4-Cl(Ph) |
| 50.180 | CH$_3$ | H | 4-CH$_3$(Ph) | N=CR$_{11}$R$_{12}$ | Ph | 4-Cl(Ph) |
| 50.181 | CH$_3$ | H | 4-NO$_2$(Ph) | N=CR$_{11}$R$_{12}$ | Ph | 4-Cl(Ph) |
| 50.182 | CH$_3$ | H | 2,4-Cl(Ph) | N=CR$_{11}$R$_{12}$ | Ph | 4-Cl(Ph) |
| 50.183 | CH$_3$ | H | 2,4-F(Ph) | N=CR$_{11}$R$_{12}$ | Ph | 4-Cl(Ph) |
| 50.184 | CH$_3$ | H | 4-CH$_3$(Ph) | N=CR$_{11}$R$_{12}$ | Ph | 4-Cl(Ph) |
| 50.185 | CH$_3$ | H | 4-NO$_2$(Ph) | N=CR$_{11}$R$_{12}$ | Ph | 4-Cl(Ph) |
| 50.186 | CH$_3$ | H | 2,4-Cl(Ph) | N=CR$_{11}$R$_{12}$ | Ph | 4-Cl(Ph) |
| 50.187 | CH$_3$ | H | 2,4-F(Ph) | N=CR$_{11}$R$_{12}$ | Ph | 4-Cl(Ph) |
| 50.188 | CH$_3$ | H | 4-CF$_3$(Ph) | N=CR$_{11}$R$_{12}$ | Ph | 4-Cl(Ph) |
| 50.189 | CH$_3$ | H | Ph | N=CR$_{11}$R$_{12}$ | Ph | 4-pyridyl |
| 50.190 | CH$_3$ | H | 4-Cl(Ph) | N=CR$_{11}$R$_{12}$ | Ph | 4-pyridyl |
| 50.191 | CH$_3$ | H | 4-Br(Ph) | N=CR$_{11}$R$_{12}$ | Ph | 4-pyridyl |
| 50.192 | CH$_3$ | H | 4-F(Ph) | N=CR$_{11}$R$_{12}$ | Ph | 4-pyridyl |
| 50.193 | CH$_3$ | H | 4-OCH$_3$(Ph) | N=CR$_{11}$R$_{12}$ | Ph | 4-pyridyl |
| 50.194 | CH$_3$ | H | 4-CH$_3$(Ph) | N=CR$_{11}$R$_{12}$ | Ph | 4-pyridyl |
| 50.195 | CH$_3$ | H | 4-NO$_2$(Ph) | N=CR$_{11}$R$_{12}$ | Ph | 4-pyridyl |
| 50.196 | CH$_3$ | H | 2 4-Cl(Ph) | N=CR$_{11}$R$_{12}$ | Ph | 4-pyridyl |
| 50.197 | CH$_3$ | H | 2,4-F(Ph) | N=CR$_{11}$R$_{12}$ | Ph | 4-pyridyl |
| 50.198 | CH$_3$ | H | 4-CF$_3$(Ph) | N=CR$_{11}$R$_{12}$ | Ph | 4-pyridyl |
| 50.199 | CH$_3$ | H | Ph | N=CR$_{11}$R$_{12}$ | CH$_3$ | N(CH$_3$)$_2$ |
| 50.200 | CH$_3$ | H | 4-Cl(Ph) | N=CR$_{11}$R$_{12}$ | CH$_3$ | N(CH$_3$)$_2$ |
| 50.201 | CH$_3$ | H | 4-Br(Ph) | N=CR$_{11}$R$_{12}$ | CH$_3$ | N(CH$_3$)$_2$ |
| 50.202 | CH$_3$ | H | 4-F(Ph) | N=CR$_{11}$R$_{12}$ | CH$_3$ | N(CH$_3$)$_2$ |
| 50.203 | CH$_3$ | H | 4-OCH$_3$(Ph) | N=CR$_{11}$R$_{12}$ | CH$_3$ | N(CH$_3$)$_2$ |
| 50.204 | CH$_3$ | H | 4-CH$_3$(Ph) | N=CR$_{11}$R$_{12}$ | CH$_3$ | N(CH$_3$)$_2$ |
| 50.205 | CH$_3$ | H | 4-NO$_2$(Ph) | N=CR$_{11}$R$_{12}$ | CH$_3$ | N(CH$_3$)$_2$ |
| 50.206 | CH$_3$ | H | 2,4-Cl(Ph) | N=CR$_{11}$R$_{12}$ | CH$_3$ | N(CH$_3$)$_2$ |
| 50.207 | CH$_3$ | H | 2,4-F(Ph) | N=CR$_{11}$R$_{12}$ | CH$_3$ | N(CH$_3$)$_2$ |
| 50.208 | CH$_3$ | H | 4-CF$_3$(Ph) | N=CR$_{11}$R$_{12}$ | CH$_3$ | N(CH$_3$)$_2$ |
| 50.209 | CH$_3$ | H | Ph | N=cyclopentyl | | |
| 50.210 | CH$_3$ | H | 4-Cl(Ph) | N=cyclopentyl | | |
| 50.211 | CH$_3$ | H | 4-Br(Ph) | N=cyclopentyl | | |
| 50.212 | CH$_3$ | H | 4-F(Ph) | N=cyclopentyl | | |
| 50.213 | CH$_3$ | H | 4-OCH$_3$(Ph) | N=cyclopentyl | | |
| 50.214 | CH$_3$ | H | 4-CH$_3$(Ph) | N=cyclopentyl | | |
| 50.215 | CH$_3$ | H | 4-NO$_2$(Ph) | N=cyclopentyl | | |
| 50.216 | CH$_3$ | H | 2,4-Cl(Ph) | N=cyclopentyl | | |
| 50.217 | CH$_3$ | H | 2,4-F(Ph) | N=cyclopentyl | | |
| 50.218 | CH$_3$ | H | 4-CF$_3$(Ph) | N=cyclopentyl | | |
| 50.219 | CH$_3$ | H | Ph | N=cyclohexyl | | |
| 50.220 | CH$_3$ | H | 4-Cl(Ph) | N=cyclohexyl | | |
| 50.221 | CH$_3$ | H | 4-Br(Ph) | N=cyclohexyl | | |
| 50.222 | CH$_3$ | H | 4-F(Ph) | N=cyclohexyl | | |
| 50.223 | CH$_3$ | H | 4-OCH$_3$(Ph) | N=cyclohexyl | | |
| 50.224 | CH$_3$ | H | 4-CH$_3$(Ph) | N=cyclohexyl | | |
| 50.225 | CH$_3$ | H | 4-NO$_2$(Ph) | N=cyclohexyl | | |
| 50.226 | CH$_3$ | H | 2,4-Cl(Ph) | N=cyclohexyl | | |
| 50.227 | CH$_3$ | H | 2,4-F(Ph) | N=cyclohexyl | | |
| 50.228 | CH$_3$ | H | 4-CF$_3$(Ph) | N=cyclohexyl | | |
| 50.229 | CH$_3$ | H | 1-napthyl | N=cyclopentyl | | |
| 50.230 | C$_2$H$_5$ | H | 1-napthyl | N=cyclopentyl | | |
| 50.231 | n-C$_3$H$_7$ | H | 1-napthyl | N=cyclopentyl | | |
| 50.232 | iso-C$_3$H$_7$ | H | 1-napthyl | N=cyclopentyl | | |
| 50.233 | cyclopropyl | H | 1-napthyl | N=cyclopentyl | | |
| 50.234 | CH$_3$ | H | 1-napthyl | N=cyclohexyl | | |
| 50.235 | C$_2$H$_5$ | H | 1-napthyl | N=cyclohexyl | | |
| 50.236 | n-C$_3$H$_7$ | H | 1-napthyl | N=cyclohexyl | | |
| 50.237 | iso-C$_3$H$_7$ | H | 1-napthyl | N=cyclohexyl | | |
| 50.238 | cyclopropyl | H | 1-napthyl | N=cyclohexyl | | |
| 50.239 | CH$_3$ | H | 2-napthyl | N=cyclopentyl | | |
| 50.240 | C$_2$H$_5$ | H | 2-napthyl | N=cyclopentyl | | |
| 50.241 | n-C$_3$H$_7$ | H | 2-napthyl | N=cyclopentyl | | |
| 50.242 | iso-C$_3$H$_7$ | H | 2-napthyl | N=cyclopentyl | | |
| 50.243 | cyclopropyl | H | 2-napthyl | N=cyclopentyl | | |
| 50.244 | CH$_3$ | H | 2-napthyl | N=cyclohexyl | | |

TABLE 50-continued

| Compd. | R$_2$ | R$_3$ | R$_7$ | R$_{10}$ | R$_{11}$ | R$_{12}$ |
|---|---|---|---|---|---|---|
| 50.245 | C$_2$H$_5$ | H | 2-napthyl | N=cyclohexyl | | |
| 50.246 | n-C$_3$H$_7$ | H | 2-napthyl | N=cyclohexyl | | |
| 50.247 | iso-C$_3$H$_7$ | H | 2-napthyl | N=cyclohexyl | | |
| 50.248 | cyclopropyl | H | 2-napthyl | N=cyclohexyl | | |
| 50.249 | CH$_3$ | H | 1-napthyl | N=CR$_{11}$R$_{12}$ | CH$_3$ | N(CH$_3$)$_2$ |
| 50.250 | C$_2$H$_5$ | H | 1-napthyl | N=CR$_{11}$R$_{12}$ | CH$_3$ | N(CH$_3$)$_2$ |
| 50.251 | n-C$_3$H$_7$ | H | 1-napthyl | N=CR$_{11}$R$_{12}$ | CH$_3$ | N(CH$_3$)$_2$ |
| 50.252 | iso-C$_3$H$_7$ | H | 1-napthyl | N=CR$_{11}$R$_{12}$ | CH$_3$ | N(CH$_3$)$_2$ |
| 50.253 | cyclopropyl | H | 1-napthyl | N=CR$_{11}$R$_{12}$ | CH$_3$ | N(CH$_3$)$_2$ |
| 50.254 | CH$_3$ | H | 2-napthyl | N=CR$_{11}$R$_{12}$ | CH$_3$ | N(CH$_3$)$_2$ |
| 50.255 | C$_2$H$_5$ | H | 2-napthyl | N=CR$_{11}$R$_{12}$ | CH$_3$ | N(CH$_3$)$_2$ |
| 50.256 | n-C$_3$H$_7$ | H | 2-napthyl | N=CR$_{11}$R$_{12}$ | CH$_3$ | N(CH$_3$)$_2$ |
| 50.257 | iso-C$_3$H$_7$ | H | 2-napthyl | N=CR$_{11}$R$_{12}$ | CH$_3$ | N(CH$_3$)$_2$ |
| 50.258 | cyclopropyl | H | 2-napthyl | N=CR$_{11}$R$_{12}$ | CH$_3$ | N(CH$_3$)$_2$ |
| 50.259 | CH$_3$ | CH$_3$ | Ph | N=CR$_{11}$R$_{12}$ | H | Ph |
| 50.260 | C$_2$H$_5$ | CH$_3$ | 4-Cl(Ph) | N=CR$_{11}$R$_{12}$ | H | Ph |
| 50.261 | n-C$_3$H$_7$ | CH$_3$ | 4-Br(Ph) | N=CR$_{11}$R$_{12}$ | H | Ph |
| 50.262 | iso-C$_3$H$_7$ | CH$_3$ | 4-F(Ph) | N=CR$_{11}$R$_{12}$ | H | Ph |
| 50.263 | CH$_3$ | CH$_3$ | Ph | N=CR$_{11}$R$_{12}$ | CH$_3$ | Ph |
| 50.264 | C$_2$H$_5$ | CH$_3$ | 4-Cl(Ph) | N=CR$_{11}$R$_{12}$ | CH$_3$ | Ph |
| 50.265 | n-C$_3$H$_7$ | CH$_3$ | 4-Br(Ph) | N=CR$_{11}$R$_{12}$ | CH | Ph |
| 50.266 | iso-C$_3$H$_7$ | CH$_3$ | 4-F(Ph) | N=CR$_{11}$R$_{12}$ | CH$_3$ | Ph |
| 50.267 | CH$_3$ | CH$_3$ | Ph | N=CR$_{11}$R$_{12}$ | Ph | Ph |
| 50.268 | C$_2$H$_5$ | CH$_3$ | 4-Cl(Ph) | N=CR$_{11}$R$_{12}$ | Ph | Ph |
| 50.269 | n-C$_3$H$_7$ | CH$_3$ | 4-Br(Ph) | N=CR$_{11}$R$_{12}$ | Ph | Ph |
| 50.270 | iso-C$_3$H$_7$ | CH$_3$ | 4-F(Ph) | N=CR$_{11}$R$_{12}$ | Ph | Ph |
| 50.271 | CH$_3$ | CH$_3$ | Ph | N=CR$_{11}$R$_{12}$ | Ph | 4-Cl(Ph) |
| 50.272 | C$_2$H$_5$ | CH$_3$ | 4-Cl(Ph) | N=CR$_{11}$R$_{12}$ | Ph | 4-Cl(Ph) |

Typical compounds encompassed by the present invention of Formula I include those compounds of Formula XII, which is Formula I with A=R$_4$=R$_5$=R$_6$=H, R$_1$=CH$_3$, X=N, Y=NH, Z=NR$_{10}$, and where R$_2$, R$_3$, R$_7$, R$_{10}$, R$_{11}$ and R$_{12}$ are defined in Table 51.

Formula XII

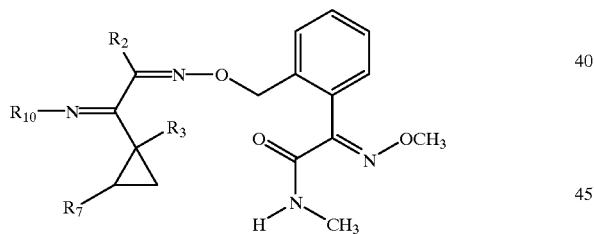

TABLE 51

| Compd. | R$_2$ | R$_3$ | R$_7$ | R$_{10}$ | R$_{11}$ | R$_{12}$ |
|---|---|---|---|---|---|---|
| 51.1 | H | H | Ph | N=CR$_{11}$R$_{12}$ | CH$_3$ | CH$_3$ |
| 51.2 | H | H | 4-Cl(Ph) | N=CR$_{11}$R$_{12}$ | CH$_3$ | CH$_3$ |
| 51.3 | H | H | 4-Br(Ph) | N=CR$_{11}$R$_{12}$ | CH$_3$ | CH$_3$ |
| 51.4 | H | H | 4-F(Ph) | N=CR$_{11}$R$_{12}$ | CH$_3$ | CH$_3$ |
| 51.5 | H | H | 4-OCH$_3$(Ph) | N=CR$_{11}$R$_{12}$ | CH$_3$ | CH$_3$ |
| 51.6 | H | H | 4-CF$_3$(Ph) | N=CR$_{11}$R$_{12}$ | CH$_3$ | CH$_3$ |
| 51.7 | H | H | Ph | N=CR$_{11}$R$_{12}$ | CH$_3$ | CH$_3$ |
| 51.8 | H | H | 4-Cl(Ph) | N=CR$_{11}$R$_{12}$ | CH$_3$ | CH$_3$ |
| 51.9 | H | H | 4-Br(Ph) | N=CR$_{11}$R$_{12}$ | CH$_3$ | CH$_3$ |
| 51.10 | H | H | 4-F(Ph) | N=CR$_{11}$R$_{12}$ | CH$_3$ | CH$_3$ |
| 51.11 | CH$_3$ | H | Ph | N=CR$_{11}$R$_{12}$ | CH$_3$ | CH$_3$ |
| 51.12 | CH$_3$ | H | 2-Cl(Ph) | N=CR$_{11}$R$_{12}$ | CH$_3$ | CH$_3$ |
| 51.13 | CH$_3$ | H | 3-Cl(Ph) | N=CR$_{11}$R$_{12}$ | CH$_3$ | CH$_3$ |
| 51.14 | CH$_3$ | H | 4-Cl(Ph) | N=CR$_{11}$R$_{12}$ | CH$_3$ | CH$_3$ |
| 51.15 | CH$_3$ | H | 2-Br(Ph) | N=CR$_{11}$R$_{12}$ | CH$_3$ | CH$_3$ |
| 51.16 | CH$_3$ | H | 3-Br(Ph) | N=CR$_{11}$R$_{12}$ | CH$_3$ | CH$_3$ |

TABLE 51-continued

| Compd. | R$_2$ | R$_3$ | R$_7$ | R$_{10}$ | R$_{11}$ | R$_{12}$ |
|---|---|---|---|---|---|---|
| 51.17 | CH$_3$ | H | 4-Br(Ph) | N=CR$_{11}$R$_{12}$ | CH$_3$ | CH$_3$ |
| 51.18 | CH$_3$ | H | Ph | N=CR$_{11}$R$_{12}$ | H | Ph |
| 51.19 | CH$_3$ | H | 2-Cl(Ph) | N=CR$_{11}$R$_{12}$ | H | Ph |
| 51.20 | CH$_3$ | H | 3-Cl(Ph) | N=CR$_{11}$R$_{12}$ | H | Ph |
| 51.21 | CH$_3$ | H | 4-Cl(Ph) | N=CR$_{11}$R$_{12}$ | H | Ph |
| 51.22 | CH$_3$ | H | 2-Br(Ph) | N=CR$_{11}$R$_{12}$ | H | Ph |
| 51.23 | CH$_3$ | H | 3-Br(Ph) | N=CR$_{11}$R$_{12}$ | H | Ph |
| 51.24 | CH$_3$ | H | 4-Br(Ph) | N=CR$_{11}$R$_{12}$ | H | Ph |
| 51.25 | CH$_3$ | H | 2-CH$_3$(Ph) | N=CR$_{11}$R$_{12}$ | H | Ph |
| 51.26 | CH$_3$ | H | 3-CH$_3$(Ph) | N=CR$_{11}$R$_{12}$ | H | Ph |
| 51.27 | CH$_3$ | H | 2-CF$_3$(Ph) | N=CR$_{11}$R$_{12}$ | H | Ph |
| 51.28 | CH$_3$ | H | 3-CF$_3$(Ph) | N=CR$_{11}$R$_{12}$ | H | Ph |
| 51.29 | CH$_3$ | H | 4-CF$_3$(Ph) | N=CR$_{11}$R$_{12}$ | H | Ph |
| 51.30 | CH$_3$ | H | 2-NO$_2$(Ph) | N=CR$_{11}$R$_{12}$ | H | Ph |
| 51.31 | CH$_3$ | H | 3-NO$_2$(Ph) | N=CR$_{11}$R$_{12}$ | H | Ph |
| 51.32 | CH$_3$ | H | 4-NO$_2$(Ph) | N=CR$_{11}$R$_{12}$ | H | Ph |
| 51.33 | CH$_3$ | H | 2,3-Cl(Ph) | N=CR$_{11}$R$_{12}$ | H | Ph |
| 51.34 | CH$_3$ | H | 2,4-Cl(Ph) | N=CR$_{11}$R$_{12}$ | H | Ph |
| 51.35 | CH$_3$ | H | 2,5-Cl(Ph) | N=CR$_{11}$R$_{12}$ | H | Ph |
| 51.36 | CH$_3$ | H | 2,6-Cl(Ph) | N=CR$_{11}$R$_{12}$ | H | Ph |
| 51.37 | CH$_3$ | H | 3,4-Cl(Ph) | N=CR$_{11}$R$_{12}$ | H | Ph |
| 51.38 | CH$_3$ | H | 3,5-Cl(Ph) | N=CR$_{11}$R$_{12}$ | H | Ph |
| 51.39 | CH$_3$ | H | Ph | N=CR$_{11}$R$_{12}$ | CH$_3$ | Ph |
| 51.40 | CH$_3$ | H | 2-Cl(Ph) | N=CR$_{11}$R$_{12}$ | CH$_3$ | Ph |
| 51.41 | CH$_3$ | H | 3-Cl(Ph) | N=CR$_{11}$R$_{12}$ | CH$_3$ | Ph |
| 51.42 | CH$_3$ | H | 4-Cl(Ph) | N=CR$_{11}$R$_{12}$ | CH$_3$ | Ph |
| 51.43 | CH$_3$ | H | 2-Br(Ph) | N=CR$_{11}$R$_{12}$ | CH$_3$ | Ph |
| 51.44 | CH$_3$ | H | 3-Br(Ph) | N=CR$_{11}$R$_{12}$ | CH$_3$ | Ph |
| 51.45 | CH$_3$ | H | 4-Br(Ph) | N=CR$_{11}$R$_{12}$ | CH$_3$ | Ph |
| 51.46 | CH$_3$ | H | 2-CH$_3$(Ph) | N=CR$_{11}$R$_{12}$ | CH$_3$ | Ph |
| 51.47 | CH$_3$ | H | 3-CH$_3$(Ph) | N=CR$_{11}$R$_{12}$ | CH$_3$ | Ph |
| 51.48 | CH$_3$ | H | 2-CF$_3$(Ph) | N=CR$_{11}$R$_{12}$ | CH$_3$ | Ph |
| 51.49 | CH$_3$ | H | 3-CF$_3$(Ph) | N=CR$_{11}$R$_{12}$ | CH$_3$ | Ph |
| 51.50 | CH$_3$ | H | 4-F(Ph) | N=CR$_{11}$R$_{12}$ | CH$_3$ | Ph |
| 51.51 | CH$_3$ | H | 4-OCH$_3$(Ph) | N=CR$_{11}$R$_{12}$ | CH$_3$ | Ph |
| 51.52 | CH$_3$ | H | 4-CH$_3$(Ph) | N=CR$_{11}$R$_{12}$ | CH$_3$ | Ph |
| 51.53 | CH$_3$ | H | 4-NO$_2$(Ph) | N=CR$_{11}$R$_{12}$ | CH$_3$ | Ph |
| 51.54 | CH$_3$ | H | 2,4-Cl(Ph) | N=CR$_{11}$R$_{12}$ | CH$_3$ | Ph |
| 51.55 | CH$_3$ | H | 2,4-F(Ph) | N=CR$_{11}$R$_{12}$ | CH$_3$ | Ph |
| 51.56 | CH$_3$ | H | Ph | N=CR$_{11}$R$_{12}$ | Ph | Ph |
| 51.57 | CH$_3$ | H | 2-Cl(Ph) | N=CR$_{11}$R$_{12}$ | Ph | Ph |
| 51.58 | CH$_3$ | H | 3-Cl(Ph) | N=CR$_{11}$R$_{12}$ | Ph | Ph |
| 51.59 | CH$_3$ | H | 4-Cl(Ph) | N=CR$_{11}$R$_{12}$ | Ph | Ph |
| 51.60 | CH$_3$ | H | 4-F(Ph) | N=CR$_{11}$R$_{12}$ | Ph | Ph |
| 51.61 | CH$_3$ | H | 3-OCH$_3$(Ph) | N=CR$_{11}$R$_{12}$ | Ph | Ph |
| 51.62 | CH$_3$ | H | 4-OCH$_3$(Ph) | N=CR$_{11}$R$_{12}$ | Ph | Ph |
| 51.63 | CH$_3$ | H | 4-CH$_3$(Ph) | N=CR$_{11}$R$_{12}$ | Ph | Ph |
| 51.64 | CH$_3$ | H | 4-NO$_2$(Ph) | N=CR$_{11}$R$_{12}$ | Ph | Ph |
| 51.65 | CH$_3$ | H | 2,4-Cl(Ph) | N=CR$_{11}$R$_{12}$ | Ph | Ph |
| 51.66 | CH$_3$ | H | 2,4-F(Ph) | N=CR$_{11}$R$_{12}$ | Ph | Ph |
| 51.67 | C$_2$H$_5$ | H | Ph | N=CR$_{11}$R$_{12}$ | CH$_3$ | CH$_3$ |
| 51.68 | C$_2$H$_5$ | H | 2-Cl(Ph) | N=CR$_{11}$R$_{12}$ | CH$_3$ | CH$_3$ |
| 51.69 | C$_2$H$_5$ | H | 3-Cl(Ph) | N=CR$_{11}$R$_{12}$ | CH$_3$ | CH$_3$ |
| 51.70 | C$_2$H$_5$ | H | 4-Cl(Ph) | N=CR$_{11}$R$_{12}$ | CH$_3$ | CH$_3$ |
| 51.71 | C$_2$H$_5$ | H | 4-Br(Ph) | N=CR$_{11}$R$_{12}$ | CH$_3$ | CH$_3$ |
| 51.72 | C$_2$H$_5$ | H | 4-F(Ph) | N=CR$_{11}$R$_{12}$ | CH$_3$ | CH$_3$ |
| 51.73 | C$_2$H$_5$ | H | 4-OCH$_3$(Ph) | N=CR$_{11}$R$_{12}$ | CH$_3$ | CH$_3$ |
| 51.74 | C$_2$H$_5$ | H | 4-CH$_3$(Ph) | N=CR$_{11}$R$_{12}$ | CH$_3$ | CH$_3$ |
| 51.75 | C$_2$H$_5$ | H | 4-NO$_2$(Ph) | N=CR$_{11}$R$_{12}$ | CH$_3$ | CH$_3$ |
| 51.76 | C$_2$H$_5$ | H | 2,4-Cl(Ph) | N=CR$_{11}$R$_{12}$ | CH$_3$ | CH$_3$ |
| 51.77 | C$_2$H$_5$ | H | 2,4-F(Ph) | N=CR$_{11}$R$_{12}$ | CH$_3$ | CH$_3$ |
| 51.78 | C$_2$H$_5$ | H | Ph | N=CR$_{11}$R$_{12}$ | CH$_3$ | CH$_3$ |
| 51.79 | C$_2$H$_5$ | H | 2-Cl(Ph) | N=CR$_{11}$R$_{12}$ | H | Ph |
| 51.80 | C$_2$H$_5$ | H | 3-Cl(Ph) | N=CR$_{11}$R$_{12}$ | H | Ph |
| 51.81 | C$_2$H$_5$ | H | 4-Cl(Ph) | N=CR$_{11}$R$_{12}$ | H | Ph |
| 51.82 | C$_2$H$_5$ | H | 4-Br(Ph) | N=CR$_{11}$R$_{12}$ | H | Ph |
| 51.83 | C$_2$H$_5$ | H | 4-F(Ph) | N=CR$_{11}$R$_{12}$ | H | Ph |
| 51.84 | C$_2$H$_5$ | H | 4-OCH$_3$(Ph) | N=CR$_{11}$R$_{12}$ | H | Ph |
| 51.85 | C$_2$H$_5$ | H | 4-CH$_3$(Ph) | N=CR$_{11}$R$_{12}$ | H | Ph |
| 51.86 | C$_2$H$_5$ | H | 4-NO$_2$(Ph) | N=CR$_{11}$R$_{12}$ | H | Ph |
| 51.87 | C$_2$H$_5$ | H | 2,4-Cl(Ph) | N=CR$_{11}$R$_{12}$ | H | Ph |
| 51.88 | C$_2$H$_5$ | H | 2,4-F(Ph) | N=CR$_{11}$R$_{12}$ | H | Ph |
| 51.89 | C$_2$H$_5$ | H | Ph | N=CR$_{11}$R$_{12}$ | CH$_3$ | Ph |
| 51.90 | C$_2$H$_5$ | H | 2-Cl(Ph) | N=CR$_{11}$R$_{12}$ | CH$_3$ | Ph |
| 51.91 | C$_2$H$_5$ | H | 3-Cl(Ph) | N=CR$_{11}$R$_{12}$ | CH$_3$ | Ph |
| 51.92 | C$_2$H$_5$ | H | 4-Cl(Ph) | N=CR$_{11}$R$_{12}$ | CH$_3$ | Ph |
| 51.93 | C$_2$H$_5$ | H | 4-F(Ph) | N=CR$_{11}$R$_{12}$ | CH$_3$ | Ph |

TABLE 51-continued

| Compd. | R$_2$ | R$_3$ | R$_7$ | R$_{10}$ | R$_{11}$ | R$_{12}$ |
|---|---|---|---|---|---|---|
| 51.94 | C$_2$H$_5$ | H | 3-OCH$_3$(Ph) | N=CR$_{11}$R$_{12}$ | CH$_3$ | Ph |
| 51.95 | C$_2$H$_5$ | H | 4-OCH$_3$(Ph) | N=CR$_{11}$R$_{12}$ | CH$_3$ | Ph |
| 51.96 | C$_2$H$_5$ | H | 4-CH$_3$(Ph) | N=CR$_{11}$R$_{12}$ | CH$_3$ | Ph |
| 51.97 | C$_2$H$_5$ | H | 4-NO$_2$(Ph) | N=CR$_{11}$R$_{12}$ | CH$_3$ | Ph |
| 51.98 | C$_2$H$_5$ | H | 2,4-Cl(Ph) | N=CR$_{11}$R$_{12}$ | CH$_3$ | Ph |
| 51.99 | C$_2$H$_5$ | H | 2,4-F(Ph) | N=CR$_{11}$R$_{12}$ | CH$_3$ | Ph |
| 51.100 | C$_2$H$_5$ | H | Ph | N=CR$_{11}$R$_{12}$ | Ph | Ph |
| 51.101 | C$_2$H$_5$ | H | 2-Cl(Ph) | N=CR$_{11}$R$_{12}$ | Ph | Ph |
| 51.102 | C$_2$H$_5$ | H | 3-Cl(Ph) | N=CR$_{11}$R$_{12}$ | Ph | Ph |
| 51.103 | C$_2$H$_5$ | H | 4-Cl(Ph) | N=CR$_{11}$R$_{12}$ | Ph | Ph |
| 51.104 | C$_2$H$_5$ | H | 4-F(Ph) | N=CR$_{11}$R$_{12}$ | Ph | Ph |
| 51.105 | C$_2$H$_5$ | H | 3-OCH$_3$(Ph) | N=CR$_{11}$R$_{12}$ | Ph | Ph |
| 51.106 | C$_2$H$_5$ | H | 4-OCH$_3$(Ph) | N=CR$_{11}$R$_{12}$ | Ph | Ph |
| 51.107 | C$_2$H$_5$ | H | 4-CH$_3$(Ph) | N=CR$_{11}$R$_{12}$ | Ph | Ph |
| 51.108 | C$_2$H$_5$ | H | 4-NO$_2$(Ph) | N=CR$_{11}$R$_{12}$ | Ph | Ph |
| 51.109 | C$_2$H$_5$ | H | 2,4-Cl(Ph) | N=CR$_{11}$R$_{12}$ | Ph | Ph |
| 51.110 | C$_2$H$_5$ | H | 2,4-F(Ph) | N=CR$_{11}$R$_{12}$ | Ph | Ph |
| 51.111 | iso-C$_3$H$_7$ | H | Ph | N=CR$_{11}$R$_{12}$ | CH$_3$ | CH$_3$ |
| 51.112 | iso-C$_3$H$_7$ | H | 2-Cl(Ph) | N=CR$_{11}$R$_{12}$ | CH$_3$ | CH$_3$ |
| 51.113 | iso-C$_3$H$_7$ | H | 3-Cl(Ph) | N=CR$_{11}$R$_{12}$ | CH$_3$ | CH$_3$ |
| 51.114 | iso-C$_3$H$_7$ | H | 4-Cl(Ph) | N=CR$_{11}$R$_{12}$ | CH$_3$ | CH$_3$ |
| 51.115 | iso-C$_3$H$_7$ | H | 4-Br(Ph) | N=CR$_{11}$R$_{12}$ | H | Ph |
| 51.116 | iso-C$_3$H$_7$ | H | 3-OCH$_3$(Ph) | N=CR$_{11}$R$_{12}$ | H | Ph |
| 51.117 | iso-C$_3$H$_7$ | H | 4-OCH$_3$(Ph) | N=CR$_{11}$R$_{12}$ | H | Ph |
| 51.118 | iso-C$_3$H$_7$ | H | 4-CH$_3$(Ph) | N=CR$_{11}$R$_{12}$ | H | Ph |
| 51.119 | iso-C$_3$H$_7$ | H | 4-NO$_2$(Ph) | N=CR$_{11}$R$_{12}$ | CH$_3$ | Ph |
| 51.120 | iso-C$_3$H$_7$ | H | 2,4-Cl(Ph) | N=CR$_{11}$R$_{12}$ | CH$_3$ | Ph |
| 51.121 | iso-C$_3$H$_7$ | H | 2,4-F(Ph) | N=CR$_{11}$R$_{12}$ | CH$_3$ | Ph |
| 51.122 | cyclopropyl | H | Ph | N=CR$_{11}$R$_{12}$ | Ph | 4-Cl(Ph) |
| 51.123 | cyclopropyl | H | 2-Cl(Ph) | N=CR$_{11}$R$_{12}$ | Ph | 4-Cl(Ph) |
| 51.124 | cyclopropyl | H | 3-Cl(Ph) | N=CR$_{11}$R$_{12}$ | Ph | 4-Cl(Ph) |
| 51.125 | cyclopropyl | H | 4-Cl(Ph) | N=CR$_{11}$R$_{12}$ | Ph | 4-Cl(Ph) |
| 51.126 | cyclopropyl | H | 4-Br(Ph) | N=CR$_{11}$R$_{12}$ | Ph | 4-Cl(Ph) |
| 51.127 | cyclopropyl | H | 4-F(Ph) | N=CR$_{11}$R$_{12}$ | Ph | 4-Cl(Ph) |
| 51.128 | cyclopropyl | H | 4-OCH$_3$(Ph) | N=CR$_{11}$R$_{12}$ | Ph | 4-pyridyl |
| 51.129 | cyclopropyl | H | 4-CH$_3$(Ph) | N=CR$_{11}$R$_{12}$ | Ph | 4-pyridyl |
| 51.130 | cyclopropyl | H | 4-NO$_2$(Ph) | N=CR$_{11}$R$_{12}$ | Ph | 4-pyridyl |
| 51.131 | cyclopropyl | H | 2,4-Cl(Ph) | N=CR$_{11}$R$_{12}$ | Ph | 4-pyridyl |
| 51.132 | cyclopropyl | H | 2,4-F(Ph) | N=CR$_{11}$R$_{12}$ | Ph | 4-pyridyl |
| 51.133 | CH$_3$ | H | 1-napthyl | N=CR$_{11}$R$_{12}$ | CH$_3$ | CH$_3$ |
| 51.134 | C$_2$H$_5$ | H | 1-napthyl | N=CR$_{11}$R$_{12}$ | CH$_3$ | CH$_3$ |
| 51.135 | n-C$_3$H$_7$ | H | 1-napthyl | N=CR$_{11}$R$_{12}$ | CH$_3$ | CH$_3$ |
| 51.136 | iso-C$_3$H$_7$ | H | 1-napthyl | N=CR$_{11}$R$_{12}$ | CH$_3$ | CH$_3$ |
| 51.137 | cyclopropyl | H | 1-napthyl | N=CR$_{11}$R$_{12}$ | CH$_3$ | CH$_3$ |
| 51.138 | CH$_3$ | H | 1-napthyl | N=CR$_{11}$R$_{12}$ | H | Ph |
| 51.139 | C$_2$H$_5$ | H | 1-napthyl | N=CR$_{11}$R$_{12}$ | H | Ph |
| 51.140 | n-C$_3$H$_7$ | H | 1-napthyl | N=CR$_{11}$R$_{12}$ | H | Ph |
| 51.141 | iso-C$_3$H$_7$ | H | 1-napthyl | N=CR$_{11}$R$_{12}$ | H | Ph |
| 51.142 | cyclopropyl | H | 1-napthyl | N=CR$_{11}$R$_{12}$ | H | Ph |
| 51.143 | CH$_3$ | H | 1-napthyl | N=CR$_{11}$R$_{12}$ | CH$_3$ | Ph |
| 51.144 | C$_2$H$_5$ | H | 1-napthyl | N=CR$_{11}$R$_{12}$ | CH$_3$ | Ph |
| 51.145 | n-C$_3$H$_7$ | H | 1-napthyl | N=CR$_{11}$R$_{12}$ | CH$_3$ | Ph |
| 51.146 | iso-C$_3$H$_7$ | H | 1-napthyl | N=CR$_{11}$R$_{12}$ | CH$_3$ | Ph |
| 51.147 | cyclopropyl | H | 1-napthyl | N=CR$_{11}$R$_{12}$ | CH$_3$ | Ph |
| 51.148 | CH$_3$ | H | 1-napthyl | N=CR$_{11}$R$_{12}$ | Ph | Ph |
| 51.149 | C$_2$H$_5$ | H | 1-napthyl | N=CR$_{11}$R$_{12}$ | Ph | Ph |
| 51.150 | n-C$_3$H$_7$ | H | 1-napthyl | N=CR$_{11}$R$_{12}$ | Ph | Ph |
| 51.151 | iso-C$_3$H$_7$ | H | 1-napthyl | N=CR$_{11}$R$_{12}$ | Ph | Ph |
| 51.152 | cyclopropyl | H | 1-napthyl | N=CR$_{11}$R$_{12}$ | Ph | Ph |
| 51.153 | CH$_3$ | H | 2-napthyl | N=CR$_{11}$R$_{12}$ | CH$_3$ | CH$_3$ |
| 51.154 | C$_2$H$_5$ | H | 2-napthyl | N=CR$_{11}$R$_{12}$ | CH$_3$ | CH$_3$ |
| 51.155 | n-C$_3$H$_7$ | H | 2-napthyl | N=CR$_{11}$R$_{12}$ | CH$_3$ | CH$_3$ |
| 51.156 | iso-C$_3$H$_7$ | H | 2-napthyl | N=CR$_{11}$R$_{12}$ | CH$_3$ | CH$_3$ |
| 51.157 | cyclopropyl | H | 2-napthyl | N=CR$_{11}$R$_{12}$ | CH$_3$ | CH$_3$ |
| 51.158 | CH$_3$ | H | 2-napthyl | N=CR$_{11}$R$_{12}$ | H | Ph |
| 51.159 | C$_2$H$_5$ | H | 2-napthyl | N=CR$_{11}$R$_{12}$ | H | Ph |
| 51.160 | n-C$_3$H$_7$ | H | 2-napthyl | N=CR$_{11}$R$_{12}$ | H | Ph |
| 51.161 | iso-C$_3$H$_7$ | H | 2-napthyl | N=CR$_{11}$R$_{12}$ | H | Ph |
| 51.162 | cyclopropyl | H | 2-napthyl | N=CR$_{11}$R$_{12}$ | H | Ph |
| 51.163 | CH$_3$ | H | 2-napthyl | N=CR$_{11}$R$_{12}$ | CH$_3$ | Ph |
| 51.164 | C$_2$H$_5$ | H | 2-napthyl | N=CR$_{11}$R$_{12}$ | CH$_3$ | Ph |
| 51.165 | n-C$_3$H$_7$ | H | 2-napthyl | N=CR$_{11}$R$_{12}$ | CH$_3$ | Ph |
| 51.166 | iso-C$_3$H$_7$ | H | 2-napthyl | N=CR$_{11}$R$_{12}$ | CH$_3$ | Ph |
| 51.167 | cyclopropyl | H | 2-napthyl | N=CR$_{11}$R$_{12}$ | CH$_3$ | Ph |
| 51.168 | CH$_3$ | H | 2-napthyl | N=CR$_{11}$R$_{12}$ | Ph | Ph |
| 51.169 | C$_2$H$_5$ | H | 2-napthyl | N=CR$_{11}$R$_{12}$ | Ph | Ph |
| 51.170 | n-C$_3$H$_7$ | H | 2-napthyl | N=CR$_{11}$R$_{12}$ | Ph | Ph |

TABLE 51-continued

| Compd. | R$_2$ | R$_3$ | R$_7$ | R$_{10}$ | R$_{11}$ | R$_{12}$ |
|---|---|---|---|---|---|---|
| 51.171 | iso-C$_3$H$_7$ | H | 2-napthyl | N=CR$_{11}$R$_{12}$ | Ph | Ph |
| 51.172 | cyclopropyl | H | 2-napthyl | N=CR$_{11}$R$_{12}$ | Ph | Ph |
| 51.173 | CH$_3$ | H | Ph | N=CR$_{11}$R$_{12}$ | Ph | 4-Cl(Ph) |
| 51.174 | CH$_3$ | H | 2-Cl(Ph) | N=CR$_{11}$R$_{12}$ | Ph | 4-Cl(Ph) |
| 51.175 | CH$_3$ | H | 3-Cl(Ph) | N=CR$_{11}$R$_{12}$ | Ph | 4-Cl(Ph) |
| 51.176 | CH$_3$ | H | 4-Cl(Ph) | N=CR$_{11}$R$_{12}$ | Ph | 4-Cl(Ph) |
| 51.177 | CH$_3$ | H | 4-Br(Ph) | N=CR$_{11}$R$_{12}$ | Ph | 4-Cl(Ph) |
| 51.178 | CH$_3$ | H | 4-F(Ph) | N=CR$_{11}$R$_{12}$ | Ph | 4-Cl(Ph) |
| 51.179 | CH$_3$ | H | 4-OCH$_3$(Ph) | N=CR$_{11}$R$_{12}$ | Ph | 4-Cl(Ph) |
| 51.180 | CH$_3$ | H | 4-CH$_3$(Ph) | N=CR$_{11}$R$_{12}$ | Ph | 4-Cl(Ph) |
| 51.181 | CH$_3$ | H | 4-NO$_2$(Ph) | N=CR$_{11}$R$_{12}$ | Ph | 4-Cl(Ph) |
| 51.182 | CH$_3$ | H | 2,4-Cl(Ph) | N=CR$_{11}$R$_{12}$ | Ph | 4-Cl(Ph) |
| 51.183 | CH$_3$ | H | 2,4-F(Ph) | N=CR$_{11}$R$_{12}$ | Ph | 4-Cl(Ph) |
| 51.184 | CH$_3$ | H | 4-CH$_3$(Ph) | N=CR$_{11}$R$_{12}$ | Ph | 4-Cl(Ph) |
| 51.185 | CH$_3$ | H | 4-NO$_2$(Ph) | N=CR$_{11}$R$_{12}$ | Ph | 4-Cl(Ph) |
| 51.186 | CH$_3$ | H | 2,4-Cl(Ph) | N=CR$_{11}$R$_{12}$ | Ph | 4-Cl(Ph) |
| 51.187 | CH$_3$ | H | 2,4-F(Ph) | N=CR$_{11}$R$_{12}$ | Ph | 4-Cl(Ph) |
| 51.188 | CH$_3$ | H | 4-CF$_3$(Ph) | N=CR$_{11}$R$_{12}$ | Ph | 4-Cl(Ph) |
| 51.189 | CH$_3$ | H | Ph | N=CR$_{11}$R$_{12}$ | Ph | 4-pyridyl |
| 51.190 | CH$_3$ | H | 4-Cl(Ph) | N=CR$_{11}$R$_{12}$ | Ph | 4-pyridyl |
| 51.191 | CH$_3$ | H | 4-Br(Ph) | N=CR$_{11}$R$_{12}$ | Ph | 4-pyridyl |
| 51.192 | CH$_3$ | H | 4-F(Ph) | N=CR$_{11}$R$_{12}$ | Ph | 4-pyridyl |
| 51.193 | CH$_3$ | H | 4-OCH$_3$(Ph) | N=CR$_{11}$R$_{12}$ | Ph | 4-pyridyl |
| 51.194 | CH$_3$ | H | 4-CH$_3$(Ph) | N=CR$_{11}$R$_{12}$ | Ph | 4-pyridyl |
| 51.195 | CH$_3$ | H | 4-NO$_2$(Ph) | N=CR$_{11}$R$_{12}$ | Ph | 4-pyridyl |
| 51.196 | CH$_3$ | H | 2,4-Cl(Ph) | N=CR$_{11}$R$_{12}$ | Ph | 4-pyridyl |
| 51.197 | CH$_3$ | H | 2,4-F(Ph) | N=CR$_{11}$R$_{12}$ | Ph | 4-pyridyl |
| 51.198 | CH$_3$ | H | 4-CF$_3$(Ph) | N=CR$_{11}$R$_{12}$ | Ph | 4-pyridyl |
| 51.199 | CH$_3$ | H | Ph | N=CR$_{11}$R$_{12}$ | CH$_3$ | N(CH$_3$)$_2$ |
| 51.200 | CH$_3$ | H | 4-Cl(Ph) | N=CR$_{11}$R$_{12}$ | CH$_3$ | N(CH$_3$)$_2$ |
| 51.201 | CH$_3$ | H | 4-Br(Ph) | N=CR$_{11}$R$_{12}$ | CH$_3$ | N(CH$_3$)$_2$ |
| 51.202 | CH$_3$ | H | 4-F(Ph) | N=CR$_{11}$R$_{12}$ | CH$_3$ | N(CH$_3$)$_2$ |
| 51.203 | CH$_3$ | H | 4-OCH$_3$(Ph) | N=CR$_{11}$R$_{12}$ | CH$_3$ | N(CH$_3$)$_2$ |
| 51.204 | CH$_3$ | H | 4-CH$_3$(Ph) | N=CR$_{11}$R$_{12}$ | CH$_3$ | N(CH$_3$)$_2$ |
| 51.205 | CH$_3$ | H | 4-NO$_2$(Ph) | N=CR$_{11}$R$_{12}$ | CH$_3$ | N(CH$_3$)$_2$ |
| 51.206 | CH$_3$ | H | 2,4-Cl(Ph) | N=CR$_{11}$R$_{12}$ | CH$_3$ | N(CH$_3$)$_2$ |
| 51.207 | CH$_3$ | H | 2,4-F(Ph) | N=CR$_{11}$R$_{12}$ | CH$_3$ | N(CH$_3$)$_2$ |
| 51.208 | CH$_3$ | H | 4-CF$_3$(Ph) | N=CR$_{11}$R$_{12}$ | CH$_3$ | N(CH$_3$)$_2$ |
| 51.209 | CH$_3$ | H | Ph | N=cyclopentyl | | |
| 51.210 | CH$_3$ | H | 4-Cl(Ph) | N=cyclopentyl | | |
| 51.211 | CH$_3$ | H | 4-Br(Ph) | N=cyclopentyl | | |
| 51.212 | CH$_3$ | H | 4-F(Ph) | N=cyclopentyl | | |
| 51.213 | CH$_3$ | H | 4-OCH$_3$(Ph) | N=cyclopentyl | | |
| 51.214 | CH$_3$ | H | 4-CH$_3$(Ph) | N=cyclopentyl | | |
| 51.215 | CH$_3$ | H | 4-NO$_2$(Ph) | N=cyclopentyl | | |
| 51.216 | CH$_3$ | H | 2,4-Cl(Ph) | N=cyclopentyl | | |
| 51.217 | CH$_3$ | H | 2,4-F(Ph) | N=cyclopentyl | | |
| 51.218 | CH$_3$ | H | 4-CF$_3$(Ph) | N=cyclopentyl | | |
| 51.219 | CH$_3$ | H | Ph | N=cyclohexyl | | |
| 51.220 | CH$_3$ | H | 4-Cl(Ph) | N=cyclohexyl | | |
| 51.221 | CH$_3$ | H | 4-Br(Ph) | N=cyclohexyl | | |
| 51.222 | CH$_3$ | H | 4-F(Ph) | N=cyclohexyl | | |
| 51.223 | CH$_3$ | H | 4-OCH$_3$(Ph) | N=cyclohexyl | | |
| 51.224 | CH$_3$ | H | 4-CH$_3$(Ph) | N=cyclohexyl | | |
| 51.225 | CH$_3$ | H | 4-NO$_2$(Ph) | N=cyclohexyl | | |
| 51.226 | CH$_3$ | H | 2,4-Cl(Ph) | N=cyclohexyl | | |
| 51.227 | CH$_3$ | H | 2,4-F(Ph) | N=cyclohexyl | | |
| 51.228 | CH$_3$ | H | 4-CF$_3$(Ph) | N=cyclohexyl | | |
| 51.229 | CH$_3$ | H | 1-napthyl | N=cyclopentyl | | |
| 51.230 | C$_2$H$_5$ | H | 1-napthyl | N=cyclopentyl | | |
| 51.231 | n-C$_3$H$_7$ | H | 1-napthyl | N=cyclopentyl | | |
| 51.232 | iso-C$_3$H$_7$ | H | 1-napthyl | N=cyclopentyl | | |
| 51.233 | cyclopropyl | H | 1-napthyl | N=cyclopentyl | | |
| 51.234 | CH$_3$ | H | 1-napthyl | N=cyclohexyl | | |
| 51.235 | C$_2$H$_5$ | H | 1-napthyl | N=cyclohexyl | | |
| 51.236 | n-C$_3$H$_7$ | H | 1-napthyl | N=cyclohexyl | | |
| 51.237 | iso-C$_3$H$_7$ | H | 1-napthyl | N=cyclohexyl | | |
| 51.238 | cyclopropyl | H | 1-napthyl | N=cyclohexyl | | |
| 51.239 | CH$_3$ | H | 2-napthyl | N=cyclopentyl | | |
| 51.240 | C$_2$H$_5$ | H | 2-napthyl | N=cyclopentyl | | |
| 51.241 | n-C$_3$H$_7$ | H | 2-napthyl | N=cyclopentyl | | |
| 51.242 | iso-C$_3$H$_7$ | H | 2-napthyl | N=cyclopentyl | | |
| 51.243 | cyclopropyl | H | 2-napthyl | N=cyclopentyl | | |
| 51.244 | CH$_3$ | H | 2-napthyl | N=cydlohexyl | | |
| 51.245 | C$_2$H$_5$ | H | 2-napthyl | N=cyclohexyl | | |
| 51.246 | n-C$_3$H$_7$ | H | 2-napthyl | N=cyclohexyl | | |
| 51.247 | iso-C$_3$H$_7$ | H | 2-napthyl | N=cyclohexyl | | |

TABLE 51-continued

| Compd. | $R_2$ | $R_3$ | $R_7$ | $R_{10}$ | $R_{11}$ | $R_{12}$ |
|---|---|---|---|---|---|---|
| 51.248 | cyclopropyl | H | 2-napthyl | N=cyclohexyl | | |
| 51.249 | $CH_3$ | H | 1-napthyl | $N=CR_{11}R_{12}$ | $CH_3$ | $N(CH_3)_2$ |
| 51.250 | $C_2H_5$ | H | 1-napthyl | $N=CR_{11}R_{12}$ | $CH_3$ | $N(CH_3)_2$ |
| 51.251 | n-$C_3H_7$ | H | 1-napthyl | $N=CR_{11}R_{12}$ | $CH_3$ | $N(CH_3)_2$ |
| 51.252 | iso-$C_3H_7$ | H | 1-napthyl | $N=CR_{11}R_{12}$ | $CH_3$ | $N(CH_3)_2$ |
| 51.253 | cyclopropyl | H | 1-napthyl | $N=CR_{11}R_{12}$ | $CH_3$ | $N(CH_3)_2$ |
| 51.254 | $CH_3$ | H | 2-napthyl | $N=CR_{11}R_{12}$ | $CH_3$ | $N(CH_3)_2$ |
| 51.255 | $C_2H_5$ | H | 2-napthyl | $N=CR_{11}R_{12}$ | $CH_3$ | $N(CH_3)_2$ |
| 51.256 | n-$C_3H_7$ | H | 2-napthyl | $N=CR_{11}R_{12}$ | $CH_3$ | $N(CH_3)_2$ |
| 51.257 | iso-$C_3H_7$ | H | 2-napthyl | $N=CR_{11}R_{12}$ | $CH_3$ | $N(CH_3)_2$ |
| 51.258 | cyclopropyl | H | 2-napthyl | $N=CR_{11}R_{12}$ | $CH_3$ | $N(CH_3)_2$ |
| 51.259 | $CH_3$ | $CH_3$ | Ph | $N=CR_{11}R_{12}$ | H | Ph |
| 51.260 | $C_2H_5$ | $CH_3$ | 4-Cl(Ph) | $N=CR_{11}R_{12}$ | H | Ph |
| 51.261 | n-$C_3H_7$ | $CH_3$ | 4-Br(Ph) | $N=CR_{11}R_{12}$ | H | Ph |
| 51.262 | iso-$C_3H_7$ | $CH_3$ | 4-F(Ph) | $N=CR_{11}R_{12}$ | H | Ph |
| 51.263 | $CH_3$ | $CH_3$ | Ph | $N=CR_{11}R_{12}$ | $CH_3$ | Ph |
| 51.264 | $C_2H_5$ | $CH_3$ | 4-Cl(Ph) | $N=CR_{11}R_{12}$ | $CH_3$ | Ph |
| 51.265 | n-$C_3H_7$ | $CH_3$ | 4-Br(Ph) | $N=CR_{11}R_{12}$ | $CH_3$ | Ph |
| 51.266 | iso-$C_3H_7$ | $CH_3$ | 4-F(Ph) | $N=CR_{11}R_{12}$ | $CH_3$ | Ph |
| 51.267 | $CH_3$ | $CH_3$ | Ph | $N=CR_{11}R_{12}$ | Ph | Ph |
| 51.268 | $C_2H_5$ | $CH_3$ | 4-Cl(Ph) | $N=CR_{11}R_{12}$ | Ph | Ph |
| 51.269 | n-$C_3H_7$ | $CH_3$ | 4-Br(Ph) | $N=CR_{11}R_{12}$ | Ph | Ph |
| 51.270 | iso-$C_3H_7$ | $CH_3$ | 4-F(Ph) | $N=CR_{11}R_{12}$ | Ph | Ph |
| 51.271 | $CH_3$ | $CH_3$ | Ph | $N=CR_{11}R_{12}$ | Ph | 4-Cl(Ph) |
| 51.272 | $C_2H_5$ | $CH_3$ | 4-Cl(Ph) | $N=CR_{11}R_{12}$ | Ph | 4-Cl(Ph) |

TABLE 52

Compounds 52.1 to 52.226 are compounds of Formula X which is Formula I with A=$R_4$=$R_5$=$R_6$=H, $R_1$=$CH_3$, X=CH, Y=O, and Z=$NR_{10}$, where $R_{10}$ is N=C(H)Ph and the substituents $R_2$, $R_3$, and $R_7$ are defined in Table 4.

TABLE 53

Compounds 53.1 to 53.226 are compounds of Formula XI which is Formula I with A=$R_4$=$R_5$=$R_6$=H, $R_1$=$CH_3$, X=N, Y=O, and Z=$NR_{10}$, where $R_{10}$ is N=C(H)Ph and the substituents $R_2$, $R_3$, and $R_7$ are defined in Table 4.

TABLE 54

Compounds 54.1 to 54.226 are compounds of Formula XII which is Formula I with A=$R_4$=$R_5$=$R_6$=H, $R_1$=$CH_3$, X=N, Y=NH, and Z=$NR_{10}$, where $R_{10}$ is N=C(H)Ph and the substituents $R_2$, $R_3$, and $R_7$ are defined in Table 4.

TABLE 55

Compounds 55.1 to 55.221 are compounds of Formula X which is Formula I with A=$R_4$=$R_5$=$R_6$=H, $R_1$=$CH_3$, X=CH, Y=O, and Z=$NR_{10}$, where $R_{10}$ is N=C($CH_3$)Ph and the substituents $R_2$, $R_3$, and $R_7$ are defined in Table 7.

TABLE 56

Compounds 56.1 to 56.221 are compounds of Formula XI which is Formula I with A=$R_4$=$R_5$=$R_6$=H, $R_1$=$CH_3$, X=N, Y=O, and Z=$NR_{10}$, where $R_{10}$ is N=C($CH_3$)Ph and the substituents $R_2$, $R_3$, and $R_7$ are defined in Table 7.

TABLE 57

Compounds 57.1 to 57.221 are compounds of Formula XII which is Formula I with A=$R_4$=$R_5$=$R_6$=H, $R_1$=$CH_3$, X=N, Y=NH, and Z=$NR_{10}$, where $R_{10}$ is N=C($CH_3$)Ph and the substituents $R_2$, $R_3$, and $R_7$ are defined in Table 7.

TABLE 58

Compounds 58.1 to 58.139 are compounds of Formula X which is Formula I with A=$R_4$=$R_5$=$R_6$=H, $R_1$=$CH_3$, X=CH, Y=O, and Z=$NR_{10}$, where $R_{10}$ is N=$CCPh_2$ and the substituents $R_2$, $R_3$, and $R_7$ are defined in Table 7.

TABLE 59

Compounds 59.1 to 59.139 are compounds of Formula XI which is Formula I with A=$R_4$=$R_5$=$R_6$=H, $R_1$=$CH_3$, X=N, Y=O, and Z=$NR_{10}$, where $R_{10}$ is N=$CCPh_2$ and the substituents $R_2$, $R_3$, and $R_7$ are defined in Table 7.

TABLE 60

Compounds 60.1 to 60.139 are compounds of Formula XII which is Formula I with A=$R_4$=$R_5$=$R_6$=H, $R_1$=$CH_3$, X=N, Y=NH, and Z=$NR_{10}$, where $R_{10}$ is N=C=$CPh_2$ and the substituents $R_2$, $R_3$, and $R_7$ are defined in Table 7.

As used in Tables 1 to 60 Ph is understood to be phenyl.

The preparation of certain bis-oximes is described in U.S. Pat. Nos. 5,756,426 and 5,863,951 and references cited therein. The specific methods for the preparation of cyclopropyl bis oximes of Formula I of the present invention are described in the following schemes. Scheme A describes the preparation of compounds of the Formula (I) where X is CH or N, and Y is O (compounds of formula XV and XVI). The cyclopropyl oximes (XIII) are reacted with the appropriately substituted benzyl derivatives (XIV) where L is a halogen, such as bromo, chloro or iodo, preferably a benzyl bromide. A cyclopropyl substituted oxime represented by the general formula (XIII) is treated, at room temperature, with an appropriate base to form an anion, followed by the addition of the benzyl bromides (XIV). Typical bases employed are metal hydrides such as sodium hydride, alkoxides such as sodium methoxide and hydroxide bases such as sodium or potassium hydroxide and alkali bases such as sodium or potassium carbonate. Typical solvents employed with hydride bases are N,N-dimethylformamide (DMF) and tetrahydrofuran (THF); with hydroxide bases DMF, THF, methyl ethyl ketone (MEK) and acetone and with alkali bases solvents such as DMF, acetone, and MEK.

As shown in Scheme A, the N—O bond in $C(R_2)=N-O-$ and

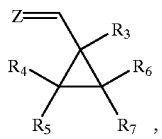

can exist as E and Z isomers. It should be recognized that the E and Z isomers can also be produced as well as mixtures. When isomers are produced they are designated isomer A (higher $R_f$ on thin layer chromatography) and isomer B (lower $R_f$ on thin layer chromatography). The determination of which isomer, A or B possesses the E or Z geometry can be made by such conventional techniques as X ray crystallography or by spectroscopic means such as nuclear magnetic resonance spectroscopy. The compounds of the of Formula I of the present invention have been produced as a single stereoisomer for the N—O bond in $C(R2)=N-O-$ and has been assigned the E configuration by nuclear magnetic resonance spectroscopy. Additionally, compounds of Formula I can exist as isomers about the Z=C. It should be recognized that the regioisomers can also be produced as well as mixtures. When isomers are produced they are designated isomer A (higher $R_f$ on thin layer chromatography) and isomer B (lower $R_f$ on thin layer chromatography). The determination of which isomer, A or B possesses the E or Z geometry can be made by such conventional techniques as X ray crystallography or by spectroscopic means such as nuclear magnetic resonance spectroscopy. When Z is $NOR_9$ the compounds designated as isomer A have the E geometry for $R_9ON=C$ and compounds designated as isomer B have the Z geometry for $R_9ON=C$. The compounds designated as A or B in the subsequent tables refer to the isomers of $NOR_9$ Scheme A

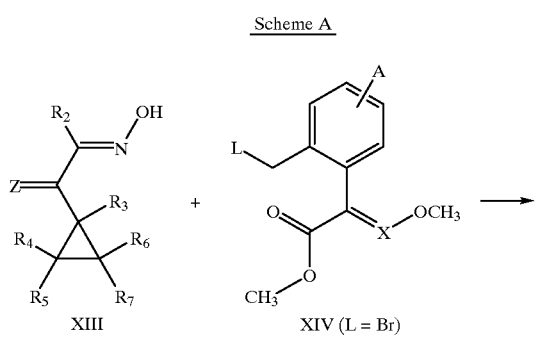

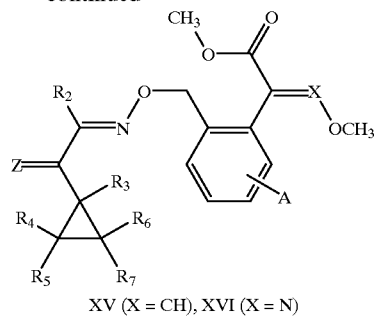

XV (X = CH), XVI (X = N)

Compounds of formula XV (X is CH) are prepared by alkylation with methyl E-α-(2-bromomethylphenyl)-β-methoxyacrylate (XIV, where A=H, X=CH and L is Br) in the presence of a base, preferably NaOH or KOH, in a solvent, preferably acetone or methyl ethyl ketone. Methyl E-α-(2-bromomethylphenyl)-β-methoxyacrylate, as a single E isomer, can be prepared in two steps from 2-methylphenylacetate as described previously in U.S. Pat. No. 4,914,128, columns 3–4. Compounds of formula XVI (X=N) are prepared by the reaction with methyl E-2-(bromomethyl)phenylglyoxylate O-methyloxime (XIV, where A=H, X=N and L is Br) in the presence of a base, preferably NaOH or KOH, in a solvent, preferably acetone or methyl ethyl ketone. Methyl 2-(bromomethyl) phenylglyoxylate O-methyloxime can be prepared as described in U.S. Pat. No. 4,999,042, columns 17–18 and 5,157,144, columns 17–18. Methyl 2-(bromomethyl) phenylglyoxylate O-methyl-oxime is prepared from methyl 2-methylphenyl-acetate by treatment with an alkyl nitrite under basic conditions to provide after methylation, methyl 2-methyl-phenyl-glyoxalate O-methyl oxime which can also be prepared from methyl 2-methyl-phenylglyoxalate by treatment with 2-hydroxylamine hydrochloride and methylation or by treatment with methoxylamine hydrochloride.

As shown in scheme B compounds of formula XVIII (X=N, Y=NH) can be prepared by the aminolysis of oximinoacetate XVI. The aminolysis of oximinoacetate to oximinoacetamides has been described in U.S. Pat. No. 5,185,342, cols. 22, 48 and 57, U.S. Pat. No. 5,221,691, cols. 26–27 and U.S. Pat. No. 5,407,902, col. 8. For example, compounds of Table 14 of formula VIII where X is N and Y is O are treated with 40% aqueous methylamine in methanol to provide compounds of Table 15 of formula IX where Y is NH. Alternatively, as is shown in scheme B intermediate cyclopropanes oximes, XIII, are reacted with N-methyl (E)-2-methoxyimino-2-[2-(bromomethyl)phenyl]-acetamide (XIV, where A=H and L=Br) in the presence of a base such as an hydroxide base preferably in a solvent such as acetone or methyl ethyl ketone to provide compounds of Table 15 of formula IX. N-methyl (E)-2-methoxy-imino-2-[2-(bromomethyl)phenyl]acetamide is described in U.S. Pat. No. 5,387,714, col. 14.

Scheme B
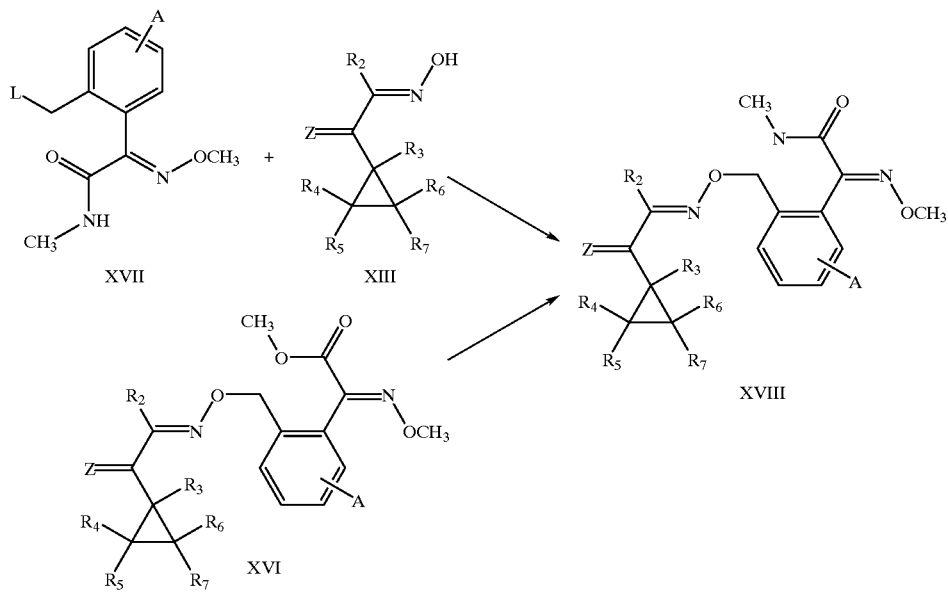
The synthesis of compounds of formula I where Z is O is described in scheme C and follow the methods of schemes A and B. In scheme C the compounds of formula IV and V (A=H) can be prepared from oxime XIX by alkylation with XIV. Compounds of formula VI (A=H) can be prepared by alkylation of XIX with bromide XVII or by aminolysis of V as described in Scheme C.
Scheme C
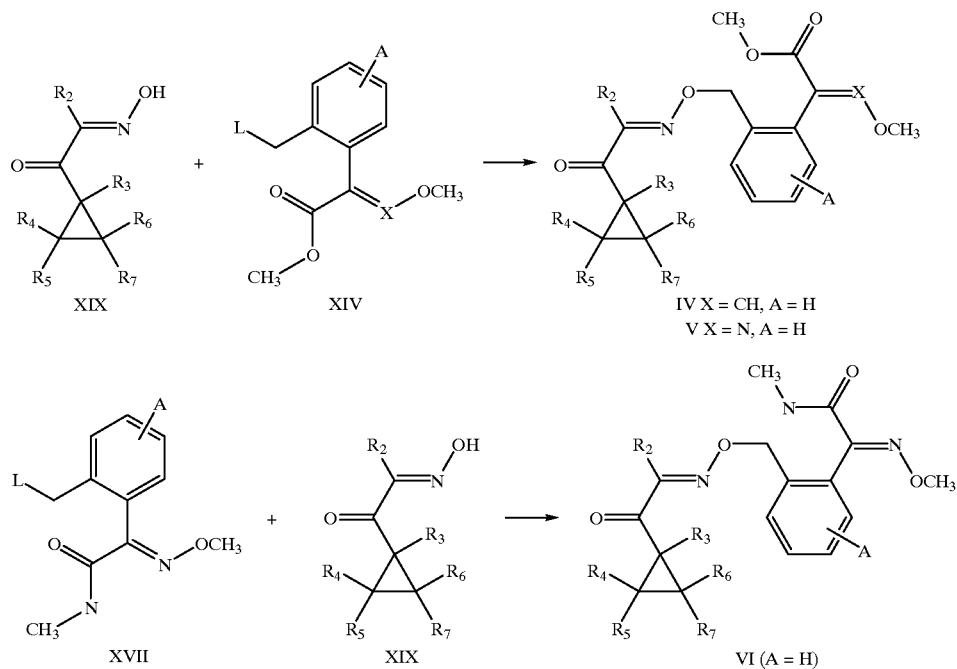

-continued

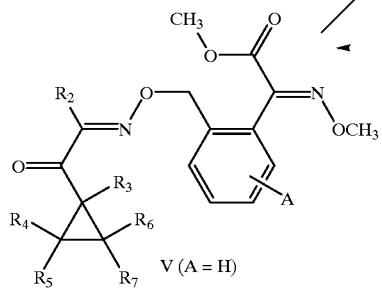

V (A = H)

Compounds of Formula I where Z is NOR$_9$ (compounds of Formula VII, VIII, IX) can be prepared, as shown in scheme D, by condensation of compounds IV, V and VI with an hydroxylamine such as R$_9$ONH$_2$. The condensation can be carried out from room temperature to reflux, preferably at room temperature, in an appropriate solvent such as methanol or ethanol in the presence of an appropriate alkali such as sodium hydroxide, potassium carbonate or pyridine. Additionally, hydroxylamine hydrochloride can be utilized (R$_9$ is hydrogen) and the compounds VII', VIII' and IX' are obtained. Alkylation with R$_9$—L where L is a leaving group such as Br or Cl provides VII, VIII and IX. The compounds of formula X, XI and XII where Z is N—R$_{10}$, such as imines and hydrazones, are prepared as shown in scheme D by condensation of the ketones IV, V and VI, with an amine or hydrazine derivative. A general description of the synthesis of oximes with and imines is described in March, *Advanced Organic Chemistry*, 4th Ed, pp. 896–897, 904–907 and references therein. The oximes, imines, hydrazones of the general formula VII to XII when obtained as a mixture of syn or anti isomers can be separated into individual isomers by conventional chromatographic techniques. The isomer with the higher Rf on thin layer chromatography is designated isomer A and the isomer with the lower Rf on thin layer chromatography is designated isomer B. The stereochemistry of isomer A and B can be determined by standard techniques such as nuclear magnetic resonance spectroscopy.

Scheme D

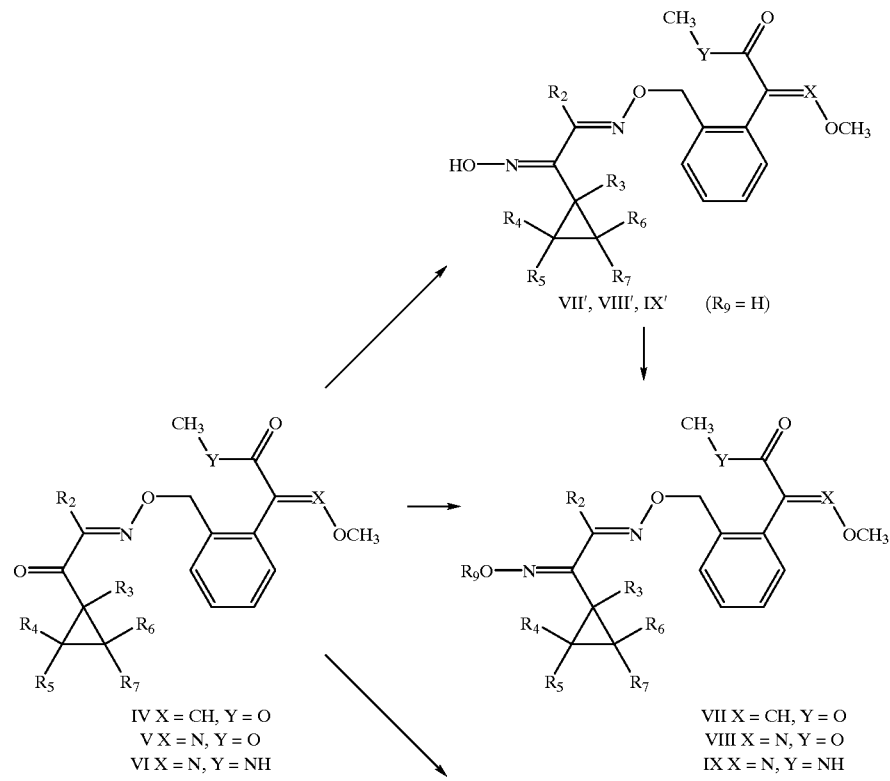

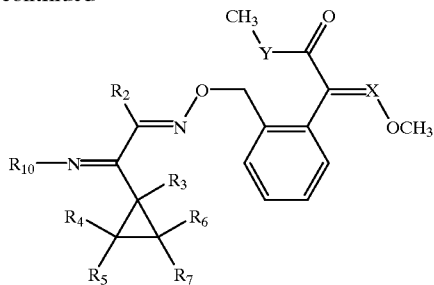

X X = CH, Y = O
XI X = N, Y = O
XII X = N, Y = NH

As is shown in scheme E the compounds of formula VII to XII can be prepared from the oxime intermediate XIX, by condensation methods described in Scheme D, leading to intermediate oximes XX and XXI. These oximes intermediates can be alkylated as described in schemes A,B and C to provide the products VII to XII.

Scheme E

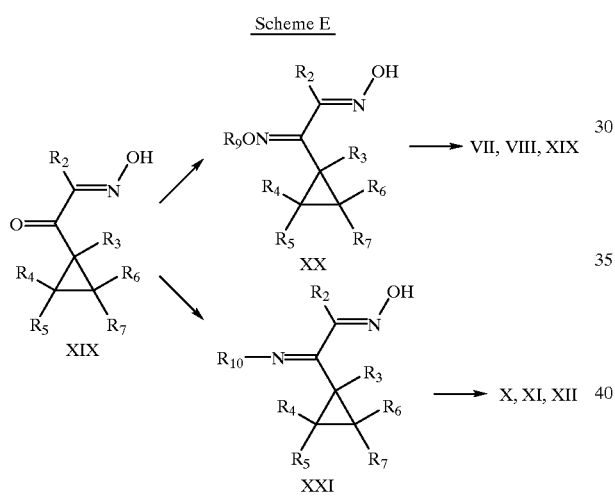

The oximes of the general formula XIX can be obtained as shown in scheme F. A general description of the synthesis of α-oximinoketones via nitrosation is described in March, *Advanced Organic Chemistry*, 4th Ed, pp. 592–593 and references therein. For the compounds of the present invention the cyclopropylketones, XXII are reacted with an alkyl nitrite such as t-butylnitrite or isoamylnitrite under basic conditions to provide the corresponding α-oximino cyclopropylketones XIX. This hydroxyimino intermediate, XIX, is typically produced as one major stereoisomer as shown in scheme F. Typically the cyclopropyl ketone in a solvent such as t-butanol and the alkyl nitrite, typically t-butylnitrite, is added to a solution t-butanol containing a base such as potassium t-butoxide and is stirred at room temperature. The α-hydroxyimino cyclopropylketones XIX are alkylated as in schemes C and E to provide compounds of the formula IV, V and VI.

Scheme F

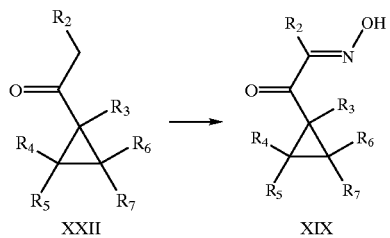

XXII → XIX

The cyclopropyl ketones XXII can be prepared by conventional techniques as is shown in scheme G. The unsaturated intermediate XXIII (scheme G) is reacted with a sulfur ylide, prepared from a dimethylsulfoxonium salt in the presence of a base, resulting in the substituted acyl cyclopropanes, XXII. The chemistry of sulfur ylides is described in Trost and Melvin, *Sulfur Ylids,* Academic Press, New York, N.Y. 1975 and in Block, *Reactions of Organosulfur Compounds,* pp. 91–123, Academic Press, New York, N.Y. 1978. Typical reaction conditions for sulfur ylide formation from a dimethylsulfoxonium salt utilizes bases such as hydroxides, metal hydrides and alkoxides in solvents such as dimethoxy-ethane, dimethylsulfoxide and water depending on the base employed. The reactions are conducted from 0 to 20° C. preferably from 10–15° C. and preferably with alkali metal hydroxides in dimethylsulfoxide. Typically dimethylsulfoxonium methylide is prepared from trimethylsulfoxonium iodide in dimethylsulfoxide in the presence of powdered sodium hydroxide at room temperature. The unsaturated ketones, XXIII, are typically added drop wise to the ylide and stirred at room temperature.

Scheme G

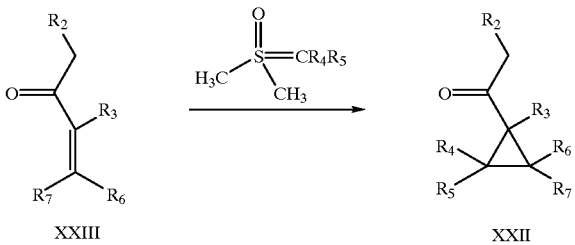

XXIII → XXII

The α,β-unsaturated ketones XXIII can be prepared by conventional condensation techniques. A extensive description of the synthesis of α,β-unsaturated ketones (enones) is described in March, *Advanced Organic Chemistry*, 4th Ed, pp. 937–955 and references therein. For example *Organic Reactions*, Volume 16 describes the general aldol condensation of ketones and aldehydes. For intermediates of formula XXIII of this invention, in general the ketones can be $R_7COR_6$ where $R_7$ and $R_6$ are defined previously. When $R_6$ is hydrogen the aldehydes are for example substituted benzaldehydes or heterocyclic aldehydes. The ketones can be $R_2CH_2COCH_2R_3$ where $R_2$ and $R_3$ are described previously. Preferably for the enones derived via a condensation reaction $R_3$ is H and is therefore a methyl ketone. Likewise $R_2$ can be hydrogen which provides enones and cyclopropanes leading to the compounds of formula I where $R_2$ is hydrogen. Typically the ketone, $R_2CH_2COCH_2R_3$, is dissolved in a hydroxylic solvent, such as methanol or ethanol, to which is added drop wise the aldehyde or ketone $R_7COR_6$ followed by the base or alternatively a solution of the aldehyde in an aqueous basic solution is added. The typical bases used can be alkali metal hydroxides, such as barium, potassium or sodium hydroxide and the drop wise addition is conducted from 0° C. to 35° C. preferably at ambient temperature. When the enone is derived from a methylketone ($R_3$ is hydrogen) the solvent can be the methylketone to which is added $R_7COR_6$ followed by the aqueous hydroxide solution.

Scheme H

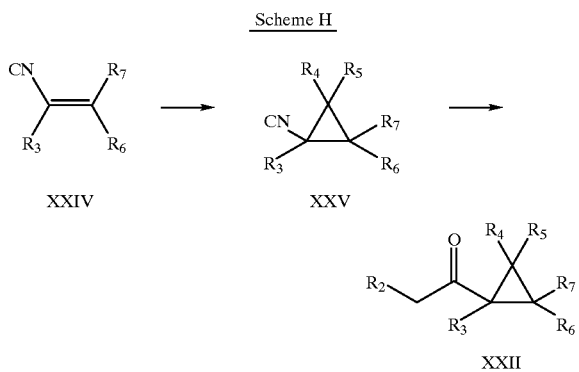

Alternatively the α,β-unsaturated cyclopropyl ketones XXII can be prepared from cyclopropyl nitriles XXV which are prepared via cyclopropanation of the acrylonitriles XXIV as is described in Scheme H. The acrylonitriles XXIV starting materials, shown in Scheme H can be prepared by conventional synthetic methods as described in March, *Advanced Organic Chemistry*, 4th Ed, pp. 937–955 and references therein.

For example the nitrile derivative $R_3CH_2CN$ is condensed with the ketone or aldehyde $R_7COR_6$, in the presence of a base to provide the acrylonitriles XXIV. Preferably $R_3$ in $R_3CH_2CN$ is an aryl or heteroaryl group as defined previously for $R_3$. Typically the nitrile is dissolved in a solvent such as ethanol and water to which is added the aldehyde or ketone followed by a base. Typical bases used can be alkali metal hydroxides, such as barium, potassium or sodium hydroxide and the mixture is stirred typically at ambient temperature. The acrylonitrile XXIV is treated as is described in Scheme H with a sulfur ylide to provide the cyclopropyl nitriles XXV. The cyclopropyl nitrile XXV is transformed to the cyclopropyl ketones by organometallic addition to the nitrile followed by hydrolysis. For example the standard Grignard reagents $R_2CH_2MgX$ or organolithium reagents, $R_2CH_2Li$ add to the nitrile functionality to provide the ketones XXII. The addition reaction to nitriles are described in March, Advanced Organic Chemistry, 4th Ed, pp.935–936 and references cited therein. When $R_2MgX$ is a methyl Grignard, such as methylmagnesium bromide the resulting methyl ketone. $R_2$=H, provides compounds of the present invention where $R_2$=H.

The compounds of this invention can be made according to the following procedures:

EXAMPLE 1

Preparation of Methyl (E)-3-methoxy-2-[2-(5-trans-(2-phenylcyclopropyl)-4-methyl-2-oxa-5-oxo-3-azahepta-3-en-1-yl)phenyl]propenoate Compound 1.11 of Table 1

Preparation of trans-1-phenyl-1-hexen-3-one

To a 250 ml round bottom flask equipped with magnetic stirrer was charged 36 g (0.5 moles) of methylethyl ketone, 100 mls of ethanol, and 10 mls of water. To this solution was then added 0.5 g of barium hydroxide monohydrate, followed by 10.6 g (0.1 moles) of benzaldehyde. The flask was stoppered and stirred overnight at ambient temperature. The reaction mixture was then poured into 200 mls of water and extracted with 3×100 mls of ethyl ether. The ether extract was washed with 100 mls of saturated aqueous sodium bisulfite solution, followed by 100 mls of water, and 100 mls of saturated aqueous sodium chloride solution. The ether extract was then dried over anhydrous magnesium sulfate, filtered and concentrated on a rotary evaporator to afford 15.1 g of a pale yellow liquid in 94% isolated yield, which was consistent with the desired product trans-1-phenyl-1-hexen-3-one upon analysis by 300 Mz $_1$H NMR.

NMR (300 MHz, $_1$H, CDCl$_3$, TMS=0 ppm) 1.17 (t, 3H), 2.7 (q, 2H), 6.7 (d, 1H), 7.4 (m, 3H), 7.6 (m, 3H)

Preparation of trans-2-phenylcyclopropylethylketone

To a 500 ml round bottom flask equipped with magnetic stirrer, nitrogen inlet, and pressure equalized addition funnel was charged 22 g (0.1 moles) of trimethylsulfoxonium iodide, 4.0 g (0.1 moles) of powdered sodium hydroxide, and 150 mls of dimethylsulfoxide. The solution was stirred at ambient temperature for 30 minutes, followed by the rapid addition of the trans-1-phenyl-1-hexen-3-one(15.1 g, 0.0945 moles) in 100 mls of dimethylsulfoxide. The reaction was then stirred for 10 minutes at ambient temperature, then poured into 200 mls of water and extracted with 3×100 mls of ethyl ether. The ether extract was washed with 2×100 mls of water, and 100 mls of saturated aqueous sodium chloride solution. The ether extract was dried over anhydrous magnesium sulfate, filtered and concentrated on a rotary evaporator to afford 12.5 g of a thick yellow liquid which was purified by high vacuum distillation. (78–85 ° C. @ 0.1 mm Hg). The pure fractions were combined to afford 8.2 g of a clear colorless liquid in an 50% isolated yield which was consistent with the desired product, trans-2-phenylcyclopropylethylketone upon analysis by 300 Mz $_1$H NMR.

NMR (300 MHz, $_1$H, CDCl$_3$, TMS=0 ppm) 1.1 (t, 3H), 1.3 (m, 1H), 1.7 (m, 1H), 2.2 (m, 1H), 2.5 (m, 1H), 2.6 (q, 2H), 7.1 (d, 2H), 7.2–7.4 (m, 3H).

Preparation of 2-hydroxyimino-1-(trans-2-phenylcyclopropyl)-1-propanone

To a dry 500 ml round bottom flask equipped with magnetic stirrer, nitrogen inlet, reflux condenser, and side arm addition funnel was charged 5.7 g. (0.0505 moles) of potassium t-butoxide and 150 ml of t-butanol. When all of the solid was dissolved, the ketone trans-2-phenyl-cyclopropylethylketone (8.0 g, 0.0459 moles)was added in on portion, followed by the drop wise addition of 5.7 g (0.0505 moles) of 90% t-butyl nitrite. The reaction was stirred for 3 hours at ambient temperature then carefully quenched with 100 mls 0.1 N aqueous hydrochloric acid solution. The mixture was extracted with 3×100 mls of ethyl ether. The ether extract was then washed with 2×100 mls of water and 100 mls of saturated aqueous sodium chloride solution, then dried over anhydrous magnesium sulfate, filtered, and concentrated on a rotary evaporator to afford 8.2 g of a thick brown liquid which was crystallized from methylene chloride and hexane. The resulting solid was collected by vacuum filtration to afford 5.1 g of a tan solid in a 55% isolated yield which was consistent with the desired product as a single hydroxyimino isomer of 2-hydroxyimino-1-(trans-2-phenyl-cyclopropyl)-1-propanone upon analysis by 300 Mz $_1$H NMR.

NMR (300 MHz, $_1$H, CDCl$_3$, TMS=0 ppm) 1.4 (m, 1H), 1.7 (m, 1H), 2.0 (s, 3H), 2.6 (m, 1H), 3.1 (m, 1H), 7.1 (d, 2H), 7.2–7.4 (m, 3H), 8.1 (bs, 1H).

Preparation of Methyl (E)-3-methoxy-2-[2-(5-trans-(2-phenylcyclopropyl)-4-methyl-2-oxa-5-oxo-3-azapentta-3-en-1-yl)phenyl]propenoate To a 250 ml round bottom flask equipped with magnetic stirrer was charged 3.0 g (0.0148 moles) of 2-hydroxyimino-1-(trans-2-phenylcyclopropyl)-1-propanone in 100 mls of anhydrous dimethylformamide, and 4.1 g (0.0295 moles) of powdered potassium carbonate. The reaction mixture was stirred at ambient temperature for a total of 0.5 hours, followed by the addition of methyl (E)-α-[2-(bromomethyl)phenyl]-β-methoxyacrylate (4.2 g, 0.0148 moles) in one portion. The reaction was stoppered and stirred overnight at ambient temperature. The reaction mixture was then was poured into 100 mls of water and extracted with 3×100 mls of ether. The ether extract was washed with 2×100 mls of water, 100 mls of saturated aqueous sodium chloride solution, dried over anhydrous magnesium sulfate, filtered, and concentrated on a rotary evaporator to afford 6.0 g of a thick amber liquid which was chromatographed on silica gel with 20% ethyl acetate, 80% hexane. The pure fractions were combined and concentrated on a rotary evaporator to afford 5.5 g of a thick pale yellow oil in 91.3% isolated yield which was consistent with the desired product as a single oximino isomer of methyl (E)-3-methoxy-2-[2-(5-trans-(2-phenylcyclopropyl)-4-methyl-2-oxa-5-oxo-3-azapenta-3-en-1-yl)phenyl]propenoate upon analysis by 300 Mz $_1$H NMR.

NMR (300 MHz, $_1$H, CDCl$_3$, TMS=0 ppm) 1.4 (m, 1H), 1.7 (m, 1H), 1.95 (s, 3H), 2.55 (m, 1H), 3.2 (m, 1H), 3.65 (s, 3H), 3.75 (s, 3H), 5.2 (s, 2H), 7.1–7.4 (m, 9H), 7.5 (s, 1H)

EXAMPLE 2

Preparation of methoxylimine isomer A Methyl (E)-3-methoxy-2-[2-(5-trans-(2-phenylcyclopropyl)-4-methyl-2,7-dioxa-3,6-diazaocta-3,5-dien-1-yl)phenyl]propenoate—Compound 13.18A of Table 13

To a 1000 ml round bottom flask equipped with magnetic stirrer was charged 56.4 g (0.138 moles) of methyl (E)-3-methoxy-2-[2-(5-trans-(2-phenylcyclopropyl)-4-methyl-2-oxa-5-oxo-3-azahepta-3-en-1-yl)phenyl]propenoate in 600 mls of anhydrous methanol, 23.2 g (0.277 moles) of methoxylamine hydrochloride, and 22 g (0.277 moles) of anhydrous pyridine. The reaction mixture was stirred at ambient temperature for a total of 24 hours, then refluxed for approximately 2 hours. The reaction mixture was then cooled and poured into 1000 mls of water and extracted with 3×200 mls of ether. The ether extract was washed with 200 mls of 0.1 N aqueous hydrochloric acid solution, 2×100 mls of water and 200 mls of saturated aqueous sodium chloride solution, dried over anhydrous magnesium sulfate, filtered, and concentrated on a rotary evaporator to afford 62 g of a thick amber liquid which was chromatographed on silica gel with 20% ethyl acetate, 80% hexane. The pure fractions were combined and concentrated on a rotary evaporator to afford 48 g of a thick pale yellow oil in a 79.8% isolated yield which was consistent with the desired product, methoxylimine isomer A, methyl (E)-3-methoxy-2-[2-(5-trans-(2-phenylcyclopropyl)-4-methyl-2,7-dioxa-3,6-diazaocta-3,5-dien-1-yl)phenyl]propenoate upon analysis by 300 Mz $_1$H NMR.

NMR (300 MHz, $_1$H, CDCl$_3$, TMS=0 ppm) 1.2 (m, 1H), 1.8 (m, 1H), 2.0 (s, 3H), 2.45 (m, 1H), 2.7 (m, 1H), 3.66 (s, 3H), 3.75 (s, 3H), 3.9 (s, 3H), 5.1 (s, 2H), 7.1–7.4 (m, 9H), 7.56 (s, 1H).

EXAMPLE 3

Preparation of (E)-Methyl 2-[2-(5-trans-(2-phenylcyclopropyl)-4-methyl-2-oxa-5-oxo-3-azapenta-3-en-1-yl)phenyl]-2-methoxyiminoacetate Compound 2.11 of Table 2

To a 250 ml round bottom flask equipped with magnetic stirrer was charged 2.0 g (0.00985 moles) of 2-hydroxyimino-1-(trans-2-phenylcyclopropyl)-1-propanone in 100 mls of anhydrous dimethylformamide, and 2.8 g (0.0197 moles) of powdered potassium carbonate. The reaction mixture was stirred at ambient temperature for a total of 0.5 hours, followed by the addition of methyl 2-(bromomethyl)phenylglyoxylate O-methyloxime (2.8 g, 0.00985 moles) in one portion. The reaction was stoppered and stirred overnight at ambient temperature. The reaction mixture was then was poured into 100 mls of water and extracted with 3×100 mls of ether. The ether extract was washed with 2×100 mls of water, 100 mls of saturated aqueous sodium chloride solution, dried over anhydrous magnesium sulfate, filtered, and concentrated on a rotary evaporator to afford 4.1 g of a thick amber liquid in a 100% isolated yield which was consistent with the desired product as a single oximino isomer of (E)-methyl 2-[2-(5-trans-(2-phenylcyclopropyl)-4-methyl-2-oxa-5-oxo-3-azapenta-3-en-1-yl)phenyl]-2-methoxy-iminoacetate upon analysis by 300 Mz $_1$H NMR.

NMR (300 MHz, $_1$H, CDCl$_3$, TMS=0 ppm) 1.4 (m, 1H), 1.7 (m, 1H), 1.95 (s, 3H), 2.55 (m, 1H), 3.1 (m, 1H), 3.8 (s, 3H), 4.0 (s, 3H), 5.15 (s, 2H), 7.1–7.4 (m, 9H)

EXAMPLE 4

Preparation of methoxylimine isomer A (E)-methyl-2-[2-(5-trans-(2-phenylcyclopropyl)-4-methyl-2,7-dioxa-3,6-diazaocta-3,5-dien-1-yl)phenyl] 2-methoxyiminoacetate—Compound 14.18A of Table 14

To a 1000 ml round bottom flask equipped with magnetic stirrer was charged 87 g (0.213 moles) of the (E)-methyl 2-[2-(5-trans-(2-phenylcyclopropyl)-4-methyl-2-oxa-5-oxo-3-azapenta-3-en-1-yl)phenyl]-2-methoxyiminoacetate 600 mls of anhydrous methanol, 35.6 g (0.426 moles) of methoxylamine hydrochloride, and 33.7 g (0.426 moles) of anhydrous pyridine. The reaction mixture was stirred at ambient temperature for a total of 24 hours, then refluxed for approximately 2 hours. The reaction mixture was then cooled and poured into 1000 mls of water and extracted with 3×200 mls of ether. The ether extract was washed with 200 mls of 0.1 N aqueous hydrochloric acid solution, 2×100 mls of water and 200 mls of saturated aqueous sodium chloride solution, dried over anhydrous magnesium sulfate, filtered, and concentrated on a rotary evaporator to afford a thick amber liquid which crystallized upon standing Slurried the solid in hexane and collected by vacuum filtration. Isolated 66.1 g of a tan solid in 71% isolated yield which was consistent with the desired product, methoxylimine isomer A, (E)-methyl-2-[2-(5-trans-(2-phenylcyclopropyl)-4-methyl-2,7-dioxa-3,6-diazaocta-3,5-dien-1-yl)phenyl] 2-methoxyiminoacetate upon analysis by 300 Mz $_1$H NMR NMR (300 MHz, $_1$H, CDCl$_3$, TMS=0 ppm) 1.1 (m, 1H), 1.8 (m, 1H), 2.0 (s, 3H), 2.45 (m, 1H), 2.7 (m, 1H), 3.8 (s, 3H), 3.9 (s, 3H), 4.0 (s, 3H), 5.0 (s, 2H), 7.0 (d, 2H), 7.1–7.4 (m, 7H)

EXAMPLE 5

Preparation of methoxylimine isomer A, N-Methyl (E)2-[2-(5-trans-(2-phenylcyclopropyl)-4-methyl-2,7-dioxa-3,6-diazaocta-3,5-dien-1-yl)phenyl] 2-methoxyiminoacetamide—Compound 1518A of Table 15

To a 1000 ml round bottom flask equipped with magnetic stirrer was charged 66.1 g (0.151 moles) of methoxylimine isomer A of (E)-methyl-2-[2-(5-trans-(2-phenylcyclopropyl)-4-methyl-2,7-dioxa-3,6-diazaocta-3,5-dien-1-yl)phenyl] 2-methoxyiminoacetate, 500 mls of anhydrous methanol, and 23.5 g (0.3 moles) of 40% aqueous methylamine solution. The reaction mixture was stirred at ambient temperature for a total of 24 hours, then poured into 1000 mls of water and extracted with 3×200 mls of ether. The ether extract was washed with 200 mls of 0.1 N aqueous hydrochloric acid solution, 2×100 mls of water and 200 mls of saturated aqueous sodium chloride solution, dried over anhydrous magnesium sulfate, filtered, and concentrated on a rotary evaporator to afford a thick amber liquid which crystallized upon standing. Isolated 62 g of a tan solid in a 94% isolated yield which was consistent with the desired product, methoxylimine isomer A: N-methyl (E)2-[2-(5-trans-(2-phenylcyclopropyl)-4-methyl-2,7-dioxa-3,6-diazaocta-3,5-dien-1-yl)phenyl] 2-methoxyiminoacetatamide upon analysis by 300 Mz $_1$H NMR.

NMR (300 MHz, $_1$H, CDCl$_3$, TMS=0 ppm) 1.2 (m, 1H), 1.8 (m, 1H), 2.0 (s, 3H), 2.45 (m, 1H), 2.8 (m, 1H), 2.9 (d, 3H), 3.9 (s, 3H), 3.92 (s, 3H), 5.0 (s, 2H), 6.8 (bs, 1H), 7.0 (d, 2H), 7.1–7.4 (m, 7H)

EXAMPLE 6

Preparation of Methyl (E)-3-methoxy-2-[2-(5-trans-(2-phenylcyclopropyl)-4-methyl-2-oxa-5-oxo-3-azapenta-3-en-1-yl)phenyl]propenoate Compound 1.67 of Table 1

Preparation of trans-5-methyl-1-phenyl-1-hexen-3-one

To a 250 ml round bottom flask equipped with magnetic stirrer was charged 11.6 g (0.116 moles) of 4-methyl-2-pentanone, 100 mls of ethanol, and 10 mls of water. To this solution was then added 0.5 g of barium hydroxide monohydrate, followed by 12.3 g (0.116 moles) of benzaldehyde. The flask was stoppered and stirred overnight at ambient temperature. The reaction mixture was then poured into 200 mls of water and extracted with 3×100 mls of ethyl ether. The ether extract was washed with 100 mls of saturated aqueous sodium bisulfite solution, followed by 100 mls of water, and 100 mls of saturated aqueous sodium chloride solution. The ether extract was then dried over anhydrous magnesium sulfate, filtered and concentrated on a rotary evaporator to afford 19.8 g of a pale yellow liquid in a 91% isolated yield which was consistent with the desired product trans-5-methyl-1-phenyl-1-hexen-3-one upon analysis by 300 Mz $_1$H NMR.

NMR (300 MHz, $_1$H, CDCl$_3$, TMS=0 ppm) 0.99 (d, 6H), 2.2 (m, 1H), 2.5 (d, 2H), 7.7 (d, 1H), 7.4 (m, 3H), 7.6 (m, 3H)

Preparation of trans-2-phenylcyclopropyl iso-butylketone

To a 500 ml round bottom flask equipped with magnetic stirrer, nitrogen inlet, and pressure equalized addition funnel was charged 23 g (0.104 moles) of trimethylsulfoxonium iodide, 4.2 g (0.104 moles) of powdered sodium hydroxide, and 150 mls of dimethylsulfoxide. The solution was stirred at ambient temperature for 30 minutes, followed by the rapid addition of trans-5-methyl-1-phenyl-1-hexen-3-one, (19.6 g, 0.104 moles) in 100 mls of dimethylsulfoxide. The reaction was then stirred for 60 minutes at ambient temperature, then poured into 200 mls of water and extracted with 3×100 mls of ethyl ether. The ether extract was washed with 2×100 mls of water, and 100 mls of saturated aqueous sodium chloride solution. The ether extract was dried over anhydrous magnesium sulfate, filtered and concentrated on a rotary evaporator to afford 18.4 g of a thick yellow liquid in a 87.6% isolated which was consistent with the desired product, trans-2-phenylcyclopropyl iso-butylketone upon analysis by 300 Mz $_1$H NMR. yield.

NMR (300 MHz, $_1$H, CDCl$_3$, TMS=0 ppm) 0.95 (d, 6H), 1.4 (m, 1H), 1.7 (m, 1H), 2.2 (m, 2H), 2.4 (d, 2H), 2.45 (m, 1H), 7.1 (d, 2H), 7.2–7.4 (m, 3

Preparation of 2-hydroxyimino-3-methyl-1-(trans-2-phenylcyclopropyl)-1-butanone

To a dry 500 ml round bottom flask equipped with magnetic stirrer, nitrogen inlet, reflux condenser, and side arm addition funnel was charged 11.2 g. (0.1 moles) of potassium t-butoxide and 150 ml of t-butanol. When all of the solid was dissolved, trans-2-phenylcyclopropyl iso-butylketone(18.4 g, 0.0911 moles)was added in on portion, followed by the drop wise addition of 32 g (0.282 moles) of 90% t-butyl nitrite. The reaction was stirred for 3 hours at ambient temperature then carefully quenched with 100 mls 0.1 N aqueous hydrochloric acid solution. The mixture was extracted with 3×100 mls of ethyl ether. The ether extract was then washed with 2×100 mls of water and 100 mls of saturated aqueous sodium chloride solution, then dried over anhydrous magnesium sulfate, filtered, and concentrated on a rotary evaporator to afford 9.1 g of a thick brown liquid which crystallized upon standing. The resulting solid was slurried in hexane and collected by vacuum filtration to afford 8.4 g of a tan solid in a 40% isolated yield which was consistent with the desired product as a single hydroxyimino isomer, 2-hydroxyimino-3-methyl-1-(trans-2-phenylcyclopropyl)-1-butanone upon analysis by 300 Mz $_1$H NMR. 40% isolated yield.

NMR (300 MHz, $_1$H NMR, CDCl$_3$, TMS=0 ppm) 1.2 (d, 6H), 1.3 (m, 1H), 1.7 (m, 1H), 2.5 (m, 1H), 3.1 (m, 1H), 3.4 (q, 1H), 7.1 (d, 2H), 7.2–7.4 (m, 3H), 8.1 (bs, 1H).

Preparation of Methyl (E)-3-methoxy-2-[2-(5-trans-(2-phenylcyclopropyl)-4-methyl-2-oxa-5-oxo-3-azahepta-3-en-1-yl)phenyl]propenoate To a 50 ml round bottom flask equipped with magnetic stirrer was charged 1.0 g (0.00432 moles) of 2-hydroxyimino-3-methyl-1-(trans-2-phenylcyclopropyl)-1-butanone, 10 mls of anhydrous dimethylformamide, and 1.2 g (0.00865 moles) of powdered potassium carbonate. The reaction mixture was stirred at ambient temperature for a total of 0.5 hours, followed by the addition of methyl (E)-α-[2-(bromomethyl)phenyl]-β-methoxyacrylate(1.3 g, 0.00432 moles) in one portion. The reaction was stoppered and stirred overnight at ambient temperature. The reaction mixture was then was poured into 100 mls of water and extracted with 3×100 mls of ether. The ether extract was washed with 2×100 mls of water, 100 mls of saturated aqueous sodium chloride solution, dried over anhydrous magnesium sulfate, filtered, and concentrated on a rotary evaporator to afford 1.8 g of a thick amber liquid which was chromatographed on silica gel with 20% ethyl acetate, 80% hexane. The pure fractions were combined and concentrated on a rotary evaporator to afford 1.2 g of a thick pale yellow oil in a 64% isolated yield which was consistent with the desired product as a single oximino isomer, methyl (E)-3-methoxy-2-[2-(5-trans-(2-phenylcyclopropyl)-4-methyl-2-oxa-5-oxo-3-azapenta-3-en-1-yl)phenyl]propenoate upon analysis by 300 Mz $_1$H NMR.

NMR (300 MHz, $_1$H NMR, CDCl$_3$, TMS=0 ppm) 1.2 (d, 6H), 1.3 (m, 1H), 1.6 (m, 1H), 2.55 (m, 1H), 3.1 (m, 1H), 3.4 (q, 1H), 3.7 (s, 3H), 3.78 (s, 3H), 5.15 (s, 2H), 7.1–7.5 (m, 9H), 7.6 (s, 1H)

EXAMPLE 7

Preparation of methoxylimine isomers A and B: Methyl (E)-3-methoxy-2-[2-(5-trans-(2-phenylcyclopropyl)-4-isopropyl-2,7-dioxa-3,6-diazaocta-3,5-dien-1-yl)phenyl]propenoate Compound 13.67A and 13.67B of Table 13

To a 100 ml round bottom flask equipped with magnetic stirrer was charged 1.0 g (0.00229 moles) of single oximino isomer of methyl (E)-3-methoxy-2-[2-(5-trans-(2-phenylcyclopropyl)-4-methyl-2-oxa-5-oxo-3-azapenta-3-en-1-yl)phenyl]propenoate 50 mls of anhydrous methanol, 1.0 g (0.0115 moles) of methoxylamine hydrochloride, and 1.0 g (0.0115 moles) of anhydrous pyridine. The reaction mixture was stirred at ambient temperature for a total of 24 hours, then refluxed for approximately 10 minutes. The reaction mixture was then cooled and poured into 100 mls of water and extracted with 3×100 mls of ether. The ether extract was washed with 100 mls of 0.1 N aqueous hydrochloric acid solution, 2×100 mls of water and 100 mls of saturated aqueous sodium chloride solution, dried over anhydrous magnesium sulfate, filtered, and concentrated on a rotary evaporator to afford 1.1 g of a thick amber liquid which was chromatographed on silica gel with 20% ethyl acetate, 80% hexane. The pure fractions were combined and concentrated on a rotary evaporator to afford 350 mg of a thick pale yellow oil consistent with the desired product as methoxylimine isomer A, methyl (E)-3-methoxy-2-[2-(5-trans-(2-phenylcyclopropyl)-4-isopropyl-2,7-dioxa-3,6-diazaocta-3,5-dien-1-yl)phenyl]propenoate upon analysis by 300 Mz $_1$H NMR, and 530 mg of a thick pale yellow oil consistent with the desired product as methoxylimine isomer B, methyl (E)-3-methoxy-2-[2-(5-trans-(2-phenylcyclopropyl)-4-isopropyl-2,7-dioxa-3,6-diazaocta-3-en-1-yl)phenyl]propenoate upon analysis by 300 Mz $_1$H NMR in a combined 85% isolated yield.

Methoxylimine Isomer A: NMR (300 MHz, $_1$H NMR, CDCl$_3$, TMS=0 ppm) 1.2 (m, 7H), 1.3 (m, 1H), 2.2 (m, 1H), 2.4 (m, 1H), 3.4 (q, 1H), 3.7 (s, 3H), 3.78 (s, 3H), 3.9 (s, 3H), 5.05 (s, 2H), 7.1–7.5 (m, 9H), 7.6 (s, 1H)

Methoxylimine Isomer B: NMR (300 MHz, $_1$H NMR, CDCl$_3$, TMS=0 ppm) 1.2 (m, 7H), 1.3 (m, 1H), 1.8 (m, 1H), 2.2 (m, 1H), 3.1 (q, 1H), 3.6 (s, 3H), 3.70 (s, 3H), 3.75 (s, 3H), 5.0 (s, 2H), 7.1–7.4 (m, 9H), 7.5 (s, 1H).

EXAMPLE 8

Preparation of hydroxylimine isomer A: Methyl (E)-3-methoxy-2-[2-(5-trans-(2-phenylcyclopropyl)-4-methyl-2,7-dioxa-3,6-diazahepta-3,5-dien-1-yl) phenyl]propenoate Compound 13.11A of Table 13

To a 100 ml round bottom flask equipped with magnetic stirrer was charged 1.0 g (0.00245 moles) a single oximino isomer of methyl (E)-3-methoxy-2-[2-(5-trans-(2-phenylcyclopropyl)-4-methyl-2-oxa-5-oxo-3-azapentta-3-en-1-yl)phenyl]propenoate, 50 mls of anhydrous methanol, 1.7 g (0.0245 moles) of hydroxylamine hydrochloride, and 1.9 g (0.0245 moles) of anhydrous pyridine. The reaction mixture was stirred at ambient temperature for a total of 24 hours, then refluxed for approximately 2 hours. The reaction mixture was then cooled and poured into 100 mls of water and extracted with 3×100 mls of ether. The ether extract was washed with 100 mls of 0.1 N aqueous hydrochloric acid solution, 2×100 mls of water and 100 mls of saturated aqueous sodium chloride solution, dried over anhydrous magnesium sulfate, filtered, and concentrated on a rotary evaporator to afford 1.1 g of a thick amber liquid which was chromatographed on silica gel with 15% ethyl acetate, 85% hexane. The pure fractions were combined and concentrated on a rotary evaporator to afford 650 mg of a thick clear colorless oil in a 63% isolated yield which was consistent with the desired product as a single hydroxyimino isomer A, methyl (E)-3-methoxy-2-[2-(5-trans-(2-phenylcyclopropyl)-4-methyl-2,7-dioxa-3,6-diazahepta-3,5-dien-1-yl)phenyl]propenoate upon analysis by 300 Mz $_1$H NMR.

NMR (300 MHz, $_1$H NMR, CDCl$_3$, TMS=0 ppm) 1.8 (m, 1H), 2.0 (s, 3H), 2.5 (m, 1H), 2.7 (m, 1H), 3.65 (s, 3H), 3.75 (s, 3H), 5.05 (s, 2H), 7.1 (d, 2H), 7.2–7.5 (m, 7H), 7.56 (s, 1H), 8.3 (bs, 1H)

EXAMPLE 9

Preparation of methoxylimine isomer A of Methyl (E)-3-methoxy-2-[2-(5-trans-(2-phenylcyclopropyl)-4-methyl-2,7-dioxa-3,6-diazadeca-3,5-dien-1-yl) phenyl]-2 propenoate Compound 13.40A of Table 13

To a 50 ml round bottom flask equipped with magnetic stirrer was charged 0.2 g, (0.000474 moles) of hydroxyimino isomer A, methyl (E)-3-methoxy-2-[2(5-trans-(2-phenylcyclopropyl)-4-methyl-2,7-dioxa-3,6-diazahepta-3,5-dien-1-yl)phenyl]propenoate 10 mls of anhydrous dimethylformamide, and 0.13 g (0.00095 moles) of powdered potassium carbonate. The reaction mixture was stirred at ambient temperature for a total of 0.5 hours, followed by the addition of the 1-bromopropane (0.065 g, 0.0005 moles) in one portion. The reaction was stopped and stirred overnight at ambient temperature The reaction mixture was then was poured into 100 mls of water and extracted with 3×100 mls of ether. The ether extract was washed with 2×100 mls of water, 100 mls of saturated aqueous sodium chloride solution, dried over anhydrous magnesium sulfate, filtered, and concentrated on a rotary evaporator to afford 0.2 g of a thick amber liquid which was chromatographed on silica gel with 20% ethyl acetate, 80% hexane. The pure fractions were combined and concentrated on a rotary evaporator to afford 120 mg of a thick clear colorless oil in a 55% isolated yield consistent with the desired product.,: methyl (E)-3-methoxy-2-[2-(5-trans-(2-phenylcyclopropyl)-4-methyl-2,7-dioxa-3,6-diazadeca-3,5-dien-1-yl)phenyl]propenoate, n-propoxyimine isomer A upon analysis by 300 Mz $_1$H NMR.

NMR (300 MHz, $_1$H NMR, CDCl$_3$, TMS=0 ppm) 0.85 (t, 3H), 1.1 (m, 1H), 1.6 (q, 2H), 1.8 (m, 1H), 2.0 (s, 3H), 2.4 (m, 1H), 2.6 (m, 1H), 3.6 (s, 3H), 3.7 (s, 3H), 4.0 (t, 2H), 5.0 (s, 2H), 7.0 (d, 2H), 7.1–7.4 (m, 7H), 7.6 (s, 1H)

EXAMPLE 10

Preparation of Methyl (E)-3-methoxy-2-[2-(5-trans-(2-phenylcyclopropyl)-4-methyl-8,8-dimethyl-2,7-dioxa-3,6-diazanona-3,5-dien-1-yl)phenyl] propenoate Compound 13.43 of Table 13

To a 100 ml round bottom flask equipped with magnetic stirrer was charged 0.5 g (0.00122 moles) of a single oximino isomer of methyl (E)-3-methoxy-2-[2-(5-trans-(2-phenylcyclopropyl)-4-methyl-2-oxa-5-oxo-3-azapentta-3-en-1-yl)phenyl]propenoate, 50 mls of anhydrous methanol, 1.5 g (0.0122 moles) of O-t-butyl hydroxylamine HCl, and 0.98 g (0.0122 moles) of anhydrous pyridine. The reaction mixture was stirred at ambient temperature for a total of 24 hours, then refluxed for approximately 2 hours. The reaction mixture was then cooled and poured into 100 mls of water and extracted with 3×100 mls of ether. The ether extract was washed with 100 mls of 0.1 N aqueous hydrochloric acid solution, 2×100 mls of water and 100 mls of saturated aqueous sodium chloride solution, dried over anhydrous magnesium sulfate, filtered, and concentrated on a rotary evaporator to afford 0.6 g of a thick yellow liquid in a 100% isolated yield which was consistent with the desired product a methyl (E)-3-methoxy-2-[2-(5-trans-(2-phenylcyclopropyl)-4-methyl-8,8-dimethyl-2,7-dioxa-3,6-diazanona-3,5-dien-1-yl)phenyl]propenoate as mixture of t-butoxyimine isomers: upon analysis by 300 Mz $_1$H NMR,.

NMR (300 MHz, $_1$H NMR,TMS=0 ppm) 1.2 (m, 10H), 1.8 (m, 1H), 2.0 (s, 3H), 2.4 (m, 1H), 2.6 (m, 1H), 3.6 (s, 3H), 3.7 (s, 3H), 4.0 (t, 2H), 5.0 (s, 2H), 7.0 (d, 2H), 7.1–7.4 (m, 7H), 7.6 (s, 1H).

Proton NMR data (300 MHz) are provided in Table 61 for typical examples of Tables 1 to 60 and are illustrative of the present invention*

TABLE 61

| Compound # | NMR DATA |
|---|---|
| 1.11 | 1.4(m, 1H), 1.8(m, 1H), 1.95(s, 3H), 2.5(m, 1H), 3.15(m, 1H), 3.65(s, 3H), 3.75(s, 3H), 5.2(s, 2H), 7.1–7.4(m, 9H), 7.55(s, 1H) |
| 1.22 | 1.5(m, 1H), 1.8(m, 1H), 1.95(s, 3H), 2.6(m, 1H), 3.1(m, 1H), 3.65(s, 3H), 3.75(s, 3H), 3.8(s, 3H), 5.2(s, 2H), 6.8(m, 3H), 7.1–7.4(m, 5H), 7.55(s, 1H) |
| 1.24 | 1.4(m, 1H), 1.75(m, 1H), 2.0(s, 3H), 2.3(s, 3H), 2.5(m, 1H), 3.1(m, 1H), 3.65(s, 3H), 3.75(s, 3H), 5.2(s, 2H), 7.1–7.4(m, 8H), 7.55(s, 1H) |
| 1.25 | 1.5(m, 1H), 1.8(m, 1H), 1.95(s, 3H), 2.35(s, 3H), 2.5(m, 1H), 3.1(m, 1H), 3.65(s, 3H), 3.75(s, 3H), 5.2(s, 2H), 7.0-7.5(m, 8H), 7.55(s, 1H) |
| 1.56 | 0.85(t, 3H), 1.4(m, 3H), 1.7(m, 1H), 2.5(m, 3H), 3.1(m, 1H), 3.7(s, 3H), 3.75(s, 3H), 5.2(s, 2H), 7.1–7.4(m, 9H); 7.6(s, 1H) |
| 1.67 | 1.2(d, 6H), 1.3(m, 1H), 1.7(m, 1H), 2.5(m, 1H), 3.1(m, 1H), 3.4(m, 1H), 3.7(s, 3H), 3.75(s, 3H), 5.15(s, 2H), 7.0-7.5(m, 9H), 7.6(s, 1H) |
| 1.78 | 0.9(t, 3H), 1.4(m, 5H), 1.8(m, 1H), 2.5(m, 3H), 3.2(m, 1H), 3.65(s, 3H), 3.75(s, 3H), 5.2(s, 2H), 7.1–7.4(m, 9H), 7.55(s, 1H) |
| 2.1 | 1.4(m, 1H), 1.8(m, 1H), 2.6(m, 1H), 3.05(m, 1H), 3.8(s, 3H), 4.0(s, 3H), 5.2(s, 2H), 7.1–7.45(m, 9H), 7.5(s, 1H) |
| 2.11 | 1.4(m, 1H), 1.8(m, 1H), 1.95(s, 3H), 2.5(m, 1H), 3.1(m, 1H), 3.8(s, 3H), 3.95(s, 3H), 5.15(s, 2H), 7.1–7.5(m, 9H) |
| 2.14 | 1.4(m, 1H), 1.8(m, 1H), 1.95(s, 3H), 2.5(m, 1H), 3.1(m, 1H), 3.9(s, 3H), 4.05(s, 3H), 5.15(s, 2H), 7.0(d, 2H), 7.1–7.5(m, 6H) |
| 2.22 | 1.45(m, 1H), 1.7(m, 1H), 1.9(s, 3H), 2.6(m, 1H), 3.1(m, 1H), 3.79(s, 3H), 3.8(s, 3H), 4.0(s, 3H), 5.2(s, 2H), 6.8(m, 3H), 7.1–7.4(m, 5H) |
| 2.24 | 1.4(m, 1H), 1.75(m, 1H), 2.0(s, 3H), 2.25(s, 3H), 2.5(m, 1H), 3.05(m, 1H), 3.8(s, 3H), 4.0(s, 3H), 5.2(s, 2H), 7.1–7.4(m, 8H) |
| 2.25 | 1.5(m, 1H), 1.8(m, 1H), 1.95(s, 3H), 2.3(s, 3H), 2.6(m, 1H), 3.1(m, 1H), 3.8(s, 3H), 4.0(s, 3H), 5.2(s,2H), 7.1–7.4(m, 8H) |
| 2.45 | 0.95(t, 3H), 1.3(m, 1H), 1.8(m, 1H), 2.5(m, 3H), 3.2(m, 1H), 3.7(s, 3H), 3.75(s, 3H), 5.2(s, 2H), 7.0-7.5(m, 9H), 7.55(s, 1H) |
| 2.45 | 1.0(t, 3H), 1.3(m, 1H), 1.8(m, 1H), 2.5(m, 3H), 3.1(m, 1H), 3.8(s, 3H), 4.0(s, 3H), 5.15(s, 2H), 7.0-7.5(m, 9H) |
| 2.56 | 0.9(t, 3H), 1.4(m, 3H), 1.7(m, 1H), 2.5(m, 3H), 3.1(m, 1H), 3.8(s, 3H), 4.0(s, 3H), 5.1(s, 2H), 7.1–7.4(m, 9H) |
| 2.67 | 1.15(d, 6H), 1.25(m, 1H), 1.7(m, 1H), 2.5(m, 1H), 3.1(m, 1H), 3.4(m, 1H), 3.8(s, 3H), 4.0(s, 3H), 5.1(s, 2H), 7.0-7.5(m, 9H) |
| 2.78 | 0.85(t, 3H), 1.4(m, 5H), 1.75(m, 1H), 2.5(m, 3H), 3.2(m, 1H), 3.8(s, 3H), 4.0(s, 3H), 5.15(s, 2H), 7.1–7.5(m, 9H) |
| 3.22 | 1.4(m, 1H), 1.7(m, 1H), 1.85(s, 3H), 2.5(m, 1H), 2.8(d, 3H), 3.1(m, 1H), 3.75(s, |

TABLE 61-continued

| Compound # | NMR DATA |
|---|---|
| | 3H), 3.85(s, 3H), 5.1(s, 2H), 6.8(m, 3H), 7.1–7.4(m, 6H) |
| 10.5 | 1.0(d, 6H), 1.3(m, 1H), 1.6(m, 2H), 3.55(m, 1H), 3.65(s, 3H), 3.75(s, 3H), 5.0(s, 2H), 7.1–7.4(m, 9H), 7.55(s, 1H) |
| 13.7 | 1.15-1.3 (m, 2H), 2.15-2.25 (m, 1H), 2.26-2.4 (m, 1H), 3.65 (s, 3H), 3.85 (s, 3H), 5.07 (s, 2H), 7.0-7.6 (m, 10H), 7.56 (s, 1H), 8.33 (s, 1H) |
| 13.11A | 1.8 (m, 1H), 2.0 (s, 3H), 2.5 (m, 1H), 2.7 (m, 1H), 3.65 (s, 3H), 3.75 (s, 3H), 5.05 (s, 2H), 7.1 (d, 2H), 7.2-7.5 (m, 7H), 7.56 (s, 1H), 8.3 bs, 1H) |
| 13.18A | 1.2 (m, 1H), 1.8 (m, 1H), 2.0 (s, 3H), 2.45 (m, 1H), 2.7 (m, 1H), 3.66 (s, 3H), 3.75 (s, 3H), 3.9 (s, 3H), 5.1 (s, 2H), 7.1–7.4 (m, 9H), 7.56 (s, 1H) |
| 13.18B | 1.2 (m, 1H), 1.4 (m, 1H), 1.8(m, 1H), 1.95 (s, 3H), 2.2 (m, 1H), 3.6 (s, 3H), 3.7 (s, 3H), 3.85 (s, 3H), 5.1 (s, 2H), 6.9 (d, 2H), 7.1–7.4 (m, 7H), 7.56 (s, 1H) |
| 13.20A | 1.1 (m, 1H), 1.8 (m, 1H), 2.0 (s, 3H), 2.4 (m, 1H), 2.7 (m, 1H), 3.6 (s, 3H), 3.7 (s, 3H), 3.85 (s, 3H), 5.0 (s, 2H), 7.0 (d, 2H), 7.1–7.4 (m, 6H), 7.6 (s, 1H) |
| 13.22A | 1.2 (m, 1H), 1.8 (m, 1H), 2.0 (s, 3H), 2.4 (m, 1H), 2.9 (m, 1H), 3.7 (s, 3H), 3.8 (s, 3H), 3.95 (s, 3H), 5.0 (s, 2H), 6.9-7.0 (m, 3H), 7.1–7.4 (m, 5H), 7.6 (s, 1H) |
| 13.23 | 1.2 (m, 1H), 1.8 (m, 1H), 2.0 (s, 3H), 2.3 (m, 1H), 2.5 (m, 1H), 3.65 (s, 3H), 3.8 (s, 3H), 3.9 (s, 3H), 5.0 (s, 2H), 6.8.0-7.0 (m, 3H), 7.1–7.4 (m, 5H), 7.6 (s, 1H) |
| 13.25A | 1.2 (m, 1H), 1.8 (m, 1H), 2.0 (s, 3H), 2.25 (s, 3H), 2.45 (m, 1H), 2.8 (m, 1H), 3.6 (s, 3H), 3.75 (s, 3H), 3.9 (s, 3H), 5.1 (s, 2H), 7.1–7.4 (m, 8H), 7.6 (s, 1H) |
| 13.26 | 1.2 (m, 1H), 1.8 (m, 1H), 2.0 (s, 3H), 2.3 (s, 3H), 2.5 (m, 1H), 2.8 (m, 1H), 3.65 (s, 3H), 3.75 (s, 3H), 3.9 (s, 3H), 5.1 (s, 2H), 6.9-7.0 (m, 3H), 7.1–7.4 (m, 5H), 7.6 (s, 1H) |
| 13.39 | 1.1 (m, 1H), 1.3 (t, 3H), 1.8 (m, 1H), 2.0 (s, 3H), 2.4 (m, 1H), 2.7 (m, 1H), 3.6 (s, 3H), 3.7 (s, 3H), 4.1 (m, 2H), 5.1 (s, 2H), 7.0 (d, 2H), 7.1–7.4 (m, 7H), 7.6 (s, 1H) |
| 13.40A | 0.85 (t, 3H), 1.1 (m, 1H), 1.6 (q, 2H), 1.8 (m, 1H), 2.0 (s, 3H), 2.4 (m, 1H), 2.6 (m, 1H), 3.6 (s, 3H), 3.7 (s, 3H), 4.0 (t, 2H), 5.0 (s, 2H), 7.0 (d, 2H), 7.1–7.4 (m, 7H), 7.6 (s, 1H) |
| 13.42A | 0.9 (t, 3H), 1.1 (m, 1H), 1.3 (m, 2H), 1.6 (m, 2H), 1.8 (m, 1H), 2.0 (s, 3H), 2.4 (m, 1H), 2.7 (m, 1H), 3.65 (s, 3H), 3.75 (s, 3H), 4.1 (t, 2H), 5.0 (s, 2H), 7.0 (d, 2H), 7.1–7.4 (m, 7H), 7.6 (s, 1H) |
| 13.43 | 1.2 (m, 10H), 1.8 (m, 1H), 2.0 (s, 3H), 2.4 (m, 1H), 2.6 (m, 1H), 3.6 (s, 3H), 3.7 (s, 3H), 4.0 (t, 2H), 5.0 (s, 2H), 7.0 (d, 2H), 7.1–7.4 (m, 7H), 7.6 (s, 1H) |
| 13.44A | 1.1 (m, 1H), 1.8 (m, 1H), 1.95 (s, 3H), 2.4 (m, 1H), 2.5 (s, 1H), 2.7 (m, 1H), 3.6 (s, 3H), 3.7 (s, 3H), 4.6 (d, 2H), 5.0 (s, 2H), 7.0 (d, 2H), 7.1–7.4 (m, 7H), 7.6 (s, 1H) |
| 13.45A | 1.0 (t, 3H), 1.1 (m, 1H), 1.3 (m, 1H), 1.8(m, 1H), 2.2 (m, 1H), 2.5 (q, 2H), 3.6 (s, 3H), 3.7 (s, 3H), 3.75 (s, 3H), 5.0 (s, 2H), 7.0 (d, 2H), 7.1–7.4 (m, 7H), 7.6 (s, 1H) |
| 13.45B | 1.0 (t, 3H), 1.1 (m, 1H), 1.3 (m, 1H), 1.7(m, 1H), 2.5 (m, 1H), 2.6 (q, 2H), 3.65 (s, 3H), 3.75 (s, 3H), 3.9 (s, 3H), 5.0 (s, 2H), 7.0 (d, 2H), 7.1–7.4 (m, 7H), 7.6 (s, 1H) |
| 13.56A | 0.95 (t, 3H), 1.2 (m, 1H), 1.5 (m, 2H), 1.7 (m, 1H), 2.45 (m, 1H), 2.7 (m, 3H), 3.65 (s, 3H), 3.75 (s, 3H), 3.9 (s, 3H), 5.0 (s, 2H), 7.0 (d, 2H), 7.1–7.4 (m, 7H), 7.6 (s, 1H) |
| 13.67A | 1.2 (m, 7H), 1.3 (m, 1H), 2.2 (m, 1H), 2.4 (m, 1H), 3.4 (q, 1H), 3.7 (s, 3H), 3.78 (s, 3H), 3.9 (s, 3H), 5.05 (s, 2H), 7.1–7.5 (m, 9H), 7.6 (s, 1H) |
| 13.67B | 1.2 (m, 7H), 1.3 (m, 1H), 1.8 (m, 1H), 2.2 (m, 1H), 3.1 (q, 1H), 3.6 (s, 3H), 3.70 (s, 3H), 3.75 (s, 3H), 5.0 (s, 2H), 7.1–7.4 (m, 9H), 7.5 (s, 1H) |
| 13.78A | 0.9 (t, 3H), 1.2 (m, 1H), 1.4 (m, 2H), 1.5 (m, 2H), 1.8 (m, 1H), 2.4 (m, 1H), 2.6 (m, 3H), 3.65 (s, 3H), 3.75 (s, 3H), 3.9 (s, 3H), 5.0 (s, 2H), 7.0 (d, 2H), 7.1–7.4 (m, 7H), 7.6 (s, 1H) |
| 14.7 | 1.10-1.25 (m, 2H), 2.10-2.20(m, 1H), 2.25-2.35 (m, 1H), 2.87-2.88 (d, 3H), 3.85 (s, 3H), , 3.92 (s, 3H), 5.05(s,2H), 6.6-6.8 (1)r s, 1H), 7.0-7.5 (m, 9H,) 8.29 (s, 1H) |
| 14.18A | 1.1 (m, 1H), 1.8 (m, 1H), 2.0 (s, 3H), 2.45 (m, 1H), 2.7 (m, 1H), 3.8 (s, 3H), 3.9 (s, 3H), 4.0 (s, 3H), 5.0 (s, 2H), 7.0 (d, 2H), 7.1–7.4 (m, 7H) |
| 14.20 | 1.2 (m, 1H), 1.8 (m, 1H), 2.0 (s, 3H), 2.4 (m, 1H), 2.6 (m, 1H), 3.8 (s, 3H), 3.9 (s, 3H), 4.0 (s, 3H), 5.0 (s, 2H), 6.9 (d, 2H), 7.1–7.4 (m, 6H) |
| 14.21 | 1.2 (m, 1H), 1.8 (m, 1H), 2.0 (s, 3H), 2.4 (m, 1H), 2.7 (m, 1H), 3.8 (s, 3H), 3.9 (s, 3H), 4.0 (s, 3H), 5.0 (s, 2H), 7.0 (d, 2H), 7.1–7.4 (m, 6H) |
| 14.22 | 1.2 (m, 1H), 1.8 (m, 1H), 2.0 (s, 3H), 2.4 (m, 1H), 2.7 (m, 1H), 3.75 (s, 3H), 3.85 (s, 3H), 3.95 (s, 3H), 5.0 (s, 2H), 6.9-7.2 (m, 3H), 7.3-7.5 (m, 5H) |
| 14.23 | 1.2 (m, 1H), 1.8 (m, 1H), 2.o (s, 3H), 2.3 (m, 1H), 2.5 (m, 1H), 3.7 (s, 3H), 3.85 (s, 3H), 3.95 (s, 3H), 4.95 (s, 2H), 6.8.0-7.0 (m, 3H), 7.1–7.4 (m, 5H) |
| 14.25A | 1.2 (m, 1H), 1.8 (m, 1H), 2.0 (s, 3H), 2.25 (s, 3H), 2.5 (m, 1H), 2.8 (m, 1H), 3.8 (s, 3H), 3.9 (s, 3H), 4.0 (s, 3H), 5.1 (s, 2H), 7.1–7.2 (m, 5H), 7.4 (m, 3H) |
| 14.26 | 1.2 (m, 1H), 1.8 (m, 1H), 2.0 (s, 3H), 2.3 (s, 3H), 2.4 (m, 1H), 2.6 (m, 1H), 3.8 (s, 3H), 3.9 (s, 3H), 4.0 (s, 3H), 5.0 (s, 2H), 7.0-7.2 (m, 3H), 7.3-7.5 (m, 5H) |
| 14.31 | 1.2 (m, 1H), 1.8 (m, 1H), 2.0 (s, 3H), 2.4 (m, 1H), 2.55 (m, 1H), 3.7 (s, 3H), 3.75 (s, 3H), 3.9 (s, 3H), 3.95 (s, 3H), 5.0 (s, 2H), 6.7 (d, 2H), 7.1–7.4 (m, 6H) |
| 14.45 | 1.1 (t, 3H), 1.2 (m, 1H), 1.8 (m, 1H), 2.4 (m, 2H), 2.5 (q, 2H), 3.8 (s, 3H), 3.9 (s, 3H), 4.0 (s, 3H), 5.0 (s, 2H), 7.0 (d, 2H), 7.1–7.4 (m, 7H) |
| 14.56A | 0.95 (t, 3H), 1.2 (m, 1H), 1.5 (m, 2H), 1.7 (m, 1H), 2.45 (m, 1H), 2.7 (m, 3H), 3.8 (s, 3H), 3.9 (s, 3H), 4.0 (s, 3H), 5.0 (s, 2H), 7.0 (d, 2H), 7.1–7.4 (m, 7H) |
| 14.67A | 1.2 (m, 7H), 1.4 (m, 1H), 2.2 (m, 1H), 2.4 (m, 1H), 3.2 (q, 1H), 3.8 (s, 3H), 3.9 (s, 3H), 4.0 (s, 3H), 5.0 (s, 2H), 7.0 (d, 2H), 7.1–7.4 (m, 7H) |
| 14.67B | 1.2 (m, 7H), 1.3 (m, 1H), 1.8 (m, 1H), 2.2 (m, 1H), 3.1 (q, 1H), 3.8 (s, 6H), 3.95 (s, 3H), 5.0 (s, 2H), 7.0 (d, 2H), 7.1–7.4 (m, 7H) |
| 14.78A | 0.9 (t, 3H), 1.2 (m, 1H), 1.4 (m, 2H), 1.5 (m, 2H), 1.7 (m, 1H), 2.4 (m, 1H), 2.6 (m, 3H), 3.8 (s, 3H), 3.9 (s, 3H), 4.0 (s, 3H), 5.0 (s, 2H), 7.0 (d, 2H), 7.1–7.4 (m, 7H) |
| 15.7 | 1.10–1.25 (m, 2H), 2.10–2.20(m, 1H), 2.25–2.25 (m, 1H), 3.82 (s, 3H), 3.85 (s, 3H), 3.99 (s, 3H), 5.04 (s,2H), 7.0–7.5 (m, 9H), 7.56 (s, 1H), 8.28 (s, 1H) |

TABLE 61-continued

| Compound # | NMR DATA |
|---|---|
| 15.21 | 1.2 (m, 1H), 1.7 (m, 1H), 1.9 (s, 3H), 2.2 (m, 1H), 2.6 (m, 1H), 2.9 (d, 3H), 3.8 (s, 3H), 3.9 (s, 3H), 5.0 (s, 2H), 6.8 bs, 1H), 7.0 (d, 2H), 7.1–7.4 (m, 6H) |
| 15.18A | 1.2 (m, 1H), 1.8 (m, 1H), 2.0 (s, 3H), 2.45 (m, 1H), 2.8 (m, 1H), 2.9 (d, 3H), 3.9 (s, 3H), 3.92 (s, 3H), 5.0 (s, 2H), 6.8 (1)s, 1H), 7.0 (d, 2H), 7.1–7.4 (m, 7H) |
| 15.18B | 1.2 (m, 1H), 1.4 (m, 1H), 1.8 (m, 1H), 1.95 (s, 3H), 2.2 (m, 1H), 2.85 (d, 3H), 3.9 (s, 3H), 3.95 (s, 3H), 5.0 (s, 2H), 6.7 bs, 1H), 7.0 (d, 2H), 7.1–7.4 (m, 7H) |
| 15.20 | 1.1 (m, 1H), 1.8 (m, 1H), 1.9 (s, 3H), 2.3 (m, 1H), 2.6 (m, 1H), 2.8 (d, 3H), 3.85 (d, 6H), 5.0 (s, 2H), 6.7 bs, 1H), 6.9–7.4 (m, 8H) |
| 15.22A | 1.1 (m, 1H), 1.8 (m, 1H), 1.9 (s, 3H), 2.3 (m, 1H), 2.8 (d, 3H), 2.9 (m, 1H), 3.85 (d, 6H), 5.0 (s, 2H), 6.7 bs, 1H), 6.9–7.4 (m, 8H) |
| 15.24 | 1.1 (m, 1H), 1.7 (m, 1H), 1.9 (s, 3H), 2.2 (m, 1H), 2.6 (m, 1H), 2.8 (d, 3H), 3.85 (d, 6H), 4.98 (s, 2H), 6.8 bs, 1H), 6.9–7.4 (m, 8H) |
| 15.25A | 1.2 (m, 1H), 1.8 (m, 1H), 2.0 (s, 3H), 2.2 (s, 3H), 2.6 (m, 1H), 2.8 (m, 1H), 2.85 (d, 3H), 3.85 (s, 6H), 4.95 (s, 2H), 6.8 bs, 1H), 7.0–7.4 (m, 8H) |
| 15.26A | 1.2 (m, 1H), 1.7 (m, 1H), 1.9 (s, 3H), 2.2 (s, 3H), 2.4 (m, 1H), 2.7 (m, 1H), 2.8 (d, 3H), 3.85 (d, 6H), 4.98 (s, 2H), 6.8 bs, 1H), 6.9–7.4 (m, 8H) |
| 15.26B | 1.1 (m, 1H), 1.4 (m, 1H), 1.8 (m, 1H), 1.9 (s, 3H), 2.1 (m, 1H), 2.2 (s, 3H), 2.8 (d, 3H), 3.75 (s, 3H), 3.85 (s, 3H), 4.95 (s, 2H), 6.7 bs, 1H), 6.8 (d, 2H), 6.9–7.4 (m, 6H) |
| 15.31 | 1.2 (m, 1H), 1.8 (m, 1H), 1.95 (s, 3H), 2.4 (m, 1H), 2.55 (m, 1H), 2.9 (d, 3H), 3.75 (s, 3H), 3.8 (s, 3H), 3.83 (s, 3H), 5.0 (s, 2H), 6.6 (d, 2H), 7.1–7.4 (m, 6H) |
| 15.45 | 1.0 (t, 3H), 1.2 (m, 1H), 1.7 (m, 1H), 2.3 (m, 2H), 2.4 (m, 1H), 2.5 (q, 2H), 2.8 (d, 2H), 3.8 (s, 3H), 3.85 (s, 3H), 4.95 (s, 2H), 6.7 bs, 1H), 6.9 (d, 2H), 7.1–7.4 (m, 7H) |
| 15.56A | 0.9 (t, 3H), 1.2 (m, 1H), 1.5 (m, 2H), 1.8 (m, 1H), 2.4 (m, 1H), 2.6 (m, 3H), 2.9 (d, 3H), 3.9 (s, 3H), 4.0 (s, 3H), 5.0 (s, 2H), 6.8 bs, 1H), 7.0 (d, 2H), 7.1–7.4 (m, 7H) |
| 15.67A | 1.1 (m, 7H), 1.2 (m, 1H), 2.2 (m, 1H), 2.4 (m, 1H), 2.9 (d, 3H), 3.1 (q, 1H), 3.8 (s, 3H), 3.9 (s, 3H), 4.95 (s, 2H), 6.8 (1,s, 1H), 7.0 (d, 2H), 7.1–7.4 (m, 7H) |
| 15.67B | 1.1 (m, 6H), 1.2 (m, 1H), 1.4 (m, 1H), 1.8 (m, 1H), 2.2 (m, 1H), 2.8 (d, 3H), 3.0 (q, 1H), 3.75 (s, 3H), 3.9 (s, 3H), 4.95 (s, 2H), 6.7 (1,s, 1H), 7.0 (d, 2H), 7.1–7.4 (m, 7H) |
| 15.78A | 0.9 (t, 3H), 1.2 (m, 1H), 1.4(m, 2H), 1.5 (m, 2H), 1.7 (m, 1H), 2.4 (m, 1H), 2.6 (m, 3H), 2.9 (d, 3H), 3.9 (s, 3H), 4.0 (s, 3H), 5.0 (s, 2H), 6.8 bs, 1H), 7.0 (d, 2H), 7.1–7.4 (m, 7H) |

*NMR data for compounds designated by A or B are data for one single stereoisomer for $R_9ON\!=\!C$ Compounds without designation are a mixture of stereoisomers and the data provided is for the major isomer.

EXAMPLE 11

Numerous compounds of this invention were tested for fungicidal activity in vivo against the diseases described below. The compounds were dissolved a 1:1 mixture of acetone and methanol or N,N-dimethylformamide and diluted with a 2:1:1 mixture of water, acetone, and methanol (by volume) or water, respectively, to achieve the appropriate concentration. The solution was sprayed onto the plants, and allowed to dry (two hours). Then the plants were inoculated with fungal spores. Each test utilized control plants which were sprayed with the appropriate solvent mixture and inoculated. For these protective tests, the plants were inoculated one day after treating the plants with the fungicide compound. The remainder of the technique of each of the tests is given below along with the results for various compounds described herein by the Compound # against the various fungi at a dose of 150 grams per hectare. The results are percent disease control are compared to the untreated check wherein one hundred was rated as complete disease control and zero as no disease control.

Wheat Leaf Rust (WLR)

*Puccinia recondita* (f. sp. *tritici*) was cultured on 7-day old wheat (cultivar Fielder) over a 12-day period in the greenhouse. Spores were collected from the leaves by settling on aluminum foil. The spores were cleaned by sieving through a 250-micron opening screen and stored dry. The dried spores were used within one month. A spore suspension was prepared from dry uredia by adding 20 mg (9.5 million spores) per ml of Soltrol oil. The suspension was dispensed into gelatin capsules (0.7 ml capacity) which attach to the oil atomizers. One capsule is used per flat of twenty 2-inch square pots of 7-day old wheat plants, cultivar Fielder After waiting for at least 15 minutes for the oil to evaporate from the wheat leaves, the plants were placed in a dark mist chamber (18–20° C. and 100% to relative humidity) for 24 hours. The plants were then placed in the greenhouse and evaluated after 12 days for disease

Wheat Leaf Blotch (SNW)

Cultures of *Septoria nodorum* was maintained on Czapek-Dox V-8 juice agar plates in an incubator at 20° C. with alternating periods of 12 hours of light and 12 hours of darkness for 2 weeks. A water suspension of the spores was obtained by shaking the portion of the plate with fungal material in deionized water and filtering through cheese-cloth. The spore-containing water suspension was diluted to a spore concentration of $3.0 \times 10^6$ spores per ml. The inoculum was dispersed by a De Vilbiss atomizer over one-week old Fielder wheat plants which had been previously sprayed with the fungicide compound. The inoculated plants were placed in a humidity cabinet at 20° C. with alternating 12 hours of light and 12 hours of darkness for 7 days. The inoculated seedlings were then moved to a controlled environment room at 20° C. for 2 days of incubation. Disease control values were recorded as percent control.

Wheat Powdery Mildew (WPM)

*Erysiphe graminis* (f. sp. *tritici*) was cultured on wheat seedlings, cultivar Fielder, in a controlled temperature room at 18° C. Mildew spores were shaken from the culture plants onto 7-day old wheat seedlings which had been previously sprayed with the fungicide compound. The inoculated seedlings were kept in a controlled temperature room at 18° C. and subirrigated. The percent disease control was rated 7 days after the inoculation.

Cucumber Powdery Mildew (CPM)

*Sphaerotheca fulginea* was maintained on cucumber plants, cultivar. Bush Champion, in the greenhouse. Inoculum was prepared by placing five to ten heavily mildewed cucumber leaves in a glass jar with 500 ml of water containing one drop of Tween 80 per 100 ml. After shaking the liquid and leaves, the inoculum was filtered through cheese cloth and misted onto the plants with a squirt bottle mister. The spore count was 100,000 spores/ml. The plants were then placed in the greenhouse for infection and incubation. The plants were scored seven days after inoculation. Disease control values were recorded as percent control.

Tomato Late Blight (TLB)

Cultures of Phytophthora infestans were maintained on green pea-amended agar for two to three weeks. The spores were washed from the agar with water and dispersed with a De Vilbiss atomizer over the leaves of 3-week old Pixie tomato plants which had been previously treated with experimental fungicides. The inoculated plants were placed in a humidity cabinet at 20° C. for 24 hours for infection. The plants were then removed to a controlled environment room at 20° C. and 90% humidity. The plants were scored for disease control after five days.

Grape Downy Mildew (GDM)

Plasmopara viticola was maintained on leaves of grape plants, cultivar. Delaware, in a controlled temperature chamber at 20° C. in humid air with moderate light intensity for 7 to 8 days. A water suspension of the spores from infested leaves was obtained and the spore concentration was adjusted to about $3 \times 10^5$ per ml of water. Delaware grape plants were inoculated by spraying the underside of leaves with a De Vilbiss atomizer until small drops were observed on the leaves. The inoculated plants were incubated in a mist chamber for 24 hours at 20° C. The plants were then removed to a controlled environmental room at 20° C. Disease control values were recorded as percent control seven days after inoculation.

Rice Blast (RB)

Cultures of Pyricularia oryzae were maintained on potato dextrose agar for two to three weeks. The spores were washed from the agar with water containing 1 drop of Tween 80 per 100 ml water. After filtering the spore suspension through two layers of cheese cloth, the spore count was adjusted to $5 \times 10_5$. The spore suspension was sprayed onto 12-day old rice plants, cultivar M-1, using a De Vilbiss atomizer. The inoculated plants were placed in a humidity cabinet at 20 C. for 36 hours to allow for infection. After the infection period, the plants were placed in the greenhouse. After 6 days, the plants were scored for disease control.

Cucumber Anthracnose (CA)

The fungal pathogen Colletotrichum lagenarium was cultured on potato dextrose agar (PDA) in the dark at 22 C for a period of 8 to 14 days. Spores of C. Lagenarium were removed from the PDA plates by flooding the plate surface with distilled water, amended with 0.5% v/w of yeast extract. The upper surface of the fungal colony was scraped with a blunt instrument until most of the spores were released into the aqueous environment. The spore suspension was filtered though cheesecloth, and the spore count was adjusted by adding more water, containing the yeast extract, until $3.0 \times 10^6$ spores per ml was achieved.

The chemically-treated cucumber plants were 15-days old, cultivar Bush Champion. The upper leaf surface of the plants were sprayed with the spore suspension until runoff, using a hand-held pump spray bottle. The plants were placed in a fluorescent-lighted mist chamber (12 hr light, 12 hr dark) for 48 hours. After that infection period, the plants were placed in a growth chamber for 3 days at 25 C and 90% humidity. The treated plants were then evaluated for disease control.

Botrytis (BOT)

The fungal pathogen Botrytis cinerea was cultured on potato dextrose agar (PDA) under fluorescent lights (12 hr on, 12 hr off) for a period of 2 to 3 weeks. Spores of B. cinerea were removed from the PDA plates by flooding the plate surface with distilled water, amended with 0.5% v/w of yeast extract. The upper surface of the fungal colony was scraped with a rubber instrument until most of the spores were released into the aqueous environment. The spore suspension was filtered though cheesecloth, and the spore count was adjusted by adding more water, containing the yeast extract, until $3.0 \times 10^6$ spores per ml was achieved.

Chemically-treated sweet bell pepper plants were 19-days old, cultivar California Wonder. The entire leaf surface of the plants were sprayed with the spore suspension until runoff, using a De Vilbiss atomizer. The plants were placed in a low light mist chamber (12 hr light, 12 hr dark) at 22 C for 4 or 5 days. The treated plants were then evaluated for disease control.

When tested against wheat leaf rust at 150 grams per hectare compounds 1.11, 1.24, 1.25, 2.24, 2.25, 3.22, 13.7, 13.11A, 13.18A, 13.18B, 13.20A, 13.22A, 13.39, 13.40A, 13.42A, 13.44A, 13.45A, 13.45B, 13.56A, 13.67B, 14.18A, 14.20, 15.7, 15.2115.18A, 15.18B, 15.20, 15.22A, 15.24, 15.31, 15.45, 15.56A, 15.67A and 15.78 exhibited 99% or better control.

When tested against septoria nodorum at 150 grams per hectare compounds 1.11, 2.14, 13.18A, 13.18B, 14.21 , 14.18A, 15.7, 15.18A and 15.18B exhibited 90% or better control.

When tested against wheat powdery mildew at 150 grams per hectare compounds 1.24, 1.25, 2.11, 2.45, 3.22, 13.7, 13.18A, 13.22A, 13.23, 14.7,14.18A 14.21, 14,22, 14.23, 14.45, 14.67A, 15.18B, 15.24, 15.26A and 15.31, exhibited 90% or better control.

When tested against cucumber powdery mildew at a dose of 150 grams per hectare, compounds, 13.18A, 13.20A, 13.22A, 13.23, 13.25A, 13.26, 13.39, 13.40A, 13.42A, 13.43, 13.44A, 13.45A, 13.56A, 13.67A, 14.20, 14.22, 14.25A, 14.26, 14.31, 14.45, 14.67A, 15.18A, 15,18B, 15.20, 15.22A, 15.24, 15.25A, 15.26A, 15.26B, 15.31, 15.45, 15.56A and 15.67A exhibited 100 % control.

When tested against tomato late blight at 150 grams/ hectare compounds 1.11, 1.22, 1.24, 1.25, 2.11, 2.45, 3.22, 13.18A, 13.23, 13.45B, 13.67A, 15.21, 15.18A 15.26A, 15.45, 15.67A and 15.67B exhibited 90% or better control.

When tested against grape downy mildew at 150 grams/ hectare compounds 2.1, 2.11, 2.14, 13.7, 13.18A, 13.18B, 14.7, 14.18A, 14.21, 15.7, 15.18A, 15.18B, 15.25A, and 15.67A exhibited 99% or better control.

When tested against rice blast at 150 grams/hectare compounds 1.11,1.22,1.24,1.25, 2.24, 13.18A, 13.18B, 13.23, 13.25A, 13.45A, 14.21, 14.18A 14.23, 14.26, 14.45, 15.18A, 15.18B, 15.21, 15.25A, 15.26A, 15.26B,16.24, 15.31 and 15.45 exhibited 90% or better control.

When tested against cucumber anthracnose at 150 grams/ hectare compounds 1.24, 13.18A, 13.18B, 13.23, 13.25A, 13.26, 13.45A, 13.67A, 14.21, 14.22, 14.26, 15,7, 15.21, 15.18A, 15.18B,15.25A, 15.26A, 15.26B, 15.45, 15.56A and 15.67A exhibited 90% or better control.

When tested against botrytis at 150 grams/hectare compounds 1.22, 3.22, 13.22A, 13.26, 14.67B, 15.7 and 15.18A exhibited 85% or better control.

The compounds of this invention are useful as agricultural fungicides and, as such, can be applied to various loci such as the seed, the soil or the foliage.

The compounds of this invention can be applied as fungicidal sprays by methods commonly employed, such as conventional high-volume hydraulic sprays, low-volume sprays, air-blast spray, aerial sprays and dusts. The dilution and rate of application will depend upon the type of equipment employed, the method of application, plants to be treated and diseases to be controlled. Generally, the compounds of this invention will be applied in amount of from about 0.005 kilogram to about 50 kilograms per hectare and preferably from about 0.025 to about 25 kilograms per hectare of the active ingredient.

As a seed protectant, the amount of toxicant coated on the seed is usually at a dosage rate of from about 0.05 to about 20, preferably from about 0.05 to about 4, and more preferably from about 0.1 to about 1 grams per hundred kilograms of seed. As a soil fungicide the chemical can be incorporated in the soil or applied to the surface usually at a rate of from about 0.02 to about 20, preferably from about 0.05 to about 10, and more preferably from about 0.1 to about 5 kilograms per hectare. As a foliar fungicide, the toxicant is usually applied to growing plants at a rate of from about 0.01 to about 10, preferably from about 0.02 to 5, and more preferably from about 0.25 to about 1 kilograms per hectare Inasmuch as the compounds of this invention display fungicidal activity, these compounds can be combined with other known fungicides to provide broad spectrum activity. Suitable fungicides include, but are not limited to, those compounds listed in U.S. Pat. No. 5,252,594 (see in particular columns 14 and 15). Other known fungicides which an be combined with the compounds of this invention are dimethomorph, famoxadone, zoxamide, cymoxanil, thifluzamide, furalaxyl, ofurace, benalaxyl, oxadixyl, propamocarb, cyprofuram, fenpiclonil, fludioxonil, pyrimethanil, cyprodinil, triticonazole, fluquinconazole, metconazole, spiroxamine, carpropamid, azoxystrobin, kresoxim-methyl, metominostrobin and trifloxystrobin.

The compounds of this invention can be advantageously employed in various ways. Since these compounds possess broad spectrum fungicidal activity, they can be employed in the storage of cereal grain. These compounds can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat *septoria nodorum,* rice sheath blight and rice blast.

EXAMPLE 12

Numerous compounds of this invention were tested for insecticidal activity in vivo against the insects described below. The following test method was used to evaluate compounds of the present invention for insecticidal activity. The compound to be evaluated was dissolved in an appropriate solvent, usually a mix of acetone, methanol and water, and sprayed over three excised leaf disks using a flat fan nozzle. After spraying, the leaf disks were allowed to dry. A disk was infested with the leaf chewing insects (southern armyworm) and a second leaf disk was already infested with the two-spotted spider mite prior to spraying. The tested insect species were:

AW southern armyworm *Spodoptera eridamia*

MTA two-spotted spider mite *Teranychus uricate*

Observations as percent control were made by visual inspection 24–48 hours after spraying.

When tested against southern army worm at 150 grams/ hectare compounds 13.20A, 13.26, 13.39, 13.40A, 13.42A and 13.45A provided 100% control.

When tested against two-spotted spider mite at 150 grams/hectare compounds 1.22, 13.20A, 13.22A, 13.26, 13.39, 13.40A, 13.42A, 13.45A, 13.56A and 15.20 provided 100% control.

The compositions and compounds of this invention can be applied directly to the locus to be protected, as for example, the area around or upon economic plants infected with insects or to plants on which infestation is to be prevented. Examples of injurious insects belong to the orders Lepidoptera, Coleoptera, Diptera, Thysanoptera, Hymenoptera, Heteroptera, Homoptera, Orthoptera, and Acarina. The compounds and compositions may be used either as contact or systemic pesticides. The compounds of the invention are applied to the insect's habitat at a rate of 0.0005 to 10 kilograms per hectare, preferably 0.05 to 5 and most preferably from 0.1 to 1 kilogram per hectare.

In the practice of the method of the invention, the active compound may be applied to the soil or foliage where it is absorbed by the plant, translocated to other plant parts and ultimately ingested by the pest or insects by means of ingestion of the plant part(s). This means of application is referred to as systemic application. Alternatively, the active compound may be applied to the soil and contacted therein with the insects and other pests to be controlled. This means of application is referred to as soil application. In another alternative, the active compound may be foliarly applied to the plants to be freed from insects and other pests which feed on the foliage.

Compositions and formulations according to the present invention may also include known pesticidal compounds. This expands the spectrum of activity of the preparation and may give rise to synergism. Suitable insecticides known in the art include those listed in U.S. Pat. No. 5,075,471, see in particular columns 14 and 15.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier is meant any substance which can be used to dissolve, disperse of diffuse the active ingredient in the composition without impairing the active ingredients effectiveness and which by itself has no significant detrimental effect on the soil, equipment, desirable plants, or agronomic environment. If desired, adjuvants such as surfactants, stabilizers, antifoam agents and anti-drift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water before or during use. In such formulations, the compounds are extended with a liquid or solid carrier and, when desired, suitable surfactants are incorporated. Baits are preparations generally comprising a food or other substance attractive to insects, that includes at least one compound of the instant invention.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art, and a discussion of adjuvants can be found in many references, such as in the John W. McCutcheon, Inc. publication "Detergents and Emulsifiers, Annual."

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001 (1:999, 999)–99 (99:1) % by weight. For compositions suitable for storage or transportation, the amount of active ingredient is preferably between about 0.5 (1:199)–90 (9:1) % by weight, and more preferably between about 1 (1:99)–75 (3:1) % by weight of the mixture. Compositions suitable for direct application or field application generally contain the active compound in an amount substantially between about 0.0001 (1:999, 999)–95 (19:1) %, preferably between about 0.0005 (1:199, 999)–90 (9:1) % by weight, and more preferably between about 0.001 (1:99, 999)–75 (3:1) % by weight of the mixture. The composition can also be stated as a ratio of the compound to the carrier. In the present invention the weight ratio of these materials active compound/carrier) can vary from 99:1 (99%) to 1:4 (20%) and more preferably from 10:1 (91%) to 1:3 (25%).

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 0% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 99%, preferably from about 40% to about 75%. A typical wettable powder is made by blending 50 parts of a compound of Formula I, 45 parts of a synthetic precipitated hydrated silicon dioxide, such as that sold under the trademark Hi-Sil®, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silicoaluminate sold under the trademark Zeolex®7.

Dusts are prepared by mixing compounds of Formula I, or the enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The active compounds can be applied as insecticide sprays by methods commonly employed, such as conventional high-gallonage hydraulic sprays, low gallonage sprays, ultra-low-volume sprays, air blast spray, aerial sprays, and dusts.

The present invention also contemplates methods of killing, combating or controlling pests which compromises contacting pests with a combative or toxic amount (i.e. a pesticidally effective amount) of at least one active compound of the invention alone or together with a carrier vehicle (composition or formulation) as noted above. The term contacting as employed in the specification and claims means applying to at least one of (a) such pests and (b) the corresponding habit at thereof (i.e., the locus to be protected, for example, to a growing crop or to an area where a crop is to be grown) the active compound of this invention alone or as a constituent of a composition or formulation.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added adhesives such as polyvinylalcohol-cellulose derivatives or other colloidal materials, such as casein, to improve the adherence of the pesticide to the surface to be protected.

We claim:
1. A compound of the formula:

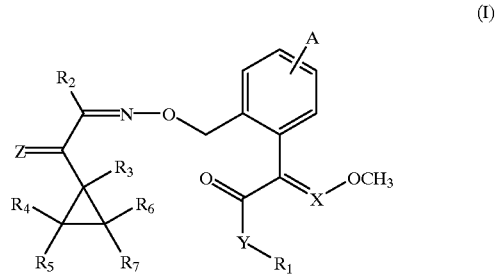

(I)

wherein
X is N or CH; Y is O, S or $NR_8$;
A is selected from the group consisting of hydrogen, halo, cyano, $(C_1–C_{12})$alkyl, and $(C_1–C_{12})$alkoxy;

Z is O, N—OR$_9$ or N—R$_{10}$;

R$_1$ and R$_8$ are independently selected from the group consisting of hydrogen and (C$_1$–C$_4$)alkyl;

R$_2$ is selected from the group consisting of hydrogen, (C$_1$–C$_{12}$)alkyl, halo(C$_1$–C$_{12}$)alkyl, (C$_3$–C$_7$)cycloalkyl, halo(C$_3$–C$_7$)cycloalkyl, (C$_2$–C$_8$)alkenyl, halo(C$_2$–C$_8$)alkenyl, (C$_2$–C$_8$)alkynyl, halo(C$_2$–C$_8$)alkynyl, cyano, (C$_1$–C$_4$)alkoxycarbonyl, aryl, aralkyl, heterocyclic, and heterocyclic(C$_1$–C$_4$)alkyl;

R$_3$ and R$_7$ are each independently selected from the group consisting of hydrogen, (C$_1$–C$_{12}$)alkyl, halo(C$_1$–C$_{12}$)alkyl, (C$_2$–C$_8$)alkenyl, halo(C$_2$–C$_8$)alkenyl, (C$_2$–C$_8$)alkynyl, halo(C$_2$–C$_8$)alkynyl, aryl, aralkyl, heterocyclic and heterocyclic(C$_1$–C$_4$)alkyl, provided that at least one of R$_3$ and R$_7$ is aryl, aralkyl, heterocyclic, or heterocyclic(C$_1$–C$_4$)alkyl;

R$_4$, R$_5$ and R$_6$ are each independently selected from the group consisting of hydrogen, (C$_1$–C$_{12}$)alkyl, halo(C$_1$–C$_{12}$)alkyl, (C$_3$–C$_7$)cycloalkyl, halo(C$_3$–C$_7$)cycloalkyl, (C$_2$–C$_8$)alkenyl, halo(C$_2$–C$_8$)alkenyl, (C$_2$–C$_8$)alkynyl, halo(C$_2$–C$_8$)alkynyl, halo, cyano, (C$_1$–C$_4$)alkoxycarbonyl, aryl, aralkyl, heterocyclic and heterocyclic(C$_1$–C$_4$)alkyl;

R$_9$ is selected from the group consisting of hydrogen, (C$_1$–C$_{12}$)alkyl, halo(C$_1$–C$_{12}$)alkyl, (C$_3$–C$_7$)cycloalkyl, halo(C$_3$–C$_7$)cycloalkyl, (C$_2$–C$_8$)alkenyl, halo(C$_2$–C$_8$)alkenyl, (C$_2$–C$_8$)alkynyl, halo(C$_2$–C$_8$)alkynyl, (C$_1$–C$_4$)alkylcarbonyl, arylcarbonyl, aralkylcarbonyl, heterocyclic carbonyl, (C$_1$–C$_4$)alkoxycarbonyl, aryl, aralkyl, heterocyclic and heterocyclic(C$_1$–C$_4$)alkyl;

R$_{10}$ is selected from the group consisting of hydrogen, (C$_1$–C$_{12}$)alkyl, halo(C$_1$–C$_{12}$)alkyl, (C$_2$–C$_8$)alkenyl, halo(C$_2$–C$_8$)alkenyl, (C$_2$–C$_8$)alkynyl, halo(C$_2$–C$_8$)alkynyl, aryl, aralkyl, heterocyclic or heterocyclic (C$_1$–C$_4$)alkyl, (C$_1$–C$_4$)alkylcarbonyl, and (C$_1$–C$_4$)alkoxycarbonyl, arylcarbonyl, aralkylcarbonyl, heterocyclic carbonyl, (C$_1$–C$_4$)alkylaminocarbonyl, arylaminocarbonyl, N—R$_8$R$_9$, N=CR$_{11}$R$_{12}$, (C$_1$–C$_4$)alkylsulfonyl, N=cyclopropyl, N=cyclobutyl, N=cyclopentyl, N=cyclohexyl, N=benzyl, and arylsulfonyl;

R$_{11}$ and R$_{12}$ are each independently selected from the group consisting of hydrogen, (C$_1$–C$_{12}$)alkyl, halo (C$_1$–C$_{12}$)alkyl, (C$_1$–C$_{12}$)alkoxy, halo(C$_1$–C$_{12}$)alkoxy, (C$_3$–C$_7$)cycloalkyl, halo(C$_3$–C$_7$)cycloalkyl, (C$_2$–C$_8$)alkenyl, halo(C$_2$–C$_8$)alkenyl, (C$_2$–C$_8$)alkynyl, halo (C$_2$–C$_8$)alkynyl, cyano, (C$_1$–C$_4$)alkoxycarbonyl, (C$_1$–C$_4$)alkylamino, aryl, aralkyl, heterocyclic, and heterocyclic(C$_1$–C$_4$)alkyl.

2. The compound of claim 1 wherein X is CH, Y is O, Z is NOR$_9$, R$_2$ is (C$_1$–C$_{12}$)alkyl, and R$_3$ is H or (C$_1$–C$_4$)alkyl.

3. The compound of claim 2 wherein R$_9$ is (C$_1$–C$_4$) and R$_7$ is selected from the group consisting of phenyl, 2-chlorophenyl, 2-fluorophenyl, 2-trifluoromethylphenyl, 3-chlorophenyl, 3-fluorophenyl, 3-trifluoromethylphenyl, 4-chlorophenyl, 4-fluorophenyl, 4-trifluoromethylphenyl 2,4-dichlorophenyl, and 2,6-dichlorophenyl.

4. The compound of claim 1 wherein X is N, Y is O or NH, Z is NOR$_9$, R$_2$ is (C$_1$–C$_{12}$)alkyl, and R$_3$ is H or (C$_1$–C$_4$) alkyl.

5. The compound of claim 4 wherein R$_9$ is (C$_1$–C$_4$) and R$_7$ is selected from the group consisting of phenyl, 2-chlorophenyl, 2-fluorophenyl, 2-trifluoromethylphenyl, 3-chlorophenyl, 3-fluorophenyl, 3-trifluoromethylphenyl, 4-chlorophenyl, 4-fluorophenyl, 4-trifluoromethylphenyl, 2,4-dichlorophenyl, and 2,6-dichlorophenyl.

6. The compound of claim 1 where the compound is where the compound is N-methyl 2-[2-(5-trans-(2-phenylcyclopropyl)-4-methyl-2,7-dioxa-3,6-diazaocta-3,5-dien-1-yl)phenyl]-2-methoxyiminoacetamide.

7. The compound of claim 1 where the compound is N-methyl 2-[2-(5-trans-(2-(4-chlorophenyl)cyclopropyl)-4-methyl-2,7-dioxa-3,6-diazaocta-3,5-dien-1-yl)phenyl]-2-methoxyiminoacetamide.

8. A fungicidal composition for controlling phytopathogenic fungi which comprises an agronomically acceptable carrier and the compound of claim 1 wherein the ratio of the carrier to the compound is between 99:1 and 1:4.

9. A method for controlling phytopathogenic fungi which comprises applying the compound of claim 1 to the locus where control is desired, at a rate of from 0.005 to 50 kilograms per hectare.

10. A method for controlling insects which comprises applying to the insects' habitat the compound of claim 1 at a rate of from 0.005 to 10 kilograms per hectare.

* * * * *

UNITED STATES PATENT AND TRADEMARK OFFICE
CERTIFICATE OF CORRECTION

PATENT NO.    : 6,313,339 B1
DATED         : November 6, 2001
INVENTOR(S)   : Ronald Ross, Jr., Duyan Vuong Nguyen and Steve Howard Shaber It is certified that error appears in the above-identified patent and that said Letters Patent is hereby corrected as shown below:

<u>Column 122,</u>
Line 24 should read as follows:
-- 6. The compound of Claim 1 where the compound is -- rather than
"6. The compound of Claim 1 where the compound is where the compound is"

Signed and Sealed this

Twenty-first Day of May, 2002

Attest:

Attesting Officer

JAMES E. ROGAN
Director of the United States Patent and Trademark Office